US012590163B2

(12) United States Patent
Trinklein et al.

(10) Patent No.: US 12,590,163 B2
(45) Date of Patent: ***Mar. 31, 2026

(54) AGONISTIC ANTI-IL-2R ANTIBODIES AND METHODS OF USE

(71) Applicant: TENEOBIO, INC., Thousand Oaks, CA (US)

(72) Inventors: Nathan Trinklein, Redwood City, CA (US); Katherine Harris, Fremont, CA (US); Kyle Lorentsen, Dublin, CA (US); Harbani Kaur Malik Chaudhry, Oakland, CA (US); Kaitlyn Loughlin, San Mateo, CA (US)

(73) Assignee: TENEOBIO, INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/457,553

(22) Filed: Aug. 29, 2023

(65) Prior Publication Data

US 2024/0018250 A1     Jan. 18, 2024

Related U.S. Application Data

(63) Continuation of application No. 18/164,442, filed on Feb. 3, 2023, now Pat. No. 11,884,735, which is a continuation of application No. PCT/US2022/023058, filed on Apr. 1, 2022.

(60) Provisional application No. 63/239,883, filed on Sep. 1, 2021, provisional application No. 63/170,383, filed on Apr. 2, 2021.

(51) Int. Cl.
*C07K 16/28*     (2006.01)
*A61K 39/00*     (2006.01)
*A61P 35/00*     (2006.01)

(52) U.S. Cl.
CPC .......... *C07K 16/2866* (2013.01); *A61P 35/00* (2018.01); *A61K 2039/505* (2013.01); *C07K 2317/31* (2013.01); *C07K 2317/522* (2013.01); *C07K 2317/524* (2013.01); *C07K 2317/526* (2013.01); *C07K 2317/53* (2013.01); *C07K 2317/565* (2013.01); *C07K 2317/569* (2013.01); *C07K 2317/62* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,510,259 A | 4/1996 | Sugamura et al. | |
| 6,103,879 A | 8/2000 | Chaovapong et al. | |
| 11,884,735 B2 * | 1/2024 | Trinklein | C07K 16/2866 |
| 2006/0165685 A1 | 7/2006 | Kreysch | |

FOREIGN PATENT DOCUMENTS

| | | |
|---|---|---|
| EP | 3428193 | 1/2019 |
| WO | 1996/021732 | 7/1996 |
| WO | 1997/043416 | 11/1997 |
| WO | 2011/127324 | 10/2011 |
| WO | 2014/087248 | 6/2014 |
| WO | 2014/182970 | 11/2014 |
| WO | 2017/021540 | 2/2017 |
| WO | 2019/092181 | 5/2019 |
| WO | 2020/094834 | 5/2020 |
| WO | 2020/094836 | 5/2020 |
| WO | 2020/160242 | 8/2020 |

OTHER PUBLICATIONS

Villareal et al. Targeting of CD122 enhances antitumor immunity by altering the tumor immune environment. Oncotarget, 2017, vol. 8, (No. 65), pp. 109151-109160.*
International Search Report for PCT Application No. PCT/US2022/023058, mailed on Jul. 7, 2022.
Written Opinion of the International Searching Authority for PCT Application No. PCT/US2022/023058, mailed on Jul. 7, 2022.
Reply from the opponent, dated Jun. 20, 2022, to patent proprietor's submission dated Nov. 22, 2021, in Opposition of EP 3428193.
Notice of Opposition of EP 3428193 filed Jun. 30, 2021.
Proprietor's Observations on the Notice of Opposition, dated Nov. 22, 2021, in EP 3428193.
Certified SG 10201506227V, filed Aug. 6, 2015.
Hechinger et al., "Therapeutic activity of multiple common-y-chain cytokine inhibition in acute and chronic GVHD," (2015) Blood 125(3):570-580.
Rudikoff et al., "Single Amino Acid Substitution Altering Antigen-binding Specificity," (1982) Proc Nat Acad Sci 79:1979-1983.
Spiess et al., "Alternative Molecular Formats and Therapeutic Applications for Bispecific Antibodies," (2015) Molecular Immunology 67:95-106.
Nelson et al., "Cytoplasmic Domains of the Interleukin-2 receptor β and γ Chains Mediate the Signal for T-cell Proliferation," (1994) Nature 369:333-336.
Ellery et al., "Activation of the Interleukin 2 Receptor: A Possible Role for Tyrosine Phosphates," (2000) Cellular Signalling 12:367-373.
Dutcher et al., "High Dose Interleukin-2 (Aldesleukin)—expert consensus on best management practices—2014," Journal for ImmunoTherapy of Cancer 2014, 2(26):1-23.
Brauer, "Interleukin-2 receptor activation by anti-IL-2β/γc bispecific," published on at Nanyang Technological University Singapore, accessed via <https://dr.ntu.edu.sg/handle/10356/66329?mode=full> on Jun. 28, 2021.

(Continued)

*Primary Examiner* — Nora M Rooney
(74) *Attorney, Agent, or Firm* — Amy C. Madl

(57) ABSTRACT

Anti-IL2R (e.g., anti-IL2RB, anti-IL2RG, anti-IL2RB/G) antibodies are disclosed, along with methods of making such antibodies, compositions, including pharmaceutical compositions, comprising such antibodies, and use of such antibodies and compositions in the treatment of diseases and disorders that are mediated by the IL2/IL2R signaling pathway.

24 Claims, 32 Drawing Sheets

Specification includes a Sequence Listing.

(56) References Cited

OTHER PUBLICATIONS

Brauer et al., "Protein Engineering for Improved Thermostability of a Bispecific IL2-mimic Antibody by phage display," Keystone Symposia, accessed via https://virutal.keystonesymposia.org/ks/articles/672/view on Jun. 28, 2021.

Nakamura et al., "Heterodimerization of the IL-2 Receptor β- and γ-chain Cytoplasmic Domains is Required for Signalling," (1994) Letters to Nature 369:330-333.

Moraga et al., "Tuning Cytokine Receptor Signaling by Re-orienting Dimer Geometry with Surrogate Ligands," (2015) Cell 160:1196-1208.

Bugelski et al., "Monoclonal Antibody-induced Cytokine-release Syndrome," (2009) Expert Rev Clin Immunol 5(5):499-521.

Skrombolas et al., "Challenges and Developing Solutions for Increasing the Benefits of IL-2 Treatment in Tumor Therapy," (2014) Expert Rev Clin Immunol 10(2):207-217.

Phelan et al., "Cutting Edge: Mechanism of Enhancement of In Vivo Cytokine Effects by Anti-cytokine Monoclonal Antibodies," (2008) J Immunol 180:44-48.

Letourneau et al., "Il-2-IL-2 Antibody Complexes Show Strong Biological Activity by Avoiding Interactions with IL-2 Receptor a Subunit CD25," (2010) PNAS 107(5):2171-2176.

Krieg et al., "Improved IL-2 Immunotherapy by Selective Stimulation of IL-2 Receptors on Lymphocytes and Endothelial Cells," (2010) PNAS 107(26):11906-11911.

Sprangler et al., "Antibodies to Interleukin-2 Elicit Selective T Cell Subset Potentiation through Distinct Conformational Mechanisms," (2015) Immunity 42:815-825.

Levin et al., "Exploiting a Natural Conformational Switch to Engineer an Interleukin-2 Superkine," (2012) Nature 484(7395):529-533.

Kontermann, "Dual Targeting Strategies with Bispecific Antibodies," (2012) mAbs 4(2):182-197.

Nakano et al., "Effective Screening Method of Agonistic Diabodies Based on Autocrine Growth," (2009) Journal of Immunological Methods 347:31-35.

Murphy et al., "Janeway's Immunobiology: Seventh Edition," New York: Garland Sciences (2008) pp. 15-16.

Saunders, "Conceptual Approaches to Modulating Antibody Effector Functions and Circulation Half-life," (2019) Frontiers in Immunology 10(1296):1-20.

Léon et al., "FoxP3+ Regulatory T Cells Promote Influenza-specific The Responses by Controlling IL-2 Availability," (2014) Nature Communications 5:3495; pp. 1-10.

Frenzel et al., "Expression of Recombinant Antibodies," (2013) Frontiers in Immunology 4(217):1-20.

Archived Website entry from bioinf.org.uk. entitled, "Antibodies, Abyss—new database," captured on Jul. 10, 2015.

Greenberg et al, "Interleukin 2 Receptor," (1998) Encyclopedia of Immunology (1998) pp. 1439-1442.

Liu et al., "Expression of Interleukin-2 Receptor γ Chain on Human Neutrophils," (1994) Blood 84(11):3870-3875.

Actor, "Cells and Organs of the Immune System," (2012) in Elsevier's Integrated Review Immunology and Microbiology (Second Edition) pp. 7-16.

Liao et al., "IL-2 Family Cytokine: New Insights into the Complex Roles of IL-2 as a Broad Regulator of T Helper Cell Differentiator," (2011) Curr Opin Immunol 23(5):598-604.

O'Shea et al., "In Search of Magic Bullets: The Golden Age of Immunotherapeutics," (2014) Cell 157(1):227-240.

Harris et al., "A bispecific antibody agonist of the IL-2 heterodimeric receptor preferentially promotes in vivo expansion of CD8 and NK cells," (2021) Scientific Reports 11(1):10592; pp. 1-15.

Molloy et al., "Cutting Edge: IL-2 Immune Complexes as a Therapy for Persistent Virus Infection," (2009) J Immunol 182(8):4512-4515.

Vabret et al., "Immunology of COVID-19: Current State of the Science," (2020) Immunity 52(6):910-941.

Narni-Mancinelli et al., "Clues that Natural Killer Cells Help to Control COVID," (2021) Nature 600:226-227, available at https://www.nature.com/articles/d41586-021-02778-y.

Schultz-Cherry, "Role of NK Cells in Influenza Infection," (2015) Curr Top Microbiol Immunol 386:109-120.

Koutsakos et al., "Human CD8+ T Cell Cross-reactivity Across Influenza A, B and C Viruses," (2019) Nature Immunology 20(5):613-625.

Vidarsson et al., "IgG Subclasses and Allotypes: From Structure to Effector Functions," (2014) Frontiers in Immunology 5(520):1-17.

Hanson et al., "ICOS Agonism by JTX-2011 (vopratelimab) Requires Initial T Cell Priming and Fc Cross-linking for Optimal T Cell Activation and Anti-tumor Immunity in Preclinical Models," (2020) PLOS One 15(9):e0239595 pp. 1-21.

Jackson et al., "Evaluation of OX40 Receptor Density, Influence of IgG Isotype and Dosing Paradigm in Anti-OX40-mediated Efficacy and Biomarker Responses with PD-1 Blockade," (2018) Abstracts Immunotherapy of Cancer 29(Suppl 8):VIII424-VIII425.

Galand et al., "AGEN2373 is CD137 Agonist Antibody Designed to Leverage Optimal CD137 and FCγR CO-targeting to Promote Antitumor Immunological Effects," (2020) J Immunother Cancer 8(Suppl 3): A229-A230.

Email correspondence with Mr. Tan (NTU Senior librarian), dated Feb. 3, 2022.

PEGS Korea Printout, The Essential Protein Engineering Summit, Sep. 2015.

Boyman et al., "The Role of Interleukin-2 During Homeostasis and Activation of the Immune System," (2012) Nature Reviews Immunology 12:180-190.

Liao et al., "Interleukin-2 at the Crossroads of Effector Responses, Tolerance and Immunotherapy," (2013) Immunity 38(1):13-25.

Olosz et al., "Molecular Basis for Binding Multiple Cytokines by yc, Implications for X-SCID and Impaired γc-Dependent Cytokine Receptor Function," from (2003) Contemporary Immunology: Cytokine Knockouts, 2nd Edition, Humana Press, Inc.

Baker et al., "The Murine Anti-human Common γ Chain Monoclonal Antibody CP.B8 Blocks the Second Step in the Formation of the Intermediate Affinity IL-2 Receptor," (1998) Biochemistry 37(41):14337-14349.

BioLegend Product Sheet, Purified Anti-human CD132 (common γ chain) Antibody, Version 1, 2012.

Piccione et al., "A Bispecific Antibody Targeting CD47 and CD20 Selectively Binds and Eliminates Dual Antigen Expressing Lymphoma Cells," (2015) mAbs 7(5):Abstract.

Piccione et al., "A Bispecific Antibody Targeting CD47 and CD20 Selectively Binds and Eliminates Dual Antigen Expressing Lymphoma Cells," (2015) mAbs 7(5):946-956.

Francois et al, "Construction of Bispecific Antibody Reacting with the α- and β-Chains of the Human IL-2 Receptor," (1993) Journal of Immunology 150(10):4610-4619.

Applicant's submission dated Jun. 3, 2019 to Exam Report mailed Jan. 25, 2019, in EP 3428193.

Wang Declaration dated Mar. 11, 2019, filed in U.S. Appl. No. 16/112,008.

Hamilton et al., "IL-2 Complex Treatment can Protect Naïve Mice from Bacterial and Viral Infection," (2010) Journal of Immunology 185(11):6584-6590.

Stephen-Victor et al., "Potential of Regulatory T-cell Based Therapies in the Management of Severe COVID-19," (2020) Eur Respir J 56:2002182.

Buelow et al., "Development of a fully human t-cell engaging bispecific antibody for the treatment of multiple myeloma," J. Clin. Oncol., vol. 36(5), Suppl., Abstract 60 and Poster (Feb. 10, 2018) (3 pages).

Clarke et al., "Multispecific Antibody Development Platform Based on Human Heavy Chain Antibodies," Frontiers in Immunology, vol. 9, pp. 3037, pp. 1-13 (2019).

Davies et al., "Affinity improvement of single antibody VH domains: residues in all three hypervariable regions affect antigen binding", Immunotechnology, vol. 2(3), pp. 169-179 (1996).

Hassanzadeh-Ghassabeh et al., "Nanobodies and their potential applications," Nanomedicine, vol. 8(6), pp. 1013-1026 (2013).

(56) References Cited

OTHER PUBLICATIONS

Koide et al., "Exploring the Capacity of Minimalist Protein Interfaces: Interface Energetics and Affinity Maturation to Picomolar KD of a Single-domain Antibody with a Flat Paratope," J. Mol. Biol., vol. 373, pp. 941-953 (2007).

Leow et al., "Single Domain Antibodies as New Biomarker Detectors," Diagnostics, vol. 7(4), pp. 52 (2017).

Tiller et al., "Facile Affinity Maturation of Antibody Variable Domains Using Natural Diversity Mutagenesis," Front. Immunol., vol. 8, Article 986, pp. 1-16 (2017).

Trinklein et al., "Abstract LB-090: Sequence-based discovery of fully human anti-CD3 and anti-PDL1 single domain antibodies using novel transgenic rats," Cancer Res. Vol. 76, No. 4, Suppl., p. 1 (Apr. 16, 2016).

Vincke et al., "General strategy to humanize a camelid single-domain antibody and identification of a universal humanized nanobody scaffold", J Biol Chem., vol. 284 (5), pp. 3273-3284 (2009).

Wagner et al., "A Two-Step Approach for the Design and Generation of Nanobodies," Int. J. Mol. Sci., vol. 19, 3444, pp. 1-16 (2018).

Yau et al., "Affinity maturation of a VHH by mutational hotspot randomization," J. Immunol. Methods, vol. 297, pp. 213-224 (2005).

Zavrtanik et al., "Structural Basis of Epitope Recognition by Heavy-Chain Camelid Antibodies," J. Mol. Biol., vol. 430(21), pp. 4369-4386 (2018).

* cited by examiner

FIG. 1

| Name | Kinetics | | | |
| --- | --- | --- | --- | --- |
| | IL2RB KD (M) | | IL2RG KD (M) | |
| | Human | Cyno | Human | Cyno |
| IL2RB_F09C**IL2RG_F16A | 1.85E-08 | 1.07E-08 | 1.79E-09 | 4.87E-09 |
| IL2RB_F09G**IL2RG_F16B | 9.34E-08 | 1.67E-08 | 1.71E-08 | 5.02E-08 |
| IL2RB_F09G**IL2RG_F16C | 9.67E-08 | 1.60E-08 | 1.43E-09 | 3.58E-09 |
| IL2RB_F09G**IL2RG_F18A | 8.24E-08 | 1.73E-08 | 2.93E-09 | 5.81E-09 |
| IL2RB_F09K**IL2RG_F16B | 1.82E-07 | 1.65E-08 | 2.01E-08 | 4.15E-08 |
| IL2RB_F18E**IL2RG_F16A | 5.38E-08 | 5.52E-08 | 1.88E-09 | 5.42E-09 |

FIG. 2C (+) Control

Bispecific pSTAT5 F/B: CD8 T-Cells

Admixture pSTAT5 F/B: CD8 T-Cells

IL2RB_F09B | IL2RB_F17A | IL2RB_F18A | IL2RB_F20A | IL2RB_F21A

IL2RG_F05B
IL2RG_F16A
IL2RG_F18A
IL2RG_F19A
IL2RG_F20A

Cell Binding
Human CD8+ T-Cells

Cell Binding
Human CD4+ T-Cells

Cell Binding
Cyno CD8+ T-Cells

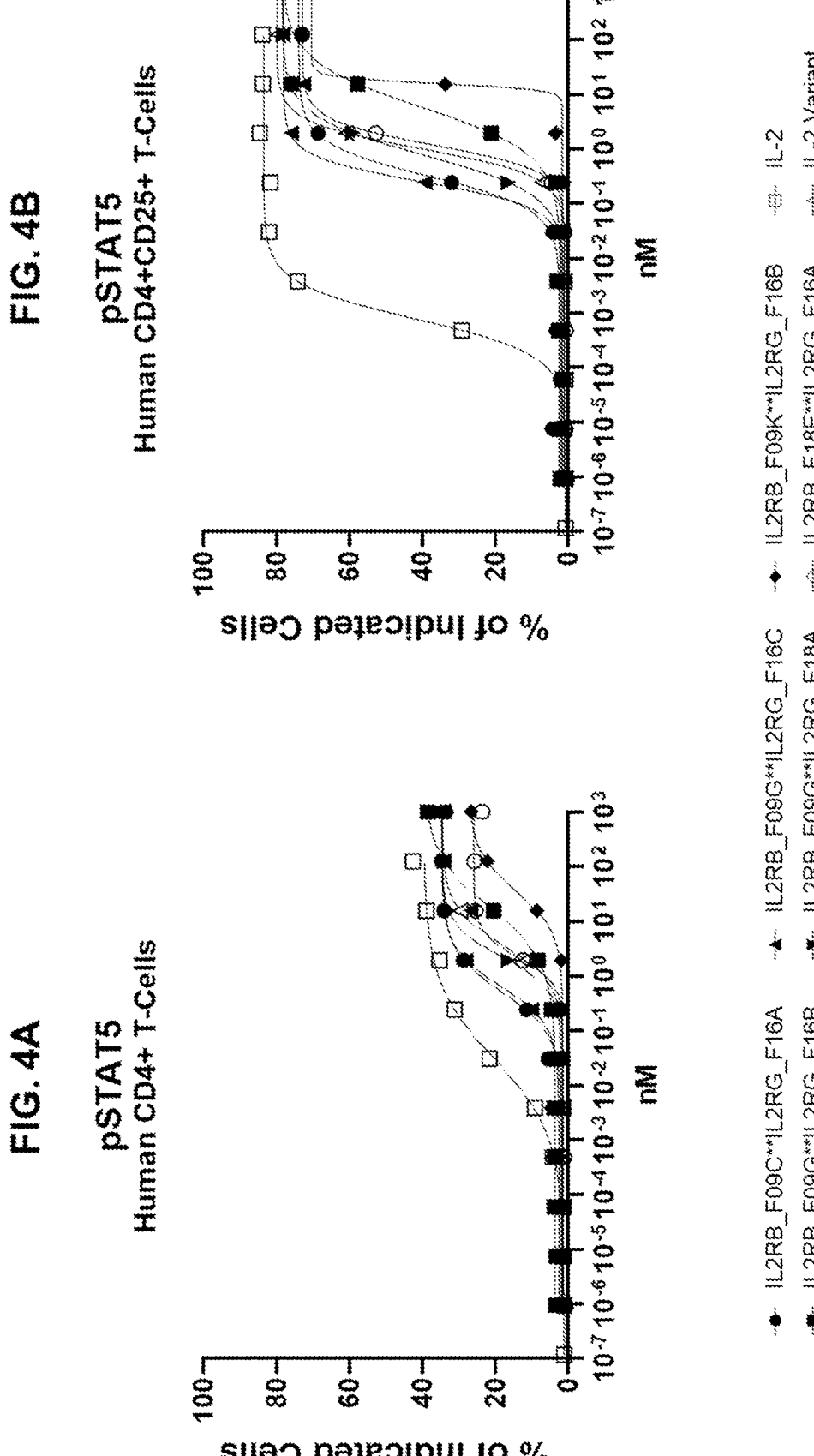

pSTAT5
Human CD56hi NK-Cells pSTAT5
Human CD8+ T-Cells pSTAT5
Cyno CD8+ T-Cells

FIG. 5A

Proliferation: Ki67%
Human CD4+ T-Cells

FIG. 5B

Proliferation: Ki67%
Human CD4+CD25+ T-Cells

Proliferation: Ki67%
Human CD56+ NK Cells

Proliferation: Ki67%
Human CD8+ T-Cells

IL2RB_F09C**IL2RG_F16A
IL2RB_F09G**IL2RG_F16B
IL2RB_F09G**IL2RG_F16C
IL2RB_F09G**IL2RG_F18A
IL2RB_F09K**IL2RG_F16B
IL2RB_F18E**IL2RG_F16A
IL-2
IL-2 Variant Cytokine Release Assay
Human Whole Blood Cytokine Release Assay
Human Whole Blood IL2RB_F09C**IL2RG_F16A
IL2RB_F09G**IL2RG_F16B
IL2RB_F09G**IL2RG_F16C
IL2RB_F09G**IL2RG_F18A
IL2RB_F09K**IL2RG_F16B
IL2RB_F18E**IL2RG_F16A
IL-2

FIG. 7B

| Molecule | t1/2 (hr) |
|---|---|
| IL2RB_F09C**IL2RG_F16A_ | 0.55 |
| IL2RB_F09G**IL2RG_F16B_ | 0.40 |
| IL2RB_F09G**IL2RG_F16C_ | 0.46 |
| IL2RB_F09G**IL2RG_F18A_ | 0.28 |
| IL2RB_F09K**IL2RG_F16B_ | 0.27 |
| IL2RB_F18E**IL2RG_F16A_ | 0.81 |

FIG. 8B

| Molecule | Dose (mg/kg) | t1/2 (hr) |
|---|---|---|
| IL2RB_F09C**IL2RG_F16A | 1 | 7.35 |
| IL2RB_F09G**IL2RG_F16B | 1 | 5.60 |
| IL2RB_F09G**IL2RG_F16C | 1 | 6.15 |
| IL2RB_F09G**IL2RG_F18A | 1 | 7.12 |
| IL2RB_F09K**IL2RG_F16B | 1 | 5.53 |
| IL2RB_F18E**IL2RG_F16A | 1 | 5.29 |

FIG. 9

| Leads | Expression | Thermal Stability | | Forced Degradation Stability (37°C) %HMW | |
|---|---|---|---|---|---|
| | Yield (g/L) | Tm (°C) | Tagg (°C) | T0 | T 1-month |
| IL2RB_F09C**IL2RG_F16A | 0.5 | 58 | 57 | 1 | 2 |
| IL2RB_F09G**IL2RG_F16B | 0.3 | 62 | 60 | 1 | 1.5 |
| IL2RB_F09G**IL2RG_F16C | 0.4 | 62 | 60 | 0.4 | 18 |
| IL2RB_F09G**IL2RG_F18A | 0.1 | 63 | 61 | 0.6 | 2 |
| IL2RB_F09K**IL2RG_F16B | 0.3 | 62 | 59 | 1.0 | 1 |
| IL2RB_F18E**IL2RG_F16A | 0.1 | 62 | 61 | 0.6 | 3 |

CD4⁺ T-Cells

CD4⁺CD25⁺Foxp3⁺ T_regs

CD8⁺ T-Cells

CD3⁻CD159a⁺ NK-Cells

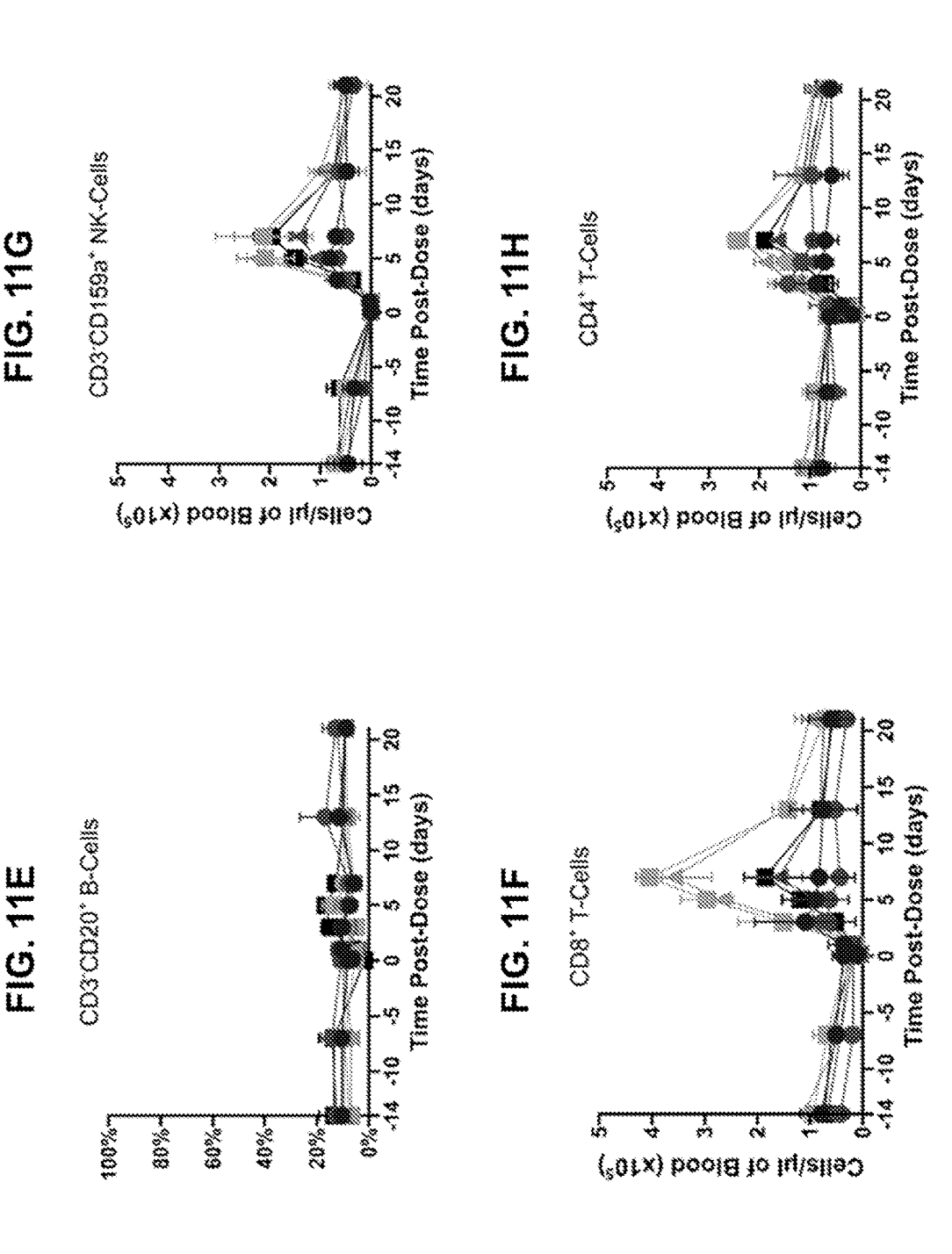

FIG. 12A

Mouse PK
IL2RB_F09K**IL2RG_F16B

Legend:
◆ 1 mg/kg
■ 10 mg/kg

Y-axis: Serum Concentration (μg/ml)
X-axis: Time (days)

FIG. 12B

| Molecule | Dose (mg/kg) | t1/2 (day) |
|---|---|---|
| IL2RB_F09K**IL2RG_F16B | 1 | 5.28 |
| IL2RB_F09K**IL2RG_F16B | 10 | 5.1 |

FIG. 15C

Percent Divided
NK-Cells

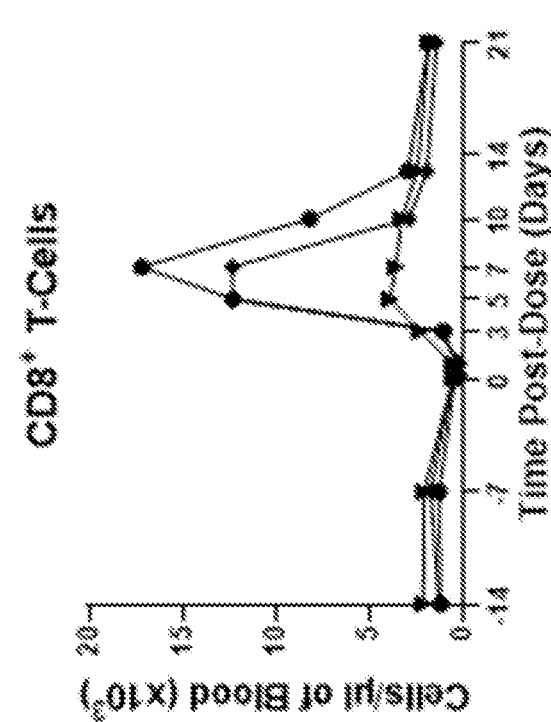
FIG. 16A
Proliferation: Ki67%
CD8+ T-Cells
FIG. 16B
Absolute Cell Concentration
CD8+ T-Cells
IL2RB_F09K*IL2RG_F16B (0.1 mg/kg)
IL2RB_F09K*IL2RG_F16B (0.3 mg/kg)
IL2RB_F09K*IL2RG_F16B (0.5 mg/kg)

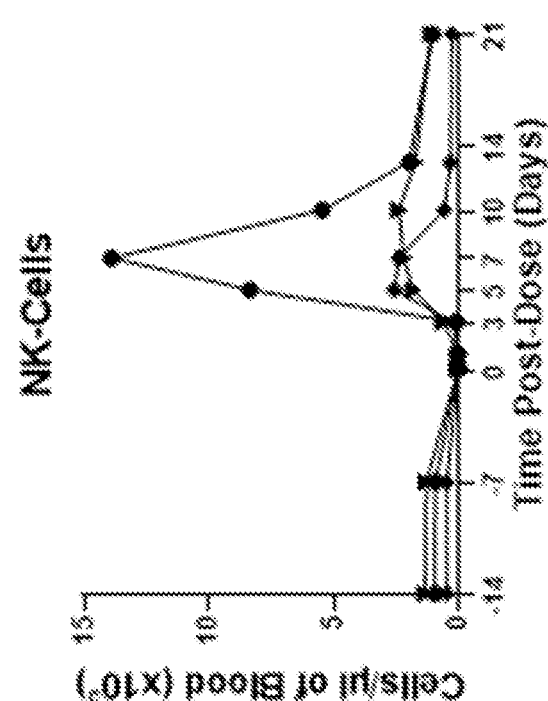
FIG. 16D
Absolute Cell Concentration
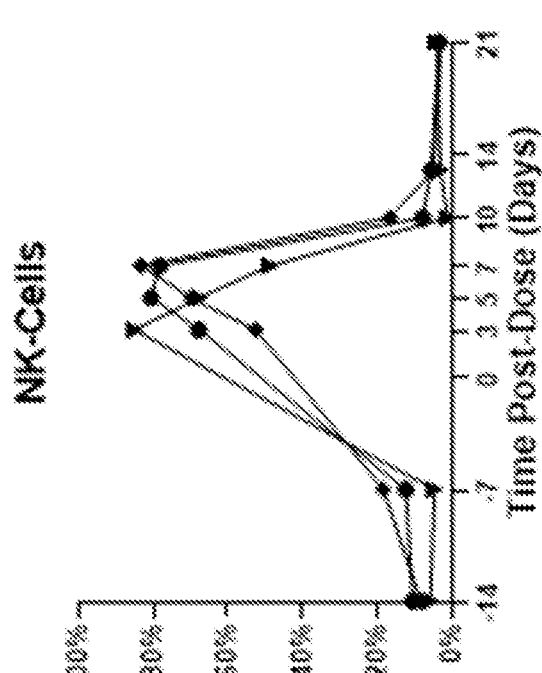
FIG. 16C
Proliferation: Ki67%
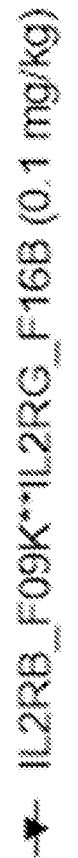
IL2RB_F09K**IL2RG_F16B (0.1 mg/kg)
IL2RB_F09K**IL2RG_F16B (0.3 mg/kg)
IL2RB_F09K**IL2RG_F16B (0.5 mg/kg)

Absolute Cell Concentration

NKT-Cells

Proliferation: Ki67%

NKT-Cells

IL2RB_F09K**IL2RG_F16B (0.1 mg/kg)

IL2RB_F09K**IL2RG_F16B (0.3 mg/kg)

IL2RB_F09K**IL2RG_F16B (0.5 mg/kg)

Absolute Cell Concentration

CD4⁺ T-Cells

Proliferation: Ki67%

CD4⁺ T-Cells

◆ IL2RB_F09K**IL2RG_F16B (0.1 mg/kg)

◆ IL2RB_F09K**IL2RG_F16B (0.3 mg/kg)

◆ IL2RB_F09K**IL2RG_F16B (0.5 mg/kg)

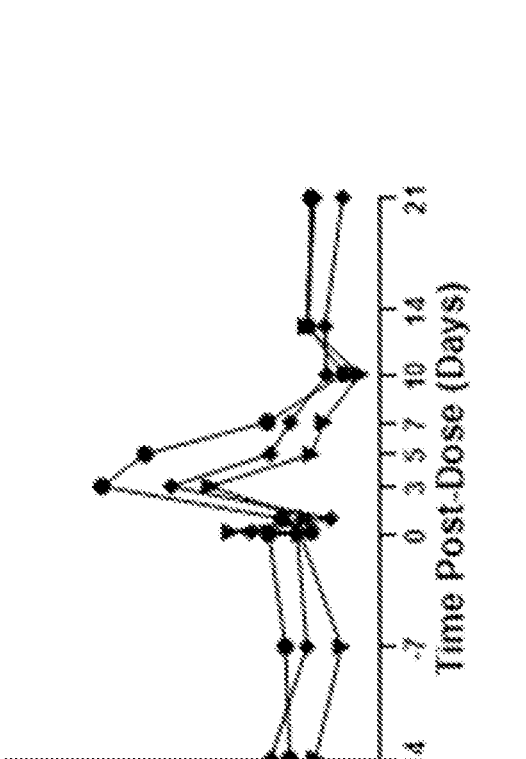

Absolute Cell Concentration

Proliferation: Ki67%

AGONISTIC ANTI-IL-2R ANTIBODIES AND METHODS OF USE

This application is a continuation application of U.S. application Ser. No. 18/164,442, filed Feb. 3, 2023, which is a bypass continuation of International Application No. PCT/US2022/023058, filed Apr. 1, 2022, which claims the benefit of priority of U.S. Provisional Application No. 63/170,383 filed Apr. 2, 2021, and U.S. Provisional Application No. 63/239,883 filed Sep. 1, 2021, the contents of each of which are incorporated by reference herein in their entireties.

The instant application contains a Sequence Listing which has been submitted electronically in XML format and is hereby incorporated by reference in its entirety. Said XML copy, created on Aug. 6, 2025, is named "A-2920-US04-CNT_Replacement Sequence_Listing" and is 101,980 bytes in size.

The present disclosure concerns antibodies that bind to the interleukin-2 (IL-2) receptor (IL2R) and exhibit agonistic activity. The disclosure further concerns methods of making such antibodies, compositions, including pharmaceutical compositions, comprising such antibodies, and the use of such antibodies and compositions in the treatment of diseases and disorders that are mediated by the IL2/IL2R signaling pathway.

Despite having potent immune-activating activity and the potential to induce durable tumor-regression in cancer patients, the success of IL-2 as an immunotherapeutic has been limited by severe dose-limiting toxicities. These adverse events are largely due to the preferential uptake of IL-2 by cells that express the high-affinity, trimeric receptor, IL-2Rαβγ, such as T-regulatory (Treg) cells and endothelial cells. The present disclosure relates to antibodies (e.g., multi-specific antibodies, multi-specific heavy-chain only antibodies, bispecific antibodies, bispecific heavy-chain only antibodies) that bind to and activate signaling through the dimeric IL-2Rβγ receptor complex that is expressed on resting T-cells and NK cells. By avoiding binding to IL-2Rα, the antibodies described herein eliminate the preferential Treg activation of native IL-2, while maintaining potent stimulatory effects on other T-cell subsets along with NK cells. Additionally, the presence of an Fc region on exemplary antibodies described herein significantly extends the in vivo half-life over that of recombinant IL-2, permitting a more convenient dosing schedule in a therapeutic context. In vivo studies in both mice and cynomolgus monkeys have confirmed the in vivo biological activity, extended pharmacokinetics, and enhanced safety profile of exemplary antibodies described herein. Together, these results support the use of such antibodies as safe and effective IL-2R agonists, as well as the use of the IL-2 signaling pathway as a therapeutic treatment approach for multiple types of cancer.

The ability to harness the immune system against tumors has been firmly established, with interleukin-2 (IL-2) being one of the first recombinant proteins to be successfully used as a treatment for cancer nearly 40 years ago. Lotze et al., *Journal of Immunology* 135(4), 2865-75 (1985); Rosenberg, S. A. *J Immunol* 192, 5451-58 (2014). IL-2 is a key regulator of immune cells, inducing both T-cell and natural killer (NK) cell proliferation. However, IL-2 is a pleiotropic cytokine that also induces the proliferation of immunosuppressive regulatory T (Treg) cells. Fontenot et al., *Nat Immunol* 6, 1142-51 (2005). The different functions of IL-2 are determined by the composition of IL-2 receptor complex subunits expressed on different target cells. Boyman et al., *Nat Rev Immunol* 12, 180-90 (2012). The high affinity IL-2 receptor complex is composed of IL-2RA (CD25), IL-2RB (CD122), and the common gamma chain receptor IL-2RG (CD132), and is expressed constitutively on CD4+FoxP3+ Tregs cells and transiently on activated T cells. Waldmann, T. A., *Nat Rev Immunol* 6, 595-601 (2006). The intermediate affinity receptor is composed of only IL-2RB and IL-2RG, and is expressed on resting T-cells, CD8+ memory effector T-cells, and NK cells. Choudhry, H. et al, *Biomed Res Int* 2018, 1-7 (2018). The IL-2RA subunit is not required for downstream JAK-STAT signaling, but its association with IL-2RB and IL-2RG provides a 100-fold higher affinity to IL-2 compared to the heterodimeric receptor composed only of IL-2RB and IL-2RG. Based on these receptor binding differences and cell-specific expression, it has been proposed that immunosuppressive Tregs serve as a buffer to consume low levels of IL-2 and create a threshold effect for IL-2-mediated expansion of effector lymphocytes. Feinerman, O. et al., *Mol Syst Biol* 6, 437 (2010).

Because of its unique signaling properties, low dose IL-2 has been used clinically to stimulate Tregs to treat autoimmunity, while high-dose IL-2 was developed and approved (Proleukin®) for the treatment of metastatic melanoma and metastatic renal cell carcinoma, with durable responses observed in 7-12% of patients. McDermott, D. F. et al., *J Clin Oncol* 23, 133-141 (2004); Payne, R. et al., *J Immunother Cancer* 2, 13 (2014); Atkins, M. B. et al., *J Clin Oncol* 17, 2105-2105 (1999); Rosenberg, S. A. et al., *Ann Surg* 228, 307-319 (1998). However, its short half-life and narrow therapeutic window have created significant challenges for the safe and effective use of IL-2 in patients. Specifically, Proleukin® has severe side effects, including vascular leak syndrome, hypotension, and liver toxicities that have limited its use in cancer immunotherapy. It has been shown that the vascular leak toxicity is related to the expression of the high affinity IL-2R on vascular endothelial cells and on lung endothelial cells, leading to pulmonary edema. Krieg, C., et al., *Proc National Acad Sci* 107, 11906-11 (2010). The anti-tumor effects of Proleukin® are further compromised by its preferential binding to the high affinity receptor on Treg cells, blunting its efficacy as an anti-cancer therapy. Schwartzentruber, D. J. et al., *New Engl J Medicine* 364, 2119-2127 (2011); Rezvani, K. et al., *Blood* 108, 1291-1297 (2006). As an example, in melanoma patients receiving high dose IL-2 therapy, costimulator-positive (ICOS+) Treg cells were found to be the most proliferative lymphocyte population in the blood after treatment with IL-2, and high numbers of ICOS+ Tregs corresponded with the worst patient outcomes. Sim, G. C. et al., *J Clin Invest* 124, 99-110 (2014).

Due to the pleiotropic nature of native IL-2 and its associated limitations as a therapeutic molecule, there has been substantial effort to engineer IL-2 variants that reduce dose-limiting toxicities and thereby broaden the therapeutic window. Murer, P. et al., *New Biotechnol* 52, 42-53 (2019); Arenas-Ramirez, N. et al., *Trends Immunol* 36, 763-77 (2015). Variant proteins that avoid the preferential activation of high-affinity IL-2R-expressing cells, such as Tregs and vascular endothelial cells, are one approach to achieving this goal. In an effort to create such a molecule, other approaches have involved mutating the IL-2RA binding interface on IL-2, attaching polyethylene glycol to the IL-2 protein, creating synthetic IL-2 proteins, and generating an antibody that blocks the IL-2RA binding domain. Silva, D.-A. et al., *Nature* 565, 186-191 (2019); Charych, D. H. et al., *Clin Cancer Res* 22, 680-690 (2016); Arenas-Ramirez, N. et al., *Sci Transl Med* 8, 367ra166-367ra166 (2016); Levin, A. M. et al., *Nature* 484, 529-533 (2012); Lopes, J. E. et al., *J Immunother Cancer* 8, e000673 (2020). As an alternative to IL-2, others have engineered IL-15 variants that bind to IL-2RB/IL-2RG subunits. The IL-15-specific receptor subunit naturally binds to IL-15 in trans from antigen presenting cells; therefore, an active IL-15 recombinant protein requires a single chain construct that expresses both IL-15 and the receptor subunit. Bernett, M. J. et al. Abstract 5565: Potency-reduced IL15/IL15Rα heterodimeric Fc-fusions display enhanced in vivo activity through increased exposure. 5565-5565 (2018) doi:10.1158/1538-7445.am2018-5565. Mutated cytokines have also been fused to antibodies or Fc domains to increase the in vivo half-life of the molecules and localize the cytokines to the tumor site. Murer, P. et al., *New Biotechnol* 52, 42-53 (2019); Klein, C. et al., *Oncoimmunology* 6:3 e1277306 (2017); Schliemann, C. et al., *Blood* 120, 3716-3716 (2012). While some of these engineered proteins have the desired functional activity, many suffer from high levels of immunogenicity in vivo and present challenges with in vivo stability and manufacturing. Brummelen, E. M. J. van et al., *Oncotarget* 9, 24737-49 (2018); Groot, A. S. D. et al., *Trends Immunol* 28, 482-90 (2007); Schellekens, H., *Nephrol Dial Transpl* 18, 1257-59 (2003); Verhoef, J. J. F., et al., *Drug Discov Today* 19, 1945-52 (2014). Therefore, creating an anti-tumor agonist of the IL-2 pathway with the desired biological activity, safety profile, and ideal drug-like properties remains a significant challenge for the field.

The molecules of the present disclosure combine the favorable drug-like properties of antibodies with the functional behavior of molecules that facilitate IL-2RB and IL-2RG association and downstream signaling. Aspects of the disclosure include antibody sequences, such as fully human antibody sequences, such as fully human multispecific (e.g., bispecific) antibodies that simultaneously bind IL-2RB and IL-2RG subunits and therefore mimic the activity of IL-2 while avoiding binding to IL-2RA. In addition to exhibiting the desired activation and expansion of immune effector cells, bispecific IL-2RB/G agonist antibodies described herein also avoid preferential expansion of suppressive Tregs, both in vitro and in vivo.

NON-LIMITING EXAMPLE EMBODIMENTS (SET 1)

Without limitation, some example embodiments/features of this disclosure include:

1. An antibody that binds to IL2RB, comprising a heavy chain variable region comprising:
   (a) a CDR1 sequence having two or fewer substitutions (e.g., 0, 1, or 2) in any one of SEQ ID NOs: 1-3; and/or
   (b) a CDR2 sequence having two or fewer substitutions (e.g., 0, 1, or 2) in any one of SEQ ID NOs: 4-6; and/or
   (c) a CDR3 sequence having two or fewer substitutions (e.g., 0, 1, or 2) in any one of SEQ ID NOs: 7-10.

2. The antibody of Feature 1, comprising:
   (a) a CDR1 sequence comprising any one of SEQ ID NOs: 1-3; and/or
   (b) a CDR2 sequence comprising any one of SEQ ID NOs: 4-6; and/or
   (c) a CDR3 sequence comprising any one of SEQ ID NOs: 7-10.

3. The antibody of Feature 1 or 2, comprising:
   (a) a CDR1 sequence comprising any one of SEQ ID NOs: 1-3; and
   (b) a CDR2 sequence comprising any one of SEQ ID NOs: 4-6; and
   (c) a CDR3 sequence comprising any one of SEQ ID NOs: 7-10.

4. The antibody of any one of Features 1-3, comprising:
   (a) a CDR1 sequence of SEQ ID NO: 1, a CDR2 sequence of SEQ ID NO: 4, and a CDR3 sequence of SEQ ID NO: 7; or
   (b) a CDR1 sequence of SEQ ID NO: 1, a CDR2 sequence of SEQ ID NO: 4, and a CDR3 sequence of SEQ ID NO: 8; or
   (c) a CDR1 sequence of SEQ ID NO: 2, a CDR2 sequence of SEQ ID NO: 5, and a CDR3 sequence of SEQ ID NO: 9; or
   (d) a CDR1 sequence of SEQ ID NO: 3, a CDR2 sequence of SEQ ID NO: 6, and a CDR3 sequence of SEQ ID NO: 10.

5. The antibody of any one of Features 1-4, comprising a heavy chain variable region having at least 95% sequence identity to any one of SEQ ID NOs: 11-14.

6. The antibody of any one of Features 1-5, comprising a heavy chain variable region sequence selected from SEQ ID NOs: 11-14.

7. An antibody that binds to IL2RB, comprising a heavy chain variable region comprising:
   (a) a CDR1 sequence comprising the formula:

$$\text{(SEQ ID NO: 26)}$$
$$\text{G G S I S S S X1 W}$$

where X1 is D or N;
   (b) a CDR2 sequence comprising the formula:

$$\text{(SEQ ID NO: 27)}$$
$$\text{I X2 H S G S T}$$

where X2 is D or S; and
   (c) a CDR3 sequence comprising the formula:

$$\text{(SEQ ID NO: 28)}$$
$$\text{X3 R G X4 W EL X5 D A F D I}$$

where X3 is G or A;
   X4 is S or Q; and
   X5 is S or T.

8. An antibody that binds to IL2RB, comprising a heavy chain variable region comprising:
   (a) a CDR1 sequence comprising the formula:

$$\text{(SEQ ID NO: 29)}$$
$$\text{G F T F S X1 Y G}$$

where X1 is S or T;
   (b) a CDR2 sequence comprising the formula:

$$\text{(SEQ ID NO: 30)}$$
$$\text{I S Y D G S N X2}$$

where X2 is K or R; and
   (c) a CDR3 sequence comprising the formula:

$$\text{(SEQ ID NO: 31)}$$
$$\text{A R D L D Y D X3 L T G D P V G G F D I}$$

where X3 is V or I.

9. An antibody that binds to IL2RG, comprising a heavy chain variable region comprising:
   (a) a CDR1 sequence having two or fewer substitutions (e.g., 0, 1, or 2) in any one of SEQ ID NOs: 15-16; and/or (b) a CDR2 sequence having two or fewer substitutions (e.g., 0, 1, or 2) in any one of SEQ ID NOs: 17-19; and/or (c) a CDR3 sequence having two or fewer substitutions (e.g., 0, 1, or 2) in any one of SEQ ID NOs: 20-21.

10. The antibody of Feature 9, comprising:

(a) a CDR1 sequence comprising any one of SEQ ID NOs: 15-16; and/or (b) a CDR2 sequence comprising any one of SEQ ID NOs: 17-19; and/or (c) a CDR3 sequence comprising any one of SEQ ID NOs: 20-21.

11. The antibody of Feature 9 or 10, comprising:

(a) a CDR1 sequence comprising any one of SEQ ID NOs: 15-16; and (b) a CDR2 sequence comprising any one of SEQ ID NOs: 17-19; and (c) a CDR3 sequence comprising any one of SEQ ID NOs: 20-21.

12. The antibody of any one of Features 9-11, comprising:

(a) a CDR1 sequence of SEQ ID NO: 15, a CDR2 sequence of SEQ ID NO: 17, and a CDR3 sequence of SEQ ID NO: 20; or (b) a CDR1 sequence of SEQ ID NO: 15, a CDR2 sequence of SEQ ID NO: 18, and a CDR3 sequence of SEQ ID NO: 20; or (c) a CDR1 sequence of SEQ ID NO: 16, a CDR2 sequence of SEQ ID NO: 18, and a CDR3 sequence of SEQ ID NO: 20; or (d) a CDR1 sequence of SEQ ID NO: 15, a CDR2 sequence of SEQ ID NO: 19, and a CDR3 sequence of SEQ ID NO: 21.

13. The antibody of any one of Features 9-12, comprising a heavy chain variable region having at least 95% sequence identity to any one of SEQ ID NOs: 22-25.

14. The antibody of any one of Features 9-13, comprising a heavy chain variable region sequence selected from SEQ ID NOs: 22-25.

15. An antibody that binds to IL2RG, comprising a heavy chain variable region comprising:

(a) a CDR1 sequence comprising the formula:

$$\text{G F X1 X2 X3 X4 Y Y} \quad \text{(SEQ ID NO: 32)}$$

where X1 is T or I;

X2 is F or V;

X3 is S, N, or G; and

X4 is D or N;

(b) a CDR2 sequence comprising the formula:

$$\text{I S X5 S G X6 X7 I} \quad \text{(SEQ ID NO: 33)}$$

where X5 is S or N;

X6 is D, S, G, or N; and

X7 is T or I; and (c) a CDR3 sequence comprising the sequence ARG-DAVSITGDY (SEQ ID NO: 20).

16. The antibody of any one of Features 1-15, wherein the CDR1, CDR2, and CDR3 sequences are present in a human VH framework.

17. The antibody of any one of Features 1-16, wherein the antibody is multi-specific.

18. The antibody of any one of Features 1-17, wherein the antibody is bispecific.

19. The antibody of any one of Features 1-18, wherein the antibody binds to IL2RB and IL2RG.

20. An antibody comprising:

a first heavy chain variable region that binds to IL2RB, comprising:

a CDR1 sequence of SEQ ID NO: 1;

a CDR2 sequence of SEQ ID NO: 4; and a CDR3 sequence of SEQ ID NO: 7; and a second heavy chain variable region that binds to IL2RG, comprising:

a CDR1 sequence of SEQ ID NO: 15;

a CDR2 sequence of SEQ ID NO: 17; and a CDR3 sequence of SEQ ID NO: 20.

21. The antibody of Feature 20, wherein the first heavy chain variable region has at least 95% sequence identity to SEQ ID NO: 11, and the second heavy chain variable region has at least 95% sequence identity to SEQ ID NO: 22.

22. The antibody of Feature 20 or 21, wherein the first heavy chain variable region comprises SEQ ID NO: 11, and the second heavy chain variable region comprises SEQ ID NO: 22.

23. The antibody of any one of Features 20-22, comprising a first polypeptide comprising SEQ ID NO: 53 and a second polypeptide comprising SEQ ID NO: 61.

24. An antibody comprising:

a first heavy chain variable region that binds to IL2RB, comprising:

a CDR1 sequence of SEQ ID NO: 1;

a CDR2 sequence of SEQ ID NO: 4; and a CDR3 sequence of SEQ ID NO: 8; and a second heavy chain variable region that binds to IL2RG, comprising:

a CDR1 sequence of SEQ ID NO: 15;

a CDR2 sequence of SEQ ID NO: 18; and a CDR3 sequence of SEQ ID NO: 20.

25. The antibody of Feature 24, wherein the first heavy chain variable region has at least 95% sequence identity to SEQ ID NO: 12, and the second heavy chain variable region has at least 95% sequence identity to SEQ ID NO: 23.

26. The antibody of Feature 24 or 25, wherein the first heavy chain variable region comprises SEQ ID NO: 12, and the second heavy chain variable region comprises SEQ ID NO: 23.

27. The antibody of any one of Features 24-26, comprising a first polypeptide comprising SEQ ID NO: 62 and a second polypeptide comprising SEQ ID NO: 63.

28. An antibody comprising:

a first heavy chain variable region that binds to IL2RB, comprising:

a CDR1 sequence of SEQ ID NO: 2;

a CDR2 sequence of SEQ ID NO: 5; and a CDR3 sequence of SEQ ID NO: 9; and a second heavy chain variable region that binds to IL2RG, comprising:

a CDR1 sequence of SEQ ID NO: 15;

a CDR2 sequence of SEQ ID NO: 18; and a CDR3 sequence of SEQ ID NO: 20.

29. The antibody of Feature 28, wherein the first heavy chain variable region has at least 95% sequence identity to SEQ ID NO: 13, and the second heavy chain variable region has at least 95% sequence identity to SEQ ID NO: 23.

30. The antibody of Feature 28 or 29, wherein the first heavy chain variable region comprises SEQ ID NO: 13, and the second heavy chain variable region comprises SEQ ID NO: 23.

31. The antibody of any one of Features 28-30, comprising a first polypeptide comprising SEQ ID NO: 64 and a second polypeptide comprising SEQ ID NO: 65.

32. An antibody comprising:
a first heavy chain variable region that binds to IL2RB, comprising:
a CDR1 sequence of SEQ ID NO: 3;
a CDR2 sequence of SEQ ID NO: 6; and
a CDR3 sequence of SEQ ID NO: 10; and
a second heavy chain variable region that binds to IL2RG, comprising:
a CDR1 sequence of SEQ ID NO: 15;
a CDR2 sequence of SEQ ID NO: 17; and
a CDR3 sequence of SEQ ID NO: 20.

33. The antibody of Feature 32, wherein the first heavy chain variable region has at least 95% sequence identity to SEQ ID NO: 14, and the second heavy chain variable region has at least 95% sequence identity to SEQ ID NO: 22.

34. The antibody of Feature 32 or 33, wherein the first heavy chain variable region comprises SEQ ID NO: 14, and the second heavy chain variable region comprises SEQ ID NO: 22.

35. The antibody of any one of Features 32-34, comprising a first polypeptide comprising SEQ ID NO: 66 and a second polypeptide comprising SEQ ID NO: 67.

36. An antibody comprising:
a first heavy chain variable region that binds to IL2RB, comprising:
a CDR1 sequence of SEQ ID NO: 1;
a CDR2 sequence of SEQ ID NO: 4; and
a CDR3 sequence of SEQ ID NO: 8; and
a second heavy chain variable region that binds to IL2RG, comprising:
a CDR1 sequence of SEQ ID NO: 16;
a CDR2 sequence of SEQ ID NO: 18; and
a CDR3 sequence of SEQ ID NO: 20.

37. The antibody of Feature 36, wherein the first heavy chain variable region has at least 95% sequence identity to SEQ ID NO: 12, and the second heavy chain variable region has at least 95% sequence identity to SEQ ID NO: 24.

38. The antibody of Feature 36 or 37, wherein the first heavy chain variable region comprises SEQ ID NO: 12, and the second heavy chain variable region comprises SEQ ID NO: 24.

39. The antibody of any one of Features 36-38, comprising a first polypeptide comprising SEQ ID NO: 34 and a second polypeptide comprising SEQ ID NO: 35.

40. An antibody comprising:
a first heavy chain variable region that binds to IL2RB, comprising:
a CDR1 sequence of SEQ ID NO: 1;
a CDR2 sequence of SEQ ID NO: 4; and
a CDR3 sequence of SEQ ID NO: 8; and
a second heavy chain variable region that binds to IL2RG, comprising:
a CDR1 sequence of SEQ ID NO: 15;
a CDR2 sequence of SEQ ID NO: 19; and
a CDR3 sequence of SEQ ID NO: 21.

41. The antibody of Feature 40, wherein the first heavy chain variable region has at least 95% sequence identity to SEQ ID NO: 12, and the second heavy chain variable region has at least 95% sequence identity to SEQ ID NO: 25.

42. The antibody of Feature 40 or 41, wherein the first heavy chain variable region comprises SEQ ID NO: 12, and the second heavy chain variable region comprises SEQ ID NO: 25.

43. The antibody of any one of Features 40-42, comprising a first polypeptide comprising SEQ ID NO: 36 and a second polypeptide comprising SEQ ID NO: 37.

44. The antibody of any one of Features 20, 24, 28, 32, 36, or 40, wherein the CDR1, CDR2, and CDR3 sequences in the first heavy chain variable region are present in a VH human framework.

45. The antibody of any one of Features 20, 24, 28, 32, 36, 40, or 44, wherein the CDR1, CDR2, and CDR3 sequences in the second heavy chain variable region are present in a VH human framework.

46. The antibody of any one of Features 1-22, 24-26, 28-30, 32-34, 36-38, 40-42, 44, or 45, wherein the antibody comprises an Fc region.

47. The antibody of Feature 46, wherein the Fc region is a variant Fc region.

48. The antibody of Feature 47, wherein the variant Fc region possesses at least about 80% (e.g., at least about 85%, at least about 90%, at least about 95%, at least about 98%, at least about 99%) homology with a native sequence Fc region.

49. The antibody of Feature 47 or 48, wherein the variant Fc region comprises heterodimerizing alterations.

50. The antibody of Feature 49, wherein the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other).

51. The antibody of Feature 49 or 50, wherein the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other).

52. The antibody of any one of Features 49-51, wherein the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

53. The antibody of any one of Features 47-52, wherein the variant Fc region is a silenced Fc region.

54. The antibody of Feature 53, wherein the silenced Fc region comprises substitution of one or more (e.g., two or more) of Fc region residues 238, 265, 269, 270, 297, 327 and 329 according to EU numbering.

55. The antibody of Feature 53 or 54, wherein the silenced Fc region comprises a substitution that alters glycosylation.

56. The antibody of any one of Features 53-55, wherein the silenced Fc region comprises an effector-less mutation (e.g., an N297A, an N297G, a DANA mutation (D265A+N297A), or a DANG mutation (D265A+N297G) in the CH2 region) and/or K322A and L234A/L235A mutations.

57. The antibody of any one of Features 1-22, 24-26, 28-30, 32-34, 36-38, 40-42, or 44-56, wherein the antibody comprises a heavy chain constant region sequence in the absence of a CH1 sequence.

58. The antibody of any one of Features 1-22, 24-26, 28-30, 32-34, 36-38, 40-42, or 44-57, wherein the antibody comprises a heavy chain constant region comprising a hinge region, a CH2 domain, and a CH3 domain.

59. The antibody of Feature 58, wherein the hinge region comprises a wild type human IgG4 hinge region sequence (SEQ ID NO: 54).

60. The antibody of Feature 58, wherein the hinge region comprises a variant human IgG4 hinge region sequence comprising an S228P mutation (SEQ ID NO: 55).

61. The antibody of any one of Features 58-60, wherein the CH2 domain comprises a wild type human IgG4 CH2 domain sequence (SEQ ID NO: 56).

62. The antibody of any one of Features 58-61, wherein the CH2 domain comprises a variant human IgG4 CH2 domain comprising an F234A mutation, an L235A mutation, or both an F234A mutation and an L235A mutation.

63. The antibody of any one of Features 58-62, wherein the CH3 domain comprises a wild type human IgG4 CH3 domain sequence (SEQ ID NO: 58).

64. The antibody of any one of Features 58-62, wherein the CH3 domain comprises a variant human IgG4 CH3 domain sequence comprising a T366W mutation.

65. The antibody of any one of Features 58-62, wherein the CH3 domain comprises a variant human IgG4 CH3 domain sequence comprising a T366S, an L368A mutation, and a Y407V mutation.

66. The antibody of any one of Features 1-65, wherein the antibody is a human antibody.

67. The antibody of any one of Features 1-66, wherein the antibody is an isolated antibody.

68. The antibody of any one of Features 1-67, wherein the antibody is an intact IgG molecule.

69. The antibody of any one of Features 1-68, wherein the antibody is an intact IgG1 molecule.

70. The antibody of any one of Features 1-68, wherein the antibody is an intact IgG2 molecule.

71. The antibody of any one of Features 1-68, wherein the antibody is an intact IgG4 molecule.

72. The antibody of any one of Features 1-67, wherein the antibody is an immunologically active portion of an intact IgG molecule.

73. The antibody of any one of Features 1-67, wherein the antibody is an immunologically active portion of an intact IgG1 molecule.

74. The antibody of any one of Features 1-67, wherein the antibody is an immunologically active portion of an intact IgG2 molecule.

75. The antibody of any one of Features 1-67, wherein the antibody is an immunologically active portion of an intact IgG4 molecule.

76. The antibody of any one of Features 1-67, wherein the antibody is a triple-chain antibody-like molecule.

77. The antibody of any one of Features 1-67, wherein the antibody is a heavy-chain only antibody.

78. The antibody of any one of Features 1-77, wherein the antibody has a Tm of from about 55° C. to about 65° C.

79. The antibody of any one of Features 1-78, wherein the antibody has a Tagg of from about 55° C. to about 65° C.

80. The antibody of any one of Features 1-79, wherein the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

81. The antibody of any one of Features 1-80, wherein the antibody has an affinity for IL2RB with a Kd of from about $10^{-8}$ M to around about $2.5 \times 10^{-7}$ M.

82. The antibody of any one of Features 1-81, wherein the antibody has an affinity for IL2RG with a Kd of from about $10^{-9}$ M to around about $2.5 \times 10^{-8}$ M.

83. The antibody of any one of Features 80-82, wherein Kd is measured using a ForteBio Octet Qk384 instrument in kinetics mode.

84. The antibody of any one of Features 80-83, wherein Kd is measured using a ForteBio Octet Qk384 instrument comprising an anti-human Fc capture (AHC, 18-5005) sensor in kinetics mode.

85. The antibody of any one of Features 80-82, wherein Kd is measured according to a method described in the Examples herein.

86. The antibody of any one of Features 1-85, wherein the antibody functions as an IL2 receptor beta/gamma agonist.

87. A pharmaceutical composition comprising:
    an antibody of any one of Features 1-86; and
    a pharmaceutically acceptable excipient.

88. The pharmaceutical composition of Feature 87, wherein the pharmaceutical composition is adapted for intravenous delivery.

89. The pharmaceutical composition of Feature 87, wherein the pharmaceutical composition is adapted for subcutaneous delivery.

90. A polynucleotide encoding an antibody of any one of Features 1-86.

91. A vector comprising a polynucleotide of Feature 90.

92. A cell (e.g., a CHO cell) comprising a vector of Feature 91.

93. A method of producing an antibody of any one of Features 1-86, the method comprising:
    growing a cell (e.g., a CHO cell) according to Feature 92 under conditions permissive for expression of the antibody; and
    isolating the antibody from the cell and/or a cell culture medium in which the cell is grown.

94. A method of making an antibody of any one of Features 1-86, the method comprising immunizing a transgenic animal (e.g., a transgenic rat, a UniRat™ animal) with IL2R and identifying IL2R-binding heavy chain sequences.

95. A kit for treating a disease or disorder in an individual in need thereof comprising:
    an antibody of any one of Features 1-86, or a pharmaceutical composition of any one of Features 87-89; and
    instructions for use.

96. The kit of Feature 95, further comprising at least one additional reagent.

97. The kit of Feature 96, wherein the at least one additional reagent comprises a chemotherapeutic drug.

98. A method of treating a disease or disorder comprising administering to an individual in need thereof an effective dose of an antibody of any one of Features 1-86, or a pharmaceutical composition of any one of Features 87-89.

99. The method of Feature 98, wherein the antibody or pharmaceutical composition is administered in conjunction with another course of therapy.

100. The method of Feature 98 or 99, wherein the antibody or pharmaceutical composition is administered in conjunction with a chemotherapy regimen.

101. Use of an antibody of any one of Features 1-86 in the preparation of a medicament for the treatment of a disease or disorder in an individual in need thereof.

102. The use of Feature 101, wherein the medicament is intended for administration in conjunction with another course of therapy.

103. The use of Feature 101 or 102, wherein the medicament is intended for administration in conjunction with a chemotherapy regimen.

104. An antibody of any one of Features 1-86, or a pharmaceutical composition of any one of Features 87-89, for use in the treatment of a disease or disorder in an individual in need thereof.

105. The antibody for use or pharmaceutical composition for use of Feature 104, wherein the antibody or pharmaceutical composition is intended for use in conjunction with another course of therapy.

106. The antibody for use or pharmaceutical composition for use of Feature 104, wherein the antibody or pharmaceutical composition is intended for use in conjunction with a chemotherapy regimen.

107. The kit, method, use, antibody for use, or pharmaceutical composition for use of any one of Features 95-106, wherein the disease or disorder is a cancer.

108. The kit, method, use, antibody for use, or pharmaceutical composition for use of Feature 107, wherein the cancer is an advanced or metastatic cancer.

109. The kit, method, use, antibody for use, or pharmaceutical composition for use of Feature 107 or 108, wherein the cancer is a solid tumor cancer.

110. The kit, method, use, antibody for use, or pharmaceutical composition for use of Feature 109, wherein the solid tumor cancer is selected from renal cell carcinoma, melanoma, urothelial cancer, triple negative breast cancer, non-small cell lung cancer (NSCLC), colorectal cancer, sarcoma, squamous cell carcinoma of the head and neck, and metastatic castration-resistant prostate cancer.

111. The kit, method, use, antibody for use, or pharmaceutical composition for use of Feature 107 or 108, wherein the cancer is a liquid cancer.

112. The kit, method, use, antibody for use, or pharmaceutical composition for use of Feature 111, wherein the liquid cancer is multiple myeloma or acute myeloid leukemia.

113. A method for stimulating IL2R signaling in an immune cell, the method comprising contacting the immune cell with an antibody of any one of Features 1-86, or a pharmaceutical composition of any one of Features 87-89.

114. A method for stimulating an IL2RB/IL2RG dimeric receptor complex on an immune cell, the method comprising contacting the immune cell with an antibody of any one of Features 1-86, or a pharmaceutical composition of any one of Features 87-89.

115. The method of Feature 113 or 114, wherein the immune cell is selected from a CD4+ T-cell, a CD8+ T-cell, and a Natural Killer (NK) cell.

116. Use of an antibody of any one of Features 1-86 in the preparation of a medicament for stimulating IL2R signaling in an immune cell in an individual in need thereof.

117. Use of an antibody of any one of Features 1-86 in the preparation of a medicament for stimulating an IL2RB/IL2RG dimeric receptor complex on an immune cell in an individual in need thereof.

118. The use of Feature 116 or 117, wherein the immune cell is selected from a CD4+ T-cell, a CD8+ T-cell, and a Natural Killer (NK) cell.

119. An antibody of any one of Features 1-86, or a pharmaceutical composition of any one of Features 87-89, for use in a method for stimulating IL2R signaling in an immune cell.

120. An antibody of any one of Features 1-86, or a pharmaceutical composition of any one of Features 87-89, for use in a method for stimulating an IL2RB/IL2RG dimeric receptor complex on an immune cell.

121. The antibody for use or pharmaceutical composition for use of Feature 119 or 120, wherein the immune cell is selected from a CD4+ T-cell, a CD8+ T-cell, and a Natural Killer (NK) cell.

NON-LIMITING EXAMPLE EMBODIMENTS
(SET 2)

Without limitation, some example embodiments/clauses of this disclosure include:

1. A heavy chain-only antibody that binds to IL2RB, comprising a heavy chain variable region comprising:
   (a) a CDR1 sequence having two or fewer substitutions in any one of SEQ ID NOs: 1-3; and/or
   (b) a CDR2 sequence having two or fewer substitutions in any one of SEQ ID NOs: 4-6; and/or
   (c) a CDR3 sequence having two or fewer substitutions in any one of SEQ ID NOs: 7-10.

2. The heavy chain-only antibody of Clause 1, wherein said CDR1, CDR2, and CDR3 sequences are present in a human VH framework.

3. The heavy chain-only antibody of Clause 1 or 2, further comprising a heavy chain constant region sequence in the absence of a CH1 sequence.

4. The heavy chain-only antibody of any one of Clauses 1-3, comprising:
   (a) a CDR1 sequence comprising any one of SEQ ID NOs: 1-3; and/or
   (b) a CDR2 sequence comprising any one of SEQ ID NOs: 4-6; and/or
   (c) a CDR3 sequence comprising any one of SEQ ID NOs: 7-10.

5. The heavy chain-only antibody of Clause 4, comprising:
   (a) a CDR1 sequence comprising any one of SEQ ID NOs: 1-3; and
   (b) a CDR2 sequence comprising any one of SEQ ID NOs: 4-6; and
   (c) a CDR3 sequence comprising any one of SEQ ID NOs: 7-10.

6. The heavy chain-only antibody of Clause 5, comprising:
   (a) a CDR1 sequence of SEQ ID NO: 1, a CDR2 sequence of SEQ ID NO: 4, and a CDR3 sequence of SEQ ID NO: 7; or (b) a CDR1 sequence of SEQ ID NO: 1, a CDR2 sequence of SEQ ID NO: 4, and a CDR3 sequence of SEQ ID NO: 8; or (c) a CDR1 sequence of SEQ ID NO: 2, a CDR2 sequence of SEQ ID NO: 5, and a CDR3 sequence of SEQ ID NO: 9; or (d) a CDR1 sequence of SEQ ID NO: 3, a CDR2 sequence of SEQ ID NO: 6, and a CDR3 sequence of SEQ ID NO: 10.

7. The heavy chain-only antibody of any one of Clauses 1-5, comprising a heavy chain variable region having at least 95% sequence identity to any one of SEQ ID NOs: 11-14.

8. The heavy chain-only antibody of Clause 7, comprising a heavy chain variable region sequence selected from the group consisting of SEQ ID NOs: 11-14.

9. A heavy chain-only antibody that binds to IL2RB, comprising a heavy chain variable region comprising:

(a) a CDR1 sequence comprising the formula:

$$\text{G G S I S S S X1 W} \qquad \text{(SEQ ID NO: 26)}$$

where X1 is D or N;

(b) a CDR2 sequence comprising the formula:

$$\text{I X2 H S G S T} \qquad \text{(SEQ ID NO: 27)}$$

where X2 is D or S; and (c) a CDR3 sequence comprising the formula:

$$\text{X3 R G X4 W E L X5 D A F D I} \qquad \text{(SEQ ID NO: 28)}$$

where X3 is G or A;

X4 is S or Q; and

X5 is S or T.

10. A heavy chain-only antibody that binds to IL2RB, comprising a heavy chain variable region comprising:

(a) a CDR1 sequence comprising the formula:

$$\text{G F T F S X1 Y G} \qquad \text{(SEQ ID NO: 29)}$$

where X1 is S or T;

(b) a CDR2 sequence comprising the formula:

$$\text{I S Y D G S N X2} \qquad \text{(SEQ ID NO: 30)}$$

where X2 is K or R; and (c) a CDR3 sequence comprising the formula:

$$\text{A R D L D Y D X3 L T G D P V G G F D I} \qquad \text{(SEQ ID NO: 31)}$$

where X3 is V or I.

11. The heavy chain-only antibody of any one of Clauses 9-10, wherein the CDR1, CDR2, and CDR3 sequences are present in a VH human framework.

12. A heavy chain-only antibody that binds to IL2RG, comprising a heavy chain variable region comprising:

(a) a CDR1 sequence having two or fewer substitutions in any one of SEQ ID NOs: 15-16; and/or (b) a CDR2 sequence having two or fewer substitutions in any one of SEQ ID NOs: 17-19; and/or (c) a CDR3 sequence having two or fewer substitutions in any one of SEQ ID NOs: 20-21.

13. The heavy chain-only antibody of Clause 12, wherein said CDR1, CDR2, and CDR3 sequences are present in a human VH framework.

14. The heavy chain-only antibody of Clause 12 or 13, further comprising a heavy chain constant region sequence in the absence of a CH1 sequence.

15. The heavy chain-only antibody of any one of Clauses 12-14, comprising:

(a) a CDR1 sequence comprising any one of SEQ ID NOs: 15-16; and/or (b) a CDR2 sequence comprising any one of SEQ ID NOs: 17-19; and/or (c) a CDR3 sequence comprising any one of SEQ ID NOs: 20-21.

16. The heavy chain-only antibody of Clause 15, comprising:

(a) a CDR1 sequence comprising any one of SEQ ID NOs: 15-16; and (b) a CDR2 sequence comprising any one of SEQ ID NOs: 17-19; and (c) a CDR3 sequence comprising any one of SEQ ID NOs: 20-21.

17. The heavy chain-only antibody of Clause 16, comprising:

(a) a CDR1 sequence of SEQ ID NO: 15, a CDR2 sequence of SEQ ID NO: 17, and a CDR3 sequence of SEQ ID NO: 20; or (b) a CDR1 sequence of SEQ ID NO: 15, a CDR2 sequence of SEQ ID NO: 18, and a CDR3 sequence of SEQ ID NO: 20; or (c) a CDR1 sequence of SEQ ID NO: 16, a CDR2 sequence of SEQ ID NO: 18, and a CDR3 sequence of SEQ ID NO: 20; or (d) a CDR1 sequence of SEQ ID NO: 15, a CDR2 sequence of SEQ ID NO: 19, and a CDR3 sequence of SEQ ID NO: 21.

18. The heavy chain-only antibody of any one of Clauses 12-16, comprising a heavy chain variable region having at least 95% sequence identity to any one of SEQ ID NOs: 22-25.

19. The heavy chain-only antibody of Clause 18, comprising a heavy chain variable region sequence selected from the group consisting of SEQ ID NOs: 22-25.

20. A heavy chain-only antibody that binds to IL2RG, comprising a heavy chain variable region comprising:

(a) a CDR1 sequence comprising the formula:

$$\text{G F X1 X2 X3 X4 Y Y} \qquad \text{(SEQ ID NO: 32)}$$

where X1 is T or I;

X2 is F or V;

X3 is S, N, or G; and

X4 is D or N;

(b) a CDR2 sequence comprising the formula:

$$\text{I S X5 S G X6 X7 I} \qquad \text{(SEQ ID NO: 33)}$$

where X5 is S or N;

X6 is D, S, G, or N; and

X7 is T or I; and

15

(c) a CDR3 sequence comprising the sequence ARG-DAVSITGDY (SEQ ID NO: 20).

21. The heavy chain-only antibody of Clause 20, wherein the CDR1, CDR2, and CDR3 sequences are present in a VH human framework.

22. The heavy chain-only antibody of any one of Clauses 1-21, which is multi-specific.

23. The heavy chain-only antibody of Clause 22, which is bispecific.

24. The heavy chain-only antibody of Clause 22 or 23, which binds to IL2RB and IL2RG.

25. The heavy chain-only antibody of any one of Clauses 1-24, further comprising a heavy chain constant region comprising a hinge region, a CH2 domain, and a CH3 domain.

26. The heavy chain-only antibody of Clause 25, wherein the hinge region comprises a wild type human IgG4 hinge region sequence (SEQ ID NO: 54).

27. The heavy chain-only antibody of Clause 25, wherein the hinge region comprises a variant human IgG4 hinge region sequence comprising an S228P mutation (SEQ ID NO: 55).

28. The heavy chain-only antibody of any one of Clauses 25-27, wherein the CH2 domain comprises a wild type human IgG4 CH2 domain sequence (SEQ ID NO: 56).

29. The heavy chain-only antibody of any one of Clauses 25-27, wherein the CH2 domain comprises a variant human IgG4 CH2 domain comprising an F234A mutation, an L235A mutation, or both an F234A mutation and an L235A mutation.

30. The heavy chain-only antibody of any one of Clauses 25-29, wherein the CH3 domain comprises a wild type human IgG4 CH3 domain sequence (SEQ ID NO: 58).

31. The heavy chain-only antibody of any one of Clauses 25-29, wherein the CH3 domain comprises a variant human IgG4 CH3 domain sequence comprising a T366W mutation.

32. The heavy chain-only antibody of any one of Clauses 25-29, wherein the CH3 domain comprises a variant human IgG4 CH3 domain sequence comprising a T366S, an L368A mutation, and a Y407V mutation.

33. The heavy chain-only antibody of any one of Clauses 22-32, which functions as an IL2 receptor beta/gamma agonist.

34. A bispecific agonistic anti-IL2R heavy chain-only antibody, comprising:
   a first heavy chain variable region that binds to IL2RB, comprising:
      a CDR1 sequence of SEQ ID NO: 1;
      a CDR2 sequence of SEQ ID NO: 4; and
      a CDR3 sequence of SEQ ID NO: 7; and
   a second heavy chain variable region that binds to IL2RG, comprising:
      a CDR1 sequence of SEQ ID NO: 15;
      a CDR2 sequence of SEQ ID NO: 17; and
      a CDR3 sequence of SEQ ID NO: 20.

35. The antibody of Clause 34, wherein the first heavy chain variable region has at least 95% sequence identity to SEQ ID NO: 11, and the second heavy chain variable region has at least 95% sequence identity to SEQ ID NO: 22.

36. The antibody of Clause 35, wherein the first heavy chain variable region comprises SEQ ID NO: 11, and the second heavy chain variable region comprises SEQ ID NO: 22.

37. The antibody of Clause 36, comprising a first polypeptide comprising SEQ ID NO: 53 and a second polypeptide comprising SEQ ID NO: 61.

38. A bispecific agonistic anti-IL2R heavy chain only antibody, comprising:
   a first heavy chain variable region that binds to IL2RB, comprising:
      a CDR1 sequence of SEQ ID NO: 1;
      a CDR2 sequence of SEQ ID NO: 4; and
      a CDR3 sequence of SEQ ID NO: 8; and
   a second heavy chain variable region that binds to IL2RG, comprising:
      a CDR1 sequence of SEQ ID NO: 15;
      a CDR2 sequence of SEQ ID NO: 18; and
      a CDR3 sequence of SEQ ID NO: 20.

39. The antibody of Clause 38, wherein the first heavy chain variable region has at least 95% sequence identity to SEQ ID NO: 12, and the second heavy chain variable region has at least 95% sequence identity to SEQ ID NO: 23.

40. The antibody of Clause 39, wherein the first heavy chain variable region comprises SEQ ID NO: 12, and the second heavy chain variable region comprises SEQ ID NO: 23.

41. The antibody of Clause 40, comprising a first polypeptide comprising SEQ ID NO: 62 and a second polypeptide comprising SEQ ID NO: 63.

42. A bispecific agonistic anti-IL2R heavy chain-only antibody, comprising:
   a first heavy chain variable region that binds to IL2RB, comprising:
      a CDR1 sequence of SEQ ID NO: 2;
      a CDR2 sequence of SEQ ID NO: 5; and
      a CDR3 sequence of SEQ ID NO: 9; and
   a second heavy chain variable region that binds to IL2RG, comprising:
      a CDR1 sequence of SEQ ID NO: 15;
      a CDR2 sequence of SEQ ID NO: 18; and
      a CDR3 sequence of SEQ ID NO: 20.

43. The antibody of Clause 42, wherein the first heavy chain variable region has at least 95% sequence identity to SEQ ID NO: 13, and the second heavy chain variable region has at least 95% sequence identity to SEQ ID NO: 23.

44. The antibody of Clause 43, wherein the first heavy chain variable region comprises SEQ ID NO: 13, and the second heavy chain variable region comprises SEQ ID NO: 23.

45. The antibody of Clause 44, comprising a first polypeptide comprising SEQ ID NO: 64 and a second polypeptide comprising SEQ ID NO: 65.

46. A bispecific agonistic anti-IL2R heavy chain-only antibody, comprising:
   a first heavy chain variable region that binds to IL2RB, comprising:
      a CDR1 sequence of SEQ ID NO: 3;
      a CDR2 sequence of SEQ ID NO: 6; and
      a CDR3 sequence of SEQ ID NO: 10; and
   a second heavy chain variable region that binds to IL2RG, comprising:
      a CDR1 sequence of SEQ ID NO: 15;
      a CDR2 sequence of SEQ ID NO: 17; and
      a CDR3 sequence of SEQ ID NO: 20.

47. The antibody of Clause 46, wherein the first heavy chain variable region has at least 95% sequence identity to SEQ ID NO: 14, and the second heavy chain variable region has at least 95% sequence identity to SEQ ID NO: 22.

48. The antibody of Clause 47, wherein the first heavy chain variable region comprises SEQ ID NO: 14, and the second heavy chain variable region comprises SEQ ID NO: 22.

49. The antibody of Clause 48, comprising a first polypeptide comprising SEQ ID NO: 66 and a second polypeptide comprising SEQ ID NO: 67.

50. A bispecific agonistic anti-IL2R heavy chain-only antibody, comprising:
  a first heavy chain variable region that binds to IL2RB, comprising:
    a CDR1 sequence of SEQ ID NO: 1;
    a CDR2 sequence of SEQ ID NO: 4; and
    a CDR3 sequence of SEQ ID NO: 8; and
  a second heavy chain variable region that binds to IL2RG, comprising:
    a CDR1 sequence of SEQ ID NO: 16;
    a CDR2 sequence of SEQ ID NO: 18; and
    a CDR3 sequence of SEQ ID NO: 20.

51. The antibody of Clause 50, wherein the first heavy chain variable region has at least 95% sequence identity to SEQ ID NO: 12, and the second heavy chain variable region has at least 95% sequence identity to SEQ ID NO: 24.

52. The antibody of Clause 51, wherein the first heavy chain variable region comprises SEQ ID NO: 12, and the second heavy chain variable region comprises SEQ ID NO: 24.

53. The antibody of Clause 52, comprising a first polypeptide comprising SEQ ID NO: 34 and a second polypeptide comprising SEQ ID NO: 35.

54. A bispecific agonistic anti-IL2R heavy chain-only antibody, comprising:
  a first heavy chain variable region that binds to IL2RB, comprising:
    a CDR1 sequence of SEQ ID NO: 1;
    a CDR2 sequence of SEQ ID NO: 4; and
    a CDR3 sequence of SEQ ID NO: 8; and
  a second heavy chain variable region that binds to IL2RG, comprising:
    a CDR1 sequence of SEQ ID NO: 15;
    a CDR2 sequence of SEQ ID NO: 19; and
    a CDR3 sequence of SEQ ID NO: 21.

55. The antibody of Clause 54, wherein the first heavy chain variable region has at least 95% sequence identity to SEQ ID NO: 12, and the second heavy chain variable region has at least 95% sequence identity to SEQ ID NO: 25.

56. The antibody of Clause 55, wherein the first heavy chain variable region comprises SEQ ID NO: 12, and the second heavy chain variable region comprises SEQ ID NO: 25.

57. The antibody of Clause 56, comprising a first polypeptide comprising SEQ ID NO: 36 and a second polypeptide comprising SEQ ID NO: 37.

58. A pharmaceutical composition comprising an antibody of any one of Clauses 1-57.

59. A polynucleotide encoding an antibody of any one of Clauses 1-57.

60. A vector comprising the polynucleotide of Clause 59.

61. A cell comprising the vector of Clause 60.

62. A method of producing an antibody of any one of Clauses 1-57, the method comprising growing a cell according to Clause 61 under conditions permissive for expression of the antibody, and isolating the antibody from the cell and/or a cell culture medium in which the cell is grown.

63. A method of making an antibody of any one of Clauses 1-57, the method comprising immunizing a UniRat animal with IL2R and identifying IL2R-binding heavy chain sequences.

64. A kit for treating a disease or disorder in an individual in need, comprising an antibody of any one of Clauses 1-57, or a pharmaceutical composition of Clause 58, and instructions for use.

65. The kit of Clause 64, further comprising at least one additional reagent.

66. The kit of Clause 65, wherein the at least one additional reagent comprises a chemotherapeutic drug.

67. A method of treatment, comprising administering to an individual in need an effective dose of an antibody of any one of Clauses 1-57, or a pharmaceutical composition of Clause 58.

68. Use of an antibody of any one of Clauses 1-57 in the preparation of a medicament for the treatment of a disease or disorder in an individual in need.

69. The antibody of any one of Clauses 1-57, or the pharmaceutical composition of Clause 58, for use in therapy in an individual in need.

70. A method for the treatment of a cancer, comprising administering to a subject with said cancer an antibody of any one of Clauses 1-57, or a pharmaceutical composition of Clause 58.

71. The method or use of any one of Clauses 67-70, wherein the cancer is an advanced or metastatic cancer.

72. The method or use of any one of Clauses 67-71, wherein the cancer is a solid tumor cancer.

73. The method or use of Clause 72, wherein the solid tumor cancer is selected from the group consisting of: renal cell carcinoma, melanoma, urothelial cancer, triple negative breast cancer, non-small cell lung cancer (NSCLC), colorectal cancer, sarcoma, squamous cell carcinoma of the head and neck, and metastatic castration-resistant prostate cancer.

74. A method for stimulating IL2R signaling in an immune cell, the method comprising contacting the immune cell with an antibody of any one of Clauses 1-57, or a pharmaceutical composition of Clause 58.

75. A method for stimulating an IL2RB/IL2RG dimeric receptor complex on an immune cell, the method comprising contacting the immune cell with an antibody of any one of Clauses 1-57, or a pharmaceutical composition of Clause 58.

76. The method of Clause 74 or 75, wherein the immune cell is selected from the group consisting of: a CD4+ T-cell, a CD8+ T-cell, and a Natural Killer (NK) cell.

IL-2R, also known as interleukin-2 receptor, is a heterodimeric protein expressed on the surface of various immune cells, which serves as a cognate ligand for interleukin 2 (IL-2). The IL-2R complex is composed of various combinations of the IL-2Rα (ILR2A), IL-2Rβ (IL2RB), and IL-2Rγ (IL2RG) protein chains. IL-2RA is also referred to as CD25, and the human IL2RA sequence (UniProtKB No. P01589) is provided herein as SEQ ID NO: 38. IL-2RB is also referred to as CD122, and the human IL2RB sequence (UniProtKB No. P14784) is provided herein as SEQ ID NO: 39. IL-2RG is also referred to as CD132, and the human IL2RG sequence (UniProtKB No. P31785) is provided herein as SEQ ID NO: 40. The human IL-2 sequence (UniProtKB No. P60568) is provided herein as SEQ ID NO: 41.

Aspects of the disclosure relate to an antibody that binds to IL2RB, comprising a heavy chain variable region comprising: (a) a CDR1 sequence having two or fewer (e.g., 0, 1, or 2) substitutions in any one of SEQ ID NOs: 1-3; and/or (b) a CDR2 sequence having two or fewer (e.g., 0, 1, or 2) substitutions in any one of SEQ ID NOs: 4-6; and/or (c) a CDR3 sequence having two or fewer (e.g., 0, 1, or 2) substitutions in any one of SEQ ID NOs: 7-10.

In some embodiments, the antibody comprises: (a) a CDR1 sequence comprising any one of SEQ ID NOs: 1-3; and/or (b) a CDR2 sequence comprising any one of SEQ ID NOs: 4-6; and/or (c) a CDR3 sequence comprising any one of SEQ ID NOs: 7-10.

In some embodiments, the antibody comprises: (a) a CDR1 sequence comprising any one of SEQ ID NOs: 1-3; and (b) a CDR2 sequence comprising any one of SEQ ID NOs: 4-6; and (c) a CDR3 sequence comprising any one of SEQ ID NOs: 7-10.

In some embodiments, the antibody comprises:

(a) a CDR1 sequence of SEQ ID NO: 1, a CDR2 sequence of SEQ ID NO: 4, and a CDR3 sequence of SEQ ID NO: 7; or (b) a CDR1 sequence of SEQ ID NO: 1, a CDR2 sequence of SEQ ID NO: 4, and a CDR3 sequence of SEQ ID NO: 8; or (c) a CDR1 sequence of SEQ ID NO: 2, a CDR2 sequence of SEQ ID NO: 5, and a CDR3 sequence of SEQ ID NO: 9; or (d) a CDR1 sequence of SEQ ID NO: 3, a CDR2 sequence of SEQ ID NO: 6, and a CDR3 sequence of SEQ ID NO: 10.

In some embodiments, the CDR1, CDR2, and CDR3 sequences are present in a human VH framework.

In some embodiments, the antibody comprises a heavy chain variable region comprising a sequence having six or fewer (e.g., five or fewer, four or fewer, three or fewer, two or fewer; six, five, four, three, two, one, zero) substitutions in any one of SEQ ID NOs: 11-14. In some embodiments, the antibody comprises a heavy chain variable region having at least 95% (e.g., at least 96%, at least 97%, at least 98%, at least 99%) sequence identity to any one of SEQ ID NOs: 11-14. In some embodiments, the antibody comprises a heavy chain variable region sequence selected from the group consisting of SEQ ID NOs: 11-14.

In some embodiments, the antibody is an isolated antibody. In some embodiments, the antibody is a human antibody. In some embodiments, the antibody is an isolated human antibody.

In some embodiments, the antibody is an intact IgG molecule. In some embodiments, the antibody is an intact IgG1 molecule. In some embodiments, the antibody is an intact IgG2 molecule. In some embodiments, the antibody is an intact IgG4 molecule. In some embodiments, the antibody is an immunologically active portion of an intact IgG molecule. In some embodiments, the antibody is an immunologically active portion of an intact IgG1 molecule. In some embodiments, the antibody is an immunologically active portion of an intact IgG2 molecule. In some embodiments, the antibody is an immunologically active portion of an intact IgG4 molecule. In some embodiments, the antibody is a triple-chain antibody-like molecule. In some embodiments, the antibody is a heavy-chain only antibody.

In some embodiments, the antibody comprises a Fc region. In some embodiments, the antibody comprises a variant Fc region. In some embodiments, the variant Fc region possesses at least about 80% homology (e.g., at least about 85%, at least about 90%, at least about 95%, at least about 98%, at least about 99%) with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, the antibody further comprises a heavy chain constant region sequence in the absence of a CH1 sequence. In some embodiments, the antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, the antibody has a Tm of from about 55° C. to about 65° C. In some embodiments, the antibody has a Tagg of from about 55° C. to about 65° C. In some embodiments, the antibody has a Tm of from about 55° C. to about 65° C. and a Tagg of from about 55° C. to about 65° C.

In some embodiments, the antibody is multi-specific. In some embodiments, the antibody is bispecific. In some embodiments, the antibody binds to IL2RB and IL2RG. In some embodiments, the antibody functions as an IL2 receptor beta/gamma agonist.

In some embodiments, the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, the antibody has an affinity for IL2RB with a Kd of from about $10^{-8}$ M to around about $2.5 \times 10^{-7}$ M.

In some embodiments, the antibody has an affinity for IL2RG with a Kd of from about $10^{-9}$ M to around about $2.5 \times 10^{-8}$ M.

In some embodiments, the antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include an antibody that binds to IL2RB, comprising a heavy chain variable region comprising:

(a) a CDR1 sequence comprising the formula:

```
                                    (SEQ ID NO: 26)
        G G S I S S S X1 W
``` where X1 is D or N;

(b) a CDR2 sequence comprising the formula:

```
                                    (SEQ ID NO: 27)
        I X2 H S G S T
``` where X2 is D or S; and (c) a CDR3 sequence comprising the formula:

```
                                    (SEQ ID NO: 28)
    X3 R G X4 W E L X5 D A F D I
``` where X3 is G or A; X4 is S or Q; and X5 is S or T.

In some embodiments, the CDR1, CDR2, and CDR3 sequences are present in a VH human framework.

In some embodiments, the antibody is an isolated antibody. In some embodiments, the antibody is a human antibody. In some embodiments, the antibody is an isolated human antibody.

In some embodiments, the antibody is an intact IgG molecule. In some embodiments, the antibody is an intact IgG1 molecule. In some embodiments, the antibody is an intact IgG2 molecule. In some embodiments, the antibody is an intact IgG4 molecule. In some embodiments, the antibody is an immunologically active portion of an intact IgG molecule. In some embodiments, the antibody is an immunologically active portion of an intact IgG1 molecule. In some embodiments, the antibody is an immunologically active portion of an intact IgG2 molecule. In some embodiments, the antibody is an immunologically active portion of an intact IgG4 molecule. In some embodiments, the antibody is a triple-chain antibody-like molecule. In some embodiments, the antibody is a heavy-chain only antibody.

In some embodiments, the antibody comprises a Fc region. In some embodiments, the antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, the antibody further comprises a heavy chain constant region sequence in the absence of a CH1 sequence. In some embodiments, the antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, the antibody has a Tm of from about 55° C. to about 65° C. In some embodiments, the antibody has a Tagg of from about 55° C. to about 65° C. In some embodiments, the antibody has a Tm of from about 55° C. to about 65° C. and a Tagg of from about 55° C. to about 65° C.

In some embodiments, the antibody is multi-specific. In some embodiments, the antibody is bispecific. In some embodiments, the antibody binds to IL2RB and IL2RG. In some embodiments, the antibody functions as an IL2 receptor beta/gamma agonist.

In some embodiments, the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, the antibody has an affinity for IL2RB with a Kd of from about $10^{-8}$ M to around about $2.5 \times 10^{-7}$ M.

In some embodiments, the antibody has an affinity for IL2RG with a Kd of from about $10^{-9}$ M to around about $2.5 \times 10^{-8}$ M.

In some embodiments, the antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include an antibody that binds to IL2RB, comprising a heavy chain variable region comprising:

(a) a CDR1 sequence comprising the formula:

(SEQ ID NO: 29)
G F T F S X1 Y G where X1 is S or T;

(b) a CDR2 sequence comprising the formula:

(SEQ ID NO: 30)
I S Y D G S N X2 where X2 is K or R; and (c) a CDR3 sequence comprising the formula:

(SEQ ID NO: 31)
A R D L D Y D X3 L T G D P V G G F D I where X3 is V or I.

In some embodiments, the CDR1, CDR2, and CDR3 sequences are present in a VH human framework.

In some embodiments, the antibody is an isolated antibody. In some embodiments, the antibody is a human antibody. In some embodiments, the antibody is an isolated human antibody.

In some embodiments, the antibody is an intact IgG molecule. In some embodiments, the antibody is an intact IgG1 molecule. In some embodiments, the antibody is an intact IgG2 molecule. In some embodiments, the antibody is an intact IgG4 molecule. In some embodiments, the antibody is an immunologically active portion of an intact IgG molecule. In some embodiments, the antibody is an immunologically active portion of an intact IgG1 molecule. In some embodiments, the antibody is an immunologically active portion of an intact IgG2 molecule. In some embodiments, the antibody is an immunologically active portion of an intact IgG4 molecule. In some embodiments, the antibody is a triple-chain antibody-like molecule. In some embodiments, the antibody is a heavy-chain only antibody.

In some embodiments, the antibody comprises a Fc region. In some embodiments, the antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, the antibody further comprises a heavy chain constant region sequence in the absence of a CH1 sequence. In some embodiments, the antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, the antibody has a Tm of from about 55° C. to about 65° C. In some embodiments, the antibody has a Tagg of from about 55° C. to about 65° C. In some embodiments, the antibody has a Tm of from about 55° C. to about 65° C. and a Tagg of from about 55° C. to about 65° C.

In some embodiments, the antibody is multi-specific. In some embodiments, the antibody is bispecific. In some embodiments, the antibody binds to IL2RB and IL2RG. In some embodiments, the antibody functions as an IL2 receptor beta/gamma agonist.

In some embodiments, the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, the antibody has an affinity for IL2RB with a Kd of from about $10^{-8}$ M to around about $2.5 \times 10^{-7}$ M.

In some embodiments, the antibody has an affinity for IL2RG with a Kd of from about $10^{-9}$ M to around about $2.5 \times 10^{-8}$ M.

In some embodiments, the antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include an antibody that binds to IL2RG, comprising a heavy chain variable region comprising: (a) a CDR1 sequence having two or fewer (e.g., 0, 1, or 2) substitutions in any one of SEQ ID NOs: 15-16; and/or (b) a CDR2 sequence having two or fewer (e.g., 0, 1, or 2) substitutions in any one of SEQ ID NOs: 17-19; and/or (c) a CDR3 sequence having two or fewer (e.g., 0, 1, or 2) substitutions in any one of SEQ ID NOs: 20-21.

In some embodiments, the antibody comprises: (a) a CDR1 sequence comprising any one of SEQ ID NOs: 15-16; and/or (b) a CDR2 sequence comprising any one of SEQ ID NOs: 17-19; and/or (c) a CDR3 sequence comprising any one of SEQ ID NOs: 20-21.

In some embodiments, the antibody comprises: (a) a CDR1 sequence comprising any one of SEQ ID NOs: 15-16; and (b) a CDR2 sequence comprising any one of SEQ ID NOs: 17-19; and (c) a CDR3 sequence comprising any one of SEQ ID NOs: 20-21.

In some embodiments, the antibody comprises:
(a) a CDR1 sequence of SEQ ID NO: 15, a CDR2 sequence of SEQ ID NO: 17, and a CDR3 sequence of SEQ ID NO: 20; or
(b) a CDR1 sequence of SEQ ID NO: 15, a CDR2 sequence of SEQ ID NO: 18, and a CDR3 sequence of SEQ ID NO: 20; or
(c) a CDR1 sequence of SEQ ID NO: 16, a CDR2 sequence of SEQ ID NO: 18, and a CDR3 sequence of SEQ ID NO: 20; or
(d) a CDR1 sequence of SEQ ID NO: 15, a CDR2 sequence of SEQ ID NO: 19, and a CDR3 sequence of SEQ ID NO: 21.

In some embodiments, the CDR1, CDR2, and CDR3 sequences are present in a VH human framework.

In some embodiments, the antibody comprises a heavy chain variable region comprising a sequence having six or fewer (e.g., five or fewer, four or fewer, three or fewer, two or fewer; six, five, four, three, two, one, zero) substitutions in any one of SEQ ID NOs: 22-25. In some embodiments, the antibody comprises a heavy chain variable region having at least 95% (e.g., at least 96%, at least 97%, at least 98%, at least 99%) sequence identity to any one of SEQ ID NOs: 22-25. In some embodiments, the antibody comprises a heavy chain variable region sequence selected from the group consisting of SEQ ID NOs: 22-25.

In some embodiments, the antibody is an isolated antibody. In some embodiments, the antibody is a human antibody. In some embodiments, the antibody is an isolated human antibody.

In some embodiments, the antibody is an intact IgG molecule. In some embodiments, the antibody is an intact IgG1 molecule. In some embodiments, the antibody is an intact IgG2 molecule. In some embodiments, the antibody is an intact IgG4 molecule. In some embodiments, the antibody is an immunologically active portion of an intact IgG molecule. In some embodiments, the antibody is an immunologically active portion of an intact IgG1 molecule. In some embodiments, the antibody is an immunologically active portion of an intact IgG2 molecule. In some embodiments, the antibody is an immunologically active portion of an intact IgG4 molecule. In some embodiments, the antibody is a triple-chain antibody-like molecule. In some embodiments, the antibody is a heavy-chain only antibody.

In some embodiments, the antibody comprises a Fc region. In some embodiments, the antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, the antibody further comprises a heavy chain constant region sequence in the absence of a CH1 sequence. In some embodiments, the antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, the antibody has a Tm of from about 55° C. to about 65° C. In some embodiments, the antibody has a Tagg of from about 55° C. to about 65° C. In some embodiments, the antibody has a Tm of from about 55° C. to about 65° C. and a Tagg of from about 55° C. to about 65° C.

In some embodiments, the antibody is multi-specific. In some embodiments, the antibody is bispecific. In some embodiments, the antibody binds to IL2RB and IL2RG. In some embodiments, the antibody functions as an IL2 receptor beta/gamma agonist.

In some embodiments, the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, the antibody has an affinity for IL2RB with a Kd of from about $10^{-8}$ M to around about $2.5 \times 10^{-7}$ M.

In some embodiments, the antibody has an affinity for IL2RG with a Kd of from about $10^{-9}$ M to around about $2.5 \times 10^{-8}$ M.

In some embodiments, the antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include an antibody that binds to IL2RG, comprising a heavy chain variable region comprising:

(a) a CDR1 sequence comprising the formula:

(SEQ ID NO: 32)

G F X1 X2 X3 X4 Y Y where X1 is T or I; X2 is F or V; X3 is S, N, or G; and X4 is D or N;

(b) a CDR2 sequence comprising the formula:

(SEQ ID NO: 33)

I S X5 S G X6 X7 I where X5 is S or N; X6 is D, S, G, or N; and X7 is T or I; and (c) a CDR3 sequence comprising the sequence ARG-DAVSITGDY (SEQ ID NO: 20).

In some embodiments, the CDR1, CDR2, and CDR3 sequences are present in a VH human framework.

In some embodiments, the antibody is multi-specific. In some embodiments, the antibody is bispecific. In some embodiments, the antibody binds to IL2RB and IL2RG.

In some embodiments, the antibody is an isolated antibody. In some embodiments, the antibody is a human antibody. In some embodiments, the antibody is an isolated human antibody.

In some embodiments, the antibody is an intact IgG molecule. In some embodiments, the antibody is an intact IgG1 molecule. In some embodiments, the antibody is an intact IgG2 molecule. In some embodiments, the antibody is an intact IgG4 molecule. In some embodiments, the antibody is an immunologically active portion of an intact IgG molecule. In some embodiments, the antibody is an immunologically active portion of an intact IgG1 molecule. In some embodiments, the antibody is an immunologically active portion of an intact IgG2 molecule. In some embodiments, the antibody is an immunologically active portion of an intact IgG4 molecule. In some embodiments, the antibody is a triple-chain antibody-like molecule. In some embodiments, the antibody is a heavy-chain only antibody.

In some embodiments, the antibody is an Fc-region-containing antibody. In some embodiments, the antibody further comprises a heavy chain constant region comprising a hinge region, a CH2 domain, and a CH3 domain. In some embodiments, the heavy chain constant region does not contain a CH1 sequence. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, the antibody has a Tm of from about 55° C. to about 65° C. In some embodiments, the antibody has a Tagg of from about 55° C. to about 65° C. In some embodiments, the antibody has a Tm of from about 55° C. to about 65° C. and a Tagg of from about 55° C. to about 65° C.

In some embodiments, the antibody functions as an IL2 receptor beta/gamma agonist.

In some embodiments, the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, the antibody has an affinity for IL2RB with a Kd of from about $10^{-8}$ M to around about $2.5 \times 10^{-7}$ M.

In some embodiments, the antibody has an affinity for IL2RG with a Kd of from about $10^{-9}$ M to around about $2.5 \times 10^{-8}$ M.

In some embodiments, the antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include an antibody, comprising:

a first heavy chain variable region that binds to IL2RB, comprising: a CDR1 sequence of SEQ ID NO: 1; a CDR2 sequence of SEQ ID NO: 4; and a CDR3 sequence of SEQ ID NO: 7; and a second heavy chain variable region that binds to IL2RG, comprising: a CDR1 sequence of SEQ ID NO: 15; a CDR2 sequence of SEQ ID NO: 17; and a CDR3 sequence of SEQ ID NO: 20.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO: 11, and the second heavy chain variable region has at least 95% (e.g., at least 96%, at least 97%, at least 98%, at least 99%) sequence identity to SEQ ID NO: 22. In some embodiments, the first heavy chain variable region comprises SEQ ID NO: 11, and the second heavy chain variable region comprises SEQ ID NO: 22.

In some embodiments, the antibody is an isolated antibody. In some embodiments, the antibody is a human antibody. In some embodiments, the antibody is an isolated human antibody.

In some embodiments, the antibody is an intact IgG molecule. In some embodiments, the antibody is an intact IgG1 molecule. In some embodiments, the antibody is an intact IgG2 molecule. In some embodiments, the antibody is an intact IgG4 molecule. In some embodiments, the antibody is an immunologically active portion of an intact IgG molecule. In some embodiments, the antibody is an immunologically active portion of an intact IgG1 molecule. In some embodiments, the antibody is an immunologically active portion of an intact IgG2 molecule. In some embodiments, the antibody is an immunologically active portion of an intact IgG4 molecule. In some embodiments, the antibody is a triple-chain antibody-like molecule. In some embodiments, the antibody is a heavy-chain only antibody.

In some embodiments, the antibody comprises a Fc region. In some embodiments, the antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, the antibody further comprises a heavy chain constant region sequence in the absence of a CH1 sequence. In some embodiments, the antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, the antibody comprises a first polypeptide comprising SEQ ID NO: 53 and a second polypeptide comprising SEQ ID NO: 61.

In some embodiments, the antibody has a Tm of from about 55° C. to about 65° C. In some embodiments, the antibody has a Tagg of from about 55° C. to about 65° C. In some embodiments, the antibody has a Tm of from about 55° C. to about 65° C. and a Tagg of from about 55° C. to about 65° C.

In some embodiments, the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, the antibody has an affinity for IL2RB with a Kd of from about $10^{-8}$ M to around about $2.5 \times 10^{-7}$ M.

In some embodiments, the antibody has an affinity for IL2RG with a Kd of from about $10^{-9}$ M to around about $2.5 \times 10^{-8}$ M.

In some embodiments, the antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include an antibody, comprising:

a first heavy chain variable region that binds to IL2RB, comprising: a CDR1 sequence of SEQ ID NO: 1; a CDR2 sequence of SEQ ID NO: 4; and a CDR3 sequence of SEQ ID NO: 8; and a second heavy chain variable region that binds to IL2RG, comprising: a CDR1 sequence of SEQ ID NO: 15; a CDR2 sequence of SEQ ID NO: 18; and a CDR3 sequence of SEQ ID NO: 20.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO: 12, and the second heavy chain variable region has at least 95% (e.g., at least 96%, at least 97%, at least 98%, at least 99%) sequence identity to SEQ ID NO: 23. In some embodiments, the first heavy chain variable region comprises SEQ ID NO: 12, and the second heavy chain variable region comprises SEQ ID NO: 23.

In some embodiments, the antibody is an isolated antibody. In some embodiments, the antibody is a human antibody. In some embodiments, the antibody is an isolated human antibody.

In some embodiments, the antibody is an intact IgG molecule. In some embodiments, the antibody is an intact IgG1 molecule. In some embodiments, the antibody is an intact IgG2 molecule. In some embodiments, the antibody is an intact IgG4 molecule. In some embodiments, the antibody is an immunologically active portion of an intact IgG molecule. In some embodiments, the antibody is an immunologically active portion of an intact IgG1 molecule. In some embodiments, the antibody is an immunologically active portion of an intact IgG2 molecule. In some embodiments, the antibody is an immunologically active portion of an intact IgG4 molecule. In some embodiments, the antibody is a triple-chain antibody-like molecule. In some embodiments, the antibody is a heavy-chain only antibody.

In some embodiments, the antibody comprises a Fc region. In some embodiments, the antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, the antibody further comprises a heavy chain constant region sequence in the absence of a CH1 sequence. In some embodiments, the antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, the antibody comprises a first polypeptide comprising SEQ ID NO: 62 and a second polypeptide comprising SEQ ID NO: 63.

In some embodiments, the antibody has a Tm of from about 55° C. to about 65° C. In some embodiments, the antibody has a Tagg of from about 55° C. to about 65° C. In some embodiments, the antibody has a Tm of from about 55° C. to about 65° C. and a Tagg of from about 55° C. to about 65° C.

In some embodiments, the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, the antibody has an affinity for IL2RB with a Kd of from about $10^{-8}$ M to around about $2.5 \times 10^{-7}$ M.

In some embodiments, the antibody has an affinity for IL2RG with a Kd of from about $10^{-9}$ M to around about $2.5 \times 10^{-8}$ M.

In some embodiments, the antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include an antibody, comprising:

a first heavy chain variable region that binds to IL2RB, comprising: a CDR1 sequence of SEQ ID NO: 2; a CDR2 sequence of SEQ ID NO: 5; and a CDR3 sequence of SEQ ID NO: 9; and a second heavy chain variable region that binds to IL2RG, comprising: a CDR1 sequence of SEQ ID NO: 15; a CDR2 sequence of SEQ ID NO: 18; and a CDR3 sequence of SEQ ID NO: 20.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO: 13, and the second heavy chain variable region has at least 95% (e.g., at least 96%, at least 97%, at least 98%, at least 99%) sequence identity to SEQ ID NO: 23. In some embodiments, the first heavy chain variable region comprises SEQ ID NO: 13, and the second heavy chain variable region comprises SEQ ID NO: 23.

In some embodiments, the antibody is an isolated antibody. In some embodiments, the antibody is a human antibody. In some embodiments, the antibody is an isolated human antibody.

In some embodiments, the antibody is an intact IgG molecule. In some embodiments, the antibody is an intact IgG1 molecule. In some embodiments, the antibody is an intact IgG2 molecule. In some embodiments, the antibody is an intact IgG4 molecule. In some embodiments, the antibody is an immunologically active portion of an intact IgG molecule. In some embodiments, the antibody is an immunologically active portion of an intact IgG1 molecule. In some embodiments, the antibody is an immunologically active portion of an intact IgG2 molecule. In some embodiments, the antibody is an immunologically active portion of an intact IgG4 molecule. In some embodiments, the antibody is a triple-chain antibody-like molecule. In some embodiments, the antibody is a heavy-chain only antibody.

In some embodiments, the antibody comprises a Fc region. In some embodiments, the antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, the antibody further comprises a heavy chain constant region sequence in the absence of a CH1 sequence. In some embodiments, the antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, the antibody comprises a first polypeptide comprising SEQ ID NO: 64 and a second polypeptide comprising SEQ ID NO: 65.

In some embodiments, the antibody has a Tm of from about 55° C. to about 65° C. In some embodiments, the antibody has a Tagg of from about 55° C. to about 65° C. In some embodiments, the antibody has a Tm of from about 55° C. to about 65° C. and a Tagg of from about 55° C. to about 65° C.

In some embodiments, the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, the antibody has an affinity for IL2RB with a Kd of from about $10^{-8}$ M to around about $2.5 \times 10^{-7}$ M.

In some embodiments, the antibody has an affinity for IL2RG with a Kd of from about $10^{-9}$ M to around about $2.5 \times 10^{-8}$ M.

In some embodiments, the antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include an antibody, comprising:

a first heavy chain variable region that binds to IL2RB, comprising: a CDR1 sequence of SEQ ID NO: 3; a CDR2 sequence of SEQ ID NO: 6; and a CDR3 sequence of SEQ ID NO: 10; and a second heavy chain variable region that binds to IL2RG, comprising: a CDR1 sequence of SEQ ID NO: 15; a CDR2 sequence of SEQ ID NO: 17; and a CDR3 sequence of SEQ ID NO: 20.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO: 14, and the second heavy chain variable region has at least 95% (e.g., at least 96%, at least 97%, at least 98%, at least 99%) sequence identity to SEQ ID NO: 22. In some embodiments, the first heavy chain variable region comprises SEQ ID NO: 14, and the second heavy chain variable region comprises SEQ ID NO: 22.

In some embodiments, the antibody is an isolated antibody. In some embodiments, the antibody is a human antibody. In some embodiments, the antibody is an isolated human antibody.

In some embodiments, the antibody is an intact IgG molecule. In some embodiments, the antibody is an intact IgG1 molecule. In some embodiments, the antibody is an intact IgG2 molecule. In some embodiments, the antibody is an intact IgG4 molecule. In some embodiments, the antibody is an immunologically active portion of an intact IgG molecule. In some embodiments, the antibody is an immunologically active portion of an intact IgG1 molecule. In some embodiments, the antibody is an immunologically active portion of an intact IgG2 molecule. In some embodiments, the antibody is an immunologically active portion of an intact IgG4 molecule. In some embodiments, the antibody is a triple-chain antibody-like molecule. In some embodiments, the antibody is a heavy-chain only antibody.

In some embodiments, the antibody comprises a Fc region. In some embodiments, the antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, the antibody further comprises a heavy chain constant region sequence in the absence of a CH1 sequence. In some embodiments, the antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, the antibody comprises a first polypeptide comprising SEQ ID NO: 66 and a second polypeptide comprising SEQ ID NO: 67.

In some embodiments, the antibody has a Tm of from about 55° C. to about 65° C. In some embodiments, the antibody has a Tagg of from about 55° C. to about 65° C. In some embodiments, the antibody has a Tm of from about 55° C. to about 65° C. and a Tagg of from about 55° C. to about 65° C.

In some embodiments, the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, the antibody has an affinity for IL2RB with a Kd of from about $10^{-8}$ M to around about $2.5 \times 10^{-7}$ M.

In some embodiments, the antibody has an affinity for IL2RG with a Kd of from about $10^{-9}$ M to around about $2.5 \times 10^{-8}$ M.

In some embodiments, the antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include an antibody, comprising:

a first heavy chain variable region that binds to IL2RB, comprising: a CDR1 sequence of SEQ ID NO: 1; a CDR2 sequence of SEQ ID NO: 4; and a CDR3 sequence of SEQ ID NO: 8; and a second heavy chain variable region that binds to IL2RG, comprising: a CDR1 sequence of SEQ ID NO: 16; a CDR2 sequence of SEQ ID NO: 18; and a CDR3 sequence of SEQ ID NO: 20.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO: 12, and the second heavy chain variable region has at least 95% (e.g., at least 96%, at least 97%, at least 98%, at least 99%) sequence identity to SEQ ID NO: 24. In some embodiments, the first heavy chain variable region comprises SEQ ID NO: 12, and the second heavy chain variable region comprises SEQ ID NO: 24.

In some embodiments, the antibody is an isolated antibody. In some embodiments, the antibody is a human antibody. In some embodiments, the antibody is an isolated human antibody.

In some embodiments, the antibody is an intact IgG molecule. In some embodiments, the antibody is an intact IgG1 molecule. In some embodiments, the antibody is an intact IgG2 molecule. In some embodiments, the antibody is an intact IgG4 molecule. In some embodiments, the antibody is an immunologically active portion of an intact IgG molecule. In some embodiments, the antibody is an immunologically active portion of an intact IgG1 molecule. In some embodiments, the antibody is an immunologically active portion of an intact IgG2 molecule. In some embodiments, the antibody is an immunologically active portion of an intact IgG4 molecule. In some embodiments, the antibody is a triple-chain antibody-like molecule. In some embodiments, the antibody is a heavy-chain only antibody.

In some embodiments, the antibody comprises a Fc region. In some embodiments, the antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, the antibody further comprises a heavy chain constant region sequence in the absence of a CH1 sequence. In some embodiments, the antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, the antibody comprises a first polypeptide comprising SEQ ID NO: 34 and a second polypeptide comprising SEQ ID NO: 35.

In some embodiments, the antibody has a Tm of from about 55° C. to about 65° C. In some embodiments, the antibody has a Tagg of from about 55° C. to about 65° C. In some embodiments, the antibody has a Tm of from about 55° C. to about 65° C. and a Tagg of from about 55° C. to about 65° C.

In some embodiments, the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, the antibody has an affinity for IL2RB with a Kd of from about $10^{-8}$ M to around about $2.5 \times 10^{-7}$ M.

In some embodiments, the antibody has an affinity for IL2RG with a Kd of from about $10^{-9}$ M to around about $2.5 \times 10^{-8}$ M.

In some embodiments, the antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include an antibody, comprising:

a first heavy chain variable region that binds to IL2RB, comprising: a CDR1 sequence of SEQ ID NO: 1; a CDR2 sequence of SEQ ID NO: 4; and a CDR3 sequence of SEQ ID NO: 8; and a second heavy chain variable region that binds to IL2RG, comprising: a CDR1 sequence of SEQ ID NO: 15; a CDR2 sequence of SEQ ID NO: 19; and a CDR3 sequence of SEQ ID NO: 21.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO: 12, and the second heavy chain variable region has at least 95% (e.g., at least 96%, at least 97%, at least 98%, at least 99%) sequence identity to SEQ ID NO: 25. In some embodiments, the first heavy chain variable region comprises SEQ ID NO: 12, and the second heavy chain variable region comprises SEQ ID NO: 25.

In some embodiments, the antibody is an isolated antibody. In some embodiments, the antibody is a human antibody. In some embodiments, the antibody is an isolated human antibody.

In some embodiments, the antibody is an intact IgG molecule. In some embodiments, the antibody is an intact IgG1 molecule. In some embodiments, the antibody is an intact IgG2 molecule. In some embodiments, the antibody is an intact IgG4 molecule. In some embodiments, the antibody is an immunologically active portion of an intact IgG molecule. In some embodiments, the antibody is an immunologically active portion of an intact IgG1 molecule. In some embodiments, the antibody is an immunologically active portion of an intact IgG2 molecule. In some embodiments, the antibody is an immunologically active portion of an intact IgG4 molecule. In some embodiments, the antibody is a triple-chain antibody-like molecule. In some embodiments, the antibody is a heavy-chain only antibody.

In some embodiments, the antibody comprises a Fc region. In some embodiments, the antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6)

D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, the antibody further comprises a heavy chain constant region sequence in the absence of a CH1 sequence. In some embodiments, the antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, the antibody comprises a first polypeptide comprising SEQ ID NO: 36 and a second polypeptide comprising SEQ ID NO: 37.

In some embodiments, the antibody has a Tm of from about 55° C. to about 65° C. In some embodiments, the antibody has a Tagg of from about 55° C. to about 65° C. In some embodiments, the antibody has a Tm of from about 55° C. to about 65° C. and a Tagg of from about 55° C. to about 65° C.

In some embodiments, the antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, the antibody has an affinity for IL2RB with a Kd of from about $10^{-8}$ M to around about $2.5 \times 10^{-7}$ M.

In some embodiments, the antibody has an affinity for IL2RG with a Kd of from about $10^{-9}$ M to around about $2.5 \times 10^{-8}$ M.

In some embodiments, the antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

In a conventional IgG antibody, the association of the heavy chain and the light chain is due in part to a hydrophobic interaction between the light chain constant region and the CH1 constant domain of the heavy chain. There are additional residues in the heavy chain framework 2 (FR2) and framework 4 (FR4) regions that also contribute to this hydrophobic interaction between the heavy and light chains.

It is known, however, that sera of camelids (sub-order Tylopoda which includes camels, dromedaries, and llamas) contain a major type of antibodies composed solely of paired H-chains (heavy-chain only antibodies or HCAbs). The heavy-chain only antibodies of Camelidae (*Camelus dromedarius, Camelus bactrianus, Lama glama, Lama guanaco, Lama alpaca* and *Lama vicugna*) have a unique structure consisting of a single variable domain (VHH), a hinge region, and two constant domains (CH2 and CH3), which are highly homologous to the CH2 and CH3 domains of classical antibodies. These heavy-chain only antibodies lack the first domain of the constant region (CH1), which is present in the genome but is spliced out during mRNA processing. The absence of the CH1 domain explains the absence of the light chain in the heavy-chain only antibodies since this domain is the anchoring place for the constant domain of the light chain. Such heavy-chain only antibodies naturally evolved to confer antigen-binding specificity and high affinity by three CDRs from conventional antibodies or fragments thereof. Muyldermans, 2001; *J Biotechnol* 74:277-302; Revets et al., 2005; *Expert Opin Biol Ther* 5:111-124. Cartilaginous fish, such as sharks, have also evolved a distinctive type of immunoglobulin, designated as IgNAR, which lacks the light polypeptide chains and is composed entirely by heavy chains. IgNAR molecules can be manipulated by molecular engineering to produce the variable domain of a single heavy chain polypeptide (vNARs). Nuttall et al. *Eur. J. Biochem.* 270, 3543-3554 (2003); Nuttall et al. *Function and Bioinformatics* 55, 187-197 (2004); Dooley et al., *Molecular Immunology* 40, 25-33 (2003).

The ability of heavy chain-only antibodies devoid of light chain to bind antigen was established in the 1960s (Jaton et al. (1968) *Biochemistry*, 7, 4185-4195). Heavy chain immunoglobulin physically separated from light chain retained 80% of antigen-binding activity relative to the tetrameric antibody. Sitia et al. (1990) *Cell*, 60, 781-790 demonstrated that removal of the CH1 domain from a rearranged mouse gene results in the production of a heavy chain-only antibody, devoid of light chain, in mammalian cell culture. The antibodies produced retained VH binding specificity and effector functions.

Heavy chain antibodies with high specificity and affinity can be generated against a variety of antigens through immunization (van der Linden, R. H., et al. *Biochim. Biophys. Acta.* 1431, 37-46 (1999)), and the VHH portion can be readily cloned and expressed in yeast (Frenken, L. G. J., et al. *J. Biotechnol.* 78, 11-21 (2000)). Their levels of expression, solubility and stability are significantly higher than those of classical F(ab) or Fv fragments. Ghahroudi, M. A. et al. *FEBS Lett.* 414, 521-526 (1997).

Mice in which the λ (lambda) light (L) chain locus and/or the λ and κ (kappa) L chain loci have been functionally silenced and antibodies produced by such mice are described in U.S. Pat. Nos. 7,541,513 and 8,367,888. Recombinant production of heavy chain-only antibodies in mice and rats has been reported, for example, in WO2006008548; U.S. Application Publication No. 20100122358; Nguyen et al., 2003, *Immunology;* 109(1), 93-101; Bruggemann et al., *Crit. Rev. Immunol.;* 2006, 26(5):377-90; and Zou et al., 2007, *J Exp Med;* 204(13): 3271-3283. The production of knockout rats via embryo microinjections of zinc-finger nucleases is described in Geurts et al., 2009, *Science,* 325(5939):433. Soluble heavy chain-only antibodies and transgenic rodents comprising a heterologous heavy chain locus producing such antibodies are described in U.S. Pat. Nos. 8,883,150 and 9,365,655. CAR-T structures comprising single-domain antibodies as binding (targeting) domains are described, for example, in Iri-Sofia et al., 2011, *Experimental Cell Research* 317:2630-2641, and Jamnani et al., 2014, *Biochim Biophys Acta,* 1840:378-386.

Aspects of the disclosure include heavy chain-only antibodies that bind to IL2RB, comprising a heavy chain variable region comprising: (a) a CDR1 sequence having two or fewer (e.g., 0, 1, or 2) substitutions in any one of SEQ ID NOs: 1-3; and/or (b) a CDR2 sequence having two or fewer (e.g., 0, 1, or 2) substitutions in any one of SEQ ID NOs: 4-6; and/or (c) a CDR3 sequence having two or fewer (e.g., 0, 1, or 2) substitutions in any one of SEQ ID NOs: 7-10.

In some embodiments, a heavy chain-only antibody comprises: (a) a CDR1 sequence comprising any one of SEQ ID NOs: 1-3; and/or (b) a CDR2 sequence comprising any one of SEQ ID NOs: 4-6; and/or (c) a CDR3 sequence comprising any one of SEQ ID NOs: 7-10.

In some embodiments, a heavy chain-only antibody comprises: (a) a CDR1 sequence comprising any one of SEQ ID NOs: 1-3; and (b) a CDR2 sequence comprising any one of SEQ ID NOs: 4-6; and (c) a CDR3 sequence comprising any one of SEQ ID NOs: 7-10.

In some embodiments, a heavy chain-only antibody comprises:

(a) a CDR1 sequence of SEQ ID NO: 1, a CDR2 sequence of SEQ ID NO: 4, and a CDR3 sequence of SEQ ID NO: 7; or (b) a CDR1 sequence of SEQ ID NO: 1, a CDR2 sequence of SEQ ID NO: 4, and a CDR3 sequence of SEQ ID NO: 8; or (c) a CDR1 sequence of SEQ ID NO: 2, a CDR2 sequence of SEQ ID NO: 5, and a CDR3 sequence of SEQ ID NO: 9; or (d) a CDR1 sequence of SEQ ID NO: 3, a CDR2 sequence of SEQ ID NO: 6, and a CDR3 sequence of SEQ ID NO: 10.

In some embodiments, the CDR1, CDR2, and CDR3 sequences are present in a human VH framework.

In some embodiments, a heavy chain-only antibody comprises a heavy chain variable region comprising a sequence having six or fewer (e.g., five or fewer, four or fewer, three or fewer, two or fewer; six, five, four, three, two, one, zero) substitutions in any one of SEQ ID NOs: 11-14. In some embodiments, a heavy chain-only antibody comprises a heavy chain variable region having at least 95% (e.g., at least 96%, at least 97%, at least 98%, at least 99%) sequence identity to any one of SEQ ID NOs: 11-14. In some embodiments, a heavy chain-only antibody comprises a heavy chain variable region sequence selected from the group consisting of SEQ ID NOs: 11-14.

In some embodiments, a heavy-chain only antibody comprises a Fc region. In some embodiments, the heavy-chain only antibody comprises a variant Fc region. In some embodiments, the variant Fc region possesses at least about 80% homology (e.g., at least about 85%, at least about 90%, at least about 95%, at least about 98%, at least about 99%) with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, a heavy chain-only antibody further comprises a heavy chain constant region sequence in the absence of a CH1 sequence. In some embodiments, the heavy chain-only antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, a heavy chain-only antibody has a Tm of from about 55° C. to about 65° C. In some embodiments, a heavy chain-only antibody has a Tagg of from about 55° C. to about 65° C. In some embodiments, a heavy chain-only antibody has a Tm of from about 55° C. to about 65° C. and a Tagg of from about 55° C. to about 65° C.

In some embodiments, a heavy chain-only antibody is multi-specific. In some embodiments, a heavy chain-only antibody is bispecific. In some embodiments, a heavy chain-only antibody binds to IL2RB and IL2RG. In some embodiments, a heavy chain-only antibody functions as an IL2 receptor beta/gamma agonist.

In some embodiments, a heavy chain-only antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, a heavy chain-only antibody has an affinity for IL2RB with a Kd of from about $10^{-8}$ M to around about $2.5 \times 10^{-7}$ M.

In some embodiments, a heavy chain-only antibody has an affinity for IL2RG with a Kd of from about $10^{-9}$ M to around about $2.5 \times 10^{-8}$ M.

In some embodiments, a heavy chain-only antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include heavy chain-only antibodies that bind to IL2RB, comprising a heavy chain variable region comprising:

(a) a CDR1 sequence comprising the formula:

(SEQ ID NO: 26)

G G S I S S S X1 W where X1 is D or N;

(b) a CDR2 sequence comprising the formula:

(SEQ ID NO: 27)

I X2 H S G S T where X2 is D or S; and (c) a CDR3 sequence comprising the formula:

(SEQ ID NO: 28)

X3 R G X4 W E L X5 D A F D I where X3 is G or A; X4 is S or Q; and X5 is S or T.

In some embodiments, the CDR1, CDR2, and CDR3 sequences are present in a VH human framework.

In some embodiments, a heavy-chain only antibody comprises a Fc region. In some embodiments, the heavy-chain only antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, a heavy chain-only antibody further comprises a heavy chain constant region sequence in the absence of a CH1 sequence. In some embodiments, the heavy chain-only antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, a heavy chain-only antibody has a Tm of from about 55° C. to about 65° C. In some embodiments, a heavy chain-only antibody has a Tagg of from about 55° C. to about 65° C. In some embodiments, a heavy chain-only antibody has a Tm of from about 55° C. to about 65° C. and a Tagg of from about 55° C. to about 65° C.

In some embodiments, a heavy chain-only antibody is multi-specific. In some embodiments, a heavy chain-only antibody is bispecific. In some embodiments, a heavy chain-only antibody binds to IL2RB and IL2RG. In some embodiments, a heavy chain-only antibody functions as an IL2 receptor beta/gamma agonist.

In some embodiments, a heavy chain-only antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, a heavy chain-only antibody has an affinity for IL2RB with a Kd of from about $10^{-8}$ M to around about $2.5 \times 10^{-7}$ M.

In some embodiments, a heavy chain-only antibody has an affinity for IL2RG with a Kd of from about $10^{-9}$ M to around about $2.5 \times 10^{-8}$ M.

In some embodiments, a heavy chain-only antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include heavy chain-only antibodies that bind to IL2RB, comprising a heavy chain variable region comprising:

(a) a CDR1 sequence comprising the formula:

(SEQ ID NO: 29)

G F T F S X1 Y G where X1 is S or T;

(b) a CDR2 sequence comprising the formula:

(SEQ ID NO: 30)

I S Y D G S N X2 where X2 is K or R; and (c) a CDR3 sequence comprising the formula:

(SEQ ID NO: 31)

A R D L D Y D X3 L T G D P V G G F D I where X3 is V or I.

In some embodiments, the CDR1, CDR2, and CDR3 sequences are present in a VH human framework.

In some embodiments, a heavy-chain only antibody comprises a Fc region. In some embodiments, the heavy-chain only antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other).

In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, a heavy chain-only antibody further comprises a heavy chain constant region sequence in the absence of a CH1 sequence. In some embodiments, the heavy chain-only antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, a heavy chain-only antibody has a Tm of from about 55° C. to about 65° C. In some embodiments, a heavy chain-only antibody has a Tagg of from about 55° C. to about 65° C. In some embodiments, a heavy chain-only antibody has a Tm of from about 55° C. to about 65° C. and a Tagg of from about 55° C. to about 65° C.

In some embodiments, a heavy chain-only antibody is multi-specific. In some embodiments, a heavy chain-only antibody is bispecific. In some embodiments, a heavy chain-only antibody binds to IL2RB and IL2RG. In some embodiments, a heavy chain-only antibody functions as an IL2 receptor beta/gamma agonist.

In some embodiments, a heavy chain-only antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, a heavy chain-only antibody has an affinity for IL2RB with a Kd of from about $10^{-8}$ M to around about $2.5 \times 10^{-7}$ M.

In some embodiments, a heavy chain-only antibody has an affinity for IL2RG with a Kd of from about $10^{-9}$ M to around about $2.5 \times 10^{-8}$ M.

In some embodiments, a heavy chain-only antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include heavy chain-only antibodies that bind to IL2RG, comprising a heavy chain variable region comprising: (a) a CDR1 sequence having two or fewer (e.g., 0, 1, or 2) substitutions in any one of SEQ ID NOs: 15-16; and/or (b) a CDR2 sequence having two or fewer (e.g., 0, 1, or 2) substitutions in any one of SEQ ID NOs: 17-19; and/or (c) a CDR3 sequence having two or fewer (e.g., 0, 1, or 2) substitutions in any one of SEQ ID NOs: 20-21.

In some embodiments, a heavy chain-only antibody comprises: (a) a CDR1 sequence comprising any one of SEQ ID NOs: 15-16; and/or (b) a CDR2 sequence comprising any one of SEQ ID NOs: 17-19; and/or (c) a CDR3 sequence comprising any one of SEQ ID NOs: 20-21.

In some embodiments, a heavy chain-only antibody comprises: (a) a CDR1 sequence comprising any one of SEQ ID NOs: 15-16; and (b) a CDR2 sequence comprising any one of SEQ ID NOs: 17-19; and (c) a CDR3 sequence comprising any one of SEQ ID NOs: 20-21.

In some embodiments, a heavy chain-only antibody comprises:

(a) a CDR1 sequence of SEQ ID NO: 15, a CDR2 sequence of SEQ ID NO: 17, and a CDR3 sequence of SEQ ID NO: 20; or (b) a CDR1 sequence of SEQ ID NO: 15, a CDR2 sequence of SEQ ID NO: 18, and a CDR3 sequence of SEQ ID NO: 20; or (c) a CDR1 sequence of SEQ ID NO: 16, a CDR2 sequence of SEQ ID NO: 18, and a CDR3 sequence of SEQ ID NO: 20; or (d) a CDR1 sequence of SEQ ID NO: 15, a CDR2 sequence of SEQ ID NO: 19, and a CDR3 sequence of SEQ ID NO: 21.

In some embodiments, the CDR1, CDR2, and CDR3 sequences are present in a VH human framework.

In some embodiments, a heavy chain-only antibody comprises a heavy chain variable region comprising a sequence having six or fewer (e.g., five or fewer, four or fewer, three or fewer, two or fewer; six, five, four, three, two, one, zero) substitutions in any one of SEQ ID NOs: 22-25. In some embodiments, a heavy chain-only antibody comprises a heavy chain variable region having at least 95% (e.g., at least 96%, at least 97%, at least 98%, at least 99%) sequence identity to any one of SEQ ID NOs: 22-25. In some embodiments, a heavy chain-only antibody comprises a heavy chain variable region sequence selected from the group consisting of SEQ ID NOs: 22-25.

In some embodiments, a heavy-chain only antibody comprises a Fc region. In some embodiments, the heavy-chain only antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, a heavy chain-only antibody further comprises a heavy chain constant region sequence in the absence of a CH1 sequence. In some embodiments, the heavy chain-only antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, a heavy chain-only antibody has a Tm of from about 55° C. to about 65° C. In some embodiments, a heavy chain-only antibody has a Tagg of from about 55° C. to about 65° C. In some embodiments, a heavy chain-only antibody has a Tm of from about 55° C. to about 65° C. and a Tagg of from about 55° C. to about 65° C.

In some embodiments, a heavy chain-only antibody is multi-specific. In some embodiments, a heavy chain-only antibody is bispecific. In some embodiments, a heavy chain-only antibody binds to IL2RB and IL2RG. In some embodiments, a heavy chain-only antibody functions as an IL2 receptor beta/gamma agonist.

In some embodiments, a heavy chain-only antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, a heavy chain-only antibody has an affinity for IL2RB with a Kd of from about $10^{-8}$ M to around about $2.5×10^{-7}$ M.

In some embodiments, a heavy chain-only antibody has an affinity for IL2RG with a Kd of from about $10^{-9}$ M to around about $2.5×10^{-8}$ M.

In some embodiments, a heavy chain-only antibody has an affinity for IL2RB with a Kd of from about $10^{-8}$ M to around about $2.5×10^{-7}$ M and an affinity for IL2RG with a Kd of from about $10^{-9}$ M to around about $2.5×10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include heavy chain-only antibodies that bind to IL2RG, comprising a heavy chain variable region comprising:

(a) a CDR1 sequence comprising the formula $$\text{(SEQ ID NO: 32)}$$
$$\text{G F X1 X2 X3 X4 Y Y}$$

where X1 is T or I; X2 is F or V; X3 is S, N, or G; and X4 is D or N;

(b) a CDR2 sequence comprising the formula:

$$\text{(SEQ ID NO: 33)}$$
$$\text{I S X5 S G X6 X7 I}$$

where X5 is S or N; X6 is D, S, G, or N; and X7 is T or I; and (c) a CDR3 sequence comprising the sequence ARG-DAVSITGDY (SEQ ID NO: 20).

In some embodiments, the CDR1, CDR2, and CDR3 sequences are present in a VH human framework.

In some embodiments, a heavy chain-only antibody is multi-specific. In some embodiments, a heavy chain-only antibody is bispecific. In some embodiments, a heavy chain-only antibody binds to IL2RB and IL2RG.

In some embodiments, a heavy chain-only antibody comprises a Fc region. In some embodiments, a heavy chain-only antibody further comprises a heavy chain constant region comprising a hinge region, a CH2 domain, and a CH3 domain. In some embodiments, the heavy chain constant region does not contain a CH1 sequence. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, a heavy chain-only antibody has a Tm of from about 55° C. to about 65° C. In some embodiments, a heavy chain-only antibody has a Tagg of from about 55° C. to about 65° C. In some embodiments, a heavy chain-only antibody has a Tm of from about 55° C. to about 65° C. and a Tagg of from about 55° C. to about 65° C.

In some embodiments, a heavy chain-only antibody functions as an IL2 receptor beta/gamma agonist.

In some embodiments, a heavy chain-only antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, a heavy chain-only antibody has an affinity for IL2RB with a Kd of from about $10^{-8}$ M to around about $2.5×10^{-7}$ M.

In some embodiments, a heavy chain-only antibody has an affinity for IL2RG with a Kd of from about $10^{-9}$ M to around about $2.5×10^{-8}$ M.

In some embodiments, a heavy chain-only antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include a bispecific agonistic anti-IL2R heavy chain-only antibody, comprising:

a first heavy chain variable region that binds to IL2RB, comprising: a CDR1 sequence of SEQ ID NO: 1; a CDR2 sequence of SEQ ID NO: 4; and a CDR3 sequence of SEQ ID NO: 7; and a second heavy chain variable region that binds to IL2RG, comprising: a CDR1 sequence of SEQ ID NO: 15; a CDR2 sequence of SEQ ID NO: 17; and a CDR3 sequence of SEQ ID NO: 20.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO: 11, and the second heavy chain variable region has at least 95% (e.g., at least 96%, at least 97%, at least 98%, at least 99%) sequence identity to SEQ ID NO: 22. In some embodiments, the first heavy chain variable region comprises SEQ ID NO: 11, and the second heavy chain variable region comprises SEQ ID NO: 22.

In some embodiments, a bispecific agonistic anti-IL2R heavy chain-only antibody comprises a Fc region. In some embodiments, a bispecific agonistic anti-IL2R heavy chain-only antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, a bispecific agonistic anti-IL2R heavy chain-only antibody further comprises a heavy chain constant region sequence in the absence of a CH1 sequence. In some embodiments, the bispecific agonistic anti-IL2R heavy chain-only antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, a bispecific agonistic anti-IL2R heavy chain-only antibody comprises a first polypeptide comprising SEQ ID NO: 53 and a second polypeptide comprising SEQ ID NO: 61.

In some embodiments, a bispecific agonistic anti-IL2R heavy chain-only antibody has a Tm of from about 55° C. to about 65° C. In some embodiments, a bispecific agonistic anti-IL2R heavy chain-only antibody has a Tagg of from about 55° C. to about 65° C. In some embodiments, a bispecific agonistic anti-IL2R heavy chain-only antibody has a Tm of from about 55° C. to about 65° C. and a Tagg of from about 55° C. to about 65° C.

In some embodiments, a bispecific agonistic anti-IL2R heavy chain-only antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, a bispecific agonistic anti-IL2R heavy chain-only antibody has an affinity for IL2RB with a Kd of from about $10^{-8}$ M to around about $2.5 \times 10^{-7}$ M.

In some embodiments, a bispecific agonistic anti-IL2R heavy chain-only antibody has an affinity for IL2RG with a Kd of from about $10^{-9}$ M to around about $2.5 \times 10^{-8}$ M.

In some embodiments, a bispecific agonistic anti-IL2R heavy chain-only antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include a bispecific agonistic anti-IL2R heavy chain-only antibody, comprising:

a first heavy chain variable region that binds to IL2RB, comprising: a CDR1 sequence of SEQ ID NO: 1; a CDR2 sequence of SEQ ID NO: 4; and a CDR3 sequence of SEQ ID NO: 8; and a second heavy chain variable region that binds to IL2RG, comprising: a CDR1 sequence of SEQ ID NO: 15; a CDR2 sequence of SEQ ID NO: 18; and a CDR3 sequence of SEQ ID NO: 20.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO: 12, and the second heavy chain variable region has at least 95% (e.g., at least 96%, at least 97%, at least 98%, at least 99%) sequence identity to SEQ ID NO: 23. In some embodiments, the first heavy chain variable region comprises SEQ ID NO: 12, and the second heavy chain variable region comprises SEQ ID NO: 23.

In some embodiments, a bispecific agonistic anti-IL2R heavy chain-only antibody comprises a Fc region. In some embodiments, a bispecific agonistic anti-IL2R heavy chain-only antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, a bispecific agonistic anti-IL2R heavy chain-only antibody further comprises a heavy chain constant region sequence in the absence of a CH1 sequence. In some embodiments, the bispecific agonistic anti-IL2R heavy chain-only antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, a bispecific agonistic anti-IL2R heavy chain-only antibody comprises a first polypeptide comprising SEQ ID NO: 62 and a second polypeptide comprising SEQ ID NO: 63.

In some embodiments, a bispecific agonistic anti-IL2R heavy chain-only antibody has a Tm of from about 55° C. to about 65° C. In some embodiments, a bispecific agonistic anti-IL2R heavy chain-only antibody has a Tagg of from about 55° C. to about 65° C. In some embodiments, a bispecific agonistic anti-IL2R heavy chain-only antibody has a Tm of from about 55° C. to about 65° C. and a Tagg of from about 55° C. to about 65° C.

In some embodiments, a bispecific agonistic anti-IL2R heavy chain-only antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, a bispecific agonistic anti-IL2R heavy chain-only antibody has an affinity for IL2RB with a Kd of from about $10^{-8}$ M to around about $2.5×10^{-7}$ M.

In some embodiments, a bispecific agonistic anti-IL2R heavy chain-only antibody has an affinity for IL2RG with a Kd of from about $10^{-9}$ M to around about $2.5×10^{-8}$ M.

In some embodiments, a bispecific agonistic anti-IL2R heavy chain-only antibody has an affinity for IL2RB with a Kd of from about $10^{-8}$ M to around about $2.5×10^{-7}$ M and an affinity for IL2RG with a Kd of from about $10^{-9}$ M to around about $2.5×10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include a bispecific agonistic anti-IL2R heavy chain-only antibody, comprising:

a first heavy chain variable region that binds to IL2RB, comprising: a CDR1 sequence of SEQ ID NO: 2; a CDR2 sequence of SEQ ID NO: 5; and a CDR3 sequence of SEQ ID NO: 9; and a second heavy chain variable region that binds to IL2RG, comprising: a CDR1 sequence of SEQ ID NO: 15; a CDR2 sequence of SEQ ID NO: 18; and a CDR3 sequence of SEQ ID NO: 20.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO:

13, and the second heavy chain variable region has at least 95% (e.g., at least 96%, at least 97%, at least 98%, at least 99%) sequence identity to SEQ ID NO: 23. In some embodiments, the first heavy chain variable region comprises SEQ ID NO: 13, and the second heavy chain variable region comprises SEQ ID NO: 23.

In some embodiments, a bispecific agonistic anti-IL2R heavy chain-only antibody comprises a Fc region. In some embodiments, a bispecific agonistic anti-IL2R heavy chain-only antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, a bispecific agonistic anti-IL2R heavy chain-only antibody further comprises a heavy chain constant region sequence in the absence of a CH1 sequence. In some embodiments, the bispecific agonistic anti-IL2R heavy chain-only antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, a bispecific agonistic anti-IL2R heavy chain-only antibody comprises a first polypeptide comprising SEQ ID NO: 64 and a second polypeptide comprising SEQ ID NO: 65.

In some embodiments, a bispecific agonistic anti-IL2R heavy chain-only antibody has a Tm of from about 55° C. to about 65° C. In some embodiments, a bispecific agonistic anti-IL2R heavy chain-only antibody has a Tagg of from about 55° C. to about 65° C. In some embodiments, a bispecific agonistic anti-IL2R heavy chain-only antibody has a Tm of from about 55° C. to about 65° C. and a Tagg of from about 55° C. to about 65° C.

In some embodiments, a bispecific agonistic anti-IL2R heavy chain-only antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, a bispecific agonistic anti-IL2R heavy chain-only antibody has an affinity for IL2RB with a Kd of from about $10^{-8}$ M to around about $2.5 \times 10^{-7}$ M.

In some embodiments, a bispecific agonistic anti-IL2R heavy chain-only antibody has an affinity for IL2RG with a Kd of from about $10^{-9}$ M to around about $2.5 \times 10^{-8}$ M.

In some embodiments, a bispecific agonistic anti-IL2R heavy chain-only antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include a bispecific agonistic anti-IL2R heavy chain-only antibody, comprising:

a first heavy chain variable region that binds to IL2RB, comprising: a CDR1 sequence of SEQ ID NO: 3; a CDR2 sequence of SEQ ID NO: 6; and a CDR3 sequence of SEQ ID NO: 10; and a second heavy chain variable region that binds to IL2RG, comprising: a CDR1 sequence of SEQ ID NO: 15; a CDR2 sequence of SEQ ID NO: 17; and a CDR3 sequence of SEQ ID NO: 20.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO: 14, and the second heavy chain variable region has at least 95% (e.g., at least 96%, at least 97%, at least 98%, at least 99%) sequence identity to SEQ ID NO: 22. In some embodiments, the first heavy chain variable region comprises SEQ ID NO: 14, and the second heavy chain variable region comprises SEQ ID NO: 22.

In some embodiments, a bispecific agonistic anti-IL2R heavy chain-only antibody comprises a Fc region. In some embodiments, a bispecific agonistic anti-IL2R heavy chain-only antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other;

12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, a bispecific agonistic anti-IL2R heavy chain-only antibody further comprises a heavy chain constant region sequence in the absence of a CH1 sequence. In some embodiments, the bispecific agonistic anti-IL2R heavy chain-only antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, a bispecific agonistic anti-IL2R heavy chain-only antibody comprises a first polypeptide comprising SEQ ID NO: 66 and a second polypeptide comprising SEQ ID NO: 67.

In some embodiments, a bispecific agonistic anti-IL2R heavy chain-only antibody has a Tm of from about 55° C. to about 65° C. In some embodiments, a bispecific agonistic anti-IL2R heavy chain-only antibody has a Tagg of from about 55° C. to about 65° C. In some embodiments, a bispecific agonistic anti-IL2R heavy chain-only antibody has a Tm of from about 55° C. to about 65° C. and a Tagg of from about 55° C. to about 65° C.

In some embodiments, a bispecific agonistic anti-IL2R heavy chain-only antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, a bispecific agonistic anti-IL2R heavy chain-only antibody has an affinity for IL2RB with a Kd of from about $10^{-8}$ M to around about $2.5\times10^{-7}$ M.

In some embodiments, a bispecific agonistic anti-IL2R heavy chain-only antibody has an affinity for IL2RG with a Kd of from about $10^{-9}$ M to around about $2.5\times10^{-8}$ M.

In some embodiments, a bispecific agonistic anti-IL2R heavy chain-only antibody has an affinity for IL2RB with a Kd of from about $10^{-8}$ M to around about $2.5\times10^{-7}$ M and an affinity for IL2RG with a Kd of from about $10^{-9}$ M to around about $2.5\times10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include a bispecific agonistic anti-IL2R heavy chain-only antibody, comprising:

a first heavy chain variable region that binds to IL2RB, comprising: a CDR1 sequence of SEQ ID NO: 1; a CDR2 sequence of SEQ ID NO: 4; and a CDR3 sequence of SEQ ID NO: 8; and a second heavy chain variable region that binds to IL2RG, comprising: a CDR1 sequence of SEQ ID NO: 16; a CDR2 sequence of SEQ ID NO: 18; and a CDR3 sequence of SEQ ID NO: 20.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO: 12, and the second heavy chain variable region has at least 95% (e.g., at least 96%, at least 97%, at least 98%, at least 99%) sequence identity to SEQ ID NO: 24. In some embodiments, the first heavy chain variable region comprises SEQ ID NO: 12, and the second heavy chain variable region comprises SEQ ID NO: 24.

In some embodiments, a bispecific agonistic anti-IL2R heavy chain-only antibody comprises a Fc region. In some embodiments, a bispecific agonistic anti-IL2R heavy chain-only antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, a bispecific agonistic anti-IL2R heavy chain-only antibody further comprises a heavy chain constant region sequence in the absence of a CH1 sequence. In some embodiments, the bispecific agonistic anti-IL2R heavy chain-only antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, a bispecific agonistic anti-IL2R heavy chain-only antibody comprises a first polypeptide comprising SEQ ID NO: 34 and a second polypeptide comprising SEQ ID NO: 35.

In some embodiments, a bispecific agonistic anti-IL2R heavy chain-only antibody has a Tm of from about 55° C. to about 65° C. In some embodiments, a bispecific agonistic anti-IL2R heavy chain-only antibody has a Tagg of from about 55° C. to about 65° C. In some embodiments, a bispecific agonistic anti-IL2R heavy chain-only antibody has a Tm of from about 55° C. to about 65° C. and a Tagg of from about 55° C. to about 65° C.

In some embodiments, a bispecific agonistic anti-IL2R heavy chain-only antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, a bispecific agonistic anti-IL2R heavy chain-only antibody has an affinity for IL2RB with a Kd of from about $10^{-8}$ M to around about $2.5 \times 10^{-7}$ M.

In some embodiments, a bispecific agonistic anti-IL2R heavy chain-only antibody has an affinity for IL2RG with a Kd of from about $10^{-9}$ M to around about $2.5 \times 10^{-8}$ M.

In some embodiments, a bispecific agonistic anti-IL2R heavy chain-only antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include a bispecific agonistic anti-IL2R heavy chain-only antibody, comprising:

a first heavy chain variable region that binds to IL2RB, comprising: a CDR1 sequence of SEQ ID NO: 1; a CDR2 sequence of SEQ ID NO: 4; and a CDR3 sequence of SEQ ID NO: 8; and a second heavy chain variable region that binds to IL2RG, comprising: a CDR1 sequence of SEQ ID NO: 15; a CDR2 sequence of SEQ ID NO: 19; and a CDR3 sequence of SEQ ID NO: 21.

In some embodiments, the CDR1, CDR2, and CDR3 sequences in the first heavy chain variable region are present in a VH human framework. In some embodiments, the CDR1, CDR2, and CDR3 sequences in the second heavy chain variable region are present in a VH human framework. In some embodiments, the CDR1, CDR2, and CDR3 sequences in the first and second heavy chain variable regions are present in VH human frameworks.

In some embodiments, the first heavy chain variable region has at least 95% (e.g., at least 96%, at least 97%, at least 98%, at least 99%) sequence identity to SEQ ID NO: 12, and the second heavy chain variable region has at least 95% (e.g., at least 96%, at least 97%, at least 98%, at least 99%) sequence identity to SEQ ID NO: 25. In some embodiments, the first heavy chain variable region comprises SEQ ID NO: 12, and the second heavy chain variable region comprises SEQ ID NO: 25.

In some embodiments, a bispecific agonistic anti-IL2R heavy chain-only antibody comprises a Fc region. In some embodiments, a bispecific agonistic anti-IL2R heavy chain-only antibody comprises a variant Fc region. In some embodiments, the variant Fc region possesses at least about 80% (e.g., at least about 85%, at least about 90%, at least about 95%, at least about 98%, at least about 99%) homology with a native-sequence Fc region.

In some embodiments, the variant Fc region comprises heterodimerizing alterations. In some embodiments, the heterodimerizing alterations comprise knob and holes substitutions (e.g., in a variant IgG1 Fc region, 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; or 9) T366W in one polypeptide of the Fc and T366S, L368A, and Y407V in the other). In some embodiments, the heterodimerizing alterations comprise substitutions that create new disulfide bridges (e.g., in a variant IgG1 Fc region, 1) Y349C in one Fc polypeptide chain and S354C in the other; 2) Y349C in one Fc polypeptide chain and E356C in the other; 3) Y349C in one Fc polypeptide chain and E357C in the other; 4) L351C in one Fc polypeptide chain and S354C in the other; 5) T394C in one Fc polypeptide chain and E397C in the other; or 6) D399C in one Fc polypeptide chain and K392C in the other). In some embodiments, the heterodimerizing alterations comprise charge pair substitutions (e.g., 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; or 17) K409D and K439D on one chain plus D399K and E356K on the other).

In some embodiments, the Fc region is a silenced Fc region. In some embodiments, the silenced Fc region comprises substitution of one or more (e.g., two or more) of Fc region residues 238, 265, 269, 270, 297, 327 and 329 according to EU numbering. In some embodiments, the silenced Fc region comprises a substitution that alters glycosylation. In some embodiments, the silenced Fc region comprises an effector-less mutation (e.g., an N297A, an N297G, a DANA mutation (D265A+N297A), or a DANG mutation (D265A+N297G) in the CH2 region). In some embodiments, the silenced Fc region comprises K322A and L234A/L235A mutations.

In some embodiments, a bispecific agonistic anti-IL2R heavy chain-only antibody further comprises a heavy chain constant region sequence in the absence of a CH1 sequence. In some embodiments, the bispecific agonistic anti-IL2R heavy chain-only antibody comprises a heavy chain constant region comprising a hinge region, a CH2 domain, and a CH3 domain. In some embodiments, the hinge region comprises a wild type human IgG4 hinge region sequence (SEQ ID NO: 54). In some embodiments, the hinge region comprises a variant human IgG4 hinge region sequence comprising an S228P mutation (SEQ ID NO: 55). In some embodiments, the CH2 domain comprises a wild type human IgG4 CH2 domain sequence (SEQ ID NO: 56). In some embodiments, the CH2 domain comprises a variant human IgG4 CH2 domain comprising an F234A mutation, an L235A mutation, or both an F234A mutation and an L235A mutation. In some embodiments, the CH3 domain comprises a wild type human IgG4 CH3 domain sequence (SEQ ID NO: 58). In some embodiments, the CH3 domain comprises a variant human IgG4 CH3 domain sequence comprising a T366W mutation. In some embodiments, the CH3 domain comprises a variant human IgG4 CH3 domain sequence comprising a T366S, an L368A mutation, and a Y407V mutation.

In some embodiments, a bispecific agonistic anti-IL2R heavy chain-only antibody comprises a first polypeptide comprising SEQ ID NO: 36 and a second polypeptide comprising SEQ ID NO: 37.

In some embodiments, a bispecific agonistic anti-IL2R heavy chain-only antibody has a Tm of from about 55° C. to about 65° C. In some embodiments, a bispecific agonistic anti-IL2R heavy chain-only antibody has a Tagg of from about 55° C. to about 65° C. In some embodiments, a bispecific agonistic anti-IL2R heavy chain-only antibody has a Tm of from about 55° C. to about 65° C. and a Tagg of from about 55° C. to about 65° C.

In some embodiments, a bispecific agonistic anti-IL2R heavy chain-only antibody has an affinity for IL2R with a Kd of from about $10^{-11}$ M to around about $10^{-6}$ M (e.g., from about $10^{-10}$ M to around about $10^{-6}$ M; from about $10^{-9}$ M to around about $10^{-6}$ M; from about $10^{-8}$ M to around about $10^{-6}$ M; from about $10^{-11}$ M to around about $10^{-8}$ M; from about $10^{-10}$ M to around about $10^{-8}$ M; from about $10^{-9}$ M to around about $10^{-8}$ M; from about $10^{-11}$ M to around about $10^{-9}$ M; from about $10^{-10}$ M to around about $10^{-9}$ M).

In some embodiments, a bispecific agonistic anti-IL2R heavy chain-only antibody has an affinity for IL2RB with a Kd of from about $10^{-8}$ M to around about $2.5 \times 10^{-7}$ M.

In some embodiments, a bispecific agonistic anti-IL2R heavy chain-only antibody has an affinity for IL2RG with a Kd of from about $10^{-9}$ M to around about $2.5 \times 10^{-8}$ M.

In some embodiments, a bispecific agonistic anti-IL2R heavy chain-only antibody has an affinity for IL2RB with a Kd of from about $10^{-8}$ M to around about $2.5 \times 10^{-7}$ M and an affinity for IL2RG with a Kd of from about $10^{-9}$ M to around about $2.5 \times 10^{-8}$ M.

In some embodiments, the Kd is measured using a ForteBio Octet Qk384 instrument in kinetics mode. In some embodiments, the Kd is measured using a ForteBio Octet Qk384 instrument comprising an anti-human Fc capture (AHC, 18-5005) sensor in kinetics mode. In some embodiments, the Kd is measured according to a method described in the Examples herein.

Aspects of the disclosure include pharmaceutical compositions comprising an antibody (e.g., a heavy chain-only antibody; a bispecific agonistic anti-IL2R heavy chain-only antibody) as described herein.

Aspects of the disclosure include polynucleotides encoding an antibody (e.g., a heavy chain-only antibody; a bispecific agonistic anti-IL2R heavy chain-only antibody) as described herein.

Aspects of the disclosure include vectors comprising a polynucleotide as described herein.

Aspects of the disclosure include cells comprising the vectors as described herein.

Aspects of the disclosure include methods of producing an antibody (e.g., a heavy chain-only antibody; a bispecific agonistic anti-IL2R heavy chain-only antibody) as described herein, the methods comprising growing a cell as described herein under conditions permissive for expression of the antibody, and isolating the antibody from the cell and/or a cell culture medium in which the cell is grown.

Aspects of the disclosure include methods of making an antibody as described herein, the methods comprising immunizing a UniRat™ animal with IL2R and identifying IL2R-binding heavy chain sequences.

Aspects of the disclosure include kits for treating a disease or disorder in an individual in need, comprising an antibody (e.g., a heavy chain-only antibody; a bispecific agonistic anti-IL2R heavy chain-only antibody) as described herein, or a pharmaceutical composition as described herein, and instructions for use.

In some embodiments, a kit further comprises at least one additional reagent. In some embodiments, the at least one additional reagent comprises a chemotherapeutic drug.

Aspects of the disclosure include methods of treatment, comprising administering to an individual in need an effective dose of an antibody (e.g., a heavy chain-only antibody; a bispecific agonistic anti-IL2R heavy chain-only antibody) as described herein, or a pharmaceutical composition as described herein.

Aspects of the disclosure include use of an antibody (e.g., a heavy chain-only antibody; a bispecific agonistic anti-IL2R heavy chain-only antibody) as described herein in the preparation of a medicament for the treatment of a disease or disorder in an individual in need. In some embodiments, the disease or disorder is a cancer. In some embodiments, the cancer is an advanced or metastatic cancer. In some embodiments, the cancer is a liquid cancer, such as, e.g., multiple myeloma or acute myeloid leukemia. In some embodiments, the cancer is a solid tumor cancer. In some embodiments, the solid tumor cancer is selected from the group consisting of renal cell carcinoma, melanoma, urothelial cancer, triple negative breast cancer, non-small cell lung cancer (NSCLC), colorectal cancer, sarcoma, squamous cell carcinoma of the head and neck, and metastatic castration-resistant prostate cancer.

Aspects of the disclosure include an antibody (e.g., a heavy chain-only antibody; a bispecific agonistic anti-IL2R heavy chain-only antibody) as described herein, or a pharmaceutical composition as described herein, for use in therapy in an individual in need.

Aspects of the disclosure include an antibody (e.g., a heavy chain-only antibody; a bispecific agonistic anti-IL2R heavy chain-only antibody) as described herein, or a pharmaceutical composition as described herein, for use in the treatment of a disease or disorder in an individual in need. In some embodiments, the disease or disorder is a cancer. In some embodiments, the cancer is an advanced or metastatic cancer. In some embodiments, the cancer is a liquid cancer, such as, e.g., multiple myeloma or acute myeloid leukemia. In some embodiments, the cancer is a solid tumor cancer. In some embodiments, the solid tumor cancer is selected from the group consisting of renal cell carcinoma, melanoma, urothelial cancer, triple negative breast cancer, non-small cell lung cancer (NSCLC), colorectal cancer, sarcoma, squamous cell carcinoma of the head and neck, and metastatic castration-resistant prostate cancer.

Aspects of the disclosure include methods for the treatment of a cancer, comprising administering to a subject with said cancer an antibody (e.g., a heavy chain-only antibody; a bispecific agonistic anti-IL2R heavy chain-only antibody) as described herein, or a pharmaceutical composition as described herein. In some embodiments, the cancer is an advanced or metastatic cancer. In some embodiments, the cancer is a liquid cancer, such as, e.g., multiple myeloma or acute myeloid leukemia. In some embodiments, the cancer is a solid tumor cancer. In some embodiments, the solid tumor cancer is selected from the group consisting of renal cell carcinoma, melanoma, urothelial cancer, triple negative breast cancer, non-small cell lung cancer (NSCLC), colorectal cancer, sarcoma, squamous cell carcinoma of the head and neck, and metastatic castration-resistant prostate cancer.

Aspects of the disclosure include methods for stimulating IL2R signaling in an immune cell, the methods comprising contacting the immune cell with an antibody (e.g., a heavy chain-only antibody; a bispecific agonistic anti-IL2R heavy chain-only antibody) as described herein, or a pharmaceutical composition as described herein.

Aspects of the disclosure include methods for stimulating an IL2RB/IL2RG dimeric receptor complex on an immune cell, the method comprising contacting the immune cell with an antibody (e.g., a heavy chain-only antibody; a bispecific agonistic anti-IL2R heavy chain-only antibody) as described herein, or a pharmaceutical composition as described herein.

In some embodiments, the immune cell is selected from the group consisting of a CD4+ T-cell, a CD8+ T-cell, and a Natural Killer (NK) cell.

These and further aspects will be further explained in the rest of the disclosure, including in the Examples.

BRIEF DESCRIPTION OF THE DRAWINGS

FIG. 1 is a table summarizing the binding kinetics of the listed bispecific antibody constructs with respect to human and cynomolgus IL2RB and IL2RG.

FIG. 2A, FIG. 2B and FIG. 2C are heatmap tables depicting fold-induction of phosphorylated STAT5 (pSTAT5) in CD8$^+$ T-cells from human PBMCs treated with: anti-IL2Rβ/γ bispecific UniAbs™ (FIG. 2A); anti-IL2Rβ and anti-IL2Rγ monospecific UniAbs™ in a 1:1 mixture or as single agents (FIG. 2B); or IL-2 as a control (FIG. 2C) at 50 nM for 1 hour. pSTAT5 levels were determined by flow cytometry and reported as geometric mean fluorescent intensity (gMFI) over the gMFI of unstimulated cells.

FIG. 4A, FIG. 4B, FIG. 4C, FIG. 4D and FIG. 4E are graphs showing STAT5 phosphorylation dose curves in human and cyno PBMCs as a function of concentration for the depicted bispecific antibody constructs and control molecules (IL-2 and IL-2 variant). pSTAT5 levels were determined by flow cytometry and reported as a percentage of the indicated cell type.

FIG. 5A, FIG. 5B, FIG. 5C and FIG. 5D are graphs showing proliferation (Ki67 dose curves) in the indicated human cells as a function of concentration for the depicted bispecific antibody constructs and control molecules (IL-2 and IL-2 variant). Ki67 levels were determined by flow cytometry and were reported as a percentage of the indicated cell type.

FIG. 7A and FIG. 7B provide cellular internalization data for the indicated bispecific antibody constructs. FIG. 7A depicts internalization of the indicated anti-IL2Rβ/γ UniAbs by CD8$^+$ T-cells from human PBMCs, as a function of time. FIG. 7B provides depicts this data in tabular format. Surface levels of UniAb were detected by flow cytometry and reported relative to cells which had not been allowed to internalize. The observed half-lives ranged from 0.27 hours to 0.81 hours. As observed here, internalization was potentially partially dependent on the specific anti-IL2RG arm of the bispecific antibody, as molecules comprising the IL2RG_F16B binding sequence internalized faster, and to a greater degree, than molecules containing different anti-IL2RG binding sequences.

FIG. 8A and FIG. 8B provide mouse model PK data in graphical (FIG. 8A) and tabular (FIG. 8B) formats. BALB/c mice (n=3 per group per time point) were administered 1 mg/kg of the indicated anti-IL2Rβ/γ UniAbs by tail-vein injection. Serum was collected at 6 time points over two weeks and tested together by ELISA for human IgG4. Results are shown as a function of time (FIG. 8A) or in tabular format (FIG. 8B).

FIG. 9 is a table summarizing several properties of the indicated bispecific antibody constructs. All constructs were expressed in an ExpiCHO expression system and were 2-step purified. Stability was determined based on percent aggregation by SE-HPLC after thermal stress. Tm and Tagg were measured using the UNcle platform. For SE-HPLC experiments, 20 μg of protein was run on TSK gel G3000 5 μm column.

FIG. 10A, FIG. 10B and FIG. 10C provide summary data from a mouse model of GVHD. Irradiated NSG mice (5 per treatment group) were engrafted with 20 million human PBMCs each. Animals were then treated with either vehicle only (100 μL), 22 μg rhIL-2 daily, or one of the two indicated bispecific antibody constructs at 1 mg/kg in 100 μL twice a week until sacrifice (20% body weight loss). FIG. 10A provides an overview of the mouse model of GVHD and subsequent dosing scheme. FIG. 10B shows animal body weights as a function of time for the indicated experimental groups. FIG. 10C depicts an analysis of cells from spleens of the mice in the study, harvested after day 5 of treatment. Proliferation of CD8+ T-cells and CD4+ T-cells was compared between the 4 treatment groups by measuring CSFE staining in the different lymphocyte populations. The two tested bispecific antibody constructs (IL2RB_F09CIL2RG_F16A (BsAb-1) and IL2RB_F09GIL2RG_F16B (BsAb-2)) both showed significantly more proliferating CD8+ T-cells compared to rhIL-2 and the vehicle control. CD4+ T-cells were expanded to a lesser extent; however, a significant increase in proliferating CD4+ T-cells was seen in IL2RB_F09GIL2RG_F16B (BsAb-2)-treated mice compared to the vehicle control (FIG. 10**C). The data demonstrate that cytokine receptor agonists promote immune effector activation and proliferation in vivo and accelerate GVHD in huPBMC-engrafted NSG mice at a rate similar to cytokine controls.

FIG. 11A, FIG. 11B, FIG. 11C, FIG. 11D, FIG. 11E, FIG. 11F, FIG. 11G, FIG. 11H, FIG. 11I, FIG. 11J and FIG. 11K are graphs summarizing in vivo pharmacodynamic (PD) data from a non-GLP cynomolgus monkey study. FIGS. 11A-11E depict the percentages of the indicated cell types as a function of time post dose. FIGS. 11F-11J depict the concentration of the indicated cell types per μL of blood ($\times 10^5$) as a function of time post dose. FIG. 11K shows the ratio of CD8+ T-cells to CD4+ T-cells as a function of time post dose.

FIG. 12A is a graph showing serum concentration as a function of time (days) for the indicated bispecific antibody. FIG. 12B is a table showing molecule, dose and half life ($t_{1/2}$) information.

FIG. 15A, FIG. 15B and FIG. 15C are graphs showing cell proliferation of the indicated cell type, measured at 5 days post-treatment, and separated into treatment groups. FIG. 15A shows results for CD8+ T-cells, FIG. 15B shows results for CD4+ T-cells, and FIG. 15C shows results for NK-cells.

FIG. 16A, FIG. 16B, FIG. 16C, FIG. 16D, FIG. 16E, FIG. 16F, FIG. 16G, FIG. 16H, FIG. 16I, FIG. 16J, FIG. 16K and FIG. 16L are graphs showing cell proliferation and absolute cell concentration for the indicated cell types under the indicated dosing conditions, as a function of time.

Figures 3A, 3B:
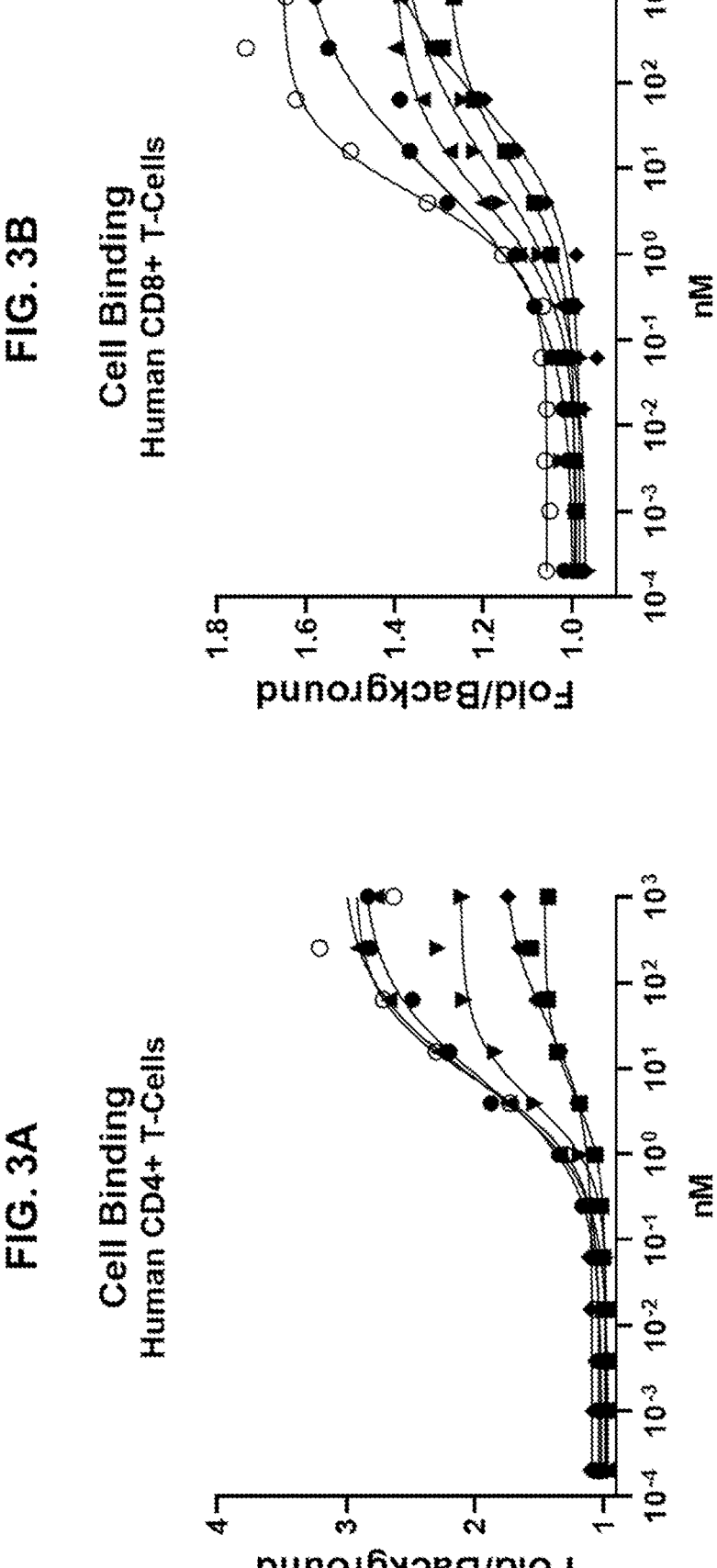
FIG. 3A, FIG. 3B, and FIG. 3C are graphs showing cell binding of the indicated cell type as a function of concentration for the depicted bispecific antibody constructs. Cell binding was determined by flow cytometry and reported as geometric mean fluorescent intensity (gMFI) over the gMFI of cells stained only with secondary detection antibody.

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Unless indicated otherwise, antibody residues herein are numbered according to the Kabat numbering system (e.g., Kabat et al., Sequences of Immunological Interest. 5th Ed. Public Health Service, National Institutes of Health, Bethesda, Md. (1991)).

In the following description, numerous specific details are set forth to provide a more thorough understanding of the present disclosure. However, it will be apparent to one of skill in the art that the present disclosure may be practiced without one or more of these specific details. In other instances, well-known features and procedures well known to those skilled in the art have not been described in order to avoid obscuring the disclosure.

All references cited throughout the disclosure, including patent applications and publications, are incorporated by reference herein in their entirety. Where there is any discrepancy in definition between the cited references and the definitions provided herein, the definitions provided herein control.

Definitions

In some embodiments, "about," when used in connection with a measurable numerical variable, refers to the indicated value of the variable and to all values of the variable that are within the experimental error of the indicated value (e.g., within the 95% confidence interval for the mean) or ±10% of the indicated value, whichever is greater. In some embodiments, numeric ranges are inclusive of the numbers defining the range.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges may independently be included in the smaller ranges also encompassed within the disclosure, subject to any specifically excluded limit in the stated range. Where the stated range includes one or both of the limits, ranges excluding either or both of those included limits are also included in the disclosure.

By "comprising", it is meant that the recited elements are required in the composition/method/kit, but other elements may be included to form the composition/method/kit etc. within the scope of the claim or embodiment.

By "consisting essentially of", it is meant a limitation of the scope of composition or method described to the specified materials or steps that do not materially affect the basic and novel characteristic(s) of the subject disclosure.

By "consisting of", it is meant the exclusion from the composition, method, or kit of any element, step, or ingredient not specified in the claim or embodiment.

Antibody residues herein are numbered according to the Kabat numbering system and the EU numbering system. The Kabat numbering system is generally used when referring to a residue in the variable domain (approximately residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies mean residue numbering by the Kabat numbering system. Unless stated otherwise herein, references to residue numbers in the constant domain of antibodies mean residue numbering by the EU numbering system.

Antibodies, also referred to as immunoglobulins, conventionally comprise at least one heavy chain and one light chain, where the amino terminal domain of the heavy and light chains is variable in sequence, and hence is commonly referred to as a variable region domain, or a variable heavy (VH) or variable light (VL) domain. The two domains conventionally associate to form a specific binding region, although as will be discussed here, specific binding can also be obtained with heavy chain-only variable sequences, and a variety of non-natural configurations of antibodies are known and used in the art.

A "functional" or "biologically active" antibody or antigen-binding molecule (including, e.g., heavy chain-only antibodies and multi-specific (e.g., bispecific) antibodies, as well as three-chain antibody-like molecules (TCAs, described herein)) is one capable of exerting one or more of its natural activities in structural, regulatory, biochemical, or biophysical events. For example, a functional antibody or other binding molecule, e.g., a TCA, may have the ability to specifically bind an antigen and the binding may in turn elicit or alter a cellular or molecular event such as signal transduction or enzymatic activity. A functional antibody or other binding molecule, e.g., a TCA, may also block ligand activation of a receptor or act as an agonist or antagonist. The capability of an antibody or other binding molecule, e.g., a TCA, to exert one or more of its natural activities depends on several factors, including proper folding and assembly of the polypeptide chains.

The term "antibody" herein is used in the broadest sense and specifically covers monoclonal antibodies, polyclonal antibodies, monomers, dimers, multimers, multispecific antibodies (e.g., bispecific antibodies), heavy chain-only antibodies, three chain antibodies, TCAs, single chain Fv (scFv), nanobodies, etc., and also includes antibody fragments, so long as they exhibit the desired biological activity. Miller et al (2003) *Jour. of Immunology* 170:4854-4861. Antibodies may be murine, human, humanized, chimeric, or derived from other species.

For example, the term "antibody" may reference a full-length heavy chain, a full-length light chain, an intact immunoglobulin molecule, or an immunologically active portion of any of these polypeptides, i.e., a polypeptide that comprises an antigen binding site that immunospecifically binds an antigen of a target of interest or part thereof, such targets including, but not limited to, a cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule, including engineered subclasses with altered Fc portions that provide for reduced or enhanced effector cell activity. Light chains of the subject antibodies can be kappa light chains (Vkappa) or lambda light chains (Vlambda). The immunoglobulins can be derived from any species. In one aspect, the immunoglobulin is of largely human origin.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies in accordance with the present disclosure can be made by the hybridoma method first described by Kohler et al. (1975) *Nature* 256:495, and can also be made via recombinant protein production methods (see, e.g., U.S. Pat. No. 4,816,567), for example.

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, MD. (1991)). The constant domains are not involved directly in binding an antibody to an antigen but exhibit various effector functions, such as participation of the antibody in antibody dependent cellular cytotoxicity (ADCC).

The term "hypervariable region", when used herein, refers to the amino acid residues of an antibody which are responsible for antigen-binding. The hypervariable region generally comprises amino acid residues from a "complementarity-determining region" or "CDR" (e.g., residues 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, MD. (1991)) and/or those residues from a "hypervariable loop" residues 26-32 (H1), 53-55 (H2) and 96-101 (H3) in the heavy chain variable domain; Chothia and Lesk *J. Mol. Biol.* 196:901-917 (1987)). In some embodiments, "CDR" means a complementarity-determining region of an antibody as defined in Lefranc, M P et al., IMGT, the International ImMunoGeneTics database, Nucleic Acids Res., 27:209-212 (1999). "Framework Region" or "FR" residues are those variable domain residues other than the hypervariable region/CDR residues as herein defined.

Exemplary CDR designations are shown herein; however, one of skill in the art will understand that a number of definitions of the CDRs are commonly in use, including the Kabat definition (see Zhao et al. "A germline knowledge based computational approach for determining antibody complementarity determining regions." *Mol Immunol.* 2010; 47:694-700), which is based on sequence variability and is the most commonly used. The Chothia definition is based on the location of the structural loop regions (Chothia et al. "Conformations of immunoglobulin hypervariable regions." *Nature.* 1989; 342:877-883). Alternative CDR definitions of interest include, without limitation, those disclosed by Honegger, "Yet another numbering scheme for immunoglobulin variable domains: an automatic modeling and analysis tool." *J Mol Biol.* 2001; 309:657-670; Ofran et al. "Automated identification of complementarity determining regions (CDRs) reveals peculiar characteristics of CDRs and B-cell epitopes." *J Immunol.* 2008; 181:6230-6235; Almagro "Identification of differences in the specificity-determining residues of antibodies that recognize antigens of different size: implications for the rational design of antibody repertoires." *J Mol Recognit.* 2004; 17:132-143; and Padlan et al. "Identification of specificity-determining residues in antibodies." *Faseb J.* 1995; 9:133-139., each of which is herein specifically incorporated by reference.

The terms "heavy chain-only antibody" and "heavy chain antibody" are used interchangeably herein and refer, in the broadest sense, to antibodies, or one or more portions of an antibody, e.g., one or more arms of an antibody, lacking the light chain of a conventional antibody (i.e., a "heavy chain antibody" may consist of an isolated portion of an antibody or an antibody format other than a conventional antibody that lacks a light chain). The terms specifically include, without limitation, homodimeric antibodies comprising the VH antigen-binding domain and the CH2 and CH3 constant domains, in the absence of the CH1 domain; functional (antigen-binding) variants of such antibodies, soluble VH variants, Ig-NAR comprising a homodimer of one variable domain (V-NAR) and five C-like constant domains (C-NAR) and functional fragments thereof; and soluble single domain antibodies (e.g., UniDabs™). In one embodiment, a heavy chain-only antibody is composed of a variable region antigen-binding domain composed of framework 1, CDR1, framework 2, CDR2, framework 3, CDR3, and framework 4. In another embodiment, a heavy chain-only antibody is composed of an antigen-binding domain, at least part of a hinge region, and CH2 and CH3 domains. In another embodiment, a heavy chain-only antibody is composed of an antigen-binding domain, at least part of a hinge region, and a CH2 domain. In a further embodiment, a heavy chain-only antibody is composed of an antigen-binding domain, at least part of a hinge region, and a CH3 domain. Heavy chain-only antibodies in which the CH2 and/or CH3 domain is truncated are also included herein. In a further embodiment, a heavy chain is composed of an antigen binding domain, and at least one CH (CH1, CH2, CH3, or CH4) domain but no hinge region. A heavy chain-only antibody can be in the form of a dimer, in which two heavy chains are disulfide bonded or otherwise, covalently or non-covalently, attached with each other. The heavy chain-only antibody may belong to the IgG subclass, but antibodies belonging to other subclasses, such as IgM, IgA, IgD and IgE subclass, are also included herein. In a particular embodiment, a heavy chain antibody may belong to the IgG1, IgG2, IgG3, or IgG4 subtype, e.g., the IgG1 or IgG4 subtype. In one embodiment, the heavy-chain antibody is of the IgG1 or IgG4 subtype, wherein one or more of the CH domains is modified to alter an effector function of the antibody. In one embodiment, a heavy-chain antibody is of the IgG4 subtype, wherein one or more of the CH domains is modified to alter an effector function of the antibody. In one embodiment, the heavy-chain antibody is of the IgG1 subtype, wherein one or more of the CH domains is modified to alter an effector function of the antibody. Modifications of CH domains that alter effector function are further described herein. Non-limiting examples of heavy-chain antibodies are described, for example, in WO2018/039180, the disclosure of which is incorporated herein by reference in its entirety.

In some embodiments, the heavy chain-only antibodies described herein are used as a binding (targeting) domain of a chimeric antigen receptor (CAR). The definition specifically includes human heavy chain-only antibodies produced by human immunoglobulin transgenic rats (e.g., UniRat™), such as, e.g., UniAbs™. The variable regions (VH) of UniAbs™ are called UniDabs™, and are versatile building blocks that can be linked to Fc regions or serum albumin for the development of novel therapeutics with multi-specificity, increased potency, and extended half-life. Since the homodimeric UniAbs™ lack a light chain and thus a VL domain, the antigen is recognized by one single domain, i.e., the variable domain of the heavy chain of a heavy-chain antibody (VH or VHH).

An "intact antibody chain" as used herein is one comprising a full-length variable region and a full length constant region (Fc). An intact "conventional" antibody comprises an intact light chain and an intact heavy chain, as well as a light chain constant domain (CL) and heavy chain constant domains, CH1, hinge, CH2 and CH3 for secreted IgG. Other isotypes, such as IgM or IgA may have different CH domains. The constant domains may be native sequence constant domains (e.g., human native sequence constant domains) or amino acid sequence variants thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors. Constant region variants include those that alter the effector profile, binding to Fc receptors, and the like.

Depending on the amino acid sequence of the Fc (constant domain) of their heavy chains, antibodies and various antigen-binding proteins can be provided as different classes. There are five major classes of heavy chain Fc regions: IgA, IgD, IgE, IgG, and IgM, and several of these may be further divided into "subclasses" (isotypes), e.g., IgG1, IgG2, IgG3, IgG4, IgA, and IgA2. The Fc constant domains that correspond to the different classes of antibodies may be referenced as α, δ, ε, γ, and μ, respectively. The subunit structures and three-dimensional configurations of different classes of immunoglobulins are well known. Ig forms include hinge-modifications or hingeless forms. Roux et al (1998) *J. Immunol.* 161:4083-4090; Lund et al (2000) *Eur. J. Biochem.* 267:7246-7256; US 2005/0048572; US 2004/0229310. The light chains of antibodies from any vertebrate species can be assigned to one of two types, called κ (kappa) and λ (lambda), based on the amino acid sequences of their constant domains. Antibodies in accordance with embodiments of the disclosure can comprise kappa light chain sequences or lambda light chain sequences.

A "functional Fc region" possesses an "effector function" of a native-sequence Fc region. Non-limiting examples of effector functions include C1q binding; CDC; Fc-receptor binding; ADCC; ADCP; down-regulation of cell-surface receptors (e.g., B-cell receptor), etc. Such effector functions generally require the Fc region to interact with a receptor, e.g., the FcγRI; FcγRIIA; FcγRIIB1; FcγRIIB2; FcγRIIIA; FcγRIIIB receptors, and the low affinity FcRn receptor; and can be assessed using various assays known in the art. A "dead" or "silenced" Fc is one that has been mutated to retain activity with respect to, for example, prolonging serum half-life, but which does not activate a high affinity Fc receptor, or which has a reduced affinity to an Fc receptor.

A "native-sequence Fc region" comprises an amino acid sequence identical to the amino acid sequence of an Fc region found in nature. Native-sequence human Fc regions include, for example, a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence that differs from that of a native-sequence Fc region by virtue of at least one amino acid modification, for example, one or more (e.g., two or more, three or more, four or more) amino acid substitution(s). Illustratively, in some embodiments, the variant Fc region has at least one amino acid substitution compared to a native-sequence Fc region or to the Fc region of a parent polypeptide, e.g., from about one to about ten amino acid substitutions, e.g., from about one to about five amino acid substitutions in a native-sequence Fc region or in the Fc region of the parent polypeptide. In some embodiments, the variant Fc region herein will possess at least about 80% homology with a native-sequence Fc region and/or with an Fc region of a parent polypeptide, e.g., at least about 85% homology therewith, e.g., at least about 90% homology therewith, e.g., at least about 95% homology therewith, e.g., at least about 99% homology therewith.

As used herein, "heterodimerizing alterations" refer to alterations in the A and B chains of an Fc region (i.e., the two chains comprising the Fc region, wherein one chain is referred to herein as the "A" chain and the other is referred to herein as the "B" chain) that facilitate the formation of heterodimeric Fc regions, that is, Fc regions in which the A chain and the B chain of the Fc region do not have identical amino acid sequences. In some embodiments, heterodimerizing alterations can be asymmetric, that is, an A chain having a certain alteration can pair with a B chain having a different alteration. These alterations facilitate heterodimerization and disfavor homodimerization. Whether hetero- or homo-dimers have formed can be assessed, for example, by size differences as determined by polyacrylamide gel electrophoresis in situations where one polypeptide chain is a dummy Fc and the other is an scFv-Fc. One non-limiting example of such paired heterodimerizing alterations are the so-called "knobs and holes" substitutions. See, e.g., U.S. Pat. No. 7,695,936 and U.S. Patent Application Publication No. 2003/0078385. As used herein, an Fc region that comprises one pair of knobs and holes substitutions, comprises one substitution in the A chain and another in the B chain. For example, the following knobs and holes substitutions in the A and B chains of an IgG1 Fc region have been found to increase heterodimer formation as compared with that found with unmodified A and B chains and may be employed in non-limiting embodiments of this disclosure: 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; and 9) T366W in one polypeptide of the Fc and T366S, L368A, and Y407V in the other. Alternatively, or in addition to such alterations, substitutions creating new disulfide bridges can facilitate heterodimer formation. See, e.g., U.S. Patent Application Publication No. 2003/0078385. Such alterations in an IgG1 Fc region include, but are not limited to, the following substitutions: Y349C in one Fc polypeptide chain and S354C in the other; Y349C in one Fc polypeptide chain and E356C in the other; Y349C in one Fc polypeptide chain and E357C in the other; L351C in one Fc polypeptide chain and S354C in the other; T394C in one Fc polypeptide chain and E397C in the other; or D399C in one Fc polypeptide chain and K392C in the other. Additionally or alternatively, substitutions changing the charge of a one or more residue(s), for example, in the CH3-CH3 interface, can enhance heterodimer formation, as described, for example, in WO 2009/089004, which is incorporated by reference herein. Such substitutions are referred to herein as "charge pair substitutions," and an Fc region comprising one pair of charge pair substitutions comprises one substitution in the A chain and a different substitution in the B chain. Non-limiting examples of charge pair substitutions include the following: 1) K409D or K409E in one chain plus D399K or D399R in the other; 2) K392D or K392E in one chain plus D399K or D399R in the other; 3) K439D or K439E in one chain plus E356K or E356R in the other; and 4) K370D or K370E in one chain plus E357K or E357R in the other. In addition, the substitutions R355D, R355E, K360D, or K360R in both chains can stabilize heterodimers when used with other heterodimerizing alterations. Specific charge pair substitutions can be used either alone or with other charge pair substitutions. Specific examples of single pairs of charge pair substitutions and combinations thereof include the following: 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; and 17) K409D and K439D on one chain plus D399K and E356K on the other. Any of these heterodimerizing alterations can be used in polypeptides comprising variant Fc regions as described herein.

In some non-limiting embodiments, variant Fc sequences may include three amino acid substitutions in the CH2 region to reduce FcγRI binding at EU index positions 234, 235, and 237 (see Duncan et al., (1988) *Nature* 332:563). Two amino acid substitutions in the complement C1q binding site at EU index positions 330 and 331 reduce complement fixation (see Tao et al., *J. Exp. Med.* 178:661 (1993) and Canfield and Morrison, *J. Exp. Med.* 173:1483 (1991)). Substitution into human IgG1 or IgG2 residues at positions 233-236 and IgG4 residues at positions 327, 330 and 331 greatly reduces ADCC and CDC (see, for example, Armour K L. et al., 1999 *Eur J Immunol.* 29(8):2613-24; and Shields R. L. et al., 2001. *J Biol Chem.* 276(9):6591-604). The human IgG4 Fc amino acid sequence (UniProtKB No. P01861) is provided herein as SEQ ID NO: 76. Silenced IgG1 is described, for example, in Boesch, A. W., et al., "Highly parallel characterization of IgG Fc binding interactions." *MAbs,* 2014. 6(4): p. 915-27, the disclosure of which is incorporated herein by reference in its entirety.

Other Fc variants are possible, including, without limitation, one in which a region capable of forming a disulfide bond is deleted, or in which certain amino acid residues are eliminated at the N-terminal end of a native Fc, or a methionine residue is added thereto. Thus, in some embodiments, one or more Fc portions of an antibody can comprise one or more mutations in the hinge region to eliminate disulfide bonding. In yet another embodiment, the hinge region of an Fc can be removed entirely. In still another embodiment, an antibody can comprise an Fc variant.

Further, an Fc variant can be constructed to remove or substantially reduce effector functions by substituting (mutating), deleting, or adding amino acid residues to effect complement binding or Fc receptor binding. For example, and not by way of limitation, a deletion may occur in a complement-binding site, such as a C1q-binding site. Techniques for preparing such sequence derivatives of the immunoglobulin Fc fragment are disclosed in International Patent Publication Nos. WO 97/34631 and WO 96/32478. In addition, the Fc domain may be modified by phosphorylation, sulfation, acylation, glycosylation, methylation, farnesylation, acetylation, amidation, and the like.

Antibodies with reduced effector function include, but are not limited to, those with substitution of one or more of Fc region residues 238, 265, 269, 270, 297, 327 and 329 according to EU numbering (see, e.g., U.S. Pat. No. 6,737, 056). In some embodiments, variant Fc regions with reduced effector function comprise substitutions at two or more of amino acid positions 265, 269, 270, 297 and 327 according to EU numbering, including the so-called "DANA" Fc mutant with substitution of residues 265 and 297 to alanine according to EU numbering (i.e., D265A and N297A according to EU numbering) (see, e.g., U.S. Pat. No. 7,332,581). In some embodiments, the variant Fc region with reduced effector function comprises the following two amino acid substitutions: D265A and N297A.

In some embodiments, effector function is reduced through a mutation in a constant region that eliminates glycosylation, e.g., an "effector-less mutation." In some embodiments, the effector-less mutation is an N297A or a DANA mutation (D265A+N297A) in the CH2 region. Shields et al., *J. Biol. Chem.* 276 (9): 6591-6604 (2001). In some embodiments, the effector-less mutation is an N297G or a DANG mutation (D265A+N297G) in the CH2 region. In some embodiments, the variant Fc region lacks glycosylation at N297, e.g., the variant Fc region is a variant Fc region lacking glycosylation at N297 as described in International Patent Publication No. WO 2014/153063, which is incorporated by reference herein. Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli*) or in host cells which result in an altered glycolsylation pattern that is ineffective or less effective at promoting effector function (e.g., Shinkawa et al., *J. Biol. Chem.* 278(5): 3466-3473 (2003)).

In some embodiments, the proline at position 329 (EU numbering) (P329) of a wild-type human Fc region is substituted with glycine or arginine or an amino acid residue large enough to destroy the proline sandwich within the Fc/Fcγ receptor interface, that is formed between the P329 of the Fc and tryptophan residues W87 and W110 of FcgRIII (Sondermann et al., *Nature* 406, 267-273 (20 Jul. 2000)). In some further embodiments, at least one further amino acid substitution in the Fc variant region is S228P, E233P, L234A, L235A, L235E, N297A, N297D, or P331S. In some embodiments, the at least one further amino acid substitution is L234A and L235A of the human IgG1 Fc region or S228P and L235E of the human IgG4 Fc region, all according to EU numbering (see, e.g., U.S. Pat. No. 8,969,526, which is incorporated by reference in its entirety).

In some embodiments, the variant Fc region has P329 of the human IgG Fc region substituted with glycine, wherein the variant Fc region comprises at least two further amino acid substitutions at L234A and L235A of the human IgG1 Fc region or S228P and L235E of the human IgG4 Fc region, and wherein the residues are numbered according to the EU numbering (see, e.g., U.S. Pat. No. 8,969,526). In some embodiments, the variant Fc region comprising the P329G, L234A and L235A (EU numbering) substitutions exhibits a reduced affinity to the human FcγRIIIA and FcγRIIA.

In some embodiments, the variant Fc region comprises a triple mutation: an amino acid substitution at position P329, a L234A, and a L235A mutation according to EU numbering (P329/LALA) (see, e.g., U.S. Pat. No. 8,969,526). In some embodiments, the variant Fc region comprises the following amino acid substitutions: P329G, L234A, and L235A according to EU numbering.

In some embodiments, an antibody comprises a variant human IgG4 CH3 domain sequence comprising a T366W mutation, which can optionally be referred to herein as an IgG4 CH3 knob sequence. In some embodiments, an antibody comprises a variant human IgG4 CH3 domain sequence comprising a T366S mutation, an L368A mutation, and a Y407V mutation, which can optionally be referred to herein as an IgG4 CH3 hole sequence. The IgG4 CH3 mutations described herein can be utilized in any suitable manner so as to place a "knob" on a first heavy chain constant region of a first monomer in an antibody dimer, and a "hole" on a second heavy chain constant region of a second monomer in an antibody dimer, thereby facilitating proper pairing (heterodimerization) of the desired pair of heavy chain polypeptide subunits in the antibody.

In some embodiments, an antibody comprises a heavy chain polypeptide subunit comprising a variant human IgG4 Fc region comprising an S228P mutation, an F234A mutation, an L235A mutation, and a T366W mutation (knob). In some embodiments, an antibody comprises a heavy chain polypeptide subunit comprising a variant human IgG4 Fc region comprising an S228P mutation, an F234A mutation, an L235A mutation, a T366S mutation, an L368A mutation, and a Y407V mutation (hole).

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, an antibody having an Fc region according to this disclosure can comprise an antibody with or without K447.

Aspects of the disclosure include antibodies comprising a heavy chain-only variable region in a monovalent or bivalent configuration. As used herein, the term "monovalent configuration", as used in reference to a heavy chain-only variable region domain, means that only one heavy chain-only variable region domain is present, having a single binding site. In contrast, the term "bivalent configuration" as used in reference to a heavy chain-only variable region domain means that two heavy chain-only variable region domains are present (each having a single binding site), and are connected by a linker sequence. Non-limiting examples of linker sequences are discussed further herein, and include, without limitation, GS linker sequences of various lengths. When a heavy chain-only variable region is in a bivalent configuration, each of the two heavy chain-only variable region domains can bind to the same antigen, or to different antigens (e.g., to different epitopes on the same protein; to two different proteins, etc.). However, unless specifically noted otherwise, a heavy chain-only variable region denoted as being in a "bivalent configuration" is understood to contain two identical heavy chain-only variable region domains, connected by a linker sequence, wherein each of the two identical heavy chain-only variable region domains binds to the same target antigen.

Aspects of the disclosure include antibodies having multi-specific configurations, which include, without limitation, bispecific, trispecific, etc. configurations. A large variety of methods and protein configurations are known and used in bispecific monoclonal antibodies (BsMAB), tri-specific antibodies, etc.

Various methods for the production of multivalent artificial antibodies have been developed by recombinantly fusing variable domains of two or more antibodies. In some embodiments, a first and a second antigen-binding domain on a polypeptide are connected by a polypeptide linker. One non-limiting example of such a polypeptide linker is a GS linker, having an amino acid sequence of four glycine residues, followed by one serine residue, and wherein the sequence is repeated n times, where n is an integer ranging from 1 to about 10 (SEQ ID NO: 68), such as 2, 3, 4, 5, 6, 7, 8, or 9. Non-limiting examples of such linkers include GGGGS (SEQ ID NO: 49) (n=1) and GGGGSGGGGS (SEQ ID NO: 50) (n=2). Other suitable linkers can also be used, and are described, for example, in Chen et al., *Adv*

*Drug Deliv Rev.* 2013 Oct. 15; 65(10): 1357-69, the disclosure of which is incorporated herein by reference in its entirety.

The term "three-chain antibody-like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy-chain only antibody comprising an Fc portion comprising CH2 and/or CH3 and/or CH4 domains, in the absence of a CH1 domain, and one or more antigen binding domains (e.g., two antigen binding domains) that binds an epitope of a second antigen or a different epitope of the first antigen, where such binding domain is derived from or has sequence identity with the variable region of an antibody heavy or light chain. Parts of such variable region may be encoded by $V_H$ and/or $V_L$ gene segments, D and $J_H$ gene segments, or $J_L$ gene segments. The variable region may be encoded by rearranged $V_H DJ_H$, $V_L DJ_H$, $V_H J_L$, or $V_L J_L$ gene segments.

A TCA binding compound makes use of a "heavy chain only antibody" or "heavy chain antibody" or "heavy chain polypeptide" which, as used herein, mean a single chain antibody comprising heavy chain constant regions CH2 and/or CH3 and/or CH4 but no CH1 domain. In one embodiment, the heavy chain antibody is composed of an antigen-binding domain, at least part of a hinge region and CH2 and CH3 domains. In another embodiment, the heavy chain antibody is composed of an antigen-binding domain, at least part of a hinge region and a CH2 domain. In a further embodiment, the heavy chain antibody is composed of an antigen-binding domain, at least part of a hinge region and a CH3 domain. Heavy chain antibodies in which the CH2 and/or CH3 domain is truncated are also included herein. In a further embodiment, the heavy chain is composed of an antigen binding domain, and at least one CH (CH1, CH2, CH3, or CH4) domain but no hinge region. The heavy chain only antibody can be in the form of a dimer, in which two heavy chains are disulfide bonded or otherwise covalently or non-covalently attached to each other, and can optionally include an asymmetric interface (e.g., a knobs-in-holes (KiH) interface) between one or more of the CH domains to facilitate proper pairing between polypeptide chains. The heavy-chain antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular the IgG1 subtype or the IgG4 subtype. Non-limiting examples of a TCA binding compound are described in, for example, WO2017/223111 and WO2018/052503, the disclosures of which are incorporated herein by reference in their entirety.

Aspects of the disclosure include antibodies that comprise a heavy chain-only variable region that is paired with a light chain variable region (VL). In some embodiments, a light chain variable region that pairs with a heavy chain-only variable region is referred to as a "fixed light chain" variable region. In certain embodiments, an antibody comprises two heavy chain-only variable regions, each of which is paired with a fixed light chain variable region. In some embodiments, a fixed light chain variable region sequence is connected to a light chain constant region sequence to form a full-length antibody light chain polypeptide. In some embodiments, an antibody comprises two full length heavy chain polypeptides and two full length light chain polypeptides. In certain embodiments, the full-length heavy chain polypeptides comprise different sequences, whereas the full length light chain polypeptides comprise the same sequence (e.g., the two full-length light chain polypeptides are identical).

Heavy-chain antibodies constitute about one fourth of the IgG antibodies produced by the camelids, e.g., camels and llamas (Hamers-Casterman C., et al. *Nature.* 363, 446-448 (1993)). These antibodies are formed by two heavy chains but are devoid of light chains. As a consequence, the variable antigen binding part is referred to as the VHH domain, and it represents the smallest naturally occurring, intact, antigen-binding site, being only around 120 amino acids in length (Desmyter, A., et al. *J. Biol. Chem.* 276, 26285-26290 (2001)). Heavy chain antibodies with a high specificity and affinity can be generated against a variety of antigens through immunization (van der Linden, R. H., et al. *Biochim. Biophys. Acta.* 1431, 37-46 (1999)), and the VHH portion can be readily cloned and expressed in yeast (Frenken, L. G. J., et al. *J. Biotechnol.* 78, 11-21 (2000)). Their levels of expression, solubility and stability are significantly higher than those of classical F(ab) or Fv fragments (Ghahroudi, M. A. et al. *FEBS Lett.* 414, 521-526 (1997)). Sharks have also been shown to have a single VH-like domain in their antibodies, termed VNAR. (Nuttall et al. *Eur. J. Biochem.* 270, 3543-3554 (2003); Nuttall et al. *Function and Bioinformatics* 55, 187-197 (2004); Dooley et al., *Molecular Immunology* 40, 25-33 (2003).)

The terms "IL2" and "IL-2" as used interchangeably herein refer to interleukin-2, which is a 15.5 to 16 kDa cytokine signaling protein molecule that regulates the activity of certain immune cells by binding to IL2 receptor complexes expressed by lymphocytes. The term "IL2" includes an IL2 protein of any human and non-human animal species, and specifically includes human IL2 as well as IL2 of non-human mammals. The human IL-2 sequence (UniProtKB No. P60568) is provided herein as SEQ ID NO: 41. The term "human IL2" as used herein includes any variants, isoforms, and species homologs of human IL2, regardless of its source or mode of preparation. Thus, "human IL2" includes human IL2 naturally expressed by cells and IL2 expressed on cells transfected with the human IL2 gene.

The terms "IL2R", "IL-2R", "IL2 receptor", and "IL-2 receptor", as used interchangeably herein refer generally to the IL2 receptor complex, which is composed of three polypeptide subunits, or chains, referred to as the alpha, A, or a chain, the beta, B, or β chain, and the gamma, G, or γ chain. The term "IL2R" includes any IL2R protein or any subunit of the IL2 receptor complex, of any human and non-human animal species, and specifically includes human IL2R as well as IL2R of non-human mammals. The term "human IL2R" as used herein includes any variants, isoforms, and species homologs of human IL2R, regardless of its source or mode of preparation. Thus, "human IL2R" includes human IL2R naturally expressed by cells and IL2R expressed on cells transfected with the human IL2R gene.

The term "IL2RA" is also referred to as CD25, and the human IL2RA sequence (UniProtKB No. P01589) is provided herein as SEQ ID NO: 38.

The term "IL2RB" IL-2RB is also referred to as CD122, and the human IL2RB sequence (UniProtKB No. P14784) is provided herein as SEQ ID NO: 39.

The term "IL2RG" IL-2RG is also referred to as CD132, and the human IL2RG sequence (UniProtKB No. P31785) is provided herein as SEQ ID NO: 40.

The terms "anti-IL2R heavy chain-only antibody," "IL2R heavy chain-only antibody," "anti-IL2R heavy chain antibody," and "IL2R heavy chain antibody" are used herein interchangeably to refer to a heavy chain-only antibody as hereinabove defined, immunospecifically binding to IL2R, including human IL2R, as hereinabove defined. The definition includes, without limitation, human heavy chain antibodies produced by transgenic animals, such as transgenic rats or transgenic mice expressing human immunoglobulin, including UniRats™ producing human anti-IL2R UniAb™ antibodies, as hereinabove defined.

The term "agonist" as used herein refers to a molecule that causes an increase in a function or activity as compared to the same function or activity in the absence of the molecule. An "agonist" of a signaling pathway is therefore a molecule whose presence causes an increase in a function or activity of the signaling pathway. The term "agonize" as used herein refers to causing an increase in a function or activity. In some embodiments, the agonist function of an antibody may be determined using an assay described herein.

The term "antagonist" as used herein refers to a molecule that causes a decrease in a function or activity as compared to the same function or activity in the absence of the molecule. An "antagonist" of a signaling pathway is therefore a molecule whose presence causes a decrease in a function or activity of the signaling pathway. The term "antagonize" as used herein refers to causing a decrease in a function or activity.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, e.g., more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, e.g., silver stain. Isolated antibody includes the antibody in situ within recombinant cells since at least one component of the antibody's natural environment will not be present. Ordinarily, however, isolated antibody will be prepared by at least one purification step.

Antibodies of the disclosure include multi-specific antibodies. Multi-specific antibodies have more than one binding specificity. The term "multi-specific" specifically includes "bispecific" and "trispecific," as well as higher-order independent specific binding affinities, such as higher-order polyepitopic specificity, as well as tetravalent antibodies and antibody fragments. The terms "multi-specific antibody," "multi-specific heavy chain-only antibody," "multi-specific heavy chain antibody," and "multi-specific UniAb™" are used herein in the broadest sense and cover all antibodies with more than one binding specificity. The multi-specific heavy chain anti-IL2R antibodies of the present disclosure specifically include antibodies immunospecifically binding to two or more non-overlapping epitopes on an IL2R protein, such as a human IL2RA, IL2RB and/or IL2RG protein. The multi-specific heavy chain anti-IL2R antibodies of the present disclosure also specifically include antibodies immunospecifically binding to an epitope on an IL2R protein, such as human IL2RB, and to an epitope on a different protein, such as, for example, an IL2RG protein, such as human IL2RG.

Antibodies of the disclosure include monospecific antibodies, having one binding specificity. Monospecific antibodies specifically include antibodies comprising a single binding specificity, as well as antibodies comprising more than one binding unit having the same binding specificity. The terms "monospecific antibody," "monospecific heavy chain-only antibody," "monospecific heavy chain antibody," and "monospecific UniAb™" are used herein in the broadest sense and cover all antibodies with one binding specificity. The monospecific heavy chain anti-IL2R antibodies of the present disclosure specifically include antibodies immuno-specifically binding to one epitope on an IL2R protein, such as a human IL2R protein, or subunit thereof (e.g., a human IL2RA, IL2RB, or IL2RG protein). The monospecific heavy chain anti-IL2R antibodies of the present disclosure also specifically include antibodies having more than one binding unit (e.g., multivalent antibodies) immunospecifically binding to an epitope on an IL2R protein, such as human IL2R. For example, a monospecific antibody in accordance with embodiments of the disclosure can include a heavy chain variable region comprising two antigen-binding domains, wherein each antigen-binding domain binds to the same epitope on an IL2R protein (i.e., an IL2RA, IL2RB, or IL2RG protein).

An "epitope" is the site on the surface of an antigen molecule to which a single antibody molecule binds. Generally, an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Polyepitopic specificity" refers to the ability to specifically bind to two or more different epitopes on the same or different target(s). As noted above, the present disclosure specifically includes anti-IL2R heavy chain antibodies with polyepitopic specificities, i.e., anti-IL2R heavy chain antibodies binding to one or more non-overlapping epitopes on a first IL2R protein, such as a human IL2RB; and anti-IL2R heavy chain antibodies binding to one or more epitopes on a first IL2R protein (e.g., an IL2RB protein) and to an epitope on a different IL2R protein, such as, for example, an IL2RG protein. The term "non-overlapping epitope(s)" or "non-competitive epitope(s)" of an antigen is defined herein to mean epitope(s) that are recognized by one member of a pair of antigen-specific antibodies but not the other member. Pairs of antibodies, or antigen-binding regions targeting the same antigen on a multi-specific antibody, recognizing non-overlapping epitopes, do not compete for binding to that antigen and are able to bind that antigen simultaneously.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term "valent" as used herein refers to a specified number of binding sites in an antibody molecule.

A "monovalent" antibody has one binding site. Thus, a monovalent antibody is also monospecific.

A "multi-valent" antibody has two or more binding sites. Thus, the terms "bivalent," "trivalent," and "tetravalent" refer to the presence of two binding sites, three binding sites, and four binding sites, respectively. Thus, a bispecific antibody according to the disclosure is at least bivalent and may be trivalent, tetravalent, or otherwise multi-valent. A bivalent antibody in accordance with embodiments of the disclosure may have two binding sites to the same epitope (i.e., bivalent, monoparatopic), or to two different epitopes (i.e., bivalent, biparatopic).

A large variety of methods and protein configurations are known and used for the preparation of bispecific monoclonal antibodies (BsMAB), tri-specific antibodies, and the like.

The term "human antibody" is used herein to include antibodies having variable and constant regions derived from human germline immunoglobulin sequences. The human antibodies herein may include amino acid residues not encoded by human germline immunoglobulin sequences, e.g., mutations introduced by random or site-specific mutagenesis in vitro or by somatic mutation in vivo. The term "human antibody" specifically includes heavy chain-only antibodies having human heavy chain variable region sequences, produced by transgenic animals, such as transgenic rats or mice, in particular UniAbs™ produced by UniRats™, as defined above.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fc-regions or artificial Fc-regions, and human idio-types. Such immunoglobulins can be isolated from animals of the disclosure that have been engineered to produce such chimeric antibodies.

As used herein, the term "effector cell" refers to an immune cell which is involved in the effector phase of an immune response, as opposed to the cognitive and activation phases of an immune response. Some effector cells express specific Fc receptors and carry out specific immune functions. In some embodiments, an effector cell such as a natural killer cell is capable of inducing antibody-dependent cellular cytotoxicity (ADCC). For example, monocytes and macrophages, which express FcR, are involved in specific killing of target cells and presenting antigens to other components of the immune system, or binding to cells that present antigens. In some embodiments, an effector cell may phagocytose a target antigen or target cell.

"Human effector cells" are leukocytes which express receptors such as T-cell receptors or FcRs and perform effector functions. For example, in some embodiments, the cells express at least FcγRIII and perform ADCC effector function. Examples of human leukocytes which mediate ADCC include natural killer (NK) cells, monocytes, cytotoxic T-cells, and neutrophils. The effector cells may be isolated from a native source thereof, e.g., from blood or PBMCs as described herein.

The term "immune cell" is used herein in the broadest sense, including, without limitation, cells of myeloid or lymphoid origin, for instance lymphocytes (such as B-cells and T-cells including cytolytic T-cells (CTLs)), killer cells, natural killer (NK) cells, macrophages, monocytes, eosinophils, polymorphonuclear cells, such as neutrophils, granulocytes, mast cells, and basophils.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity (CDC); Fc receptor binding; antibody-dependent cell-mediated cytotoxicity (ADCC); phagocytosis; down regulation of cell surface receptors (e.g., B-cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (*USA*) 95:652-656 (1998).

"Complement dependent cytotoxicity" or "CDC" refers to the ability of a molecule to lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., *J. Immunol. Methods* 202:163 (1996), may be performed.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art. Low-affinity antibodies generally bind antigen slowly and tend to dissociate readily, whereas high-affinity antibodies generally bind antigen faster and tend to remain bound.

As used herein, the "Kd" or "Kd value" refers to a dissociation constant determined by BioLayer Interferometry, using an Octet QK384 instrument (Fortebio Inc., Menlo Park, CA) in kinetics mode. For example, anti-mouse Fc sensors are loaded with mouse-Fc fused antigen and then dipped into antibody-containing wells to measure concentration dependent association rates (kon). Antibody dissociation rates (koff) are measured in the final step, where the sensors are dipped into wells containing buffer only. The Kd is the ratio of koff/kon. (For further details see, Concepcion, J, et al., *Comb Chem High Throughput Screen,* 12(8), 791-800, 2009).

The terms "treatment," "treating," and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during, or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates, or otherwise causes an improvement in the pathological symptoms, disease progression, or physiological conditions associated with a disease or which improves resistance to a disorder.

The term "mediated by activation of IL2R signaling in immune cells" broadly refers to any disease or disorder in which the IL2/IL2R signaling pathway is associated with or involved with one or more pathological processes that are characteristic of the disease or disorder. Such disorders include, but are not limited to, infectious diseases, autoimmune disorders (e.g., Crohn's disease, multiple sclerosis), cancer, inflammatory diseases (e.g., arthritis), or diseases or disorders associated with deficient IL-2-mediated signaling, deficient T cell proliferation, or T cell dysfunction.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g., mouse, rat, etc.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (e.g., vehicles, additives) are those which can reasonably be administered to a subject mammal to provide an effective dose of the active ingredient employed.

A "sterile" formulation is aseptic or free or essentially free from all living microorganisms and their spores. A "frozen" formulation is one at a temperature below 0° C.

A "stable" formulation is one in which the protein therein essentially retains its physical stability and/or chemical stability and/or biological activity upon storage. In some embodiments, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301. Vincent Lee Ed., Marcel Dekker, Inc., New York, N.Y., Pubs. (1991) and Jones. A. *Adv. Drug Delivery Rev.* 10: 29-90) (1993), for example. Stability can be measured at a selected temperature for a selected time period. Stability can be evaluated qualitatively and/or quantitatively in a variety of different ways, including evaluation of aggregate formation (for example, using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g., Asn deamidation), oxidation (e.g., Met oxidation), isomerization (e.g., Asp isomerization), clipping/hydrolysis/fragmentation (e.g., hinge region fragmentation), succinimide formation, unpaired cysteine(s), N-terminal extension, C-terminal processing, glycosylation differences, etc.

Anti-IL2R Antibodies

The present disclosure provides various families of antibodies that bind to human IL2R. Aspects of the disclosure include closely related antibody families whose members bind to a particular IL2R subunit, or chain, e.g., that bind to IL2RB or IL2RG, or a combination thereof.

In some embodiments, an anti-IL2RB antibody comprises CDR sequences having the following sequence formulae. An X indicates a variable amino acid, which may, in some embodiments, be the specific amino acid listed below:

```
CDR1 (IL2RB_F09)
                               (SEQ ID NO: 26)
    G G S I S S S X1 W
``` where X1 is D or N;

```
CDR2 (IL2RB_F09)
                               (SEQ ID NO: 27)
    I X2 H S G S T
``` where X2 is D or S; and

```
CDR3 (IL2RB_F09)
                               (SEQ ID NO: 28)
    X3 R G X4 W E L X5 D A F D I
``` where:
  X3 is G or A;
  X4 is S or Q; and
  X5 is S or T.

In some embodiments, an anti-IL2RB antibody comprises any combination of CDR1, and CDR2 and CDR3 sequences comprising the sequence formulae of SEQ ID NOs: 26, 27, and 28, respectively. Antibodies of this family can be referred to herein as IL2RB_F09 antibodies.

In some embodiments, an anti-IL2RB antibody comprises CDR sequences having the following sequence formulae. An X indicates a variable amino acid, which may, in some embodiments, be the specific amino acid listed below:

```
CDR1 (IL2RB_F18)
                               (SEQ ID NO: 29)
    G F T F S X1 Y G
``` where X1 is S or T;

```
CDR2 (IL2RB_F18)
                               (SEQ ID NO: 30)
    I S Y D G S N X2
``` where X2 is K or R; and

```
CDR3 (IL2RB_F18)
                               (SEQ ID NO: 31)
    A R D L D Y D X3 L T G D P V G G F D I
``` where X3 is V or I.

In some embodiments, an anti-IL2RB antibody comprises any combination of CDR1, CDR2, and CDR3 sequences comprising the sequence formulae of SEQ ID NOs: 29, 30, and 31, respectively. Antibodies of this family can be referred to herein as IL2RB_F18 antibodies.

Antibodies in accordance with embodiments of the disclosure that bind to IL2RB can comprise a set of CDR sequences as defined herein and exemplified by the provided heavy chain CDR1, CDR2 and CDR3 sequences set forth in Table 1, and the heavy chain variable region (VH) sequences set forth in Table 2. These antibodies provide a number of benefits that contribute to utility as clinically therapeutic agent(s). The antibodies include members with a range of binding affinities, allowing the selection of a specific sequence with a desired binding affinity.

TABLE 1

| Anti-IL2RB Heavy Chain Antibody Unique CDR Amino Acid Sequences | | | | |
| --- | --- | --- | --- | --- |
| Clone ID No. | Family ID No. | CDR1 | CDR2 | CDR3 |
| 387205 | IL2RB_F09C | GGSISSSDW (SEQ ID NO: 1) | IDHSGST (SEQ ID NO: 4) | GRGSWELSDAFDI (SEQ ID NO: 7) |
| 387172 | IL2RB_F09G | GGSISSSDW (SEQ ID NO: 1) | IDHSGST (SEQ ID NO: 4) | ARGSWELTDAFDI (SEQ ID NO: 8) |

TABLE 1-continued

| Anti-IL2RB Heavy Chain Antibody Unique CDR Amino Acid Sequences | | | | |
|---|---|---|---|---|
| Clone ID No. | Family ID No. | CDR1 | CDR2 | CDR3 |
| 387111 | IL2RB_F09K | GGSISSSNW (SEQ ID NO: 2) | ISHSGST (SEQ ID NO: 5) | GRGSWELTDAFDI (SEQ ID NO: 9) |
| 388252 | IL2RB_F18E | GFTFSSYG (SEQ ID NO: 3) | ISYDGSNK (SEQ ID NO: 6) | ARDLDYDVLTGDPVGGFDI (SEQ ID NO: 10) |

TABLE 2

| Anti-IL2RB Heavy Chain Antibody Variable Region Amino Acid Sequences | | |
|---|---|---|
| Clone ID No. | Family ID No. | VH sequence |
| 387205 | IL2RB_F09C | QVQLQESGPGLVKPSGTLSLTCAVSGGSISSSDWWSWVRQPP GKGLEWIGEIDHSGSTNYNPSLMSRVTISVDKSKNQFSLKLSS VTAADTAVYFCGRGSWELSDAFDIRGQGTLVTVSS (SEQ ID NO: 11) |
| 387172 | IL2RB_F09G | QVQLQESGPGLVKSSETLSLTCTVSGGSISSSDWWSWVRQPPG KGLEWIGEIDHSGSTNYNPSLMSRVTISVDKSKNQFSLKLSSV TAADTAVYFCARGSWELTDAFDIRGQGTLVTVSS (SEQ ID NO: 12) |
| 387111 | IL2RB_F09K | QVQLQESSPGLVKPSETLSLTCTVSGGSISSSNWWSWVRQPPG KGLEWIGEISHSGSTNYNPSLKSRVTISVDKSKNQFSLRLSSVT AADTAVYFCGRGSWELTDAFDIRGQGTLVTVSS (SEQ ID NO: 13) |
| 388252 | IL2RB_F18E | QVQLVESGGGVVQPGRSLRLSCAASGFTFSSYGMHWVRQAP GKEREWVAVISYDGSNKYYTDSVKGRFTISRDNSKNTLYLEM NSLRAEDTAVYYCARDLDYDVLTGDPVGGFDIWGQGTLVTV SS (SEQ ID NO: 14) |

In some embodiments, an anti-IL2RG antibody comprises CDR sequences having the following sequence formulae. An X indicates a variable amino acid, which may, in some embodiments, be the specific amino acid listed below:

```
            CDR1 (IL2RG_F16)
                                (SEQ ID NO: 32)
            G F X1 X2 X3 X4 Y Y
``` where:

X1 is T or I;

X2 is F or V;

X3 is S, N, or G; and

X4 is D or N;

```
            CDR2 (IL2RG_F16)
                                (SEQ ID NO: 33)
            I S X5 S G X6 X7 I
``` where:

X5 is S or N;

X6 is D, S, G, or N; and

X7 is T or I; and

```
    CDR3 (IL2RG_F16)
                        (SEQ ID NO: 20)
    ARGDAVSITGDY.
```

In some embodiments, an anti-IL2RG antibody comprises any combination of CDR1, and CDR2 and CDR3 sequences comprising the sequence formulae of SEQ ID NOs: 32, 33, and 34, respectively. Antibodies of this family can be referred to herein as IL2RG_F16 antibodies.

In some embodiments, an anti-IL2RG antibody comprises a CDR1 sequence comprising GFTFSDYY (SEQ ID NO: 15), a CDR2 (IL2RG_F18) sequence comprising ISSSGTTT (SEQ ID NO: 19), and a CDR3 (IL2RG_F18) sequence comprising ARGAAVAPGFDS (SEQ ID NO: 21). Antibodies of this family can be referred to herein as IL2RG_F18 antibodies.

Antibodies in accordance with embodiments of the disclosure that bind to IL2RG comprise a set of CDR sequences as defined herein and exemplified by the provided heavy chain CDR1, CDR2, and CDR3 sequences set forth in Table 3, and the heavy chain variable region (VH) sequences set forth in Table 4. This family of antibodies provides a number of benefits that contribute to utility as clinically therapeutic agent(s). The antibodies include members with a range of binding affinities, allowing the selection of a specific sequence with a desired binding affinity.

TABLE 3

Anti-IL2RG Heavy Chain Antibody CDR1, CDR2 and CDR3 Amino Acid Sequences

| Clone ID No. | Family ID No. | CDR1 | CDR2 | CDR3 |
|---|---|---|---|---|
| 363256 | IL2RG_F16A | GFTFSDYY (SEQ ID NO: 15) | ISSSGDTI (SEQ ID NO: 17) | ARGDAVSITGDY (SEQ ID NO: 20) |
| 363544 | IL2RG_F16B | GFTFSDYY (SEQ ID NO: 15) | ISSSGSTI (SEQ ID NO: 18) | ARGDAVSITGDY (SEQ ID NO: 20) |
| 388582 | IL2RG_F16C | GFTFNDYY (SEQ ID NO: 16) | ISSSGSTI (SEQ ID NO: 18) | ARGDAVSITGDY (SEQ ID NO: 20) |
| 363435 | IL2RG_F18A | GFTFSDYY (SEQ ID NO: 15) | ISSSGTTT (SEQ ID NO: 19) | ARGAAVAPGFDS (SEQ ID NO: 21) |

TABLE 4

Anti-IL2RG Heavy Chain Antibody Variable Region Amino Acid Sequences

| Clone ID No. | Family ID No. | VH Sequence |
|---|---|---|
| 363256 | IL2RG_F16A | QVQLVESGGGLVKPGGSLRLSCAASGFTFSDYYMSWIRQAPGK GLEWVSSISSSGDTIYYADSVQGRFTLSRDNAENSLFLQMNSLR AEDTAVYYCARGDAVSITGDYRGQGTLVTVSS (SEQ ID NO: 22) |
| 363544 | IL2RG_F16B | QVQLVESGGGLVKPGGSLRLSCAASGFTFSDYYMSWIRQAPGK GLEWVSYISSSGSTIYYADSVKGRFTISRDNAKNSLYLQMNSLR AEDTAVYYCARGDAVSITGDYRGQGTLVTVSS (SEQ ID NO: 23) |
| 388582 | IL2RG_F16C | QVQLVESGGGLVKPGGSLRLSCAASGFTFNDYYMSWIRQAPGK GLEWVSHISSSGSTIYYADSVKGRFTVSRDNANNSLYLQMHSLR AEDTAVYYCARGDAVSITGDYRGQGTLVTVSS (SEQ ID NO: 24) |
| 363435 | IL2RG_F18A | QVQLVESGGDLVKPGGSLRLSCAASGFTFSDYYMSWLRQAPGK ELEWVSHISSSGTTTYYADSVEGRFTITRDNAKNSLYLQMNSLR AEDTAVYYCARGAAVAPGFDSRGQGTLVTVSS (SEQ ID NO: 25) |

A suitable antibody may be selected from those provided herein for development and therapeutic or other use, including, without limitation, use as a multispecific antibody, such as a bispecific antibody.

Determination of affinity for a candidate protein can be performed using methods known in the art, such as Biacore measurements. Members of the antibody families described herein may have an affinity for IL2R with a Kd of from about $10^{-6}$ to around about $10^{-11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g., agonizing, an IL2R biological activity, including in vitro assays, pre-clinical models, and clinical trials, as well as assessment of potential toxicity.

Members of the antibody families described herein are cross-reactive with the IL2R protein of Cynomolgus macaque, which facilitates the use of Cynomolgus macaque as an animal model for validating, e.g., mechanism of action, pharmacokinetics, toxicology, and other attributes of the antibodies described herein.

In some embodiments, the IL2R-specific antibodies herein comprise a VH domain, comprising CDR1, CDR2, and CDR3 sequences in a human VH framework. The CDR sequences may be situated, as an example, in the region of around amino acid residues 26-33; 51-58; and 97-116 for CDR1, CDR2, and CDR3, respectively, of the provided exemplary variable region sequences set forth in SEQ ID NOs: 11-14 and 22-25. It will be understood by one of ordinary skill in the art that the CDR sequences may be in different positions if a different framework sequence is selected, although generally the order of the sequences will remain the same.

In a particular embodiment, an anti-IL2RB antibody comprises a CDR1 sequence of any one of SEQ ID NOs: 1-3. In a particular embodiment, the CDR1 sequence comprises SEQ ID NO: 1. In a particular embodiment, the CDR1 sequence comprises SEQ ID NO: 2. In a particular embodiment, the CDR1 sequence comprises SEQ ID NO: 3.

In a particular embodiment, an anti-IL2RB antibody comprises a CDR2 sequence of any one of SEQ ID NOs: 4-6. In a particular embodiment, the CDR2 sequence comprises SEQ ID NO: 4. In a particular embodiment, the CDR2 sequence comprises SEQ ID NO: 5. In a particular embodiment, the CDR2 sequence comprises SEQ ID NO: 6.

In a particular embodiment, an anti-IL2RB antibody comprises a CDR3 sequence of any one of SEQ ID NOs: 7-10. In a particular embodiment, the CDR3 sequence comprises SEQ ID NO: 7. In a particular embodiment, the CDR2 sequence comprises SEQ ID NO: 8. In a particular embodiment, the CDR2 sequence comprises SEQ ID NO: 9. In a particular embodiment, the CDR2 sequence comprises SEQ ID NO: 10.

In a further embodiment, an anti-IL2RB heavy chain-only antibody comprises the CDR1 sequence of SEQ ID NO: 1; the CDR2 sequence of SEQ ID NO: 4; and the CDR3 sequence of SEQ ID NO: 7.

In a further embodiment, an anti-IL2RB antibody comprises the CDR1 sequence of SEQ ID NO: 1; the CDR2 sequence of SEQ ID NO: 4; and the CDR3 sequence of SEQ ID NO: 8.

In a further embodiment, an anti-IL2RB antibody comprises the CDR1 sequence of SEQ ID NO: 2; the CDR2 sequence of SEQ ID NO: 5; and the CDR3 sequence of SEQ ID NO: 9.

In a further embodiment, an anti-IL2RB antibody comprises the CDR1 sequence of SEQ ID NO: 3; the CDR2 sequence of SEQ ID NO: 6; and the CDR3 sequence of SEQ ID NO: 10.

In a further embodiment, an anti-IL2RB antibody comprises any of the heavy chain variable region amino acid sequences of SEQ ID NOs: 11-14 (Table 2).

In a still further embodiment, an anti-IL2RB antibody comprises the heavy chain variable region sequence of SEQ ID NO: 11. In a still further embodiment, an anti-IL2RB antibody comprises the heavy chain variable region sequence of SEQ ID NO: 12. In a still further embodiment, an anti-IL2RB antibody comprises the heavy chain variable region sequence of SEQ ID NO: 13. In a still further embodiment, an anti-IL2RB antibody comprises the heavy chain variable region sequence of SEQ ID NO: 14.

In some embodiments, a CDR sequence in an anti-IL2RB antibody of the disclosure comprises one or two amino acid substitutions relative to a CDR1, CDR2, and/or CDR3 sequence or set of CDR1, CDR2 and CDR3 sequences in any one of SEQ ID NOs: 1-10 (Table 1).

In some embodiments, an anti-IL2RB antibody comprises a heavy chain variable domain (VH) in which the CDR3 sequence has greater than or equal to 80%, such as at least 85%, at least 90%, at least 95%, or at least 99% sequence identity at the amino acid level to a CDR3 sequence of any one of the antibodies whose CDR3 sequences are provided in Table 1, and binds to IL2RB.

In some embodiments, an anti-IL2RB antibody comprises a heavy chain variable domain (VH) in which the full set of CDRs 1, 2, and 3 (combined) has greater than or equal to eighty-five percent (85%) (e.g., ≥90%, ≥95%, ≥98%, ≥99%) sequence identity at the amino acid level to the CDRs 1, 2, and 3 (combined) of the antibodies whose CDR sequences are provided in Table 1, and binds to IL2RB.

In some embodiments, an anti-IL2RB antibody comprises a heavy chain variable region sequence with at least about 80% identity, at least 85% identity, at least 90% identity, at least 95% identity, at least 98% identity, or at least 99% identity to any of the heavy chain variable region sequences of SEQ ID NOs: 11-14 (shown in Table 2), and binds to IL2RB.

In some embodiments, an anti-IL2RB antibody comprises a heavy chain variable region sequence as described herein, paired with a fixed light chain sequence. In some embodiments, the fixed light chain comprises a CDR1 sequence of SEQ ID NO: 44, a CDR2 sequence of SEQ ID NO: 45, and a CDR3 sequence of SEQ ID NO: 46, in a human VL framework. Together, the anti-IL2RB VH region and the fixed light chain variable region have binding affinity for IL2RB. In some embodiments, a fixed light chain comprises a light chain variable region sequence of SEQ ID NO: 47. In some embodiments, a fixed light chain comprises a sequence having at least about 80%, at least about 85%, at least about 90%, at least about 95%, or at least about 99% percent identity to the heavy chain variable region sequence of SEQ ID NO: 47. In some embodiments, a fixed light chain further comprises a light chain constant region sequence (CL). In some embodiments, a fixed light chain comprises the sequence of SEQ ID NO: 48.

In some embodiments, an anti-IL2RB antibody is a heavy chain-only antibody comprising a heavy chain variable region sequence as described herein, which is not paired with a light chain sequence.

In a particular embodiment, an anti-IL2RG antibody comprises a CDR1 sequence of any one of SEQ ID NOs: 15-16. In a particular embodiment, the CDR1 sequence comprises SEQ ID NO: 15. In a particular embodiment, the CDR1 sequence comprises SEQ ID NO: 16.

In a particular embodiment, an anti-IL2RG antibody comprises a CDR2 sequence of any one of SEQ ID NOs: 17-19. In a particular embodiment, the CDR2 sequence comprises SEQ ID NO: 17. In a particular embodiment, the CDR2 sequence comprises SEQ ID NO: 18. In a particular embodiment, the CDR2 sequence comprises SEQ ID NO: 19.

In a particular embodiment, an anti-IL2RG antibody comprises a CDR3 sequence of any one of SEQ ID NOs: 20-21. In a particular embodiment, the CDR3 sequence comprises SEQ ID NO: 20. In a particular embodiment, the CDR2 sequence comprises SEQ ID NO: 21.

In a further embodiment, an anti-IL2RG heavy chain-only antibody comprises the CDR1 sequence of SEQ ID NO: 15; the CDR2 sequence of SEQ ID NO: 17; and the CDR3 sequence of SEQ ID NO: 20.

In a further embodiment, an anti-IL2RG antibody comprises the CDR1 sequence of SEQ ID NO: 15; the CDR2 sequence of SEQ ID NO: 18; and the CDR3 sequence of SEQ ID NO: 20.

In a further embodiment, an anti-IL2RG antibody comprises the CDR1 sequence of SEQ ID NO: 16; the CDR2 sequence of SEQ ID NO: 18; and the CDR3 sequence of SEQ ID NO: 20.

In a further embodiment, an anti-IL2RG antibody comprises the CDR1 sequence of SEQ ID NO: 15; the CDR2 sequence of SEQ ID NO: 19; and the CDR3 sequence of SEQ ID NO: 21.

In a further embodiment, an anti-IL2RG antibody comprises any of the heavy chain variable region amino acid sequences of SEQ ID NOs: 22-25 (Table 4).

In a still further embodiment, an anti-IL2RG antibody comprises the heavy chain variable region sequence of SEQ ID NO: 22. In a still further embodiment, an anti-IL2RB antibody comprises the heavy chain variable region sequence of SEQ ID NO: 23. In a still further embodiment, an anti-IL2RB antibody comprises the heavy chain variable region sequence of SEQ ID NO: 24. In a still further embodiment, an anti-IL2RB antibody comprises the heavy chain variable region sequence of SEQ ID NO: 25.

In some embodiments, a CDR sequence in an anti-IL2RG antibody of the disclosure comprises one or two amino acid substitutions relative to a CDR1, CDR2 and/or CDR3 sequence or set of CDR1, CDR2 and CDR3 sequences in any one of SEQ ID NOs: 15-21 (Table 3).

In some embodiments, an anti-IL2RG antibody comprises a heavy chain variable domain (VH) in which the CDR3 sequence has greater than or equal to 80%, such as at least 85%, at least 90%, at least 95%, or at least 99% sequence identity at the amino acid level to a CDR3 sequence of any one of the antibodies whose CDR3 sequences are provided in Table 3, and binds to IL2RG.

In some embodiments, an anti-IL2RG antibody comprises a heavy chain variable domain (VH) in which the full set of CDRs 1, 2, and 3 (combined) has greater than or equal to eighty-five percent (85%) (e.g., ≥90%, ≥95%, ≥98%, ≥99%) sequence identity at the amino acid level to the CDRs 1, 2, and 3 (combined) of the antibodies whose CDR sequences are provided in Table 3, and binds to IL2RG.

In some embodiments, an anti-IL2RG antibody comprises a heavy chain variable region sequence with at least about 80% identity, at least 85% identity, at least 90% identity, at least 95% identity, at least 98% identity, or at least 99% identity to any of the heavy chain variable region sequences of SEQ ID NOs: 22-25 (shown in Table 4), and binds to IL2RG.

In some embodiments, an anti-IL2RG antibody comprises a heavy chain variable region sequence as described herein, paired with a fixed light chain sequence. In some embodiments, the fixed light chain comprises a CDR1 sequence of SEQ ID NO: 44, a CDR2 sequence of SEQ ID NO: 45, and a CDR3 sequence of SEQ ID NO: 46, in a human VL framework. Together, the anti-IL2RG VH region and the fixed light chain variable region have binding affinity for IL2RG. In some embodiments, a fixed light chain comprises a light chain variable region sequence of SEQ ID NO: 47. In some embodiments, a fixed light chain comprises a sequence having at least about 80%, at least about 85%, at least about 90%, at least about 95%, or at least about 99% percent identity to the heavy chain variable region sequence of SEQ ID NO: 47. In some embodiments, a fixed light chain further comprises a light chain constant region sequence (CL). In some embodiments, a fixed light chain comprises the sequence of SEQ ID NO: 48.

In some embodiments, an anti-IL2RG antibody is a heavy chain-only antibody comprising a heavy chain variable region sequence as described herein, which is not paired with a light chain sequence.

Multispecific Antibodies

Aspects of the disclosure include multispecific, e.g., bispecific, antibodies, which may have any of the configurations discussed herein, including, without limitation, a bispecific, bivalent heavy-chain antibody comprising two non-identical heavy chain polypeptide subunits that are associated with one another via an asymmetric (e.g., knobs-in-holes (KiH)) interface. In certain embodiments, a bispecific, bivalent heavy chain antibody can comprise two non-identical heavy chain polypeptide subunits that are associated with one another via an asymmetric interface, and may optionally further include two identical fixed light chain polypeptide subunits, each of which associates with one of the two heavy chain polypeptide subunits.

In some embodiments, a bispecific antibody comprises at least one heavy chain variable region that binds to a first IL2R subunit, and at least one heavy chain variable region that binds to a second IL2R subunit. In some embodiments, a bispecific antibody comprises at least one heavy chain variable region that binds to IL2RB, and at least one heavy chain variable region that binds to IL2RG. In some embodiments, a multispecific antibody further comprises an Fc portion comprising CH2 and/or CH3 and/or CH4 domains, in the absence of a CH1 domain.

Various formats of multispecific antibodies are within the ambit of the disclosure, including, without limitation, single chain polypeptides, two chain polypeptides, three chain polypeptides, four chain polypeptides, and multiples thereof. The multispecific antibodies herein specifically include those binding to IL2RB and IL2RG.

In some embodiments, a multispecific antibody comprises a first variable region comprising a member of the IL2RB_F09 family, comprising a CDR1 sequence comprising SEQ ID NO: 26, a CDR2 sequence comprising SEQ ID NO: 27, and a CDR3 sequence comprising SEQ ID NO: 28, and a second variable region comprising a member of the IL2RG_F16 family, comprising a CDR1 sequence comprising SEQ ID NO: 32, a CDR2 sequence comprising SEQ ID NO: 33, and a CDR3 sequence comprising SEQ ID NO: 20.

In some embodiments, a multispecific antibody comprises a first variable region comprising a member of the IL2RB_F09 family, comprising a CDR1 sequence comprising SEQ ID NO: 26, a CDR2 sequence comprising SEQ ID NO: 27, and a CDR3 sequence comprising SEQ ID NO: 28, and a second variable region comprising a member of the IL2RG_F18 family, comprising a CDR1 sequence comprising SEQ ID NO: 15, a CDR2 sequence comprising SEQ ID NO: 19, and a CDR3 sequence comprising SEQ ID NO: 21.

In some embodiments, a multispecific antibody comprises a first variable region comprising a member of the IL2RB_F18 family, comprising a CDR1 sequence comprising SEQ ID NO: 29, a CDR2 sequence comprising SEQ ID NO: 30, and a CDR3 sequence comprising SEQ ID NO: 31, and a second variable region comprising a member of the IL2RG_F16 family, comprising a CDR1 sequence comprising SEQ ID NO: 32, a CDR2 sequence comprising SEQ ID NO: 33, and a CDR3 sequence comprising SEQ ID NO: 20.

In some embodiments, a multispecific antibody comprises a first variable region comprising a member of the IL2RB_F18 family, comprising a CDR1 sequence comprising SEQ ID NO: 29, a CDR2 sequence comprising SEQ ID NO: 30, and a CDR3 sequence comprising SEQ ID NO: 31, and a second variable region comprising a member of the IL2RG_F18 family, comprising a CDR1 sequence comprising SEQ ID NO: 15, a CDR2 sequence comprising SEQ ID NO: 19, and a CDR3 sequence comprising SEQ ID NO: 21.

In some embodiments, a bispecific antibody comprises a first variable region that binds to IL2RB, comprising a CDR1 sequence of SEQ ID NO: 1, a CDR2 sequence of SEQ ID NO: 4, and a CDR3 sequence of SEQ ID NO: 7, and a second variable region that binds to IL2RG, comprising a CDR1 sequence of SEQ ID NO: 15, a CDR2 sequence of SEQ ID NO: 17, and a CDR3 sequence of SEQ ID NO: 20.

In some embodiments, a bispecific antibody comprises a first variable region that binds to IL2RB, comprising a CDR1 sequence of SEQ ID NO: 1, a CDR2 sequence of SEQ ID NO: 4, and a CDR3 sequence of SEQ ID NO: 8, and a second variable region that binds to IL2RG, comprising a CDR1 sequence of SEQ ID NO: 15, a CDR2 sequence of SEQ ID NO: 18, and a CDR3 sequence of SEQ ID NO: 20.

In some embodiments, a bispecific antibody comprises a first variable region that binds to IL2RB, comprising a CDR1 sequence of SEQ ID NO: 2, a CDR2 sequence of SEQ ID NO: 5, and a CDR3 sequence of SEQ ID NO: 9, and a second variable region that binds to IL2RG, comprising a CDR1 sequence of SEQ ID NO: 15, a CDR2 sequence of SEQ ID NO: 18, and a CDR3 sequence of SEQ ID NO: 20.

In some embodiments, a bispecific antibody comprises a first variable region that binds to IL2RB, comprising a CDR1 sequence of SEQ ID NO: 3, a CDR2 sequence of SEQ ID NO: 6, and a CDR3 sequence of SEQ ID NO: 10, and a second variable region that binds to IL2RG, comprising a CDR1 sequence of SEQ ID NO: 15, a CDR2 sequence of SEQ ID NO: 17, and a CDR3 sequence of SEQ ID NO: 20.

In some embodiments, a bispecific antibody comprises a first variable region that binds to IL2RB, comprising a CDR1 sequence of SEQ ID NO: 1, a CDR2 sequence of SEQ ID NO: 4, and a CDR3 sequence of SEQ ID NO: 8, and a second variable region that binds to IL2RG, comprising a CDR1 sequence of SEQ ID NO: 16, a CDR2 sequence of SEQ ID NO: 18, and a CDR3 sequence of SEQ ID NO: 20.

In some embodiments, a bispecific antibody comprises a first variable region that binds to IL2RB, comprising a CDR1 sequence of SEQ ID NO: 1, a CDR2 sequence of SEQ ID NO: 4, and a CDR3 sequence of SEQ ID NO: 8, and a second variable region that binds to IL2RG, comprising a CDR1 sequence of SEQ ID NO: 15, a CDR2 sequence of SEQ ID NO: 19, and a CDR3 sequence of SEQ ID NO: 21.

Table 5 provides a summary of various CDR combinations of bispecific IL2RB×IL2RG antibodies in accordance with embodiments of the disclosure.

TABLE 5

Bispecific IL2RB x IL2RG Antibodies, CDR Sequence Combinations

| Family ID No. Combination | CDR1 | CDR2 | CDR3 |
|---|---|---|---|
| IL2RB_F09C ** | GGSISSSDW (SEQ ID NO: 1) | IDHSGST (SEQ ID NO: 4) | GRGSWELSDAFDI (SEQ ID NO: 7) |
| IL2RG_F16A | GFTFSDYY (SEQ ID NO: 15) | ISSSGDTI (SEQ ID NO: 17) | ARGDAVSITGDY (SEQ ID NO: 20) |
| IL2RB_F09G ** | GGSISSSDW (SEQ ID NO: 1) | IDHSGST (SEQ ID NO: 4) | ARGSWELTDAFDI (SEQ ID NO: 8) |
| IL2RG_F16B | GFTFSDYY (SEQ ID NO: 15) | ISSSGSTI (SEQ ID NO: 18) | ARGDAVSITGDY (SEQ ID NO: 20) |
| IL2RB_F09K ** | GGSISSSNW (SEQ ID NO: 2) | ISHSGST (SEQ ID NO: 5) | GRGSWELTDAFDI (SEQ ID NO: 9) |
| IL2RG_F16B | GFTFSDYY (SEQ ID NO: 15) | ISSSGSTI (SEQ ID NO: 18) | ARGDAVSITGDY (SEQ ID NO: 20) |
| IL2RB_F18E ** | GFTFSSYG (SEQ ID NO: 3) | ISYDGSNK (SEQ ID NO: 6) | ARDLDYDVLTGDPVGGFDI (SEQ ID NO: 10) |
| IL2RG_F16A | GFTFSDYY (SEQ ID NO: 15) | ISSSGDTI (SEQ ID NO: 17) | ARGDAVSITGDY (SEQ ID NO: 20) |
| IL2RB_F09G ** | GGSISSSDW (SEQ ID NO: 1) | IDHSGST (SEQ ID NO: 4) | ARGSWELTDAFDI (SEQ ID NO: 8) |
| IL2RG_F16C | GFTFNDYY (SEQ ID NO: 16) | ISSSGSTI (SEQ ID NO: 18) | ARGDAVSITGDY (SEQ ID NO: 20) |
| IL2RB_F09G | GGSISSSDW (SEQ ID NO: 1) | IDHSGST (SEQ ID NO: 4) | ARGSWELTDAFDI (SEQ ID NO: 8) |
| IL2RG_F18A | GFTFSDYY (SEQ ID NO: 15) | ISSSGTTT (SEQ ID NO: 19) | ARGAAVAPGFDS (SEQ ID NO: 21) |

In some embodiments, a bispecific antibody comprises a first variable region that binds to IL2RB, comprising a heavy chain variable region sequence of SEQ ID NO: 11, and a second variable region that binds to IL2RG, comprising a heavy chain variable region sequence of SEQ ID NO: 22.

In some embodiments, a bispecific antibody comprises a first variable region that binds to IL2RB, comprising a heavy chain variable region sequence of SEQ ID NO: 12, and a second variable region that binds to IL2RG, comprising a heavy chain variable region sequence of SEQ ID NO: 23.

In some embodiments, a bispecific antibody comprises a first variable region that binds to IL2RB, comprising a heavy chain variable region sequence of SEQ ID NO: 13, and a second variable region that binds to IL2RG, comprising a heavy chain variable region sequence of SEQ ID NO: 23.

In some embodiments, a bispecific antibody comprises a first variable region that binds to IL2RB, comprising a heavy chain variable region sequence of SEQ ID NO: 14, and a second variable region that binds to IL2RG, comprising a heavy chain variable region sequence of SEQ ID NO: 22.

In some embodiments, a bispecific antibody comprises a first variable region that binds to IL2RB, comprising a heavy chain variable region sequence of SEQ ID NO: 12, and a second variable region that binds to IL2RG, comprising a heavy chain variable region sequence of SEQ ID NO: 24.

In some embodiments, a bispecific antibody comprises a first variable region that binds to IL2RB, comprising a heavy chain variable region sequence of SEQ ID NO: 12, and a second variable region that binds to IL2RG, comprising a heavy chain variable region sequence of SEQ ID NO: 25.

Table 6 provides a summary of various heavy chain variable region combinations of bispecific IL2RB×IL2RG antibodies in accordance with embodiments of the disclosure.

TABLE 6

Bispecific IL2RB x IL2RG antibodies, VH Sequence Combinations

| Family ID No. Combination | VH Sequences |
|---|---|
| IL2RB_F09C ** IL2RG_F16A | QVQLQESGPGLVKPSGTLSLTCAVSGGSISSSDWWSWVRQPPGKGLEWIG EIDHSGSTNYNPSLMSRVTISVDKSKNQFSLKLSSVTAADTAVYFCGRGS WELSDAFDIRGQGTLVTVSS (SEQ ID NO: 11) QVQLVESGGGLVKPGGSLRLSCAASGFTFSDYYMSWIRQAPGKGLEWVS SISSSGDTIYYADSVQGRFTLSRDNAENSLFLQMNSLRAEDTAVYYCARG DAVSITGDYRGQGTLVTVSS (SEQ ID NO: 22) |
| IL2RB_F09G ** | QVQLQESGPGLVKSSETLSLTCTVSGGSISSSDWWSWVRQPPGKGLEWIG EIDHSGSTNYNPSLMSRVTISVDKSKNQFSLKLSSVTAADTAVYFCARGS |

TABLE 6-continued

| Bispecific IL2RB x IL2RG antibodies, VH Sequence Combinations |
| --- |

| Family ID No. Combination | VH Sequences |
| --- | --- |
| IL2RG_F16B | WELTDAFDIRGQGTLVTVSS (SEQ ID NO: 12)<br>QVQLVESGGGLVKPGGSLRLSCAASGFTFSDYYMSWIRQAPGKGLEWVS<br>YISSSGSTIYYADSVKGRFTISRDNAKNSLYLQMNSLRAEDTAVYYCARG<br>DAVSITGDYRGQGTLVTVSS (SEQ ID NO: 23) |
| IL2RB_F09K<br>**<br>IL2RG_F16B | QVQLQESSPGLVKPSETLSLTCTVSGGSISSSNWWSWVRQPPGKGLEWIG<br>EISHSGSTNYNPSLKSRVTISVDKSKNQFSLRLSSVTAADTAVYFCGRGSW<br>ELTDAFDIRGQGTLVTVSS (SEQ ID NO: 13)<br>QVQLVESGGGLVKPGGSLRLSCAASGFTFSDYYMSWIRQAPGKGLEWVS<br>YISSSGSTIYYADSVKGRFTISRDNAKNSLYLQMNSLRAEDTAVYYCARG<br>DAVSITGDYRGQGTLVTVSS (SEQ ID NO: 23) |
| IL2RB_F18E<br>**<br>IL2RG_F16A | QVQLVESGGGVVQPGRSLRLSCAASGFTFSSYGMHWVRQAPGKEREWV<br>AVISYDGSNKYYTDSVKGRFTISRDNSKNTLYLEMNSLRAEDTAVYYCA<br>RDLDYDVLTGDPVGGFDIWGQGTLVTVSS (SEQ ID NO: 14)<br>QVQLVESGGGLVKPGGSLRLSCAASGFTFSDYYMSWIRQAPGKGLEWVS<br>SISSSGDTIYYADSVQGRFTLSRDNAENSLFLQMNSLRAEDTAVYYCARG<br>DAVSITGDYRGQGTLVTVSS (SEQ ID NO: 22) |
| IL2RB_F09G<br>**<br>IL2RG_F16C | QVQLQESGPGLVKSSETLSLTCTVSGGSISSSDWWSWVRQPPGKGLEWIG<br>EIDHSGSTNYNPSLMSRVTISVDKSKNQFSLKLSSVTAADTAVYFCARGS<br>WELTDAFDIRGQGTLVTVSS (SEQ ID NO: 12)<br>QVQLVESGGGLVKPGGSLRLSCAASGFTFNDYYMSWIRQAPGKGLEWVS<br>HISSSGSTIYYADSVKGRFTVSRDNANNSLYLQMHSLRAEDTAVYYCARG<br>DAVSITGDYRGQGTLVTVSS (SEQ ID NO: 24) |
| IL2RB_F09G<br>**<br>IL2RG_F18A | QVQLQESGPGLVKSSETLSLTCTVSGGSISSSDWWSWVRQPPGKGLEWIG<br>EIDHSGSTNYNPSLMSRVTISVDKSKNQFSLKLSSVTAADTAVYFCARGS<br>WELTDAFDIRGQGTLVTVSS (SEQ ID NO: 12)<br>QVQLVESGGDLVKPGGSLRLSCAASGFTFSDYYMSWLRQAPGKELEWVS<br>HISSSGTTTYYADSVEGRFTITRDNAKNSLYLQMNSLRAEDTAVYYCARG<br>AAVAPGFDSRGQGTLVTVSS (SEQ ID NO: 25) |

In some embodiments, a multispecific antibody includes a first and a second polypeptide, i.e., a first and a second polypeptide subunit, wherein each polypeptide comprises an antigen-binding domain of a heavy-chain antibody. In some embodiments, each of the first and second polypeptides further includes a hinge region, or at least a portion of a hinge region, which can facilitate formation of at least one disulfide bond between the first and second polypeptides. In some embodiments, each of the first and second polypeptides further includes at least one heavy chain constant region (CH) domain, such as a CH2 domain, and/or a CH3 domain, and/or a CH4 domain. In certain embodiments, the CH domain lacks a CH1 domain. The antigen-binding domain of each of the first and second polypeptides can incorporate any of the CDR sequences and/or variable region sequences described herein in order to impart antigen-binding capability on the multispecific antibody. As such, in certain embodiments, each polypeptide subunit in a multispecific antibody can include an antigen-binding domain that binds to a different IL2R subunit, or chain (e.g., IL2RB and IL2RG).

In some embodiments, a multispecific antibody comprises a variant human IgG4 Fc domain comprising a first heavy chain constant region sequence comprising an S228P mutation, an F234A mutation, an L235A mutation, and a T366W mutation (knob), and a second heavy chain constant region sequence comprising an S228P mutation, an F234A mutation, an L235A mutation, a T366S mutation, an L368A mutation, and a Y407V mutation (hole). This variant, or modified, IgG4 Fc domain prevents unwanted Fab exchange, reduces effector function of the antibody, and also facilitates heterodimerization of the heavy chain polypeptide subunits to form the multispecific (e.g., bispecific) antibody.

The components of the multispecific antibodies described herein (i.e., CDR sequences, variable region sequences, and Fc domain sequences (e.g., hinge, CH2, and CH3 domain sequences) can be combined in various ways to generate multispecific antibodies that bind to IL2R, e.g., to IL2RB and IL2RG, and that have beneficial properties, e.g., reduced effector function activity, increased IL2R agonistic activity, etc.

Table 7 provides the sequences of human IgG1 and IgG4 Fc region sequences, as well as versions of these sequences that incorporate additional mutations (variants) that impart additional desired properties.

TABLE 7

| Human IgG1 and IgG4 Fc Region Sequences and Variants Thereof | |
| --- | --- |
| Polypeptide Name | Amino Acid Sequence |
| Human IgG1<br>(UniProt No. P01857) | ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKKVEPKSCDKTHTCPPCPAPELLGG<br>PSVFLFPPKPKDTLMISRTPEVTCVVVDVSHEDPEVKFNW<br>YVDGVEVHNAKTKPREEQYNSTYRVVSVLTVLHQDWLNGK |

TABLE 7-continued

Human IgG1 and IgG4 Fc Region Sequences and Variants Thereof

| Polypeptide Name | Amino Acid Sequence |
|---|---|
| | EYKCKVSNKALPAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHYT QKSLSLSPGK (SEQ ID NO: 42) |
| Human IgG4 (UniProt No. P01861) | ASTKGPSVFPLAPCSRSTSESTAALGCLVKDYFPEPVTVS WNSGALTSGVHTFPAVLQSSGLYSLSSVVTVPSSSLGTKT YTCNVDHKPSNTKVDKRVESKYGPPCPSCPAPEFLGGPSV FLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTK NQVSLTCLVKGFYPSDIAVEWESNGQPENNYKTTPPVLDS DGSFFLYSRLTVDKSRWQEGNVFSCSVMHEALHNHYTQKS LSLSLGK (SEQ ID NO: 43) |
| Human IgG1 with silencing mutations (Fc region) | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNTK VDKKVEPKSCDKTHTCPPCPAPEAAGGPSVFLFPPKPKDTLMISRTP EVTCVVVDVSHEDPEVKFNWYVDGVEVHNAKTKPREEQYNSTYR VVSVLTVLHQDWLNGKEYKCKVSNKALPAPIEKTISKAKGQPREP QVYTLPPSREEMTKNQVSLTCLVKGFYPSDIAVEWESNGQPENNY KTTPPVLDSDGSFFLYSKLTVDKSRWQQGNVFSCSVMHEALHNHY TQKSLSLSPGK (SEQ ID NO: 51) |
| Human IgG4 with silencing mutations (Fc region) | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEAAGGPSVFLFPPKPKDTLMISRTPEV TCVVVDVSQEDPEVQFNWYVDGVEVHNAKTKPREEQFNSTYRVV SVLTVLHQDWLNGKEYKCKVSNKGLPSSIEKTISKAKGQPREPQVY TLPPSQEEMTKNQVSLTCLVKGFYPSDIAVEWESNGQPENNYKTTP PVLDSDGSFFLYSRLTVDKSRWQEGNVFSCSVMHEALHNHYTQKS LSLSLGK (SEQ ID NO: 52) |
| Human IgG4 hinge region (wild type) | ESKYGPPCPSCPA (SEQ ID NO: 54) |
| Human IgG4 hinge region (S228P) | ESKYGPPCPPCPA (SEQ ID NO: 55) |
| Human IgG4 CH2 domain sequence (wild type) | APEFLGGPSVFLFPPKPKDTLMISRTPEVTCVVVDVSQEDPEVQFN WYVDGVEVHNAKTKPREEQFNSTYRVVSVLTVLHQDWLNGKEY KCKVSNKGLPSSIEKTISKAK (SEQ ID NO: 56) |
| Human IgG4 CH2 domain sequence (F234A, L235A) | APEAAGGPSVFLFPPKPKDTLMISRTPEVTCVVVDVSQEDPEVQFN WYV̲DGVEVHNAKTKPREEQFNSTYRVVSVLTVLHQDWLNGKEY KCKVSNKGLPSSIEKTISKAK (SEQ ID NO: 57) |
| Human IgG4 CH3 domain sequence (wild type) | GQPREPQVYTLPPSQEEMTKNQVSLTCLVKGFYPSDIAVEWESNGQ PENNYKTTPPVLDSDGSFFLYSRLTVDKSRWQEGNVFSCSVMHEA LHNHYTQKSLSLSLGK (SEQ ID NO: 58) |
| Human IgG4 CH3 domain sequence (knob, T366W) | GQPREPQVYTLPPSQEEMTKNQVSLWCLVKGFYPSDIAVEWESNG QPENNYKTTPPVLDSDGSFFLYSRL̲TVDKSRWQEGNVFSCSVMHE ALHNHYTQKSLSLSLGK (SEQ ID NO: 59) |
| Human IgG4 CH3 domain sequence (hole, T366S, L368A, Y407V) | GQPREPQVYTLPPSQEEMTKNQVSLSCAVKGFYPSDIAVEWESNG QPENNYKTTPPVLDSDGSFFLVSRL̲T̲V̲DKSRWQEGNVFSCSVMHE ALHNHYTQKSLSLSLGK (SE̲Q ID NO: 60) |

In some embodiments, a bispecific antibody comprises a first heavy chain polypeptide subunit comprising a variable region that binds to IL2RB, wherein the first heavy chain polypeptide subunit comprises the sequence of SEQ ID NO: 53, and a second heavy chain polypeptide subunit comprising a variable region that binds to IL2RG, wherein the second heavy chain polypeptide subunit comprises the sequence of SEQ ID NO: 61.

In some embodiments, a bispecific antibody comprises a first heavy chain polypeptide subunit comprising a variable region that binds to IL2RB, wherein the first heavy chain polypeptide subunit comprises the sequence of SEQ ID NO:

62, and a second heavy chain polypeptide subunit comprising a variable region that binds to IL2RG, wherein the second heavy chain polypeptide subunit comprises the sequence of SEQ ID NO: 63.

In some embodiments, a bispecific antibody comprises a first heavy chain polypeptide subunit comprising a variable region that binds to IL2RB, wherein the first heavy chain polypeptide subunit comprises the sequence of SEQ ID NO: 64, and a second heavy chain polypeptide subunit comprising a variable region that binds to IL2RG, wherein the second heavy chain polypeptide subunit comprises the sequence of SEQ ID NO: 65.

In some embodiments, a bispecific antibody comprises a first heavy chain polypeptide subunit comprising a variable region that binds to IL2RB, wherein the first heavy chain polypeptide subunit comprises the sequence of SEQ ID NO: 66, and a second heavy chain polypeptide subunit comprising a variable region that binds to IL2RG, wherein the second heavy chain polypeptide subunit comprises the sequence of SEQ ID NO: 67.

In some embodiments, a bispecific antibody comprises a first heavy chain polypeptide subunit comprising a variable region that binds to IL2RB, wherein the first heavy chain polypeptide subunit comprises the sequence of SEQ ID NO: 34, and a second heavy chain polypeptide subunit comprising a variable region that binds to IL2RG, wherein the second heavy chain polypeptide subunit comprises the sequence of SEQ ID NO: 35.

In some embodiments, a bispecific antibody comprises a first heavy chain polypeptide subunit comprising a variable region that binds to IL2RB, wherein the first heavy chain polypeptide subunit comprises the sequence of SEQ ID NO: 36, and a second heavy chain polypeptide subunit comprising a variable region that binds to IL2RG, wherein the second heavy chain polypeptide subunit comprises the sequence of SEQ ID NO: 37.

Table 8 provides a summary of various heavy chain polypeptide subunit sequence combinations of bispecific IL2RB×IL2RG antibodies in accordance with embodiments of the disclosure.

TABLE 8

| Bispecific IL2RB x IL2RG Antibodies, Full Length Polypeptide Sequence Combinations | | |
| --- | --- | --- |
| Family ID No. Combination | Polypeptide Name | Full Length Sequences |
| IL2RB_F09C hole ** IL2RG_F16A knob | IL2RB_F09C IgG4 hole | QVQLQESGPGLVKPSGTLSLTCAVSGGSISSSDWWSWV RQPPGKGLEWIGEIDHSGSTNYNPSLMSRVTISVDKSKN QFSLKLSSVTAADTAVYFCGRGSWELSDAFDIRGQGTL VTVSSESKYGPPCPPCPAPEAAGGPSVFLFPPKPKDTLMI SRTPEVTCVVVDVSQEDPEVQFNWYVDGVEVHNAKTK PREEQFNSTYRVVSVLTVLHQDWLNGKEYKCKVSNKG LPSSIEKTISKAKGQPREPQVYTLPPSQEEMTKNQVSLSC AVKGFYPSDIAVEWESNGQPENNYKTTPPVLDSDGSFFL VSRLTVDKSRWQEGNVFSCSVMHEALHNHYTQKSLSLS LGK (SEQ ID NO: 53) |
| | IL2RG_F16A IgG4 knob | QVQLVESGGGLVKPGGSLRLSCAASGFTFSDYYMSWIR QAPGKGLEWVSSISSSGDTIYYADSVQGRFTLSRDNAEN SLFLQMNSLRAEDTAVYYCARGDAVSITGDYRGQGTLV TVSSESKYGPPCPPCPAPEAAGGPSVFLFPPKPKDTLMIS RTPEVTCVVVDVSQEDPEVQFNWYVDGVEVHNAKTKP REEQFNSTYRVVSVLTVLHQDWLNGKEYKCKVSNKGL PSSIEKTISKAKGQPREPQVYTLPPSQEEMTKNQVSLWC LVKGFYPSDIAVEWESNGQPENNYKTTPPVLDSDGSFFL YSRLTVDKSRWQEGNVFSCSVMHEALHNHYTQKSLSLS LGK (SEQ ID NO: 61) |
| IL2RB_F09G hole ** IL2RG_F16B knob | IL2RB_F09G IgG4 hole | QVQLQESGPGLVKSSETLSLTCTVSGGSISSSDWWSWVR QPPGKGLEWIGEIDHSGSTNYNPSLMSRVTISVDKSKNQ FSLKLSSVTAADTAVYFCARGSWELTDAFDIRGQGTLVT VSSESKYGPPCPPCPAPEAAGGPSVFLFPPKPKDTLMISR TPEVTCVVVDVSQEDPEVQFNWYVDGVEVHNAKTKPR EEQFNSTYRVVSVLTVLHQDWLNGKEYKCKVSNKGLPS SIEKTISKAKGQPREPQVYTLPPSQEEMTKNQVSLSCAV KGFYPSDIAVEWESNGQPENNYKTTPPVLDSDGSFFLVS RLTVDKSRWQEGNVFSCSVMHEALHNHYTQKSLSLSLG K (SEQ ID NO: 62) |
| | IL2RG_F16B IgG4 knob | QVQLVESGGGLVKPGGSLRLSCAASGFTFSDYYMSWIR QAPGKGLEWVSYISSSGSTIYYADSVKGRFTISRDNAKN SLYLQMNSLRAEDTAVYYCARGDAVSITGDYRGQGTL VTVSSESKYGPPCPPCPAPEAAGGPSVFLFPPKPKDTLMI SRTPEVTCVVVDVSQEDPEVQFNWYVDGVEVHNAKTK PREEQFNSTYRVVSVLTVLHQDWLNGKEYKCKVSNKG LPSSIEKTISKAKGQPREPQVYTLPPSQEEMTKNQVSLW CLVKGFYPSDIAVEWESNGQPENNYKTTPPVLDSDGSFF LYSRLTVDKSRWQEGNVFSCSVMHEALHNHYTQKSLSL SLGK (SEQ ID NO: 63) |
| IL2RB_F09K hole ** IL2RG_F16B knob | IL2RB_F09K IgG4 hole | QVQLQESSPGLVKPSETLSLTCTVSGGSISSSNWWSWVR QPPGKGLEWIGEISHSGSTNYNPSLKSRVTISVDKSKNQF SLRLSSVTAADTAVYFCGRGSWELTDAFDIRGQGTLVT VSSESKYGPPCPPCPAPEAAGGPSVFLFPPKPKDTLMISR TPEVTCVVVDVSQEDPEVQFNWYVDGVEVHNAKTKPR EEQFNSTYRVVSVLTVLHQDWLNGKEYKCKVSNKGLPS SIEKTISKAKGQPREPQVYTLPPSQEEMTKNQVSLSCAV KGFYPSDIAVEWESNGQPENNYKTTPPVLDSDGSFFLVS RLTVDKSRWQEGNVFSCSVMHEALHNHYTQKSLSLSLG K (SEQ ID NO: 64) |

TABLE 8-continued

Bispecific IL2RB x IL2RG Antibodies, Full Length Polypeptide Sequence Combinations

| Family ID No. Combination | Polypeptide Name | Full Length Sequences |
|---|---|---|
| | IL2RG_F16B IgG4 knob | QVQLVESGGGLVKPGGSLRLSCAASGFTFSDYYMSWIR QAPGKGLEWVSYISSSGSTIYYADSVKGRFTISRDNAKN SLYLQMNSLRAEDTAVYYCARGDAVSITGDYRGQGTL VTVSSESKYGPPCPPCPAPEAAGGPSVFLFPPKPKDTLMI SRTPEVTCVVVDVSQEDPEVQFNWYVDGVEVHNAKTK PREEQFNSTYRVVSVLTVLHQDWLNGKEYKCKVSNKG LPSSIEKTISKAKGQPREPQVYTLPPSQEEMTKNQVSLW CLVKGFYPSDIAVEWESNGQPENNYKTTPPVLDSDGSFF LYSRLTVDKSRWQEGNVFSCSVMHEALHNHYTQKSLSL SLGK (SEQ ID NO: 65) |
| IL2RB_F18E hole ** IL2RG_F16A knob | IL2RB_F18E IgG4 hole | QVQLVESGGGVVQPGRSLRLSCAASGFTFSSYGMHWVR QAPGKEREWVAVISYDGSNKYYTDSVKGRFTISRDNSK NTLYLEMNSLRAEDTAVYYCARDLDYDVLTGDPVGGF DIWGQGTLVTVSSESKYGPPCPPCPAPEAAGGPSVFLFPP KPKDTLMISRTPEVTCVVVDVSQEDPEVQFNWYVDGVE VHNAKTKPREEQFNSTYRVVSVLTVLHQDWLNGKEYK CKVSNKGLPSSIEKTISKAKGQPREPQVYTLPPSQEEMTK NQVSLSCAVKGFYPSDIAVEWESNGQPENNYKTTPPVL DSDGSFFLVSRLTVDKSRWQEGNVFSCSVMHEALHNHY TQKSLSLSLGK (SEQ ID NO: 66) |
| | IL2RG_F16A IgG4 knob | QVQLVESGGGLVKPGGSLRLSCAASGFTFSDYYMSWIR QAPGKGLEWVSSISSSGDTIYYADSVQGRFTLSRDNAEN SLFLQMNSLRAEDTAVYYCARGDAVSITGDYRGQGTLV TVSSESKYGPPCPPCPAPEAAGGPSVFLFPPKPKDTLMIS RTPEVTCVVVDVSQEDPEVQFNWYVDGVEVHNAKTKP REEQFNSTYRVVSVLTVLHQDWLNGKEYKCKVSNKGL PSSIEKTISKAKGQPREPQVYTLPPSQEEMTKNQVSLWC LVKGFYPSDIAVEWESNGQPENNYKTTPPVLDSDGSFFL YSRLTVDKSRWQEGNVFSCSVMHEALHNHYTQKSLSLS LGK (SEQ ID NO: 67) |
| IL2RB_F09G hole ** IL2RG_F16C knob | IL2RB_F09G IgG4 hole | QVQLQESGPGLVKSSETLSLTCTVSGGSISSSDWWSWVR QPPGKGLEWIGEIDHSGSTNYNPSLMSRVTISVDKSKNQ FSLKLSSVTAADTAVYFCARGSWELTDAFDIRGQGTLVT VSSESKYGPPCPPCPAPEAAGGPSVFLFPPKPKDTLMISR TPEVTCVVVDVSQEDPEVQFNWYVDGVEVHNAKTKPR EEQFNSTYRVVSVLTVLHQDWLNGKEYKCKVSNKGLPS SIEKTISKAKGQPREPQVYTLPPSQEEMTKNQVSLSCAV KGFYPSDIAVEWESNGQPENNYKTTPPVLDSDGSFFLVS RLTVDKSRWQEGNVFSCSVMHEALHNHYTQKSLSLSLG K (SEQ ID NO: 34) |
| | IL2RG_F16C IgG4 knob | QVQLVESGGGLVKPGGSLRLSCAASGFTFNDYYMSWIR QAPGKGLEWVSHISSSGSTIYYADSVKGRFTVSRDNANN SLYLQMHSLRAEDTAVYYCARGDAVSITGDYRGQGTL VTVSSESKYGPPCPPCPAPEAAGGPSVFLFPPKPKDTLMI SRTPEVTCVVVDVSQEDPEVQFNWYVDGVEVHNAKTK PREEQFNSTYRVVSVLTVLHQDWLNGKEYKCKVSNKG LPSSIEKTISKAKGQPREPQVYTLPPSQEEMTKNQVSLW CLVKGFYPSDIAVEWESNGQPENNYKTTPPVLDSDGSFF LYSRLTVDKSRWQEGNVFSCSVMHEALHNHYTQKSLSL SLGK (SEQ ID NO: 35) |
| IL2RB_F09G hole ** IL2RG_F18A knob | IL2RB_F09G IgG4 hole | QVQLQESGPGLVKSSETLSLTCTVSGGSISSSDWWSWVR QPPGKGLEWIGEIDHSGSTNYNPSLMSRVTISVDKSKNQ FSLKLSSVTAADTAVYFCARGSWELTDAFDIRGQGTLVT VSSESKYGPPCPPCPAPEAAGGPSVFLFPPKPKDTLMISR TPEVTCVVVDVSQEDPEVQFNWYVDGVEVHNAKTKPR EEQFNSTYRVVSVLTVLHQDWLNGKEYKCKVSNKGLPS SIEKTISKAKGQPREPQVYTLPPSQEEMTKNQVSLSCAV KGFYPSDIAVEWESNGQPENNYKTTPPVLDSDGSFFLVS RLTVDKSRWQEGNVFSCSVMHEALHNHYTQKSLSLSLG K (SEQ ID NO: 36) |
| | IL2RG_F18A IgG4 knob | QVQLVESGGDLVKPGGSLRLSCAASGFTFSDYYMSWLR QAPGKELEWVSHISSSGTTTYYADSVEGRFTITRDNAKN SLYLQMNSLRAEDTAVYYCARGAAVAPGFDSRGQGTL VTVSSESKYGPPCPPCPAPEAAGGPSVFLFPPKPKDTLMI SRTPEVTCVVVDVSQEDPEVQFNWYVDGVEVHNAKTK PREEQFNSTYRVVSVLTVLHQDWLNGKEYKCKVSNKG LPSSIEKTISKAKGQPREPQVYTLPPSQEEMTKNQVSLW CLVKGFYPSDIAVEWESNGQPENNYKTTPPVLDSDGSFF LYSRLTVDKSRWQEGNVFSCSVMHEALHNHYTQKSLSL SLGK (SEQ ID NO: 37) |

Additional sequences referred to herein are provided in Tables 9 and 10 for reference.

cells, where internalization is at least about 10%, at least about 20%, at least about 30%, at least about 40%, at least

TABLE 9

Additional Sequences

| Protein Name | UniProt KB No. | Amino Acid Sequence |
|---|---|---|
| Human IL2RA | P01589 | MDSYLLMWGLLTFIMVPGCQAELCDDDPPEIPHATFKAMAY KEGTMLNCECKRGFRRIKSGSLYMLCTGNSSHSSWDNQCQC TSSATRNTTKQVTPQPEEQKERKTTEMQSPMQPVDQASLPG HCREPPPWENEATERIYHFVVGQMVYYQCVQGYRALHRGP AESVCKMTHGKTRWTQPQLICTGEMETSQFPGEEKPQASPE GRPESETSCLVTTTDFQIQTEMAATMETSIFTTEYQVAVAGC VFLLISVLLLSGLTWQRRQRKSRRTI (SEQ ID NO: 38) |
| Human IL2RB | P14784 | MAAPALSWRLPLLILLLPLATSWASAAVNGTSQFTCFYNSRA NISCVWSQDGALQDTSCQVHAWPDRRRWNQTCELLPVSQA SWACNLILGAPDSQKLTTVDIVTLRVLCREGVRWRVMAIQD FKPFENLRLMAPISLQVVHVETHRCNISWEISQASHYFERHLE FEARTLSPGHTWEEAPLLTLKQKQEWICLETLTPDTQYEFQV RVKPLQGEFTTWSPWSQPLAFRTKPAALGKDTIPWLGHLLV GLSGAFGFIILVYLLINCRNTGPWLKKVLKCNTPDPSKFFSQL SSEHGGDVQKWLSSPFPSSSFSPGGLAPEISPLEVLERDKVTQ LLLQQDKVPEPASLSSNHSLTSCFTNQGYFFFHLPDALEIEAC QVYFTYDPYSEEDPDEGVAGAPTGSSPQPLQPLSGEDDAYCT FPSRDDLLLFSPSLLGGPSPPSTAPGGSGAGEERMPPSLQERV PRDWDPQPLGPPTPGVPDLVDFQPPPELVLREAGEEVPDAGP REGVSFPWSRPPGQGEFRALNARLPLNTDAYLSLQELQGQDP THLV (SEQ ID NO: 39) |
| Human IL2RG | P31785 | MLKPSLPFTSLLFLQLPLLGVGLNTTILTPNGNEDTTADFFLT TMPTDSLSVSTLPLPEVQCFVFNVEYMNCTWNSSSEPQPTNL TLHYWYKNSDNDKVQKCSHYLFSEEITSGCQLQKKEIHLYQ TFVVQLQDPREPRRQATQMLKLQNLVIPWAPENLTLHKLSES QLELNWNNRFLNHCLEHLVQYRTDWDHSWTEQSVDYRHKF SLPSVDGQKRYTFRVRSRFNPLCGSAQHWSEWSHPIHWGSN TSKENPFLFALEAVVISVGSMGLIISLLCVYFWLERTMPRIPTL KNLEDLVTEYHGNFSAWSGVSKGLAESLQPDYSERLCLVSEI PPKGGALGEGPGASPCNQHSPYWAPPCYTLKPET (SEQ ID NO: 40) |
| Human IL2 | P60568 | MYRMQLLSCIALSLALVTNSAPTSSSTKKTQLQLEHLLLDLQ MILNGINNYKNPKLTRMLTFKFYMPKKATELKHLQCLEEEL KPLEEVLNLAQSKNFHLRPRDLISNINVIVLELKGSETTFMCE YADETATIVEFLNRWITFCQSIISTLT (SEQ ID NO: 41) |

TABLE 10

Additional Sequences

| Protein Name | Amino Acid Sequence |
|---|---|
| Fixed light chain, CDR1 sequence | QSVSSN (SEQ ID NO: 44) |
| Fixed light chain, CDR2 sequence | GAS (SEQ ID NO: 45) |
| Fixed light chain, CDR3 sequence | QQYNNWPWT (SEQ ID NO: 46) |
| Fixed light chain, VL sequence | EIVMTQSPATLSVSPGERATLSCRASQSVSSNLAWYQQKPGQAPRLL IYGASTRATGIPARFSGSGSGTEFTLTISSLQSEDFAVYYCQQYNNWP WTFGQGTKVEIK (SEQ ID NO: 47) |
| Fixed light chain, full length sequence (VL + CL) | EIVMTQSPATLSVSPGERATLSCRASQSVSSNLAWYQQKPGQAPRLL IYGASTRATGIPARFSGSGSGTEFTLTISSLQSEDFAVYYCQQYNNWP WTFGQGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC (SEQ ID NO: 48) |

Cellular Internalization

In some embodiments, the antibodies of the disclosure, once bound to a binding target (e.g., IL2R), internalize into about 50%, at least about 60%, at least about 70%, at least about 80%, or at least about 90%, at least about 100%, at least about 110%, at least about 120%, at least about 130%, at least about 140%, at least about 150%, at least about 160%, at least about 170%, at least about 180%, at least about 190%, or at least about 200% or more, in comparison to one or more control antibodies that do not internalize. In some embodiments, aspects of the methods described herein involve internalizing an antibody as described herein within a cell to achieve a desired effect, e.g., to act as an IL2R agonist.

Figure 7A:
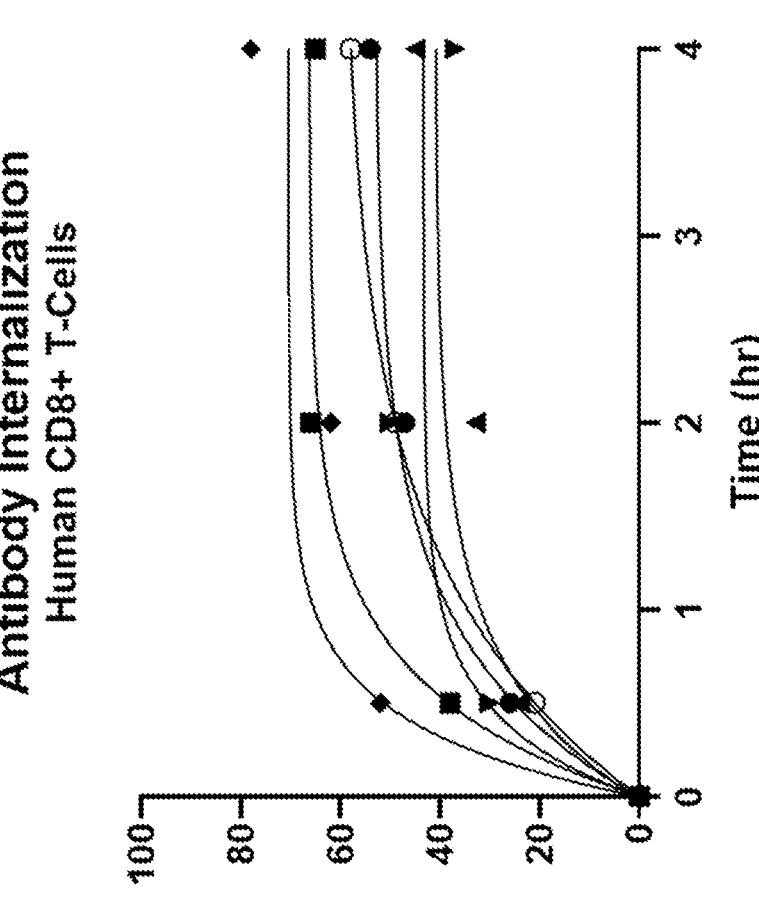

Cellular internalization results are provided in FIG. 7A and FIG. 7B. FIG. 7A depicts internalization of the indicated anti-IL2Rβ/γ UniAbs™ by CD8⁺ T-cells from human PBMCs, as a function of time. FIG. 7B depicts this data in tabular format. Surface levels of UniAb™ were detected by flow cytometry and reported relative to cells which had not been allowed to internalize. The observed half-lives ranged from 0.27 hours to 0.81 hours. As observed here, internalization was potentially partially dependent on the specific anti-IL2RG arm of the bispecific antibody, as molecules comprising the IL2RG_F16B binding sequence internalized faster, and to a greater degree, than molecules containing different anti-IL2RG binding sequences.

Preparation of Anti-IL2R Antibodies

The antibodies of the present disclosure can be prepared by methods known in the art. In some embodiments, the antibodies herein are produced by transgenic animals, including transgenic mice and rats, e.g., transgenic rats, in which the endogenous immunoglobulin genes are knocked out or disabled. In some embodiments, the heavy chain antibodies herein are produced in a UniRat™. UniRat™ have their endogenous immunoglobulin genes silenced and use a human immunoglobulin heavy-chain translocus to express a diverse, naturally optimized repertoire of fully human HCAbs. While endogenous immunoglobulin loci in rats can be knocked out or silenced using a variety of technologies, in UniRat™ the zinc-finger (endo)nuclease (ZNF) technology was used to inactivate the endogenous rat heavy chain J-locus, light chain Cκ locus and light chain C locus. ZNF constructs for microinjection into oocytes can produce IgH and IgL knock out (KO) lines. For details, see, e.g., Geurts et al., 2009, *Science* 325:433. Characterization of Ig heavy chain knockout rats has been reported by Menoret et al., 2010, *Eur. J. Immunol.* 40:2932-2941. Advantages of the ZNF technology are that non-homologous end joining to silence a gene or locus via deletions up to several kb can also provide a target site for homologous integration (Cui et al., 2011, *Nat Biotechnol* 29:64-67). Human heavy chain antibodies produced in UniRat™ are called UniAbs™ and can bind epitopes that cannot be attacked with conventional antibodies. Their high specificity, affinity, and small size make them ideal for mono- and poly-specific applications.

In addition to UniAbs™, specifically included herein are heavy chain-only antibodies lacking the camelid VHH framework and mutations, and their functional VH regions. Such heavy chain-only antibodies can, for example, be produced in transgenic rats or mice which comprise fully human heavy chain-only gene loci as described, e.g., in WO2006/008548, but other transgenic mammals, such as rabbit, guinea pig, and rat can also be used. Heavy chain-only antibodies, including their VHH or VH functional fragments, can also be produced by recombinant DNA technology, by expression of the encoding nucleic acid in a suitable eukaryotic or prokaryotic host, including, for example, mammalian cells (e.g., CHO cells), *E. coli*, or yeast.

Domains of heavy chain-only antibodies combine advantages of antibodies and small molecule drugs: can be monoor multi-valent; have low toxicity; and are cost-effective to manufacture. Due to their small size, these domains are easy to administer, including oral or topical administration, are characterized by high stability, including gastrointestinal stability; and their half-life can be tailored to the desired use or indication. In addition, VH and VHH domains of HCAbs can be manufactured in a cost-effective manner.

In a particular embodiment, the heavy chain antibodies of the present disclosure, including UniAbs™, have the native amino acid residue at the first position of the FR4 region (amino acid position 101 according to the Kabat numbering system), substituted by another amino acid residue, which is capable of disrupting a surface-exposed hydrophobic patch comprising or associated with the native amino acid residue at that position. Such hydrophobic patches are normally buried in the interface with the antibody light chain constant region but become surface exposed in HCAbs and are, at least partially, for the unwanted aggregation and light chain association of HCAbs. In some embodiments, the substituted amino acid residue is charged. In some embodiments, the substituted amino acid residue is positively charged, such as lysine (Lys, K), arginine (Arg, R) or histidine (His, H), e.g., arginine (R). In some embodiments, the heavy chain-only antibodies derived from the transgenic animals contain a Trp to Arg mutation at position 101. In some embodiments, the resultant HCAbs have high antigen-binding affinity and solubility under physiological conditions in the absence of aggregation.

As part of the present disclosure, human IgG anti-IL2R heavy chain antibodies with unique sequences from Uni-Rat™ animals (UniAb™) were identified that bind to human IL2R in ELISA protein and cell-binding assays. The identified heavy chain variable region (VH) sequences are positive for human IL2R protein binding and/or for binding to IL2R+ cells, and are all negative for binding to cells that do not express IL2R.

Heavy chain antibodies binding to non-overlapping epitopes on an IL2R protein, e.g., UniAbs™ can be identified by competition binding assays, such as enzyme-linked immunoassays (ELISA assays) or flow cytometric competitive binding assays. For example, one can use competition between known antibodies binding to the target antigen and the antibody of interest. By using this approach, one can divide a set of antibodies into those that compete with the reference antibody and those that do not. The non-competing antibodies are identified as binding to a distinct epitope that does not overlap with the epitope bound by the reference antibody. Often, one antibody is immobilized, the antigen is bound, and a second, labeled (e.g., biotinylated) antibody is tested in an ELISA assay for ability to bind the captured antigen. This can be performed also by using surface plasmon resonance (SPR) platforms, including ProteOn XPR36 (BioRad, Inc), Biacore 2000 and Biacore T200 (GE Healthcare Life Sciences), and MX96 SPR imager (Ibis technologies B.V.), as well as on biolayer interferometry platforms, such as Octet Red384 and Octet HTX (ForteBio, Pall Inc). For further details, see the Examples herein.

Typically, an antibody "competes" with a reference antibody if it causes about 15-100% reduction in the binding of the reference antibody to the target antigen, as determined by standard techniques, such as by the competition binding assays described above. In some embodiments, competitive binding is measured using an enzyme-linked immunoassay (ELISA assay). In some embodiments, one antibody is immobilized, the antigen is bound, and a second, labeled (e.g., biotinylated) antibody is tested in an ELISA assay for ability to bind the captured antigen. This can be performed, for example, using a surface plasmon resonance (SPR) platform, such as, for example, ProteOn XPR36 (BioRad, Inc), Biacore 2000 and Biacore T200 (GE Healthcare Life Sciences), and MX96 SPR imager (Ibis technologies B.V.), as well as on biolayer interferometry platforms, such as Octet Red384 and Octet HTX (ForteBio, Pall Inc). In some embodiments, competitive binding is measured using a flow cytometric competitive binding assay.

In various embodiments, the relative inhibition is at least about 15%, at least about 20%, at least about 25%, at least about 30%, at least about 35%, at least about 40%, at least about 45%, at least about 50% at least about 55%, at least about 60%, at least about 65%, at least about 70%, at least about 75%, at least about 80%, at least about 85%, at least about 90%, at least about 95% or higher.

Pharmaceutical Compositions

It is another aspect of the present disclosure to provide pharmaceutical compositions comprising one or more antibodies of the present disclosure in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

In one embodiment, a pharmaceutical composition comprises a heavy chain antibody (e.g., UniAb™) that binds to IL2R. In another embodiment, a pharmaceutical composition comprises a multi-specific (including bispecific) heavy chain antibody (e.g., UniAb™) that binds to two or more non-overlapping epitopes on an IL2R protein (e.g., a first epitope on a first IL2R polypeptide chain (e.g., IL2RB) and a second epitope on a second IL2R polypeptide chain (e.g., IL2RG). In some embodiments, a pharmaceutical composition comprises a multi-specific (including bispecific) heavy chain antibody (e.g., UniAb™) that binds to IL2RB and IL2RG.

Pharmaceutical compositions of the antibodies used in accordance with the present disclosure are prepared for storage by mixing proteins having the desired degree of purity with optional pharmaceutically acceptable carriers, excipients or stabilizers (see, e.g. Remington's Pharmaceutical Sciences 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG). In some embodiments, pharmaceutical compositions for parenteral administration are sterile and substantially isotonic and manufactured under Good Manufacturing Practice (GMP) conditions. Pharmaceutical compositions can be provided in unit dosage form (i.e., the dosage for a single administration). The formulation depends on the route of administration chosen. The antibodies herein can be administered by intravenous injection or infusion or subcutaneously. For injection administration, the antibodies herein can be formulated in aqueous solutions, e.g., in physiologically-compatible buffers to reduce discomfort at the site of injection. The solution can contain carriers, excipients, or stabilizers as discussed above. Alternatively, antibodies can be in lyophilized form for constitution with a suitable vehicle, e.g., sterile pyrogen-free water, before use.

Antibody formulations are disclosed, for example, in U.S. Pat. No. 9,034,324. Similar formulations can be used for the heavy chain antibodies, including UniAbs™, of the present disclosure. Subcutaneous antibody formulations are described, for example, in US20160355591 and US20160166689.

Methods of Use

The anti-IL2R antibodies and pharmaceutical compositions described herein can be used for the treatment of diseases and conditions that are mediated by activation of IL2R signaling in immune cells, such as immune effector cells, such as effector T and natural killer (NK) cells. In some embodiments, the disease or condition can be an infectious disease, an autoimmune disorder (e.g., Crohn's disease, Multiple Sclerosis), a cancer, an inflammatory disease (e.g., arthritis), a disease or disorder associated with deficient IL-2-mediated signaling, deficient T cell proliferation, or T cell dysfunction.

In some embodiments, a disease or disorder is one in which increased IL-2-mediated signaling is therapeutic to the patient. In some embodiments, a disease or disorder is associated with a deficient T cell response, e.g., a deficient CD8+ T cell response.

In some embodiments, a treatment is aimed at preventing or treating a disease or disorder by: increasing the number of CD3+ T cells, increasing the number of CD4+ T cells, increasing the number of CD8+ T cells, increasing the number of CD8+ effector T cells (e.g., CTLs), increasing the number NK cells, increasing the ratio of CD8+ T cells to CD4+ T cells, decreasing the proportion of Tregs, or any combination thereof.

In some embodiments, a disease or disorder can manifest as an infection, or as an inability to mount an effective immune response against an infection. The infection may be chronic, persistent, latent, or slow, and may be the result of bacterial, viral, fungal, or parasitic infection. As such, treatment may be provided to patients having a bacterial, viral, or fungal infection. Non-limiting examples of bacterial infections include infection with *Helicobacter pylori*. Non-limiting examples of viral infections include infection with EBV, HIV, hepatitis B or hepatitis C.

In some embodiments, a disease or disorder can be associated with a cancer, such as, e.g., tumor immune escape. Many human tumors express tumor-associated antigens recognised by T cells and capable of inducing an immune response. Cancers may also be treated where there is no indication of a T-cell dysfunctional disorder, but the use of an antibody described herein promotes an effective immune response.

In some embodiments, a treatment is aimed at prevention of a disease or disorder associated with deficient and/or reduced IL-2-mediated signaling. As such, the antibodies described herein can be used to formulate pharmaceutical compositions or medicaments, and subjects may be prophylactically treated against development of a disease state. This may take place before the onset of symptoms of the disease state, and/or such treatment can be given to subjects considered to be at greater risk of the disease or disorder.

In certain embodiments, the methods herein involve inducing activation of immune effector cells without preferentially activating regulatory T-cells (Tregs). Without being held to theory, the inventors have discovered that multispecific antibodies that simultaneously target both the beta and gamma subunits of the IL2 receptor to induce activation (i.e., act as agonists) of IL2R signaling in human immune effector cells without preferentially activating Tregs, shifting the balance to the activation of T-effector and NK cells, lead to improved treatment outcomes in diseases and disorders that are mediated by activation of IL2R signaling.

Accordingly, aspects of the disclosure include methods of treatment wherein a subject's immune response is boosted or aided by administering a therapeutically effective amount of the one or more of the antibodies described herein. In some embodiments, the methods involve administering an antibody described herein to achieve an immune response that destroys cancerous cells. In certain embodiments, the antibodies described herein act as agonists of the IL2R signaling pathway to achieve such results. Methods in accordance with embodiments of the disclosure also include combination therapy, wherein a subject is administered an antibody as described herein, in conjunction with another course of therapy, e.g., a chemotherapy regimen.

In one aspect, a multispecific (e.g., bispecific) antibody as described herein, having agonist activity for the IL2R signaling pathway, is used for treating cancer. Cancers that are amenable to such treatment include, but are not limited to, advanced or metastatic cancers. In some embodiments, a cancer is a solid tumor cancer. Solid tumor cancers in accordance with embodiments of the disclosure include, but are not limited to, renal cell carcinoma, melanoma, urothelial cancer, triple negative breast cancer, non-small cell lung cancer (NSCLC), colorectal cancer, sarcoma, squamous cell carcinoma of the head and neck, and metastatic castration-resistant prostate cancer.

Aspects of the disclosure also include methods for stimulating IL2R signaling in an immune cell, wherein the methods involve contacting the immune cell with an antibody as described herein (e.g., with an agonistic bispecific antibody as described herein). In certain embodiments, the methods involve stimulating an IL2RB/IL2RG dimeric receptor complex on an immune cell by contacting the immune cell with a multispecific (e.g., bispecific) antibody that binds to both IL2RB and IL2RG, and acts as an agonist of the IL2R complex. Any of a variety of immune cells that express IL2R can be involved in the subject methods, including, but not limited to: CD4+ T-cells, CD8+ T-cells, and Natural Killer (NK) cells.

Effective doses of the compositions of the present disclosure for the treatment of disease vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g., companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage the agent may range from about 0.0001 to 100 mg/kg, and more usually 0.01 to 5 mg/kg, of the host body weight. For example, dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present disclosure are usually administered on multiple occasions. Intervals between single dosages can be weekly, monthly, or yearly. Intervals can also be irregular as indicated by measuring blood levels of the therapeutic entity in the patient. Alternatively, therapeutic entities of the present disclosure can be administered as a sustained release formulation, in which case less frequent administration is required. Dosage and frequency vary depending on the half-life of the polypeptide in the patient.

Typically, compositions are prepared as injectables, either as liquid solutions or suspensions; solid forms suitable for solution in, or suspension in, liquid vehicles prior to injection can also be prepared. The pharmaceutical compositions herein are suitable for intravenous or subcutaneous administration, directly or after reconstitution of solid (e.g., lyophilized) compositions. The preparation also can be emulsified or encapsulated in liposomes or micro particles such as polylactide, polyglycolide, or copolymer for enhanced adjuvant effect, as discussed above. Langer, *Science* 249: 1527, 1990 and Hanes, *Advanced Drug Delivery Reviews* 28: 97-119, 1997. The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the antibodies and antibody structures described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in humans. In some embodiments, the dosage of the antibodies described herein lies within a range of circulating concentrations that include the effective dose with little or no toxicity. The dosage can vary within this range depending upon the dosage form employed and the route of administration utilized. The exact formulation, route of administration, and dosage can be chosen by the individual physician in view of the patient's condition.

The compositions for administration will commonly comprise an antibody or other ablative agent dissolved in a pharmaceutically acceptable carrier, e.g., an aqueous carrier. A variety of aqueous carriers can be used, e.g., buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents, and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the disclosure are kits comprising the active agents and formulations thereof, of the disclosure and instructions for use. The kit can further contain a least one additional reagent, e.g., a chemotherapeutic drug, etc. Kits typically include a label indicating the intended use of the contents of the kit. The term "label" as used herein includes any writing, or recorded material supplied on or with a kit, or which otherwise accompanies a kit Example embodiments now being fully described, it will be apparent to one of ordinary skill in the art that various changes and modifications can be made without departing from the spirit or scope of the disclosure.

EXAMPLES

Materials and Methods

Antibody Construct Names

The following table (Table 11) provides shorthand nomenclature for six bispecific antibody constructs evaluated herein:

TABLE 11

| Shorthand Nomenclature | |
| --- | --- |
| Shorthand Name | Sequence Name |
| BsAb-1 | IL2RB_F09C**IL2RG_F16A |
| BsAb-2 | IL2RB_F09G**IL2RG_F16B |
| BsAb-3 | IL2RB_F09G**IL2RG_F16C |
| BsAb-4 | IL2RB_F09G**IL2RG_F18A |
| BsAb-5 | IL2RB_F09K**IL2RG_F16B |
| BsAb-6 | IL2RB_F18E**IL2RG_F16A |

Immunizations, Next-Generation Sequencing, Clonotype Analysis and Cloning

Methods essentially as described in Harris et al. *Front Immunol.* 2018 Apr. 24; 9:889(60). In brief, UniRat animals were immunized using standard adjuvants (Complete Freunds or Titermax/Ribi) along with recombinant protein antigens in a 48-day protocol or DNA immunizations. For protein immunizations, boosts consisted of 10 μg of recombinant protein injected into each leg of each animal with the appropriate adjuvant. In the case of DNA immunizations, gold particles were coated with vectors containing cDNA of the target antigen, which were subsequently administered subcutaneously every 7 days, using a gene gun. Plasma samples were collected post-immunization to assess serum titers against the antigen by ELISA.

After approximately 7 weeks (protein antigen) or 10 weeks (DNA antigen) of immunization, draining lymph nodes were harvested and total RNA was isolated. Ig heavy chain sequences were amplified using first strand cDNA synthesis and 5' RACE by PCR, following methods similar to those previously described in Harris et al. *Front Immunol.* 2018 Apr. 24; 9:889 and then purified by gel extraction.

Next-generation sequencing was completed using the MiSeq platform (Illumina) with 2×300 paired-end reads. To enable multiplexing of samples, indexing labels were added by primer extension. Approximately 100,000 paired reads covered each sample, and those that showed alignment of less than 20 nucleotides to a human Ig locus were discarded. Merged forward and reverse reads of VH regions were translated into open reading frames and framework and CDR regions identified by IGBLAST (https://www.ncbi.nlm.nih.gov/igblast/). Clonotypes (defined by CDR3 protein sequences with at least 80% sequence similarity) were determined for samples using agglomerative clustering. CDR3 clonotypes were ranked by the percent of total reads in a sample defined by that clonotype. Those with the greatest abundance were prioritized for high-throughput cloning into an expression vector containing a CH1-deleted human IgG1 Fc region and validated by Sanger sequencing. Plasmids were transformed into *E. coli* grown in LB culture media and then purified to enable transient transfection of HEK 293 cells in 96-well format. Following several days of expression, supernatants containing antibody were harvested and clarified by centrifugation.

High-Throughput ELISA

Methods are essentially as described in Harris et al. *Front Immunol.* 2018 Apr. 24; 9:889. Briefly, recombinant proteins were coated overnight at 4° C. in 96-well plates using BupH Carbonate-Bicarbonate buffer (human IL-2Rβ, Acrobiosystems; cynomolgus IL-2Rβ, Sino Biological). Plates were then washed with TBST (20 mM Tris, 150 mM NaCl, 0.05% Tween-20, pH 7.6) and blocked with blocking buffer (TBST with 1% dry milk powder). HEK 293 supernatants containing antibodies were diluted 1:100 in blocking buffer and added to antigen-coated plates. Detection of bound antibodies was accomplished using an HRP-labeled anti-human Ig secondary antibody together with chemiluminescent substrate.

Luminescence was quantified (SpectraMax i3X, Molecular devices) and the signal for each well was normalized by dividing by the average background luminescence of antigen-coated wells that had been incubated with supernatant from untransfected HEK 293 cells.

Cell Lines and PBMCs

M07e cells were obtained from DSMZ and were grown in RPMI medium containing 10% Fetal Bovine Serum (FBS), 1% Penicillin/Streptomycin, and 10 ng/mL rhGM-CSF. HSC-F cells were obtained from The Nonhuman Primate Reagent Resource and cultured in RPMI medium supplemented with 20% FBS, 1% Penicillin/Streptomycin and 55 M β-Mercaptoethanol. 293-F were obtained from Gibco and grown according to their recommendations.

For creating stable cell lines expressing human IL-2Rβ or cynomolgus IL-2Rβ, expression constructs carried the full-length cDNA for the antigen and a NeoR selection cassette. Each expression construct was then linearized and used to electroporate CHO cells. Three days after transfection, cells were put under selection for 3-6 weeks using Geneticin treatments. At the end of the selection period, all untransfected and negative control cell lines were killed, while all transfected pools showed regrowth as expected for successfully transfected pools. Four pools of each target were then assayed by flow cytometry for binding to a positive control antibody. The culture media for the CHO cells was EX-CELL® 325 PF CHO media containing 8 mM L-glutamine, 0.1 µg/L IGF-1, 5% dialyzed FBS, 0.45 mg/mL geneticin, and 0.45 mg/mL hygromycin. The cells were grown in suspension and maintained at a concentration between 0.5× $10^6$/mL to 2×$10^6$/mL.

Human PBMCs were isolated in-house from fresh leukapheresis packs (StemCell) by Ficoll® Paque Premium (GE Healthcare Life Sciences) density gradient centrifugation.

Cell Binding by Flow Cytometry

All washes and dilutions of cells, antibodies, and reagents were performed using flow buffer (1×PBS, 1% BSA, 0.1% NaN3, pH 7.4). Staining was performed in a round-bottom 96-well plate (Corning) seeded at 100,000 cells/well and all incubations were performed at 4° C. or on ice. For primary and secondary screens, the cells were incubated for 30 minutes with pre-diluted test antibodies (secondary screen and dose-curves) or 1:5 diluted HEK 293 supernatants containing antibodies (for primary screens and diversity screens) in a total volume of 50 µL. The cells were washed twice with 200 µL flow buffer. The cells were then incubated for 30 minutes with detection antibody (Goat F(ab')2 Anti-Human IgG-PE, Southern Biotech) at 0.625 µg/mL in flow buffer. Following 2 more washes, the cells were resuspended in a final volume of 150 µL of flow buffer. The cells were analyzed on a BD FACSCelesta or a Guava easyCyte 8-HT flow cytometer. At least 3000 events were collected, and PE geometric mean fluorescence intensity was plotted as a fold over background (cells incubated with secondary detection antibody only). In some secondary screens involving human or cynomolgus PBMCs, an additional CD4 antibody (BioLegend) and/or CD8 antibody (BioLegend) was included to further characterize cell binding.

pSTAT5 Detection by Flow Cytometry

For detection of pSTAT5 by flow cytometry, PBMCs were prepared from either frozen whole blood (cynomolgus) or frozen LeukoPak (human). Cells were thawed, washed twice with complete RPMI medium and resuspended at 5×$10^6$ cells/mL. 100 µL/well of these cells was then transferred to a sterile, round-bottom, 96-well plate (Corning) and sealed with an AeraSeal™ (Excel Scientific). The plate was then incubated at 37° C. and 5% $CO_2$ for 1 hour. After the incubation, 100 µL of pre-diluted antibodies (or IL-2/IL-2 variant) was added to the appropriate wells. A final concentration of 10 nM IL-2 (R&D Systems) was used in control wells to ensure detectable pSTAT5. The plate was then resealed and returned to the incubator for an additional 1 hour. After the incubation, the cells were centrifuged and washed twice with PBS pre-chilled to 4° C. The cells were then blocked with Human TruStain FcX (BioLegend) and then subsequently stained for 30 minutes with Fixable Viability Dye (Invitrogen) and antibodies against CD3, CD4, CD8, CD25, and/or CD56. After staining, the cells were again centrifuged and washed twice with pre-chilled PBS. The cells were then fixed with the addition of 200 µL/well Fixation Buffer (BioLegend) and incubated at room temp for 30 minutes. After fixation, the cells were centrifuged and washed twice with Flow Buffer (1×PBS, 1% BSA, 0.1% $NaN_3$, pH 7.4). Next, the cells were permeabilized by resuspending in 200 µL/well True-Phos buffer (BioLegend) pre-chilled to −20° C. and transferred to a −20° C. freezer overnight. The following morning, the cells were centrifuged, washed twice with flow buffer, and subsequently stained for 30 minutes with anti-pSTAT5 (BD Biosciences). After two additional washes, the cells were resuspended in 125 µL/well flow buffer and acquired on a BD FACSCelesta.

Ki67 Detection by Flow Cytometry

For detection of Ki67 by flow cytometry, frozen human PBMCs (previously isolated in-house from a LeukoPak) were thawed and rested overnight in complete RPMI medium at 1×$10^6$ cells/mL. The morning of the assay, the PBMCs were washed with complete RPMI and resuspended at 1e6 cells/mL. Then, to each well of a sterile 96-well plate, 100 µL of PBMCs, 50 µL of 0.16×ImmunoCult (StemCellTech), and 50 µL of diluted antibody or rhIL-2 (R&D Systems) was added. 0.5×ImmunoCult was used for staining controls to ensure detectable Ki67 and CD25 signal for compensation. The plate was then covered and incubated at 37° C. and 5% $CO_2$. After 3 days, the media was refreshed with 100 µL/well of the corresponding concentration antibody and ImmunoCult and then returned to the incubator. After 3 more days (6 days total), the cells were centrifuged and washed twice with PBS pre-chilled to 4° C. The cells were then blocked with Human TruStain FcX (BioLegend) and then subsequently stained for 30 minutes with Fixable Viability Dye (Invitrogen) and antibodies against CD3, CD4, CD8, CD25, and/or CD56. After staining, the cells were again centrifuged and washed twice with pre-chilled PBS. The cells were then fixed and permeabilized for 1 hour with 200 µL/well FoxP3/Transcription Factor Staining Buffer working solution (Invitrogen). After permeabilization, the cells were centrifuged, washed twice with permeabilization buffer, and subsequently stained for 30 minutes with anti-FoxP3 (BioLegend) and anti-Ki67 (BioLegend). After two additional washes, the cells were resuspended in 125 µL/well flow buffer and acquired on a BD FACSCelesta.

Whole Blood Cytokine Release Assay

Cytokine secretion was detected using fresh human whole blood (heparinized) obtained from AllCells. The following method was adapted from B. Wolf et al. *Cytokine* 60 (2012) 828-837(61). 12.5 µL of 20× concentrated (diluted in 1×PBS) test article was added to each well of a sterile 96-well round bottom plate. To this, 237.5 µL of fresh, human whole blood was added to each well with minimal pipetting to reduce non-specific activation. The plate was the covered and incubated at 37° C. and 5% $CO_2$ overnight. The following morning, the plate was centrifugated at 1800×g for 10 minutes and then 50 µL of serum was transferred to a 96-well microplate. The serum was then immediately tested by MSD (#K15010K-1 or a custom U-Plex plate) or frozen at −80° C. for later testing.

Mouse Pharmacokinetic (PK) Evaluation

The PK of BsAb-1 and BsAb-2 were each evaluated in 6 male BALB/c mice following a single tail vein injection of 1 mg/kg (n=3*6 groups, Aragen Biosciences, Morgan Hill, CA). Serum samples were collected at selected time points over the course of 14 days post-dose.

The PK of BsAb-5 was evaluated in two groups of nine female BALB/c mice following a single tail vein injection of 1 mg/kg or 10 mg/kg (9 mice per dosing group, CrownBio, San Diego, CA). Serum samples were collected at selected time points over the course of 14 days post-dose.

Mouse Accelerated GVHD Study

Each immune-compromised NSG mouse (8-9 weeks old from Charles River, France) was irradiated with 1.5 Gy on study day −1. Mice were divided into 4 groups (n=5) and 2 independent experiments were conducted using 2 different PBMC donors. On study day 0, each mouse was adoptively transferred IV with 20 million human PBMCs from one of the 2 donors and each mouse was treated with either vehicle control (100 µL), 22 µg rhIL-2 (350,000 UI/mice, Proleukin, Novartis) daily, 1 mg/kg BsAb-1 twice a week or 1 mg/kg BsAb-2 twice a week. GVHD was assessed by measuring weight loss over time in all animals. Animals were euthanized when body weight loss of 20% was observed.

In the second experiment, NSG mice (8-9 weeks old from Charles River, France) were irradiated with 1.5 Gy on study day −1. Mice were divided into 4 groups and 2 independent experiments were conducted using 2 different PBMC donors. On study day 0, each mouse was adoptively transferred IV with 20 million CSFE-labelled human PBMCs from one of the 2 donors and each mouse was treated with either vehicle control (100 μL) (n=7), 22 μg rhIL-2 (350,000 UI/mice) daily (n=6), 1 mg/kg BsAb-1 twice a week (n=6) or 1 mg/kg BsAb-2 twice a week (n=6). All animals were sacrificed on study day 5.

Immunophenotyping of the engrafted PBMCs by flow cytometry was performed on single-cell suspensions prepared from the mouse spleen on the day of sacrifice. The method of detection was largely the same as the above method for Ki67 detection by flow cytometry, but with different panels of antibodies to better distinguish the human PBMCs from the host cells. Cells were surface stained with anti-human CD45, CD3, CD4, CD8, CD25, CD16, CD19, and/or CD69. Following fixation and permeabilization, some of the cells were stained with anti-human FoxP3. The samples were then collected on a flow cytometer and analyzed using FlowJo analysis software.

For BsAb-5, 10 million PBMCs were transferred instead of 20 million, and mice were divided into 3 groups.

Cynomolgus Pharmacodynamic (PD) Study

The PD profiles of BsAb-1 and BsAb-2 were evaluated in twelve 2-4 years old naïve cynomolgus monkeys following a single IV (slow bolus) dose of 0.03, 0.1 or 0.3 mg/kg. Each treatment group contained 1 male and 1 female cynomolgus monkey (Charles River Lab, USA, Reno, NV). Blood samples were collected at selected time points for 21 days after dosing for analyses of hematology, serum chemistry, cytokines, and PD endpoints. After study termination, animals from the study were returned to the general colony. All procedures were approved by CRL IACUC and were performed in compliance with the Animal Welfare Act, the Guide for Care and Use of Laboratory Animals and the Office of Laboratory Animal Welfare.

Cynomolgus Blood Immunophenotyping

A portion of the blood from each collected time point was used for immunophenotyping and quantification by flow cytometry. The method for Ki67 detection by flow cytometry was largely the same as described above, but with a different panel of cyno-reactive antibodies. Cells were surface stained with antibodies against CD3, CD4, CD8, CD20, CD25, and CD159a. After fixation and permeabilization, the cells were stained with antibodies against FoxP3 and Ki67. The samples were then collected on a flow cytometer and analyzed using FlowJo analysis software.

Simultaneously, a portion of each blood sample was transferred to BD TruCount tubes and stained with CD45 for real time quantification of peripheral blood cell absolute counts. The cell subset percentages from the above blood analysis were applied to the total cell numbers from the corresponding TruCount tube.

αIgG4 ELISA

Serum concentrations of BsAb-1 and BsAb-2 in mouse serum were determined using an antigen capture ELISA. All washes and dilutions were performed with freshly made TBS-T (Accuris). All volumes should be assumed to be 100 μL/well except for coating, blocking and washing, which are at 200 μL/well. The night before the assay, Nunc Maxi-Sorp™ flat-bottom plates (Invitrogen) were coated with recombinant human IL2Rγ protein diluted to 1 μg/mL in carbonate-bicarbonate buffer (Thermo Scientific) and left at 4° C. The next day, the plates were washed 5 times and then blocked with 1% BSA for 30 minutes. The plates were washed once and then multiple dilutions of the serum samples were added, along with a reference standard. Stocks of known concentration for BsAb-1 and BsAb-2 were used to make the standard curve. After 1 hour at room temp, the plate was washed 8 times and then biotinylated anti-human IgG4-Fc (MABTECH) diluted to 3 μg/mL was added. The plates were incubated at room temp for another 30 minutes and then washed again 8 times. Next, the plates were incubated for 30 minutes with HRP-Streptavidin (Thermo Scientific) diluted 1:4000. Following an additional 8 washes, the plates were incubated in the dark for 6 minutes with room-temperature 1-Step Ultra TMB (Thermo Scientific). The reaction was stopped with 100 μL/well 2 N sulfuric acid. Absorbance was assessed at 450 nm and 570 nm.

Protein Expression and Purification

Monospecific UniAbs were expressed in ExpiCHO cells following the manufacturer's instructions (ThermoFisher A29133, Standard Protocol). Clarified supernatants were harvested on day 7 and purified using Protein A magnetic beads, using the KingFisher Flex Platform (ThermoFisher). Antibodies were eluted in 0.1 M citrate, 0.1 M NaCl, 10% glycerol, 10% sucrose, pH 3.5.

To express bispecific UniAbs, ExpiCHO cells were transfected with two expression vectors (knob and hole vectors, knob vectors contain C-terminal His-tag) and were expressed in the ExpiCHO cells according to manufacturer's instructions using the high titer protocol. Clarified supernatants were harvested and the antibodies were purified by IMAC (Ni Sepharose® Excel, Cytive Life Sciences), using an imidazole gradient for elution. The IL-2Rβγ bispecific UniAbs containing fractions were pooled, concentrated, and further purified on cation exchange to remove any product-related impurities (Mono S® 10/100 GL column (Cytiva Life Sciences)). All antibodies were analyzed by SEC-UPLC and SDS-PAGE to confirm their size and purity.

The cynomolgus IL-2Rγ sequence was obtained from Uniprot.org (UniProt Accession ID: G7Q2Z6,) and the extracellular domain (aa Met1-Asn254) was cloned into a proprietary vector containing the endogenous leader sequence and a C-terminal His-tag. The IL-2Rγ reagent was expressed in ExpiCHO cells, according to the vendors instructions (high titer protocol, ThermoFisher). Cells were harvested on day 8 and supernatant was run on SDS-PAGE (NuPAGE 4-12% Bis Tris Gel) to verify target protein expression. Clarified harvest was purified by IMAC using Ni-Sepharose Excel resin (Cytiva Life Sciences), using an imidazole gradient for elution. The peaks were pooled and quantified using QiaXpert (Qiagen).

The cloning, expression, and purification of mutant IL-2 protein (T3A, F42A, Y45A, L72G, C125A) was completed at Lake Pharma. A C-terminal His-tag was added to enable purification by IMAC using standard procedures and elution with an imidazole gradient.

Octet-Based Off-Rate Measurements

All off-rate measurements were performed on an Octet Qk384 instrument (ForteBio), in 96-well microplates at 25° C. using anti-human IgG Fc capture (AHC, 18-5005) sensors with a shake speed of 1000 rpm. For off-rate determination, the antibodies were loaded on the AHC sensors at 5 g/mL. Following a short baseline in kinetics buffer (0.02% Tween20, 0.1% BSA, 0.05% sodium azide, 1×PBS). Offrate measurements were done for the following: human IL-2Rβ (AcroBiosystems), human IL-2Rγ (Sino Biological), cynomolgus IL-2Rβ (Sino Biological), cynomolgus IL-2Rγ (expressed and purified in house using ExpiCHO expression system followed by Ni-NTA His-tag purification), mouse IL-2Rγ (Sino Biological), mouse IL-2Rβ (Sino Biological), human IL-2Rα (Sino Biological), IL-4R (Sino Biological), IL-7R (Sino Biological), IL-9R (R&D Systems) and IL-21R (Sino Biological). The following antibodies were used as positive controls to verify target binding and reagent quality: anti-human IL-9R (R&D Systems), anti-human IL-21R (R&D Systems), anti-human IL-7R (R&D Systems) and anti-human IL-4Ra (R&D Systems). The loaded sensors were then submerged in wells containing antigen at 100 nM concentration for association step. Dissociation was monitored in kinetics buffer. The capture surfaces were regenerated for 60 s. ForteBio data analysis software was used to fit the data to a 1:1 binding model to extract an association rate and dissociation rate.

Octet-Based Kinetics Measurements

All kinetics measurement experiments were performed on a ForteBio Octet Qk384 instrument using anti-human Fc capture (AHC, 18-5005) sensors. The bispecific UniAbs and antigens were diluted to final concentrations in Kinetics buffer (0.02% Tween20, 0.1% BSA, 0.05% sodium azide, 1×PBS). Kinetics measurements were against the following antigens: human IL-2RB (AcroBiosystems), human IL-2RG (AcroBiosystems), cynomolgus IL-2RB (Sino Biological), cynomolgus IL-2RG (expressed and purified in house using ExpiCHO expression system followed by Ni-NTA his-tag purification). The antibodies were loaded on the AHC sensors at 5 g/mL for maximum loading. Following a short baseline in Kinetics buffer, the sensors were exposed to a series of analyte concentrations (7.8 nM to 500 nM) for association step and background subtraction was used to correct for sensor drifting. Dissociation was monitored in Kinetics buffer. The capture surfaces were regenerated for 60s. All experiments were performed with shaking at 1000 rpm. ForteBio's data analysis software was used to fit the data to a 1:1 binding model to extract an association rate and dissociation rate. The KD was calculated using the ratio kd/ka. Kinetics data for six bispecific antibody constructs is provided in FIG. 1.

Biophysical Characterization Assay (Tm, Tagg)

Tm and Tagg were measured on the UNcle platform. Briefly, 9 µL of each sample was loaded in duplicate in a Uni (UNcle cassette) and run with a thermal ramp from 20° C. to 70° C. at a constant rate of 1° C./min. UNcle Analysis 3.1 software, was used to calculate the Tm of each sample using the first derivative of the barycentric mean (BCM) of the fluorescence intensity. The Tagg for each sample was calculated using the intensity of scattered light at 266 nm.

Thermal Stress and Stability Characterization

Bispecific UniAb molecules were concentrated to 10 mg/mL in 20 mM citrate and 0.1 M NaCl pH 6.2. Presence of high and low molecular weight species (% HMW and % LMW) was determined before and after temperature stress for 1 month at 2-8° C. and 37° C. by SEC on an analytical ThermoFisher UltiMate™ 3000 UPLC.

Example 1: Identification of IL-2Rβγ Bispecific Antibody Combinations with Agonist Activity The activation of the IL-2 receptor complex triggers a signaling cascade that results in the phosphorylation of STAT5 (pSTAT5), translocation of pSTAT5 dimers to the nucleus, and transcription of STAT5-regulated genes (M. Rickert, et al., Science 308, 1477-1480 (2005); G. C. Sim, et al., Cytokine Growth FR 25, 377-390 (2014)). As a primary assay to determine if bispecific antibodies targeting the beta and gamma subunits of IL-2R could induce activation of IL-2R signaling, 5 anti-IL-2Rβ binding arms from unique CDR3 families and 5 anti-IL-2Rγ binding arms from unique CDR3 families were combined to make 25 bispecific UniAbs for conducting an all-by-all screen of agonist activity. The bispecific UniAbs were expressed on a silenced and stabilized human IgG4 Fc (CH1 domain deleted) using knobs-into-holes technology to facilitate heavy-chain heterodimer formation, with a single anti-IL-2Rγ VH on the knob arm and a single anti-IL-2Rβ VH on the hole arm (J. B. B. Ridgway et al., Protein Eng Des Sel 9, 617-621 (1996); S. M. Canfield, et al., J Exp Medicine 173, 1483-1491 (1991); D. Xu et al., Cell Immunol 200, 16-26 (2000); J. W. Bloom et al., Protein Sci 6, 407-415 (1997); M. P. Reddy et al., J Immunol 164, 1925-1933 (2000); A. M. Merchant et al., Nat Biotechnol 16, 677-681 (1998)).

Figures 2A, 2B, 2C:
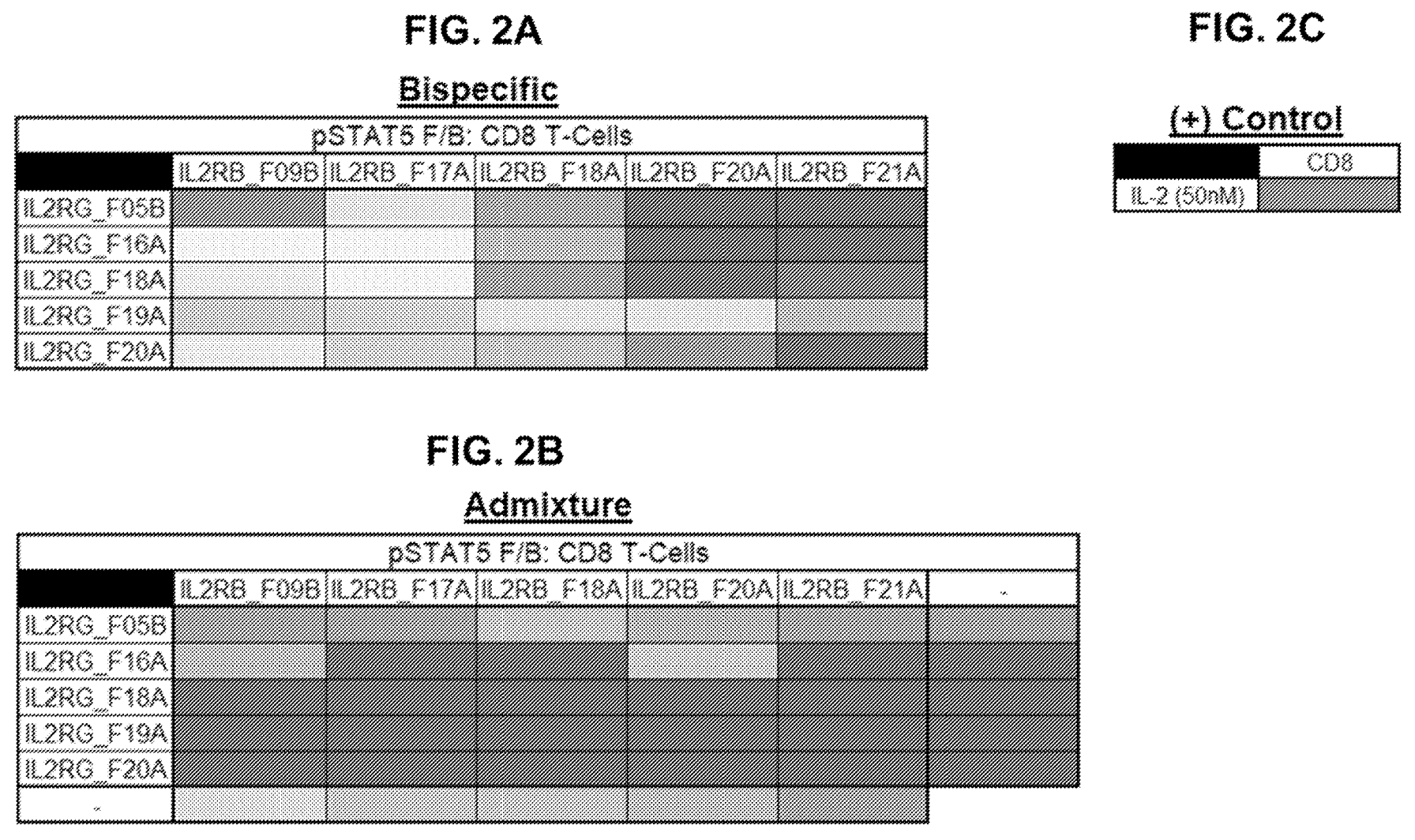

A phospho-flow cytometry assay was used to measure and compare the phosphorylation of STAT5 by the 25 IL-2Rβγ UniAb combinations compared to rhIL-2 on human CD8+ T-cells. STAT5 phosphorylation was not observed with any of the anti-IL-2Rβ or anti-IL-2Rγ monospecific UniAbs. Similarly, STAT5 phosphorylation was also not observed when anti-IL-2Rβ and anti-IL-2Rγ monospecific UniAbs were tested as a mixture in the pSTAT5 assay (FIG. 2B). In contrast, the bispecific UniAbs with one anti-IL-2Rβ arm and one anti-IL-2Rγ arm exhibited varying levels of agonist activity, summarized in FIG. 2A. Interestingly, the ability to induce phosphorylation of STAT5 agonist activity seemed highly dependent on the anti-IL-2Rβ arm present in the bispecific combination, while the degree of agonism appeared to be dependent on the anti-IL-2Rγ arm. Control data is shown in FIG. 2C.

To identify antibodies with a greater range of agonist activity, a secondary diversity screen was initiated to survey other unique VH sequences in 3 of the 4 lead CDR3 clonotype families identified in the bispecific screen for STAT5 activity. These additional VH sequences were selected from the lead CDR3 clonotype families and contain sequence variation in CDR1, CDR2 and framework regions. In total, an additional 157 unique family members underwent a second round of high-throughput gene assembly, expression and were assessed for binding to IL-2R expressing cells. For IL-2Rβ, an additional 33 IL-2Rβ family F09 members and an additional 22 IL-2Rβ family F18 members that bound to human and cynomolgus IL-2Rβ cells were identified in the diversity screen. A further 29 IL-2Rγ family F16 members were identified that bound to human and cynomolgus IL-2Rγ recombinant protein and on cells in the diversity screen. This large and diverse set of novel IL-2R binding UniAbs enabled subsequent efforts to identify a set of lead IL-2Rβγ bispecific combinations with a range of functional activity.

Example 2: In Vitro Characterization of IL-2Rβγ Bispecific UniAbs

Figure 3C:
Figure 3C:
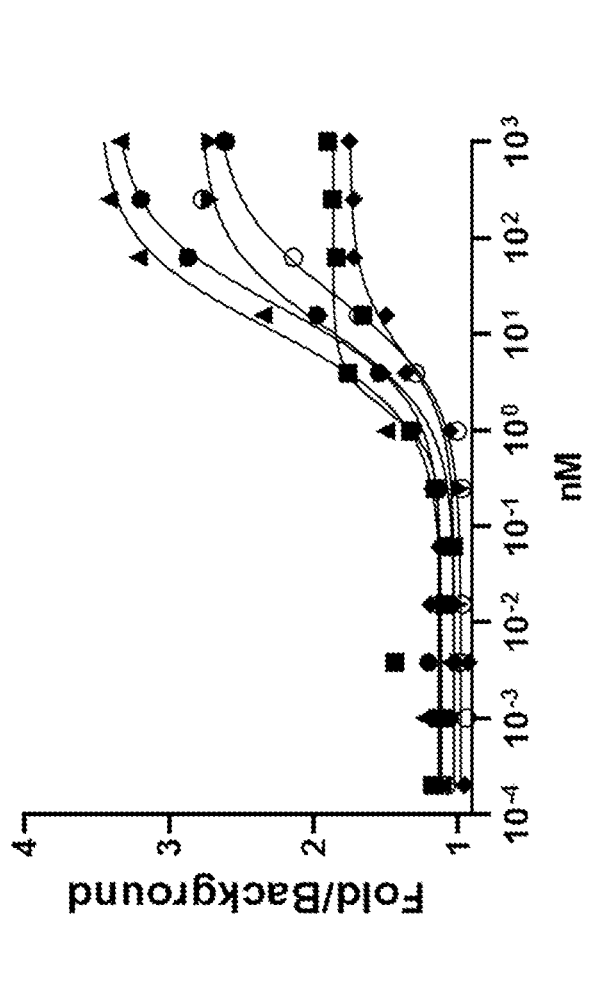

Based on the primary and secondary binding screening results as well as the STAT5 phosphorylation seen in the all-by-all bispecific UniAb screen, 6 IL-2Rβγ bispecific UniAb molecules were selected for additional in vitro characterization. The 6 IL-2Rβγ bispecific UniAbs bound efficiently to both human and cynomolgus T-cells with a range of EC50 values (FIG. 3). None of the 6 bispecific UniAbs bound to other common gamma chain partners (IL-4R, IL-7R, IL-9R or IL-21R) or IL-2Rα by Octet off-rate analysis.

Figures 4C, 4D:
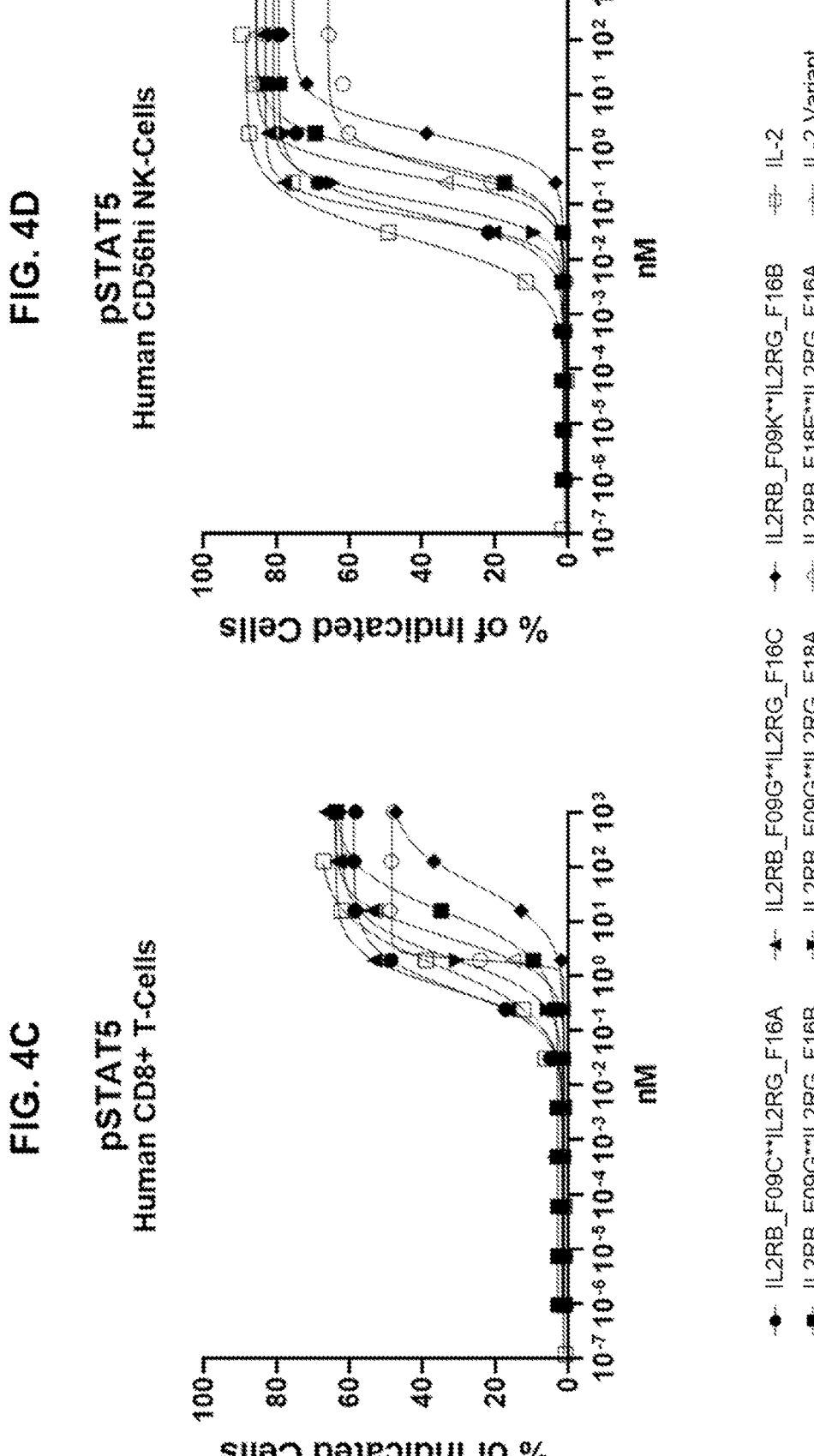
Figure 4E:
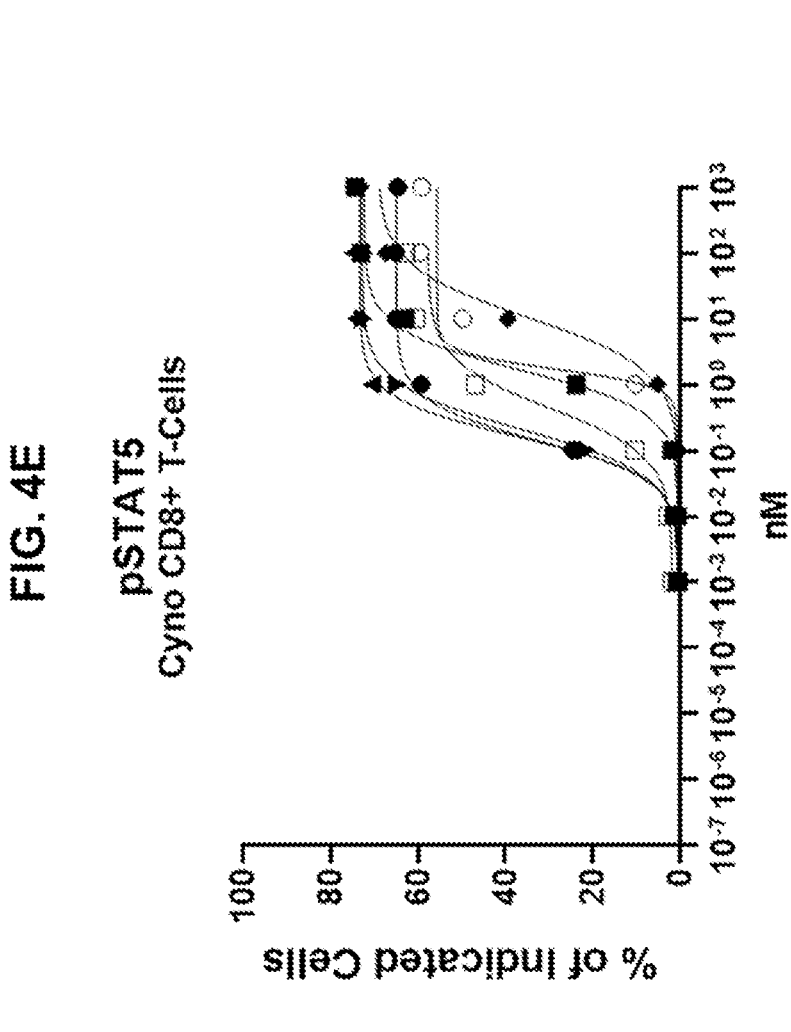

The ability of the IL-2Rβγ bispecific UniAbs to stimulate IL-2R signaling in human CD4+ T, CD8+ T, and NK-cells was confirmed by a dose-dependent increase of STAT5 phosphorylation compared to rhIL-2 and an rhIL-2 variant which contains mutations (F42A, Y45A, L72G) that have been shown to disrupt binding to IL-2Rα while retaining the ability to bind and activate the intermediate affinity IL-2Rβγ receptor (FIGS. 4A-4C) (C. Klein et al., *Oncoimmunology* 6:3 e1277306 (2017)). On CD8+ T-cells, the bispecific UniAbs exhibit a range of EC50 values in the pSTAT5 assay, with multiple constructs (BsAb-1, BsAb-3, BsAb-4) showing near equivalent activity with rhIL-2 and the rhIL-2 variant (FIG. 4A). However, this is in stark contrast to the level of pSTAT5 in CD4+CD25+FoxP3+ T-regulatory cells, where the bispecific UniAbs show significantly lower potency compared to rhIL-2 on cells that express high levels of IL-2Rα (FIGS. 4C-4D). Thus, IL-2Rβγ bispecific UniAbs avoid the preferential activation of T-regs, which is a key functional criterion for these molecules. All 6 bispecific UniAbs were also confirmed to activate IL-2R signaling on cynomolgus T-cells, establishing cynomolgus monkeys as a suitable non-human primate model in subsequent studies (FIG. 4E).

Figures 5A, 5B:
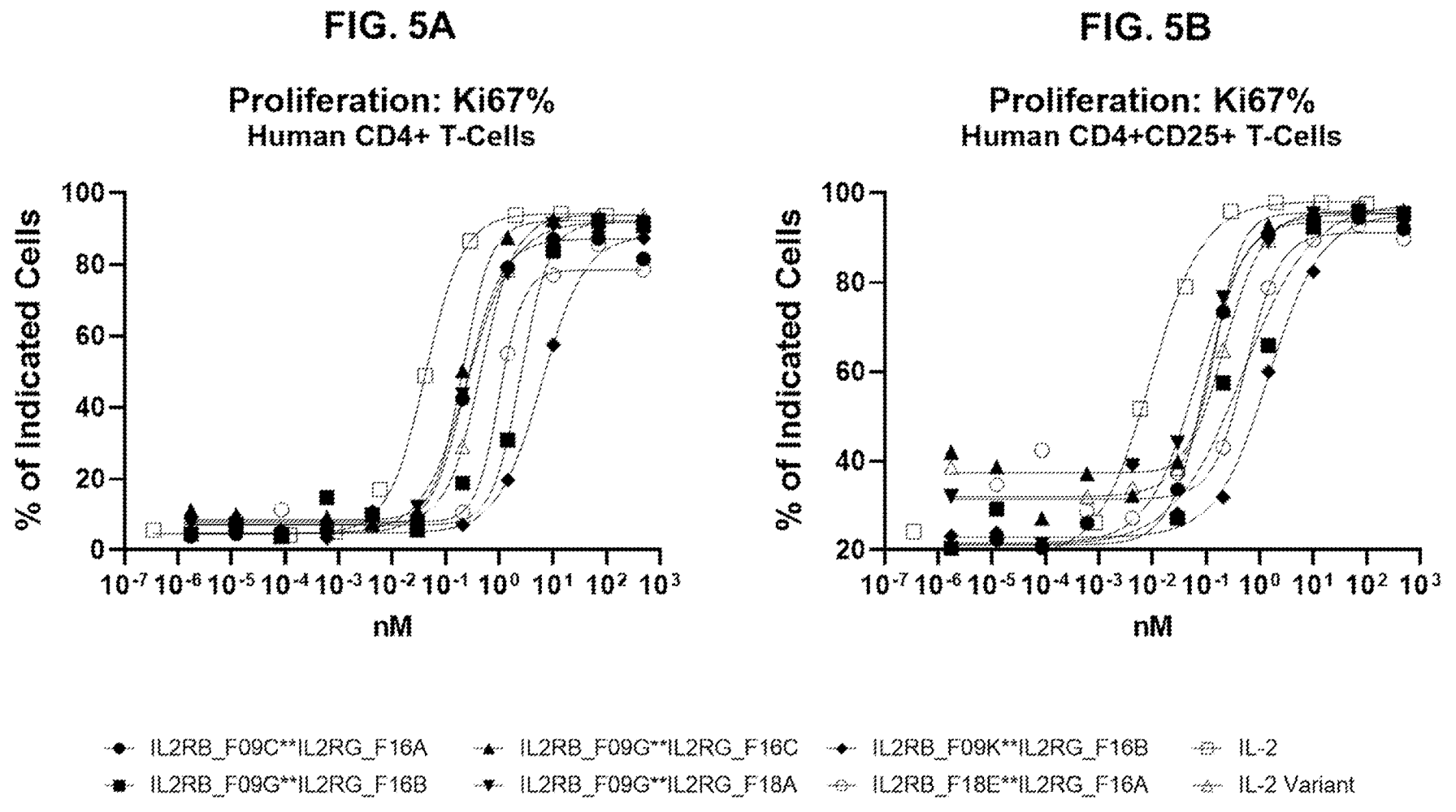
Figures 5C, 5D:
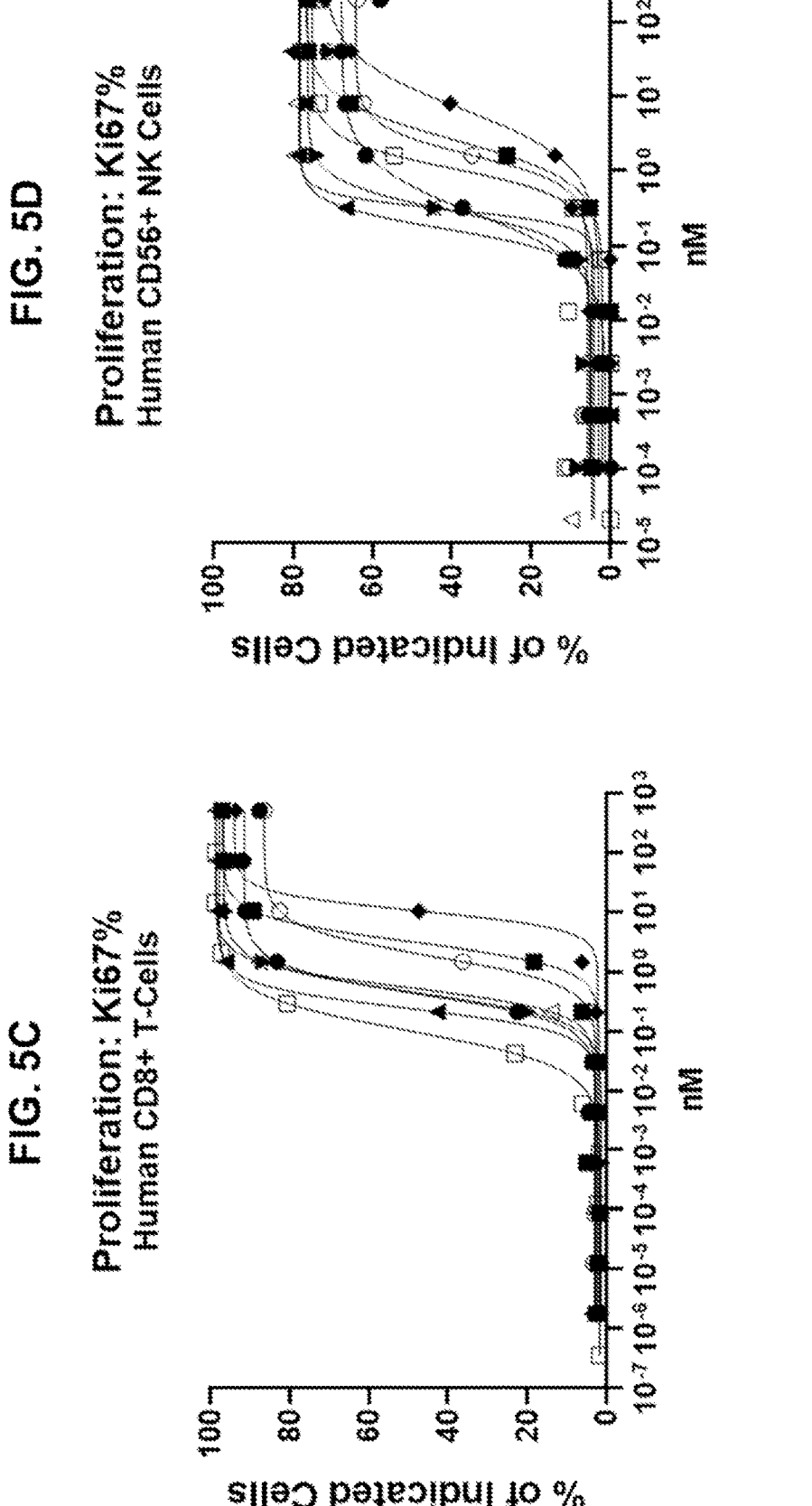
Figures 6A, 6B:
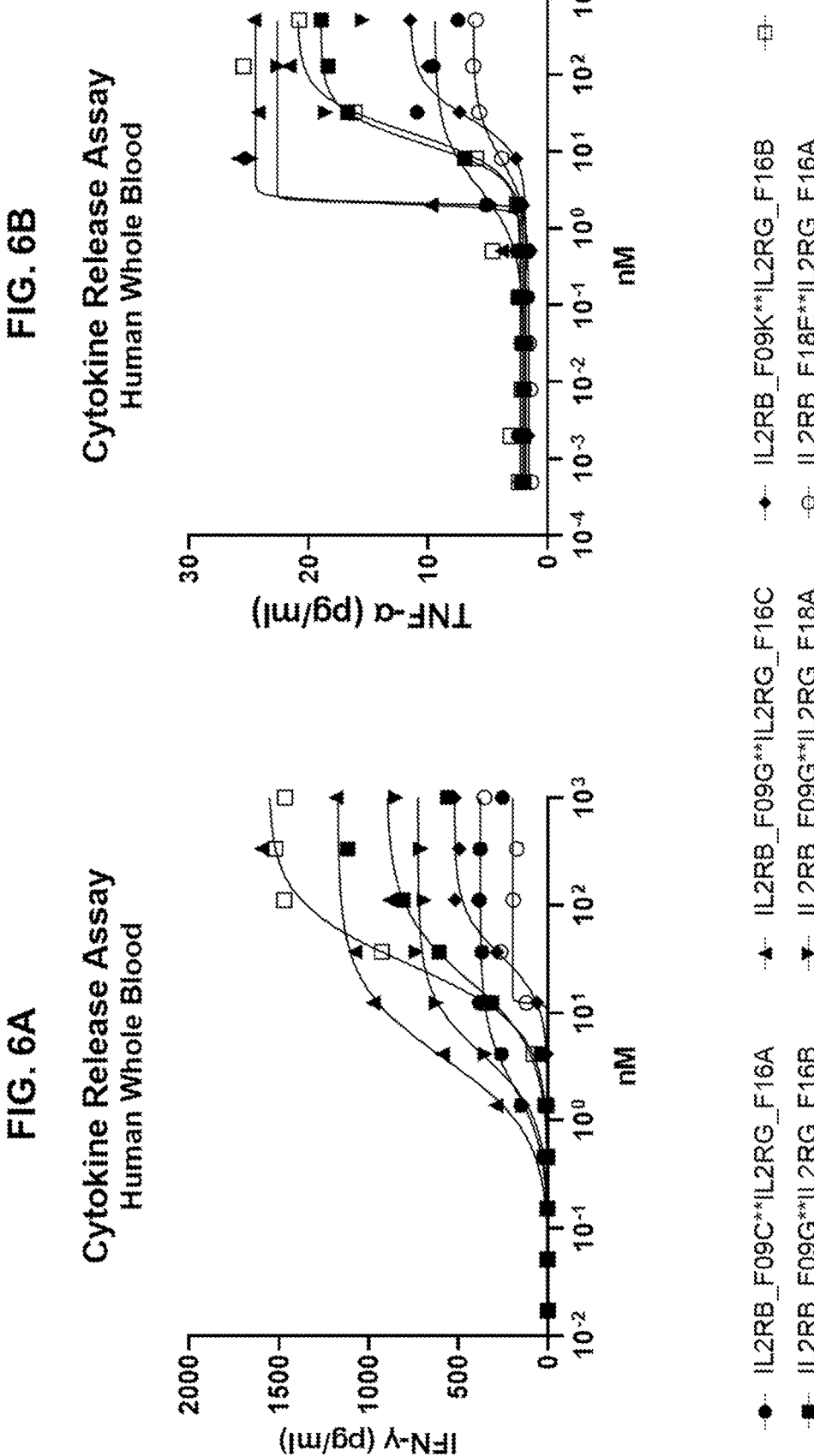
FIG. 6A, FIG. 6B, FIG. 6C and FIG. 6D are graphs showing cytokine secretion in human whole blood as a function of concentration for the depicted bispecific antibody constructs and control molecules (IL-2).
Figures 6C, 6D:
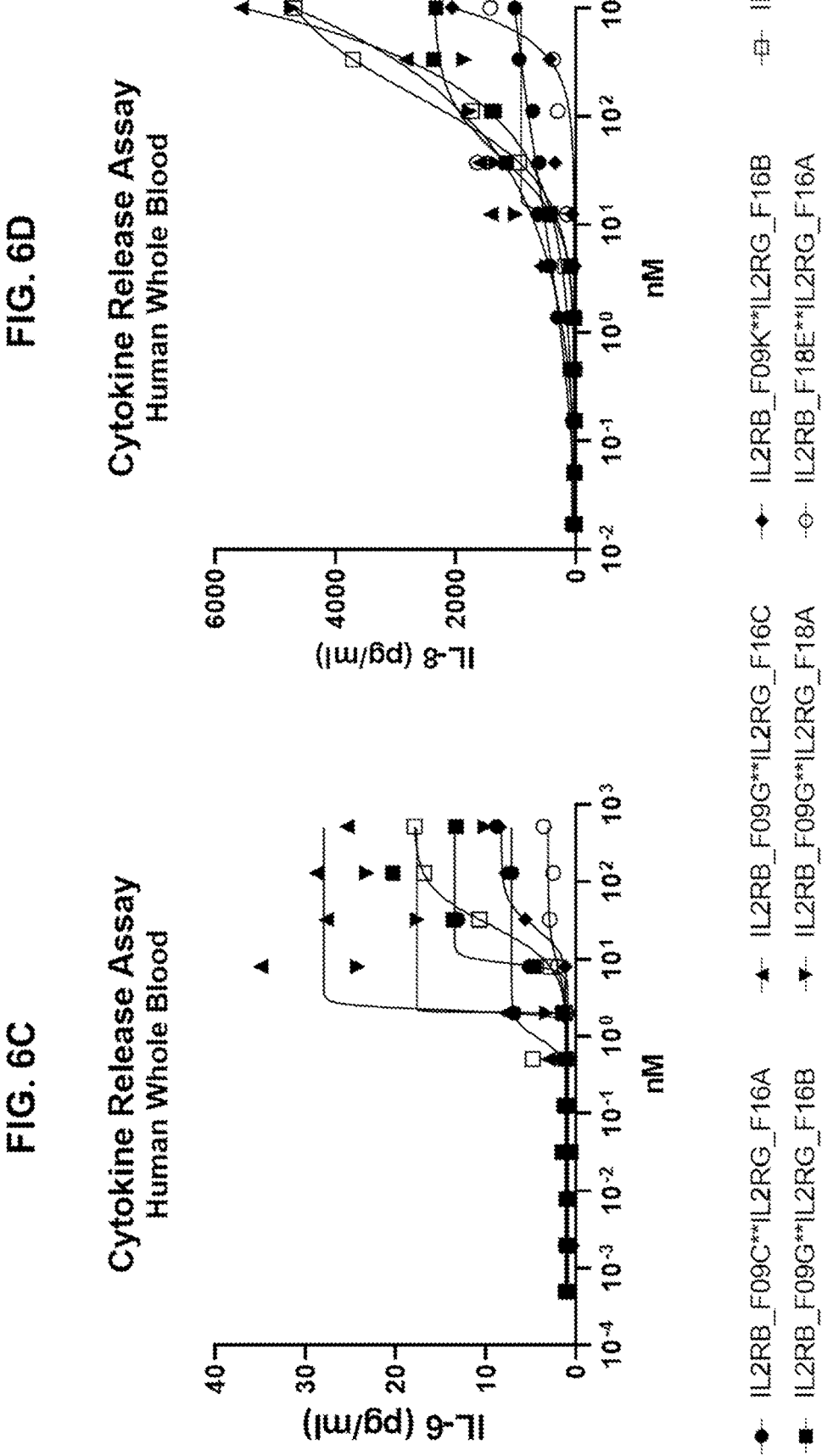

To further compare the functional activity among the 6 bispecific UniAbs and rhIL-2, a cell proliferation assay was performed. In response to treatment with the bispecific IL-2R agonist UniAbs, or the IL-2 cytokine controls, immune effector cells (T and NK-cells derived from healthy donor PBMCs) demonstrated dose dependent proliferation (FIGS. 5A-D). While a range of potencies was observed in the proliferation of CD8+ T-cells and NK-cells in PBMCs treated with the IL-2Rβγ bispecific UniAbs, several (BsAb-1, BsAb-3, BsAb-4) showed induction of proliferation at levels similar to rhIL-2 and the rhIL-2 variant control, while all molecules achieved similar levels of maximum proliferation (FIGS. 5A-5B). In contrast, rhIL-2 was more active than the bispecific agonist UniAbs and the rhIL-2 variant control on CD4+ cells (including T-regs) (FIGS. 5C-5D).

Cytokine release profiles of the bispecific IL-2R agonist UniAbs compared to rhIL-2 were assessed in an ex vivo human whole blood assay. After a 24-hour incubation in the presence of the IL-2Rβγ bispecific UniAbs or rhIL-2, a dose-dependent increase in IFN-γ, TNF-α, IL-6, and IL-8 was observed for all test articles (FIGS. 6A-6D). Two of the bispecific UniAbs (BsAb-3 and BsAb-4) induced cytokine levels (max concentration or EC50) at or above that of rhIL-2 in all tested cytokines, but the remaining four induced levels lower than the cytokine control.

In summary, six bispecific IL-2Rβγ antibodies were identified with a range of agonist activity. BsAb-1 demonstrates agonist activity at a similar level to that seen with rhIL-2 in immune effector cells measured by phosphorylation of STAT5 and in the proliferation assay. In contrast, in the same in vitro assays, BsAb-2 shows reduced potency compared to rhIL-2 and BsAb-1. Both antibodies showed low aggregation measured by SEC, had favorable melting temperatures, and were stable at 37° C. for one month (FIG. 9). These results combined with the favorable cytokine release profiles of BsAb-1 and BsAb-2 led to the selection of these two bispecific antibodies for further in vivo characterization.

Example 3: In Vivo Characterization of IL-2Rβγ Bispecific UniAbs BsAb-1 and BsAb-2

Figure 8A:
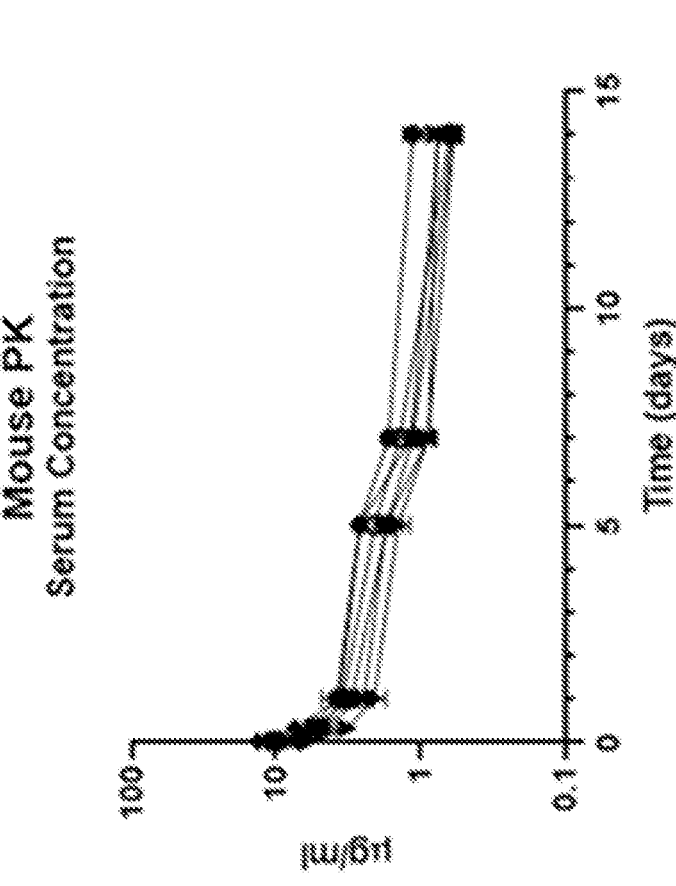
Figures 10A, 10B:
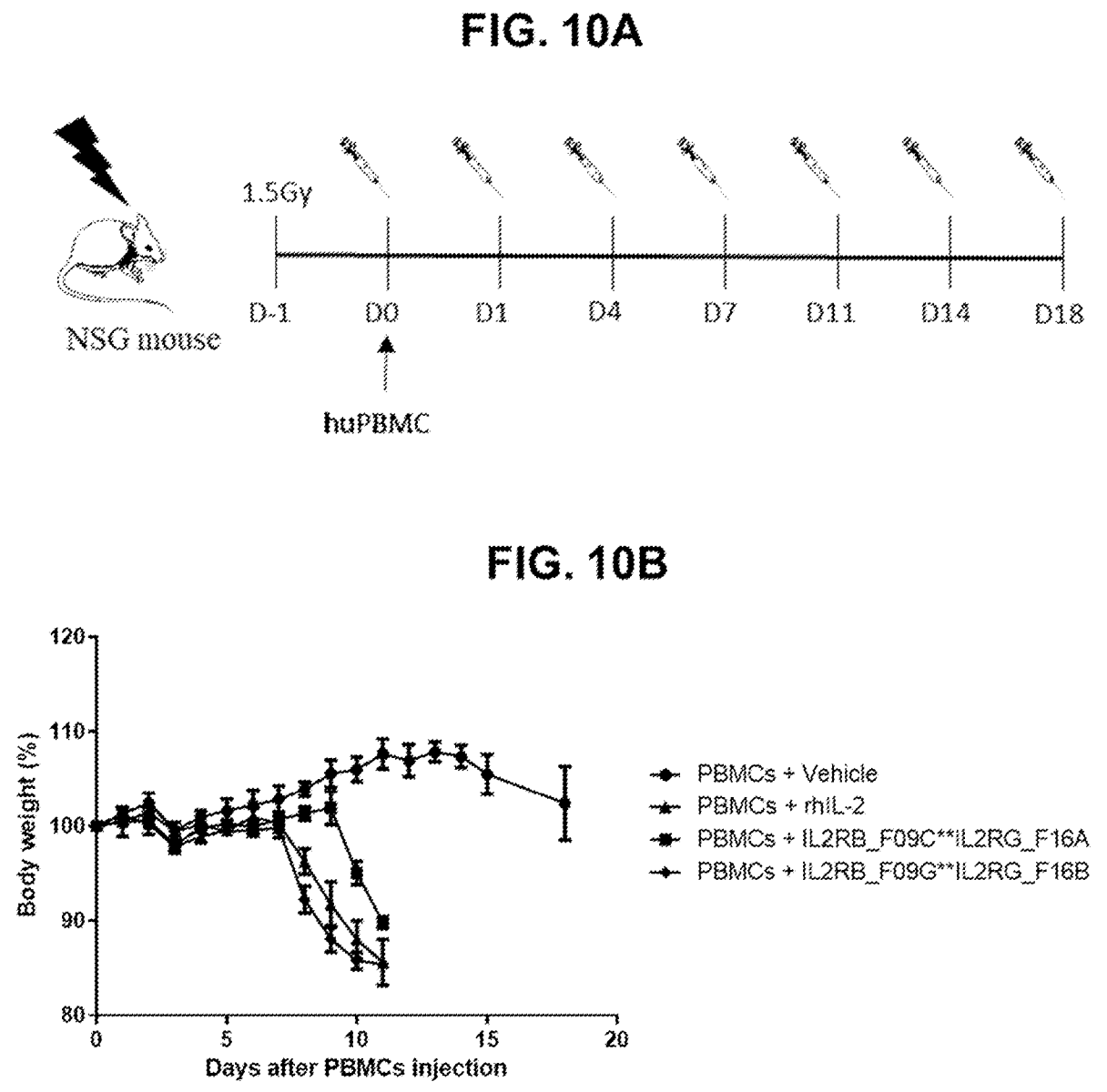
Figure 10C:
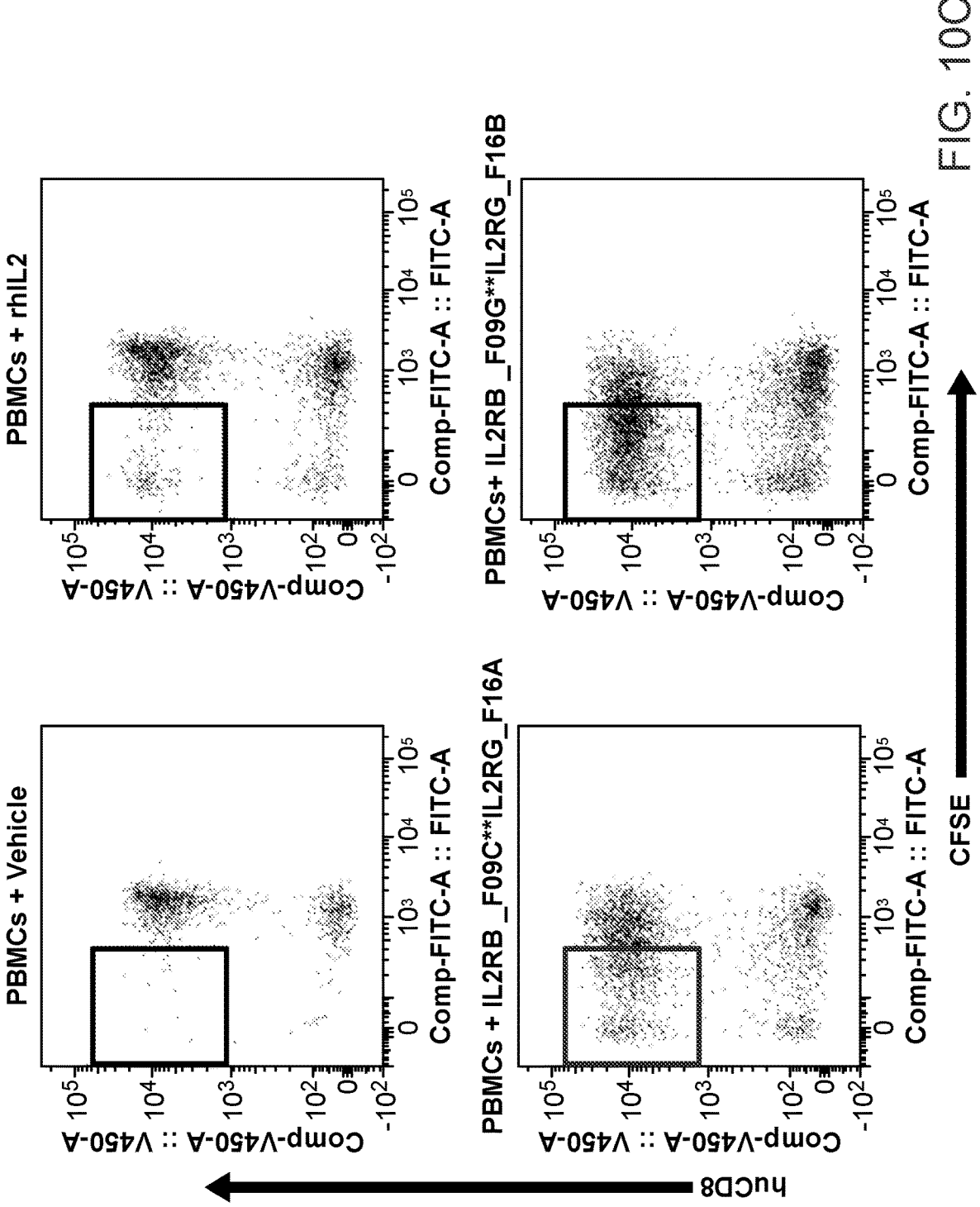

Prior to conducting in vivo functional studies, the in vivo stability and pharmacokinetics of the bispecific antibodies were measured in mice. The observed 5-7 day half-life of each bispecific antibody is consistent with the half-life of a human IgG4 antibody in mice (FIG. 8A) (R. Deng et al., *Mabs* 3, 61-66 (2011)). To assess the in vivo functional activity of the bispecific antibodies, an accelerated graph versus host disease (GVHD) model was used to compare the functional activity of BsAb-1, BsAb-2 and rhIL-2 (FIGS. 10A-10C). In the first experiment, irradiated NSG mice were engrafted with human PBMCs, and the mice were subsequently treated with either vehicle, rhIL-2 daily, or one of the two bispecific agonist antibodies twice a week until sacrifice. As expected, animals treated with the vehicle control showed onset of GVHD, measured by body weight loss, around day 20 and were sacrificed with 20% body weight loss at approximately day 35. In contrast, the bispecific IL-2Rβγ agonist antibodies (BsAb-1, BsAb-2) as well as rhIL-2-treated animals exhibited onset of GVHD at approximately day 8 and were sacrificed with 20% body weight loss between days 9 and 13, indicating an acceleration of GVHD compared to the vehicle control, consistent with the enhanced activation of immune effector cells in treated mice (FIG. 10B).

A second study was conducted to directly measure the ability of BsAb-1 and BsAb-2 to stimulate the proliferation of immune effector cells in vivo. Similar to the first experiment, irradiated NSG mice were engrafted with human PBMCs that were labeled with CSFE and treated with vehicle, rhIL-2, BsAb-1, or BsAb-2. After day 5 of treatment, spleens were harvested and the proliferation of CD8+ T and CD4+ T-cells was compared between the 4 treatment groups by measuring CSFE staining in the different lymphocyte populations. BsAb-1 and BsAb-2 both showed significantly more proliferating CD8+ T-cells compared to rhIL-2 and the vehicle control (FIG. 10C). CD4+ T-cells were expanded to a lesser extent; however, a significant increase in proliferating CD4+ T-cells was seen in BsAb-2 treated mice compared to the vehicle control.

Figures 11A, 11B, 11C, 11D:
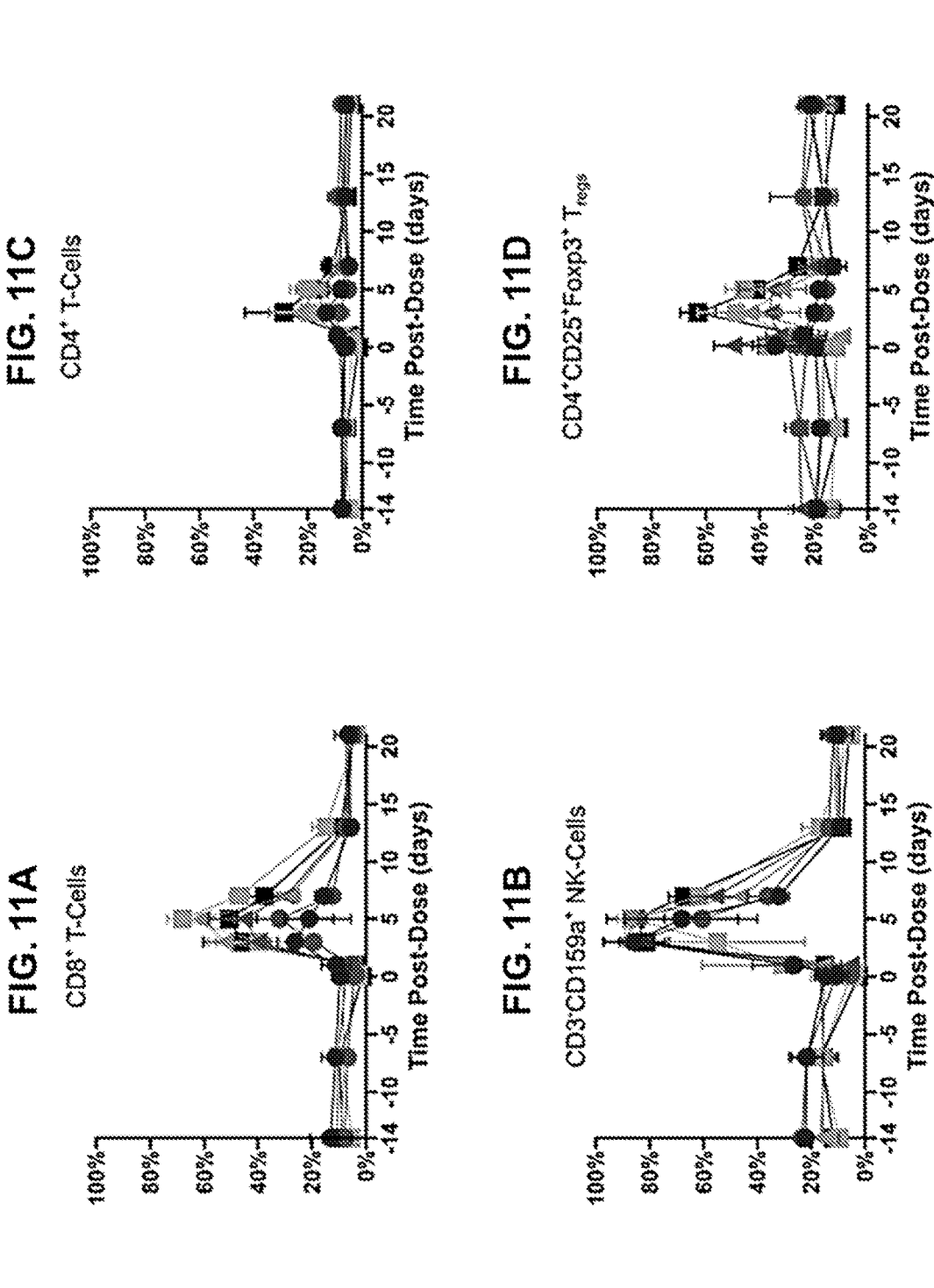
Figures 11I, 11J, 11K:
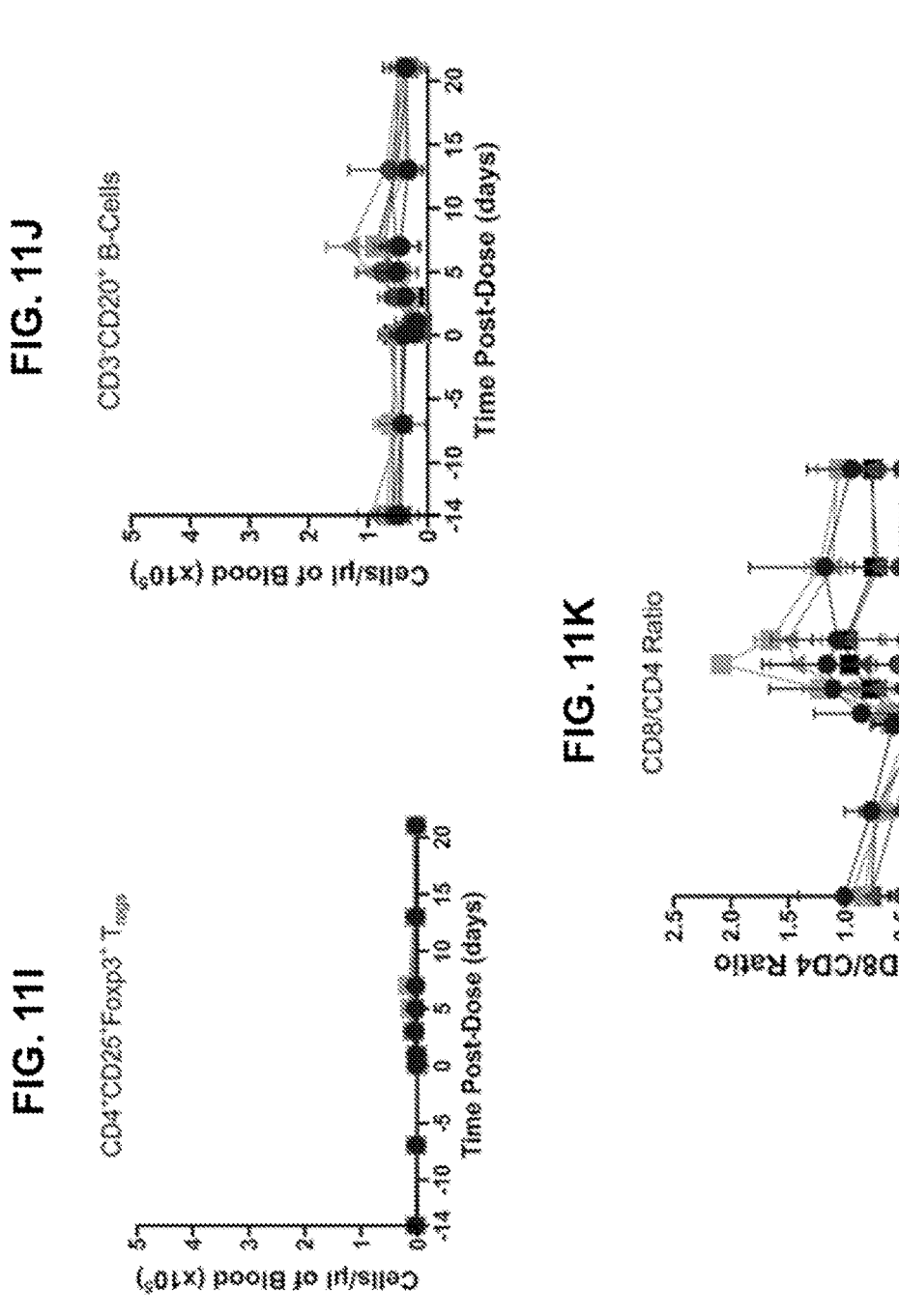

An important aspect of the preclinical evaluation of the bispecific antibody agonists was establishing cynomolgus monkeys as an appropriate in vivo model for measuring the pharmacodynamics of the molecules. To determine human and cynomolgus functional equivalency, the bispecific antibodies were confirmed to activate pSTAT5 signaling ex vivo in cynomolgus primary T-cells at a similar level as seen in primary human T-cells (FIG. 4C and FIG. 4E). After establishing functional equivalency between human and cynomolgus, a non-GLP cynomolgus study was conducted to further investigate the activity of BsAb-1 and BsAb-2 in vivo in a non-human primate model. The two bispecific agonist antibodies were administered to cynomolgus monkeys in groups of 2 that received a single intravenous (slow bolus) dose of 0.03, 0.1 or 0.3 mg/kg of either BsAb-1 or BsAb-2. At all doses with both molecules, a marked expansion of peripheral CD8+ T and NK-cells was observed (FIGS. 11A-11K). After an initial transient drop in lymphocyte numbers, CD8+ T, NK-cells, and to a lesser degree, CD4+ T-cells, showed dose dependent proliferation and expansion in the blood, peaking around day 4-7 before returning to baseline levels around day 14 (FIGS. 11A-11C and 11F-11H). Importantly, no pronounced expansion of CD4+CD25+FoxP3+ T-regulatory cells was seen, consistent with the bispecific agonist antibodies avoiding preferential activation of the trimeric IL-2 receptor (FIG. 11D and FIG. 11I). This effect was further confirmed by the ratio of CD8+:CD4+ T-cells which was skewed in favor of the CD8+ T-cell subset (FIG. 11K). Moreover, the IL-2Rβγ agonist antibodies were well tolerated in the monkeys at all dose levels tested, with no indication of vascular leak syndrome or other overt toxicities.

Example 4: In Vivo Characterization of IL-2Rβγ Bispecific UniAb BsAb-5

Figure 13:
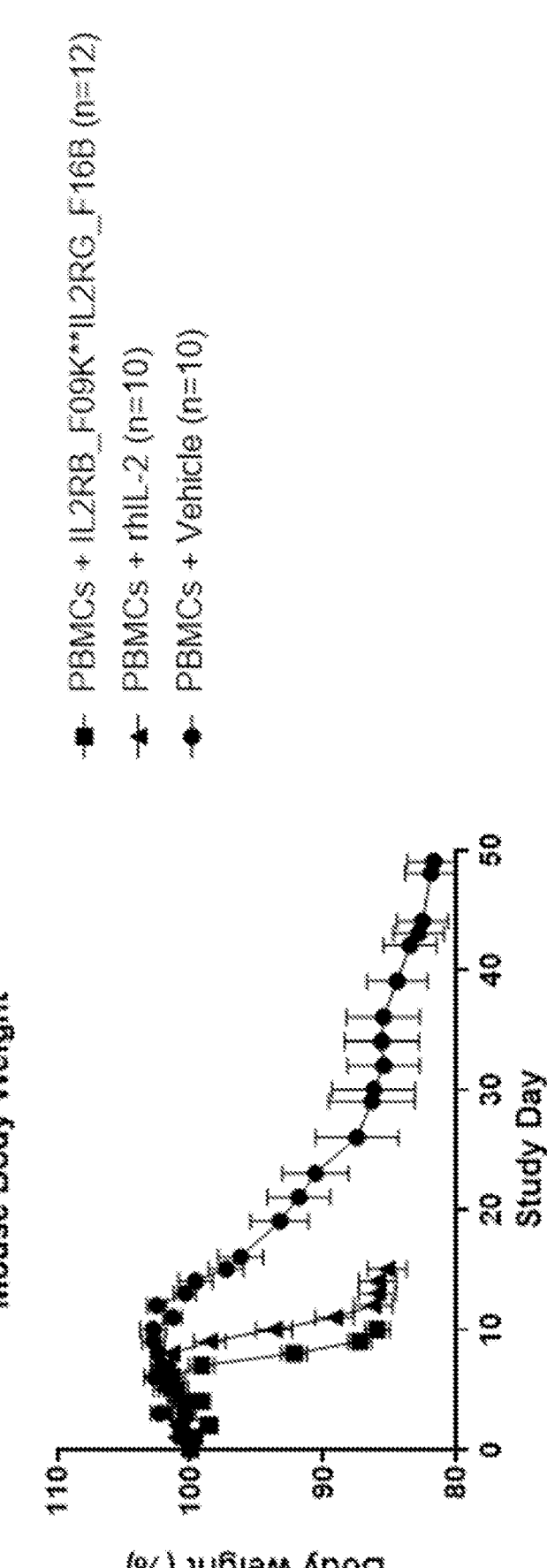
FIG. 13 is a graph showing body weight (%) as a function of time (study day) for animals in an accelerated GVHD model.
Figure 14:
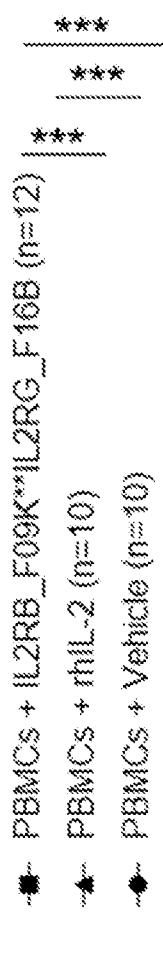
FIG. 14 is a graph showing probability of survival as a function of time (study day) for animals in an accelerated GVHD model.
Figure 14:
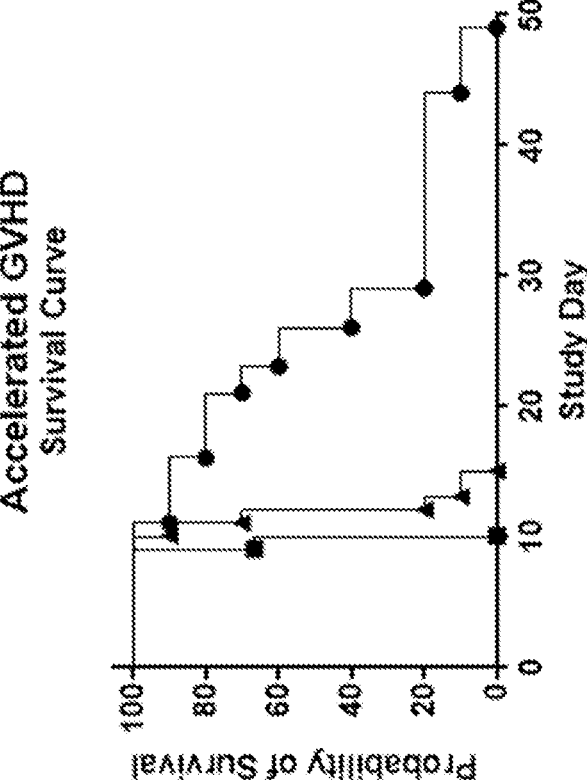

Prior to conducting in vivo functional studies, the in vivo stability and pharmacokinetics of the bispecific antibodies were measured in mice at two dose-levels: 1 mg/kg and 10 mg/kg. The observed 5-day half-life of BsAb-5 (IL2RB_F09K**IL2RG_F16B) is consistent with the half-life of a human IgG4 antibody in mice (FIGS. 12A-12B) (R. Deng et al., *Mabs* 3, 61-66 (2011)). To assess the in vivo functional activity of the bispecific antibody, an accelerated graph versus host disease (GVHD) model was used to compare the functional activity of BsAb-5 and rhIL-2 (FIGS. 13-14). In the first experiment, irradiated NSG mice were engrafted with human PBMCs, and the mice were subsequently treated with either vehicle, rhIL-2 daily, or BsAb-5 twice a week until sacrifice. As expected, animals treated with the vehicle control showed onset of GVHD, measured by body weight loss, around day 20 and were sacrificed with 20% body weight loss at approximately day 35. In contrast, BsAb-5-treated animals, as well as rhIL-2-treated animals, exhibited onset of GVHD at approximately day 8 and were sacrificed with 20% body weight loss between days 9 and 13, indicating an acceleration of GVHD compared to the vehicle control, consistent with the enhanced activation of immune effector cells in treated mice (FIG. 14).

Figures 15A, 15B:
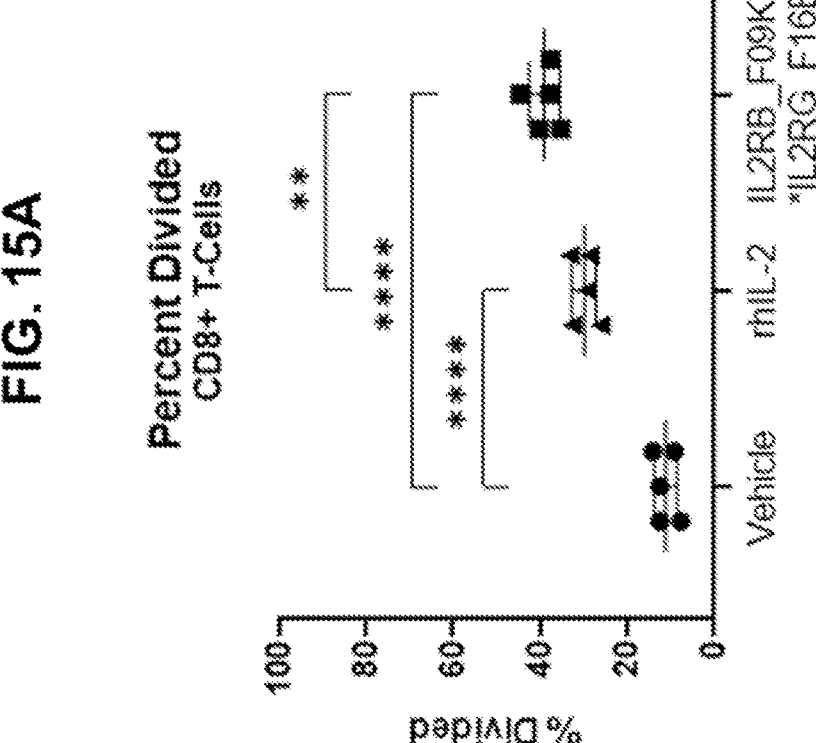
Figure 15C:
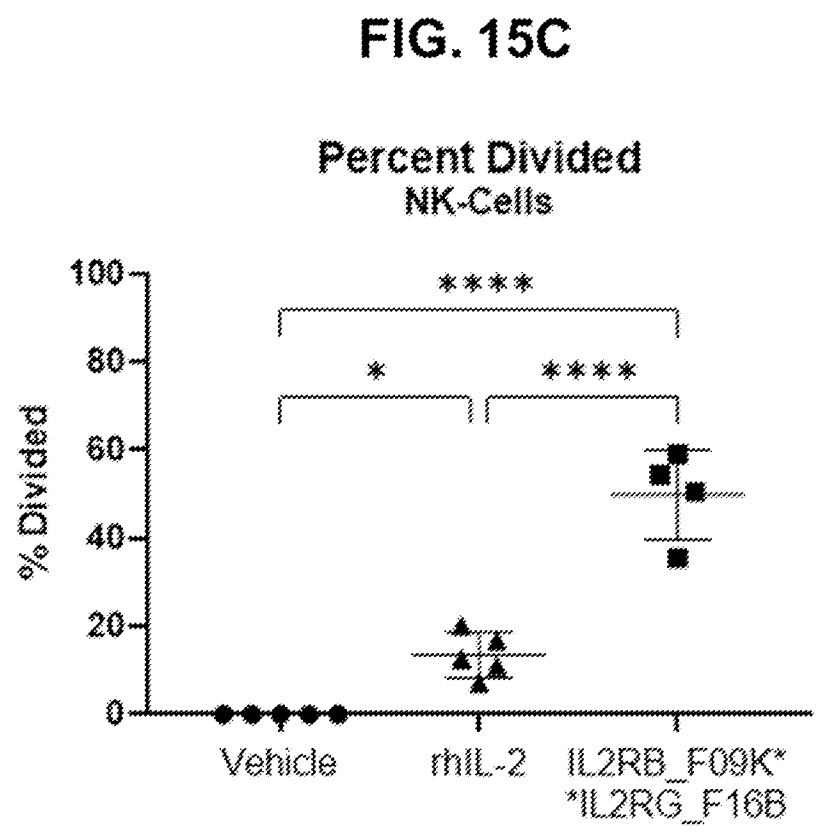

A second study was conducted to directly measure the ability of BsAb-5 to stimulate the proliferation of immune effector cells in vivo. Similar to the first experiment, irradiated NSG mice were engrafted with human PBMCs that were labeled with CPD450 and treated with vehicle, rhIL-2, or BsAb-5. After day 5 of treatment, spleens were harvested and the proliferation of CD8+ T-cells, CD4+ T-cells, and NK-cells were compared between the 3 treatment groups by measuring CPD450 dilutions in the different populations. In all three measured cell types, BsAb-5 induced significantly more proliferation than rhIL-2 or the vehicle control (FIGS. 15A-15C).

Figures 16E, 16F:
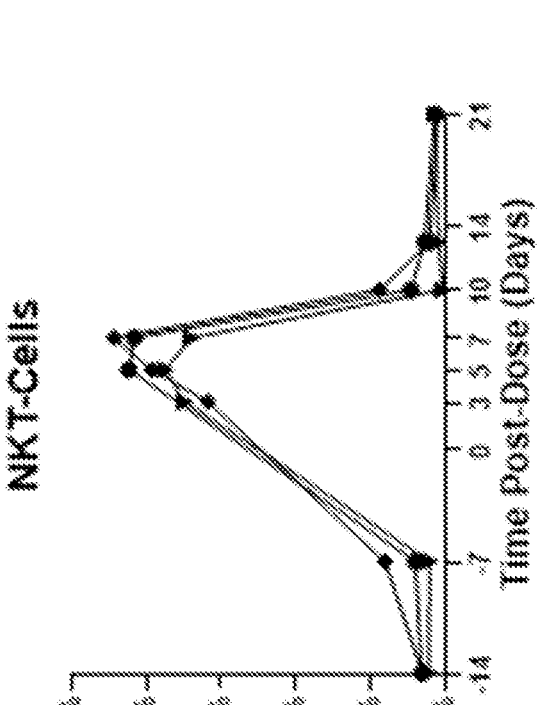
Figure 16H:
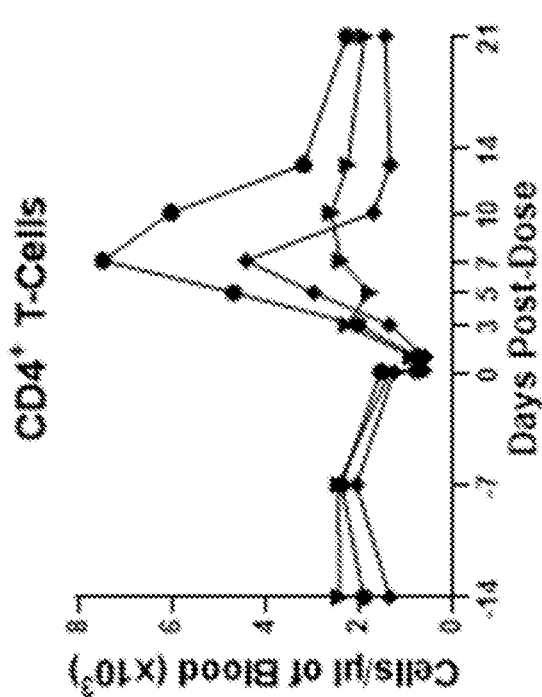
Figure 16G:
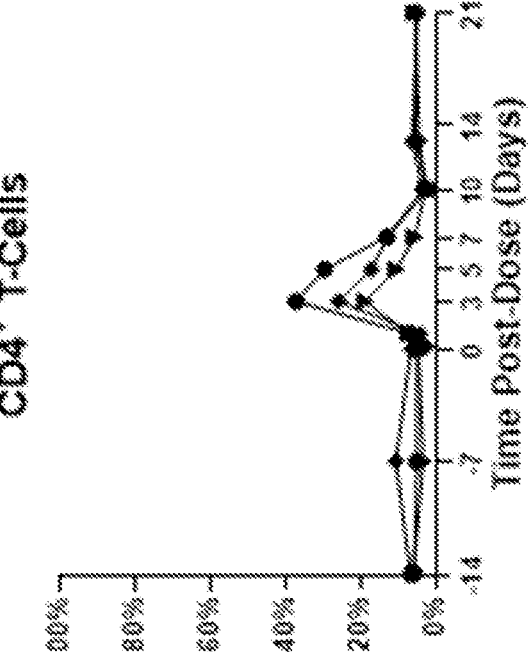
Figures 16K, 16L:
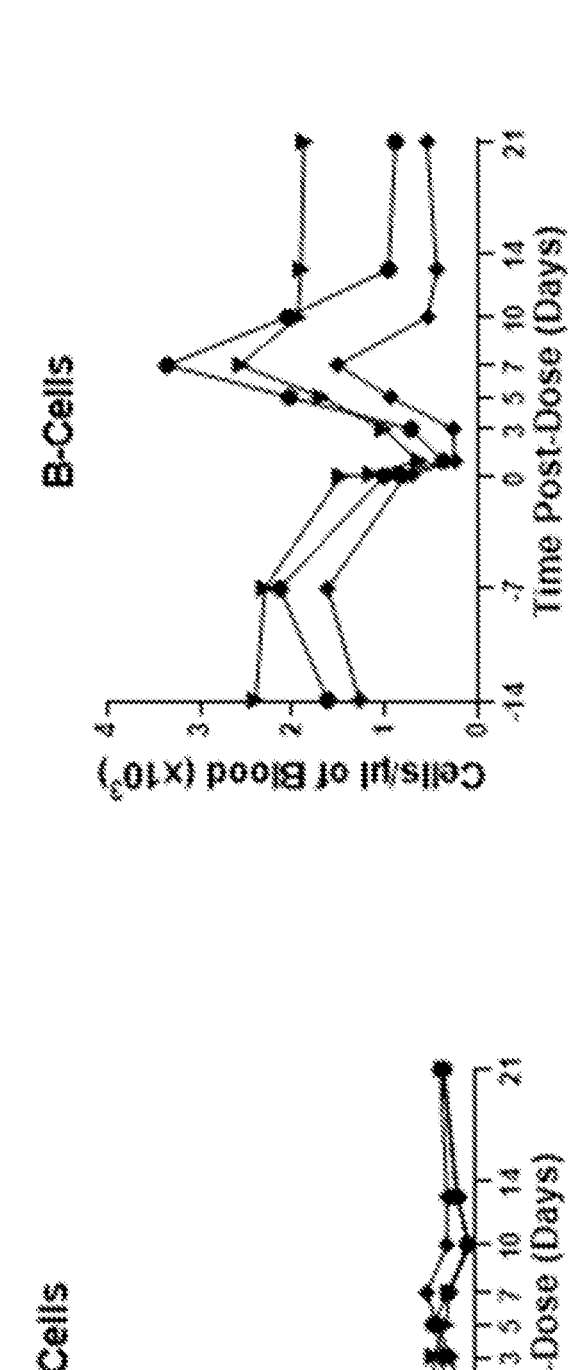

An important aspect of the preclinical evaluation of the bispecific antibody agonists was establishing cynomolgus monkeys as an appropriate in vivo model for measuring the pharmacodynamics of the molecules. To determine human and cynomolgus functional equivalency, the bispecific antibodies were confirmed to activate pSTAT5 signaling ex vivo in cynomolgus primary T-cells at a similar level as seen in primary human T-cells (FIG. 4C and FIG. 4E). After establishing functional equivalency between human and cynomolgus, a non-GLP cynomolgus study was conducted to further investigate the activity of BsAb-5 in vivo in a non-human primate model. BsAb-5 was administered to cynomolgus monkeys in a single intravenous (slow bolus) dose of 0.1, 0.3, or 0.5 mg/kg. The monkeys were dosed in groups of 2 for the first two dose levels, and in a group of 4 for the 0.5 mg/kg dose level. At all dose levels, a marked expansion of peripheral CD8+ T-, NK-, and NKT-cells was observed (FIGS. 16A-16F). After an initial transient drop in lymphocyte numbers, CD8+ T-, NK-, NKT-cells, and to a lesser degree, CD4+ T-cells, showed dose dependent proliferation and expansion in the blood, peaking around day 4-7 before returning to baseline levels around day 14 (FIGS. 16A-16H). Importantly, no preferential expansion of CD4+ CD25+Foxp3+ T-regulatory cells was observed, consistent with the bispecific agonist antibodies avoiding preferential activation of the trimeric IL-2 receptor (FIGS. 16A-16J). Additionally, B-cells, which serve as a useful negative control due to their lack of IL-2 receptor expression, did not proliferate in response to BsAb-5 (FIGS. 16K-16L). Moreover, the IL-2Rβγ agonist antibodies were well tolerated in the monkeys up to 0.5 mg/kg, with no indication of vascular leak syndrome or other overt toxicities.

While non-limiting example embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

The invention claimed is:

1. A method of treating a cancer comprising administering to an individual in need thereof an effective dose of a heavy chain-only antibody comprising:

a first heavy chain variable region that binds to IL2RB, comprising:

a CDR1 sequence comprising the formula:

$$\text{G G S I S S S X1 W} \quad \text{(SEQ ID NO: 26)}$$

wherein X1 is D or N; and a CDR2 sequence comprising the formula:

$$\text{I X2 H S G S T} \quad \text{(SEQ ID NO: 27)}$$

wherein X2 is D or S; and a CDR3 sequence comprising the formula:

$$\text{X3 R G X4 W E L X5 D A F D I} \quad \text{(SEQ ID NO: 28)}$$

wherein X3 is G or A;

X4 is S or Q; and

X5 is S or T; and a second heavy chain variable region that binds to IL2RG, comprising:

a CDR1 sequence comprising the formula:

$$\text{G F X1 X2 X3 X4 Y Y} \quad \text{(SEQ ID NO: 32)}$$

wherein X1 is T or I;

X2 is F or V;

X3 is S, N, or G; and

X4 is D or N; and a CDR2 sequence comprising the formula:

$$\text{I S X5 S G X6 X7 I} \quad \text{(SEQ ID NO: 33)}$$

wherein X5 is S or N;

X6 is D, S, G, or N; and

X7 is T or I; and a CDR3 sequence comprising the sequence ARG-DAVSITGDY (SEQ ID NO: 20).

2. The method of claim 1, wherein:

the first heavy chain variable region comprises:

(a) a CDR1 sequence of SEQ ID NO: 1, a CDR2 sequence of SEQ ID NO: 4, and a CDR3 sequence of SEQ ID NO: 7; or (b) a CDR1 sequence of SEQ ID NO: 1, a CDR2 sequence of SEQ ID NO: 4, and a CDR3 sequence of SEQ ID NO: 8; or (c) a CDR1 sequence of SEQ ID NO: 2, a CDR2 sequence of SEQ ID NO: 5, and a CDR3 sequence of SEQ ID NO: 9; and the second heavy chain variable region comprises:

(a) a CDR1 sequence of SEQ ID NO: 15, a CDR2 sequence of SEQ ID NO: 17, and a CDR3 sequence of SEQ ID NO: 20; or (b) a CDR1 sequence of SEQ ID NO: 15, a CDR2 sequence of SEQ ID NO: 18, and a CDR3 sequence of SEQ ID NO: 20; or (c) a CDR1 sequence of SEQ ID NO: 16, a CDR2 sequence of SEQ ID NO: 18, and a CDR3 sequence of SEQ ID NO: 20.

3. The method of claim 1, wherein the first heavy chain variable region has at least 95% sequence identity to any one of SEQ ID NOs: 11-13.

4. The method of claim 1, wherein the first heavy chain variable region sequence is selected from SEQ ID NOs: 11-13.

5. The method of claim 1, wherein the second heavy chain variable region has at least 95% sequence identity to any one of SEQ ID NOs: 22-24.

6. The method of claim 1, wherein the second heavy chain variable region sequence is selected from SEQ ID NOs: 22-24.

7. The method of claim 1, wherein:

the first heavy chain variable region comprises a CDR1 sequence of SEQ ID NO: 1, a CDR2 sequence of SEQ ID NO: 4, and a CDR3 sequence of SEQ ID NO: 7; and the second heavy chain variable region comprises a CDR1 sequence of SEQ ID NO: 15, a CDR2 sequence of SEQ ID NO: 17, and a CDR3 sequence of SEQ ID NO: 20.

8. The method of claim 7, wherein the first heavy chain variable region has at least 95% sequence identity to SEQ ID NO: 11, and the second heavy chain variable region has at least 95% sequence identity to SEQ ID NO: 22.

9. The method of claim 7, wherein the first heavy chain variable region comprises SEQ ID NO: 11, and the second heavy chain variable region comprises SEQ ID NO: 22.

10. The method of claim 7, wherein the heavy chain-only antibody comprises a first polypeptide comprising SEQ ID NO: 53 and a second polypeptide comprising SEQ ID NO: 61.

11. The method of claim 1, wherein:

the first heavy chain variable region comprises a CDR1 sequence of SEQ ID NO: 1, a CDR2 sequence of SEQ ID NO: 4, and a CDR3 sequence of SEQ ID NO: 8; and the second heavy chain variable region comprises a CDR1 sequence of SEQ ID NO: 15, a CDR2 sequence of SEQ ID NO: 18, and a CDR3 sequence of SEQ ID NO: 20.

12. The method of claim 11, wherein the first heavy chain variable region has at least 95% sequence identity to SEQ ID NO: 12, and the second heavy chain variable region has at least 95% sequence identity to SEQ ID NO: 23.

13. The method of claim 11, wherein the first heavy chain variable region comprises SEQ ID NO: 12, and the second heavy chain variable region comprises SEQ ID NO: 23.

14. The method of claim 11, wherein the heavy chain-only antibody comprises a first polypeptide comprising SEQ ID NO: 62 and a second polypeptide comprising SEQ ID NO: 63.

15. The method of claim 1, wherein:

the first heavy chain variable region comprises a CDR1 sequence of SEQ ID NO: 2, a CDR2 sequence of SEQ ID NO: 5, and a CDR3 sequence of SEQ ID NO: 9; and the second heavy chain variable region comprises a CDR1 sequence of SEQ ID NO: 15, a CDR2 sequence of SEQ ID NO: 18, and a CDR3 sequence of SEQ ID NO: 20.

16. The method of claim 15, wherein the first heavy chain variable region has at least 95% sequence identity to SEQ ID NO: 13, and the second heavy chain variable region has at least 95% sequence identity to SEQ ID NO: 23.

17. The method of claim 15, wherein the first heavy chain variable region comprises SEQ ID NO: 13, and the second heavy chain variable region comprises SEQ ID NO: 23.

18. The method of claim 15, wherein the heavy chain-only antibody comprises a first polypeptide comprising SEQ ID NO: 64 and a second polypeptide comprising SEQ ID NO: 65.

19. The method of claim 1, wherein:

the first heavy chain variable region comprises a CDR1 sequence of SEQ ID NO: 1, a CDR2 sequence of SEQ ID NO: 4, and a CDR3 sequence of SEQ ID NO: 8; and the second heavy chain variable region comprises a CDR1 sequence of SEQ ID NO: 16, a CDR2 sequence of SEQ ID NO: 18, and a CDR3 sequence of SEQ ID NO: 20.

20. The method of claim 19, wherein the first heavy chain variable region has at least 95% sequence identity to SEQ ID NO: 12, and the second heavy chain variable region has at least 95% sequence identity to SEQ ID NO: 24.

21. The method of claim 19, wherein the first heavy chain variable region comprises SEQ ID NO: 12, and the second heavy chain variable region comprises SEQ ID NO: 24.

22. The method of claim 19, wherein the heavy chain-only antibody comprises a first polypeptide comprising SEQ ID NO: 34 and a second polypeptide comprising SEQ ID NO: 35.

23. The method of claim 1, wherein the heavy chain-only antibody is administered in conjunction with another course of therapy.

24. The method of claim 1, wherein the heavy chain-only antibody is administered in conjunction with a chemo-therapy regimen.

* * * * *

SEQUENCE LISTING

```
Sequence total quantity: 68
SEQ ID NO: 1          moltype = AA  length = 9
FEATURE               Location/Qualifiers
REGION                1..9
                      note = source = /note="Description of Artificial Sequence:
                       Synthetic peptide"
source                1..9
                      mol_type = protein
                      organism = synthetic construct
SEQUENCE: 1
GGSISSSDW                                                             9

SEQ ID NO: 2          moltype = AA  length = 9
FEATURE               Location/Qualifiers
REGION                1..9
                      note = source = /note="Description of Artificial Sequence:
                       Synthetic peptide"
source                1..9
                      mol_type = protein
                      organism = synthetic construct
SEQUENCE: 2
GGSISSSNW                                                             9
```

-continued

```
SEQ ID NO: 3          moltype = AA  length = 8
FEATURE               Location/Qualifiers
REGION                1..8
                      note = source = /note="Description of Artificial Sequence:
                       Synthetic peptide"
source                1..8
                      mol_type = protein
                      organism = synthetic construct
SEQUENCE: 3
GFTFSSYG                                                                    8

SEQ ID NO: 4          moltype = AA  length = 7
FEATURE               Location/Qualifiers
REGION                1..7
                      note = source = /note="Description of Artificial Sequence:
                       Synthetic peptide"
source                1..7
                      mol_type = protein
                      organism = synthetic construct
SEQUENCE: 4
IDHSGST                                                                     7

SEQ ID NO: 5          moltype = AA  length = 7
FEATURE               Location/Qualifiers
REGION                1..7
                      note = source = /note="Description of Artificial Sequence:
                       Synthetic peptide"
source                1..7
                      mol_type = protein
                      organism = synthetic construct
SEQUENCE: 5
ISHSGST                                                                     7

SEQ ID NO: 6          moltype = AA  length = 8
FEATURE               Location/Qualifiers
REGION                1..8
                      note = source = /note="Description of Artificial Sequence:
                       Synthetic peptide"
source                1..8
                      mol_type = protein
                      organism = synthetic construct
SEQUENCE: 6
ISYDGSNK                                                                    8

SEQ ID NO: 7          moltype = AA  length = 13
FEATURE               Location/Qualifiers
REGION                1..13
                      note = source = /note="Description of Artificial Sequence:
                       Synthetic peptide"
source                1..13
                      mol_type = protein
                      organism = synthetic construct
SEQUENCE: 7
GRGSWELSDA FDI                                                              13

SEQ ID NO: 8          moltype = AA  length = 13
FEATURE               Location/Qualifiers
REGION                1..13
                      note = source = /note="Description of Artificial Sequence:
                       Synthetic peptide"
source                1..13
                      mol_type = protein
                      organism = synthetic construct
SEQUENCE: 8
ARGSWELTDA FDI                                                              13

SEQ ID NO: 9          moltype = AA  length = 13
FEATURE               Location/Qualifiers
REGION                1..13
                      note = source = /note="Description of Artificial Sequence:
                       Synthetic peptide"
source                1..13
                      mol_type = protein
                      organism = synthetic construct
SEQUENCE: 9
GRGSWELTDA FDI                                                              13

SEQ ID NO: 10         moltype = AA  length = 19
FEATURE               Location/Qualifiers
```

-continued

```
REGION                     1..19
                           note = source = /note="Description of Artificial Sequence:
                            Synthetic peptide"
source                     1..19
                           mol_type = protein
                           organism = synthetic construct
SEQUENCE: 10
ARDLDYDVLT GDPVGGFDI                                              19

SEQ ID NO: 11              moltype = AA  length = 120
FEATURE                    Location/Qualifiers
REGION                     1..120
                           note = source = /note="Description of Artificial Sequence:
                            Synthetic polypeptide"
source                     1..120
                           mol_type = protein
                           organism = synthetic construct
SEQUENCE: 11
QVQLQESGPG LVKPSGTLSL TCAVSGGSIS SSDWWSWVRQ PPGKGLEWIG EIDHSGSTNY  60
NPSLMSRVTI SVDKSKNQFS LKLSSVTAAD TAVYFCGRGS WELSDAFDIR GQGTLVTVSS  120

SEQ ID NO: 12              moltype = AA  length = 120
FEATURE                    Location/Qualifiers
REGION                     1..120
                           note = source = /note="Description of Artificial Sequence:
                            Synthetic polypeptide"
source                     1..120
                           mol_type = protein
                           organism = synthetic construct
SEQUENCE: 12
QVQLQESGPG LVKSSETLSL TCTVSGGSIS SSDWWSWVRQ PPGKGLEWIG EIDHSGSTNY  60
NPSLMSRVTI SVDKSKNQFS LKLSSVTAAD TAVYFCARGS WELTDAFDIR GQGTLVTVSS  120

SEQ ID NO: 13              moltype = AA  length = 120
FEATURE                    Location/Qualifiers
REGION                     1..120
                           note = source = /note="Description of Artificial Sequence:
                            Synthetic polypeptide"
source                     1..120
                           mol_type = protein
                           organism = synthetic construct
SEQUENCE: 13
QVQLQESSPG LVKPSETLSL TCTVSGGSIS SSNWWSWVRQ PPGKGLEWIG EISHSGSTNY  60
NPSLKSRVTI SVDKSKNQFS LRLSSVTAAD TAVYFCGRGS WELTDAFDIR GQGTLVTVSS  120

SEQ ID NO: 14              moltype = AA  length = 126
FEATURE                    Location/Qualifiers
REGION                     1..126
                           note = source = /note="Description of Artificial Sequence:
                            Synthetic polypeptide"
source                     1..126
                           mol_type = protein
                           organism = synthetic construct
SEQUENCE: 14
QVQLVESGGG VVQPGRSLRL SCAASGFTFS SYGMHWVRQA PGKEREWVAV ISYDGSNKYY  60
TDSVKGRFTI SRDNSKNTLY LEMNSLRAED TAVYYCARDL DYDVLTGDPV GGFDIWGQGT  120
LVTVSS                                                            126

SEQ ID NO: 15              moltype = AA  length = 8
FEATURE                    Location/Qualifiers
REGION                     1..8
                           note = source = /note="Description of Artificial Sequence:
                            Synthetic peptide"
source                     1..8
                           mol_type = protein
                           organism = synthetic construct
SEQUENCE: 15
GFTFSDYY                                                          8

SEQ ID NO: 16              moltype = AA  length = 8
FEATURE                    Location/Qualifiers
REGION                     1..8
                           note = source = /note="Description of Artificial Sequence:
                            Synthetic peptide"
source                     1..8
                           mol_type = protein
                           organism = synthetic construct
SEQUENCE: 16
GFTFNDYY                                                          8
```

-continued

```
SEQ ID NO: 17              moltype = AA   length = 8
FEATURE                    Location/Qualifiers
REGION                     1..8
                           note = source = /note="Description of Artificial Sequence:
                            Synthetic peptide"
source                     1..8
                           mol_type = protein
                           organism = synthetic construct
SEQUENCE: 17
ISSSGDTI                                                                    8

SEQ ID NO: 18              moltype = AA   length = 8
FEATURE                    Location/Qualifiers
REGION                     1..8
                           note = source = /note="Description of Artificial Sequence:
                            Synthetic peptide"
source                     1..8
                           mol_type = protein
                           organism = synthetic construct
SEQUENCE: 18
ISSSGSTI                                                                    8

SEQ ID NO: 19              moltype = AA   length = 8
FEATURE                    Location/Qualifiers
REGION                     1..8
                           note = source = /note="Description of Artificial Sequence:
                            Synthetic peptide"
source                     1..8
                           mol_type = protein
                           organism = synthetic construct
SEQUENCE: 19
ISSSGTTT                                                                    8

SEQ ID NO: 20              moltype = AA   length = 12
FEATURE                    Location/Qualifiers
REGION                     1..12
                           note = source = /note="Description of Artificial Sequence:
                            Synthetic peptide"
source                     1..12
                           mol_type = protein
                           organism = synthetic construct
SEQUENCE: 20
ARGDAVSITG DY                                                               12

SEQ ID NO: 21              moltype = AA   length = 12
FEATURE                    Location/Qualifiers
REGION                     1..12
                           note = source = /note="Description of Artificial Sequence:
                            Synthetic peptide"
source                     1..12
                           mol_type = protein
                           organism = synthetic construct
SEQUENCE: 21
ARGAAVAPGF DS                                                               12

SEQ ID NO: 22              moltype = AA   length = 119
FEATURE                    Location/Qualifiers
REGION                     1..119
                           note = source = /note="Description of Artificial Sequence:
                            Synthetic polypeptide"
source                     1..119
                           mol_type = protein
                           organism = synthetic construct
SEQUENCE: 22
QVQLVESGGG LVKPGGSLRL SCAASGFTFS DYYMSWIRQA PGKGLEWVSS ISSSGDTIYY   60
ADSVQGRFTL SRDNAENSLF LQMNSLRAED TAVYYCARGD AVSITGDYRG QGTLVTVSS    119

SEQ ID NO: 23              moltype = AA   length = 119
FEATURE                    Location/Qualifiers
REGION                     1..119
                           note = source = /note="Description of Artificial Sequence:
                            Synthetic polypeptide"
source                     1..119
                           mol_type = protein
                           organism = synthetic construct
SEQUENCE: 23
QVQLVESGGG LVKPGGSLRL SCAASGFTFS DYYMSWIRQA PGKGLEWVSY ISSSGSTIYY   60
ADSVKGRFTI SRDNAKNSLY LQMNSLRAED TAVYYCARGD AVSITGDYRG QGTLVTVSS    119
```

```
SEQ ID NO: 24            moltype = AA  length = 119
FEATURE                  Location/Qualifiers
REGION                   1..119
                         note = source = /note="Description of Artificial Sequence:
                          Synthetic polypeptide"
source                   1..119
                         mol_type = protein
                         organism = synthetic construct
SEQUENCE: 24
QVQLVESGGG LVKPGGSLRL SCAASGFTFN DYYMSWIRQA PGKGLEWVSH ISSSGSTIYY   60
ADSVKGRFTV SRDNANNSLY LQMHSLRAED TAVYYCARGD AVSITGDYRG QGTLVTVSS    119

SEQ ID NO: 25            moltype = AA  length = 119
FEATURE                  Location/Qualifiers
REGION                   1..119
                         note = source = /note="Description of Artificial Sequence:
                          Synthetic polypeptide"
source                   1..119
                         mol_type = protein
                         organism = synthetic construct
SEQUENCE: 25
QVQLVESGGD LVKPGGSLRL SCAASGFTFS DYYMSWLRQA PGKELEWVSH ISSSGTTTYY   60
ADSVEGRFTI TRDNAKNSLY LQMNSLRAED TAVYYCARGA AVAPGFDSRG QGTLVTVSS    119

SEQ ID NO: 26            moltype = AA  length = 9
FEATURE                  Location/Qualifiers
REGION                   1..9
                         note = source = /note="Description of Artificial Sequence:
                          Synthetic peptide"
source                   1..9
                         mol_type = protein
                         organism = synthetic construct
SEQUENCE: 26
GGSISSSBW                                                           9

SEQ ID NO: 27            moltype = AA  length = 7
FEATURE                  Location/Qualifiers
VARIANT                  2
                         note = X = D or S
SITE                     1..7
                         note = /note="Variant residues given in the sequence have
                          no preference with respect to those in the annotations for
                          variant positions"
REGION                   1..7
                         note = source = /note="Description of Artificial Sequence:
                          Synthetic peptide"
source                   1..7
                         mol_type = protein
                         organism = synthetic construct
SEQUENCE: 27
IXHSGST                                                             7

SEQ ID NO: 28            moltype = AA  length = 13
FEATURE                  Location/Qualifiers
VARIANT                  1
                         note = X = G or A
VARIANT                  4
                         note = X = S or Q
VARIANT                  8
                         note = X = S or T
SITE                     1..13
                         note = /note="Variant residues given in the sequence have
                          no preference with respect to those in the annotations for
                          variant positions"
REGION                   1..13
                         note = source = /note="Description of Artificial Sequence:
                          Synthetic peptide"
source                   1..13
                         mol_type = protein
                         organism = synthetic construct
SEQUENCE: 28
XRGXWELXDA FDI                                                      13

SEQ ID NO: 29            moltype = AA  length = 8
FEATURE                  Location/Qualifiers
VARIANT                  6
                         note = X = S or T
SITE                     1..8
```

-continued

```
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 29
GFTFSXYG                                                                    8

SEQ ID NO: 30           moltype = AA  length = 8
FEATURE                 Location/Qualifiers
VARIANT                 8
                        note = X = K or R
SITE                    1..8
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 30
ISYDGSNX                                                                    8

SEQ ID NO: 31           moltype = AA  length = 19
FEATURE                 Location/Qualifiers
VARIANT                 8
                        note = X = V or I
SITE                    1..19
                        note = /note="Variant residues given in the sequence have
                         no preference with respect to those in the annotations for
                         variant positions"
REGION                  1..19
                        note = source = /note="Description of Artificial Sequence:
                         Synthetic peptide"
source                  1..19
                        mol_type = protein
                        organism = synthetic construct
SEQUENCE: 31
ARDLDYDXLT GDPVGGFDI                                                        19

SEQ ID NO: 32           moltype = AA  length = 8
FEATURE                 Location/Qualifiers
VARIANT                 3
                        note = X = T or I
VARIANT                 4
                        note = X = F or V
VARIANT                 5
                        note = X = S, N, or G
SITE                    1..8
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 32
GFXXXBYY                                                                    8

SEQ ID NO: 33           moltype = AA  length = 8
FEATURE                 Location/Qualifiers
VARIANT                 3
                        note = X = S or N
VARIANT                 6
                        note = X = D, S, G, or N
VARIANT                 7
                        note = X = T or I
SITE                    1..8
                        note = /note="Variant residues given in the sequence have
                         no preference with respect to those in the annotations for
                         variant positions"
```

-continued

```
REGION                    1..8
                          note = source = /note="Description of Artificial Sequence:
                          Synthetic peptide"
source                    1..8
                          mol_type = protein
                          organism = synthetic construct
SEQUENCE: 33
ISXSGXXI                                                                          8

SEQ ID NO: 34             moltype = AA   length = 349
FEATURE                   Location/Qualifiers
REGION                    1..349
                          note = source = /note="Description of Artificial Sequence:
                          Synthetic polypeptide"
source                    1..349
                          mol_type = protein
                          organism = synthetic construct
SEQUENCE: 34
QVQLQESGPG LVKSSETLSL TCTVSGGSIS SSDWWSWVRQ PPGKGLEWIG EIDHSGSTNY  60
NPSLMSRVTI SVDKSKNQFS LKLSSVTAAD TAVYFCARGS WELTDAFDIR GQGTLVTVSS  120
ESKYGPPCPP CPAPEAAGGP SVFLFPPKPK DTLMISRTPE VTCVVVDVSQ EDPEVQFNWY  180
VDGVEVHNAK TKPREEQFNS TYRVVSVLTV LHQDWLNGKE YKCKVSNKGL PSSIEKTISK  240
AKGQPREPQV YTLPPSQEEM TKNQVSLSCA VKGFYPSDIA VEWESNGQPE NNYKTTPPVL  300
DSDGSFFLVS RLTVDKSRWQ EGNVFSCSVM HEALHNHYTQ KSLSLSLGK              349

SEQ ID NO: 35             moltype = AA   length = 348
FEATURE                   Location/Qualifiers
REGION                    1..348
                          note = source = /note="Description of Artificial Sequence:
                          Synthetic polypeptide"
source                    1..348
                          mol_type = protein
                          organism = synthetic construct
SEQUENCE: 35
QVQLVESGGG LVKPGGSLRL SCAASGFTFN DYYMSWIRQA PGKGLEWVSH ISSSGSTIYY  60
ADSVKGRFTV SRDNANNSLY LQMHSLRAED TAVYYCARGD AVSITGDYRG QGTLVTVSSE  120
SKYGPPCPPC PAPEAAGGPS VFLFPPKPKD TLMISRTPEV TCVVVDVSQE DPEVQFNWYV  180
DGVEVHNAKT KPREEQFNST YRVVSVLTVL HQDWLNGKEY KCKVSNKGLP SSIEKTISKA  240
KGQPREPQVY TLPPSQEEMT KNQVSLWCLV KGFYPSDIAV EWESNGQPEN NYKTTPPVLD  300
SDGSFFLYSR LTVDKSRWQE GNVFSCSVMH EALHNHYTQK SLSLSLGK               348

SEQ ID NO: 36             moltype = AA   length = 349
FEATURE                   Location/Qualifiers
REGION                    1..349
                          note = source = /note="Description of Artificial Sequence:
                          Synthetic polypeptide"
source                    1..349
                          mol_type = protein
                          organism = synthetic construct
SEQUENCE: 36
QVQLQESGPG LVKSSETLSL TCTVSGGSIS SSDWWSWVRQ PPGKGLEWIG EIDHSGSTNY  60
NPSLMSRVTI SVDKSKNQFS LKLSSVTAAD TAVYFCARGS WELTDAFDIR GQGTLVTVSS  120
ESKYGPPCPP CPAPEAAGGP SVFLFPPKPK DTLMISRTPE VTCVVVDVSQ EDPEVQFNWY  180
VDGVEVHNAK TKPREEQFNS TYRVVSVLTV LHQDWLNGKE YKCKVSNKGL PSSIEKTISK  240
AKGQPREPQV YTLPPSQEEM TKNQVSLSCA VKGFYPSDIA VEWESNGQPE NNYKTTPPVL  300
DSDGSFFLVS RLTVDKSRWQ EGNVFSCSVM HEALHNHYTQ KSLSLSLGK              349

SEQ ID NO: 37             moltype = AA   length = 348
FEATURE                   Location/Qualifiers
REGION                    1..348
                          note = source = /note="Description of Artificial Sequence:
                          Synthetic polypeptide"
source                    1..348
                          mol_type = protein
                          organism = synthetic construct
SEQUENCE: 37
QVQLVESGGD LVKPGGSLRL SCAASGFTFS DYYMSWLRQA PGKELEWVSH ISSSGTTTYY  60
ADSVEGRFTI TRDNAKNSLY LQMNSLRAED TAVYYCARGA AVAPGFDSRG QGTLVTVSSE  120
SKYGPPCPPC PAPEAAGGPS VFLFPPKPKD TLMISRTPEV TCVVVDVSQE DPEVQFNWYV  180
DGVEVHNAKT KPREEQFNST YRVVSVLTVL HQDWLNGKEY KCKVSNKGLP SSIEKTISKA  240
KGQPREPQVY TLPPSQEEMT KNQVSLWCLV KGFYPSDIAV EWESNGQPEN NYKTTPPVLD  300
SDGSFFLYSR LTVDKSRWQE GNVFSCSVMH EALHNHYTQK SLSLSLGK               348

SEQ ID NO: 38             moltype = AA   length = 272
FEATURE                   Location/Qualifiers
source                    1..272
                          mol_type = protein
                          organism = Homo sapiens
SEQUENCE: 38
```

```
MDSYLLMWGL LTFIMVPGCQ AELCDDDPPE IPHATFKAMA YKEGTMLNCE CKRGFRRIKS    60
GSLYMLCTGN SSHSSWDNQC QCTSSATRNT TKQVTPQPEE QKERKTTEMQ SPMQPVDQAS   120
LPGHCREPPP WENEATERIY HFVVGQMVYY QCVQGYRALH RGPAESVCKM THGKTRWTQP   180
QLICTGEMET SQFPGEEKPQ ASPEGRPESE TSCLVTTTDF QIQTEMAATM ETSIFTTEYQ   240
VAVAGCVFLL ISVLLLSGLT WQRRQRKSRR TI                                 272

SEQ ID NO: 39              moltype = AA  length = 551
FEATURE                    Location/Qualifiers
source                     1..551
                           mol_type = protein
                           organism = Homo sapiens
SEQUENCE: 39
MAAPALSWRL PLLILLLPLA TSWASAAVNG TSQFTCFYNS RANISCVWSQ DGALQDTSCQ    60
VHAWPDRRRW NQTCELLPVS QASWACNLIL GAPDSQKLTT VDIVTLRVLC REGVRWRVMA   120
IQDFKPFENL RLMAPISLQV VHVETHRCNI SWEISQASHY FERHLEFEAR TLSPGHTWEE   180
APLLTLKQKQ EWICLETLTP DTQYEFQVRV KPLQGEFTTW SPWSQPLAFR TKPAALGKDT   240
IPWLGHLLVG LSGAFGFIIL VYLLINCRNT GPWLKKVLKC NTPDPSKFFS QLSSEHGGDV   300
QKWLSSPFPS SSFSPGGLAP EISPLEVLER DKVTQLLLQQ DKVPEPASLS SNHSLTSCFT   360
NQGYFFFHLP DALEIEACQV YFTYDPYSEE DPDEGVAGAP TGSSPQPLQP LSGEDDAYCT   420
FPSRDDLLLF SPSLLGGPSP PSTAPGGSGA GEERMPPSLQ ERVPRDWDPQ PLGPPTPGVP   480
DLVDFQPPPE LVLREAGEEV PDAGPREGVS FPWSRPPGQG EFRALNARLP LNTDAYLSLQ   540
ELQGQDPTHL V                                                        551

SEQ ID NO: 40              moltype = AA  length = 369
FEATURE                    Location/Qualifiers
source                     1..369
                           mol_type = protein
                           organism = Homo sapiens
SEQUENCE: 40
MLKPSLPFTS LLFLQLPLLG VGLNTTILTP NGNEDTTADF FLTTMPTDSL SVSTLPLPEV    60
QCFVFNVEYM NCTWNSSSEP QPTNLTLHYW YKNSDNDKVQ KCSHYLFSEE ITSGCQLQKK   120
EIHLYQTFVV QLQDPREPRR QATQMLKLQN LVIPWAPENL TLHKLSESQL ELNWNNRFLN   180
HCLEHLVQYR TDWDHSWTEQ SVDYRHKFSL PSVDGQKRYT FRVRSRFNPL CGSAQHWSEW   240
SHPIHWGSNT SKENPFLFAL EAVVISVGSM GLIISLLCVY FWLERTMPRI PTLKNLEDLV   300
TEYHGNFSAW SGVSKGLAES LQPDYSERLC LVSEIPPKGG ALGEGPGASP CNQHSPYWAP   360
PCYTLKPET                                                           369

SEQ ID NO: 41              moltype = AA  length = 153
FEATURE                    Location/Qualifiers
source                     1..153
                           mol_type = protein
                           organism = Homo sapiens
SEQUENCE: 41
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLT                                153

SEQ ID NO: 42              moltype = AA  length = 330
FEATURE                    Location/Qualifiers
source                     1..330
                           mol_type = protein
                           organism = Homo sapiens
SEQUENCE: 42
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 43              moltype = AA  length = 327
FEATURE                    Location/Qualifiers
source                     1..327
                           mol_type = protein
                           organism = Homo sapiens
SEQUENCE: 43
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 44              moltype = AA  length = 6
FEATURE                    Location/Qualifiers
REGION                     1..6
                           note = source = /note="Description of Artificial Sequence:
                            Synthetic peptide"
source                     1..6
```

-continued

```
                         mol_type = protein
                         organism = synthetic construct
SEQUENCE: 44
QSVSSN                                                          6

SEQ ID NO: 45            moltype =    length =
SEQUENCE: 45
000

SEQ ID NO: 46            moltype = AA   length = 9
FEATURE                  Location/Qualifiers
REGION                   1..9
                         note = source = /note="Description of Artificial Sequence:
                          Synthetic peptide"
source                   1..9
                         mol_type = protein
                         organism = synthetic construct
SEQUENCE: 46
QQYNNWPWT                                                       9

SEQ ID NO: 47            moltype = AA   length = 107
FEATURE                  Location/Qualifiers
REGION                   1..107
                         note = source = /note="Description of Artificial Sequence:
                          Synthetic polypeptide"
source                   1..107
                         mol_type = protein
                         organism = synthetic construct
SEQUENCE: 47
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPWTFGQ GTKVEIK            107

SEQ ID NO: 48            moltype = AA   length = 214
FEATURE                  Location/Qualifiers
REGION                   1..214
                         note = source = /note="Description of Artificial Sequence:
                          Synthetic polypeptide"
source                   1..214
                         mol_type = protein
                         organism = synthetic construct
SEQUENCE: 48
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNWPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                           214

SEQ ID NO: 49            moltype = AA   length = 5
FEATURE                  Location/Qualifiers
REGION                   1..5
                         note = source = /note="Description of Artificial Sequence:
                          Synthetic peptide"
source                   1..5
                         mol_type = protein
                         organism = synthetic construct
SEQUENCE: 49
GGGGS                                                           5

SEQ ID NO: 50            moltype = AA   length = 10
FEATURE                  Location/Qualifiers
REGION                   1..10
                         note = source = /note="Description of Artificial Sequence:
                          Synthetic peptide"
source                   1..10
                         mol_type = protein
                         organism = synthetic construct
SEQUENCE: 50
GGGGSGGGGS                                                      10

SEQ ID NO: 51            moltype = AA   length = 330
FEATURE                  Location/Qualifiers
REGION                   1..330
                         note = source = /note="Description of Artificial Sequence:
                          Synthetic polypeptide"
source                   1..330
                         mol_type = protein
                         organism = synthetic construct
SEQUENCE: 51
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
```

-continued

```
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 52             moltype = AA   length = 327
FEATURE                   Location/Qualifiers
REGION                    1..327
                          note = source = /note="Description of Artificial Sequence:
                           Synthetic polypeptide"
source                    1..327
                          mol_type = protein
                          organism = synthetic construct
SEQUENCE: 52
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEAAGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 53             moltype = AA   length = 349
FEATURE                   Location/Qualifiers
REGION                    1..349
                          note = source = /note="Description of Artificial Sequence:
                           Synthetic polypeptide"
source                    1..349
                          mol_type = protein
                          organism = synthetic construct
SEQUENCE: 53
QVQLQESGPG LVKPSGTLSL TCAVSGGSIS SSDWWSWVRQ PPGKGLEWIG EIDHSGSTNY   60
NPSLMSRVTI SVDKSKNQFS LKLSSVTAAD TAVYFCGRGS WELSDAFDIR GQGTLVTVSS   120
ESKYGPPCPP CPAPEAAGGP SVFLFPPKPK DTLMISRTPE VTCVVVDVSQ EDPEVQFNWY   180
VDGVEVHNAK TKPREEQFNS TYRVVSVLTV LHQDWLNGKE YKCKVSNKGL PSSIEKTISK   240
AKGQPREPQV YTLPPSQEEM TKNQVSLSCA VKGFYPSDIA VEWESNGQPE NNYKTTPPVL   300
DSDGSFFLVS RLTVDKSRWQ EGNVFSCSVM HEALHNHYTQ KSLSLSLGK               349

SEQ ID NO: 54             moltype = AA   length = 13
FEATURE                   Location/Qualifiers
source                    1..13
                          mol_type = protein
                          organism = Homo sapiens
SEQUENCE: 54
ESKYGPPCPS CPA                                                      13

SEQ ID NO: 55             moltype = AA   length = 13
FEATURE                   Location/Qualifiers
REGION                    1..13
                          note = source = /note="Description of Artificial Sequence:
                           Synthetic peptide"
source                    1..13
                          mol_type = protein
                          organism = synthetic construct
SEQUENCE: 55
ESKYGPPCPP CPA                                                      13

SEQ ID NO: 56             moltype = AA   length = 110
FEATURE                   Location/Qualifiers
source                    1..110
                          mol_type = protein
                          organism = Homo sapiens
SEQUENCE: 56
APEFLGGPSV FLFPPKPKDT LMISRTPEVT CVVVDVSQED PEVQFNWYVD GVEVHNAKTK   60
PREEQFNSTY RVVSVLTVLH QDWLNGKEYK CKVSNKGLPS SIEKTISKAK              110

SEQ ID NO: 57             moltype = AA   length = 110
FEATURE                   Location/Qualifiers
REGION                    1..110
                          note = source = /note="Description of Artificial Sequence:
                           Synthetic polypeptide"
source                    1..110
                          mol_type = protein
                          organism = synthetic construct
SEQUENCE: 57
APEAAGGPSV FLFPPKPKDT LMISRTPEVT CVVVDVSQED PEVQFNWYVD GVEVHNAKTK   60
PREEQFNSTY RVVSVLTVLH QDWLNGKEYK CKVSNKGLPS SIEKTISKAK              110

SEQ ID NO: 58             moltype = AA   length = 107
FEATURE                   Location/Qualifiers
```

-continued

```
source                      1..107
                            mol_type = protein
                            organism = Homo sapiens
SEQUENCE: 58
GQPREPQVYT LPPSQEEMTK NQVSLTCLVK GFYPSDIAVE WESNGQPENN YKTTPPVLDS  60
DGSFFLYSRL TVDKSRWQEG NVFSCSVMHE ALHNHYTQKS LSLSLGK                107

SEQ ID NO: 59               moltype = AA   length = 107
FEATURE                     Location/Qualifiers
REGION                      1..107
                            note = source = /note="Description of Artificial Sequence:
                             Synthetic polypeptide"
source                      1..107
                            mol_type = protein
                            organism = synthetic construct
SEQUENCE: 59
GQPREPQVYT LPPSQEEMTK NQVSLWCLVK GFYPSDIAVE WESNGQPENN YKTTPPVLDS  60
DGSFFLYSRL TVDKSRWQEG NVFSCSVMHE ALHNHYTQKS LSLSLGK                107

SEQ ID NO: 60               moltype = AA   length = 107
FEATURE                     Location/Qualifiers
REGION                      1..107
                            note = source = /note="Description of Artificial Sequence:
                             Synthetic polypeptide"
source                      1..107
                            mol_type = protein
                            organism = synthetic construct
SEQUENCE: 60
GQPREPQVYT LPPSQEEMTK NQVSLSCAVK GFYPSDIAVE WESNGQPENN YKTTPPVLDS  60
DGSFFLVSRL TVDKSRWQEG NVFSCSVMHE ALHNHYTQKS LSLSLGK                107

SEQ ID NO: 61               moltype = AA   length = 348
FEATURE                     Location/Qualifiers
REGION                      1..348
                            note = source = /note="Description of Artificial Sequence:
                             Synthetic polypeptide"
source                      1..348
                            mol_type = protein
                            organism = synthetic construct
SEQUENCE: 61
QVQLVESGGG LVKPGGSLRL SCAASGFTFS DYYMSWIRQA PGKGLEWVSS ISSSGDTIYY  60
ADSVQGRFTL SRDNAENSLF LQMNSLRAED TAVYYCARGD AVSITGDYRG QGTLVTVSSE  120
SKYGPPCPPC PAPEAAGGPS VFLFPPKPKD TLMISRTPEV TCVVVDVSQE DPEVQFNWYV  180
DGVEVHNAKT KPREEQFNST YRVVSVLTVL HQDWLNGKEY KCKVSNKGLP SSIEKTISKA  240
KGQPREPQVY TLPPSQEEMT KNQVSLWCLV KGFYPSDIAV EWESNGQPEN NYKTTPPVLD  300
SDGSFFLYSR LTVDKSRWQE GNVFSCSVMH EALHNHYTQK SLSLSLGK              348

SEQ ID NO: 62               moltype = AA   length = 349
FEATURE                     Location/Qualifiers
REGION                      1..349
                            note = source = /note="Description of Artificial Sequence:
                             Synthetic polypeptide"
source                      1..349
                            mol_type = protein
                            organism = synthetic construct
SEQUENCE: 62
QVQLQESGPG LVKSSETLSL TCTVSGGSIS SSDWWSWVRQ PPGKGLEWIG EIDHSGSTNY  60
NPSLMSRVTI SVDKSKNQFS LKLSSVTAAD TAVYFCARGS WELTDAFDIR GQGTLVTVSS  120
ESKYGPPCPP CPAPEAAGGP SVFLFPPKPK DTLMISRTPE VTCVVVDVSQ EDPEVQFNWY  180
VDGVEVHNAK TKPREEQFNS TYRVVSVLTV LHQDWLNGKE YKCKVSNKGL PSSIEKTISK  240
AKGQPREPQV YTLPPSQEEM TKNQVSLSCA VKGFYPSDIA VEWESNGQPE NNYKTTPPVL  300
DSDGSFFLVS RLTVDKSRWQ EGNVFSCSVM HEALHNHYTQ KSLSLSLGK             349

SEQ ID NO: 63               moltype = AA   length = 348
FEATURE                     Location/Qualifiers
REGION                      1..348
                            note = source = /note="Description of Artificial Sequence:
                             Synthetic polypeptide"
source                      1..348
                            mol_type = protein
                            organism = synthetic construct
SEQUENCE: 63
QVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARGD AVSITGDYRG QGTLVTVSSE  120
SKYGPPCPPC PAPEAAGGPS VFLFPPKPKD TLMISRTPEV TCVVVDVSQE DPEVQFNWYV  180
DGVEVHNAKT KPREEQFNST YRVVSVLTVL HQDWLNGKEY KCKVSNKGLP SSIEKTISKA  240
KGQPREPQVY TLPPSQEEMT KNQVSLWCLV KGFYPSDIAV EWESNGQPEN NYKTTPPVLD  300
SDGSFFLYSR LTVDKSRWQE GNVFSCSVMH EALHNHYTQK SLSLSLGK              348
```

-continued

```
SEQ ID NO: 64            moltype = AA   length = 349
FEATURE                  Location/Qualifiers
REGION                   1..349
                         note = source = /note="Description of Artificial Sequence:
                         Synthetic polypeptide"
source                   1..349
                         mol_type = protein
                         organism = synthetic construct
SEQUENCE: 64
QVQLQESSPG LVKPSETLSL TCTVSGGSIS SSNWWSWVRQ PPGKGLEWIG EISHSGSTNY   60
NPSLKSRVTI SVDKSKNQFS LRLSSVTAAD TAVYFCGRGS WELTDAFDIR GQGTLVTVSS  120
ESKYGPPCPP CPAPEAAGGP SVFLFPPKPK DTLMISRTPE VTCVVVDVSQ EDPEVQFNWY  180
VDGVEVHNAK TKPREEQFNS TYRVVSVLTV LHQDWLNGKE YKCKVSNKGL PSSIEKTISK  240
AKGQPREPQV YTLPPSQEEM TKNQVSLSCA VKGFYPSDIA VEWESNGQPE NNYKTTPPVL  300
DSDGSFFLVS RLTVDKSRWQ EGNVFSCSVM HEALHNHYTQ KSLSLSLGK             349

SEQ ID NO: 65            moltype = AA   length = 348
FEATURE                  Location/Qualifiers
REGION                   1..348
                         note = source = /note="Description of Artificial Sequence:
                         Synthetic polypeptide"
source                   1..348
                         mol_type = protein
                         organism = synthetic construct
SEQUENCE: 65
QVQLVESGGG LVKPGGSLRL SCAASGFTFS DYYMSWIRQA PGKGLEWVSY ISSSGSTIYY   60
ADSVKGRFTI SRDNAKNSLY LQMNSLRAED TAVYYCARGD AVSITGDYRG QGTLVTVSSE  120
SKYGPPCPPC PAPEAAGGPS VFLFPPKPKD TLMISRTPEV TCVVVDVSQE DPEVQFNWYV  180
DGVEVHNAKT KPREEQFNST YRVVSVLTVL HQDWLNGKEY KCKVSNKGLP SSIEKTISKA  240
KGQPREPQVY TLPPSQEEMT KNQVSLWCLV KGFYPSDIAV EWESNGQPEN NYKTTPPVLD  300
SDGSFFLYSR LTVDKSRWQE GNVFSCSVMH EALHNHYTQK SLSLSLGK              348

SEQ ID NO: 66            moltype = AA   length = 355
FEATURE                  Location/Qualifiers
REGION                   1..355
                         note = source = /note="Description of Artificial Sequence:
                         Synthetic polypeptide"
source                   1..355
                         mol_type = protein
                         organism = synthetic construct
SEQUENCE: 66
QVQLVESGGG VVQPGRSLRL SCAASGFTFS SYGMHWVRQA PGKEREWVAV ISYDGSNKYY   60
TDSVKGRFTI SRDNSKNTLY LEMNSLRAED TAVYYCARDL DYDVLTGDPV GGFDIWGQGT  120
LVTVSSESKY GPPCPPCPAP EAAGGPSVFL FPPKPKDTLM ISRTPEVTCV VVDVSQEDPE  180
VQFNWYVDGV EVHNAKTKPR EEQFNSTYRV VSVLTVLHQD WLNGKEYKCK VSNKGLPSSI  240
EKTISKAKGQ PREPQVYTLP PSQEEMTKNQ VSLSCAVKGF YPSDIAVEWE SNGQPENNYK  300
TTPPVLDSDG SFFLVSRLTV DKSRWQEGNV FSCSVMHEAL HNHYTQKSLS LSLGK      355

SEQ ID NO: 67            moltype = AA   length = 348
FEATURE                  Location/Qualifiers
REGION                   1..348
                         note = source = /note="Description of Artificial Sequence:
                         Synthetic polypeptide"
source                   1..348
                         mol_type = protein
                         organism = synthetic construct
SEQUENCE: 67
QVQLVESGGG LVKPGGSLRL SCAASGFTFS DYYMSWIRQA PGKGLEWVSS ISSSGDTIYY   60
ADSVQGRFTL SRDNAENSLF LQMNSLRAED TAVYYCARGD AVSITGDYRG QGTLVTVSSE  120
SKYGPPCPPC PAPEAAGGPS VFLFPPKPKD TLMISRTPEV TCVVVDVSQE DPEVQFNWYV  180
DGVEVHNAKT KPREEQFNST YRVVSVLTVL HQDWLNGKEY KCKVSNKGLP SSIEKTISKA  240
KGQPREPQVY TLPPSQEEMT KNQVSLWCLV KGFYPSDIAV EWESNGQPEN NYKTTPPVLD  300
SDGSFFLYSR LTVDKSRWQE GNVFSCSVMH EALHNHYTQK SLSLSLGK              348

SEQ ID NO: 68            moltype = AA   length = 50
FEATURE                  Location/Qualifiers
SITE                     1..50
                         note = /note="This sequence may encompass 1-10 'Gly Gly Gly
                         Gly Ser' repeating units"
REGION                   1..50
                         note = source = /note="Description of Artificial Sequence:
                         Synthetic polypeptide"
source                   1..50
                         mol_type = protein
                         organism = synthetic construct
SEQUENCE: 68
GGGGSGGGGS GGGGSGGGGS GGGGSGGGGS GGGGSGGGGS GGGGSGGGGS             50
```